(12) United States Patent
Tsun et al.

(10) Patent No.: US 11,498,972 B2
(45) Date of Patent: Nov. 15, 2022

(54) ANTI-OX40 ANTIBODY AND USE THEREOF

(71) Applicant: Innovent Biologics (Suzhou) Co., Ltd., Suzhou (CN)

(72) Inventors: Andy Tsun, Suzhou (CN); Hemanta Baruah, Suzhou (CN); Xiaolin Liu, Suzhou (CN); Cheng Chen, Suzhou (CN); Junjian Liu, Suzhou (CN); Bingliang Chen, Suzhou (CN); Weifeng Huang, Suzhou (CN)

(73) Assignee: Innovent Biologics (Suzhou) Co., Ltd., Suzhou (CN)

( * ) Notice: Subject to any disclaimer, the term of this patent is extended or adjusted under 35 U.S.C. 154(b) by 178 days.

(21) Appl. No.: 16/496,019

(22) PCT Filed: Mar. 23, 2018

(86) PCT No.: PCT/CN2018/080315
§ 371 (c)(1),
(2) Date: Sep. 20, 2019

(87) PCT Pub. No.: WO2018/177220
PCT Pub. Date: Oct. 4, 2018

(65) Prior Publication Data
US 2020/0140562 A1 May 7, 2020

(30) Foreign Application Priority Data
Mar. 25, 2017 (CN) .......................... 201710185400.8

(51) Int. Cl.
*A61K 39/395* (2006.01)
*C07K 16/28* (2006.01)
(Continued)

(52) U.S. Cl.
CPC ...... *C07K 16/2878* (2013.01); *A61K 47/6803* (2017.08); *A61P 35/00* (2018.01);
(Continued)

(58) Field of Classification Search
None
See application file for complete search history.

(56) References Cited

U.S. PATENT DOCUMENTS

| 5,500,362 A | 3/1996 | Robinson et al. |
| 5,591,828 A | 1/1997 | Bosslet et al. |
(Continued)

FOREIGN PATENT DOCUMENTS

| CN | 105229032 A | 2/2016 |
| EP | 0404097 | 6/1990 |
(Continued)

OTHER PUBLICATIONS

Yan et al., Construction of a synthetic phage-displayed nonaobody library with CDR3 regions randomized by trinucleotide cassesttes for diagonostic applications, J. Transl. Med. 12:343, 12 pages, 2014.*

(Continued)

*Primary Examiner* — Claire Kaufman
(74) *Attorney, Agent, or Firm* — Stinson LLP

(57) ABSTRACT

The present invention relates to an antibody and antibody fragment that specifically binds to OX40 and to a composition comprising said antibody or antibody fragment thereof. In addition, the present invention relates to a nucleic acid encoding the antibody or antibody fragment thereof and a host cell comprising the same, and to a related use thereof. In addition, the present invention relates to the use of the antibody and antibody fragment for treatment and diagnosis.

24 Claims, 8 Drawing Sheets
Specification includes a Sequence Listing.

(51) Int. Cl.
  *A61K 47/68*  (2017.01)
  *A61P 35/00*  (2006.01)
  *A61K 39/00*  (2006.01)

(52) U.S. Cl.
  CPC .... *A61K 2039/507* (2013.01); *C07K 2317/21* (2013.01); *C07K 2317/565* (2013.01); *C07K 2317/732* (2013.01); *C07K 2317/75* (2013.01); *C07K 2317/92* (2013.01)

(56) References Cited

U.S. PATENT DOCUMENTS

| | | | |
|---|---|---|---|
| 5,648,237 | A | 7/1997 | Carter |
| 5,789,199 | A | 8/1998 | Joly et al. |
| 5,821,337 | A | 10/1998 | Carter et al. |
| 5,840,523 | A | 11/1998 | Simmons et al. |
| 6,171,586 | B1 | 1/2001 | Lam et al. |
| 6,267,958 | B1 | 7/2001 | Andya et al. |
| 6,737,056 | B1 | 5/2004 | Presta |
| 8,236,930 | B2 | 8/2012 | Min et al. |
| 9,790,281 | B2* | 10/2017 | Simons ............... C07K 16/30 |
| 10,273,307 | B2 | 4/2019 | Simmons et al. |
| 10,851,173 | B2 | 12/2020 | Liu et al. |
| 2009/0214560 | A1 | 8/2009 | Min et al. |

FOREIGN PATENT DOCUMENTS

| | | | |
|---|---|---|---|
| JP | 2013538057 | A | 10/2013 |
| WO | 9301161 | A1 | 1/1993 |
| WO | 9942585 | A1 | 8/1999 |
| WO | 2005103081 | A2 | 11/2005 |
| WO | 2006044908 | A2 | 4/2006 |
| WO | 2006121167 | A1 | 11/2006 |
| WO | 2007005874 | A2 | 1/2007 |
| WO | 2009036379 | A2 | 3/2009 |
| WO | 2009114335 | A2 | 9/2009 |
| WO | 2010027827 | A2 | 3/2010 |
| WO | 2010077634 | A1 | 7/2010 |
| WO | 2010105256 | A1 | 9/2010 |
| WO | 2011066342 | A2 | 6/2011 |
| WO | 2012009567 | A2 | 1/2012 |
| WO | 2012009568 | A2 | 1/2012 |
| WO | 2015153513 | A1 | 10/2015 |
| WO | 2016179517 | A1 | 11/2016 |
| WO | 2016196228 | A1 | 12/2016 |
| WO | 2018195386 | A1 | 10/2018 |

OTHER PUBLICATIONS

Al-Shamkhani et al., OX40 is differentially expressed on activated rat and mouse T cells and is the sole receptor for the OX40 ligand; Eur. J. Immunol., 1996, vol. 26, pp. 1696-1699.
Almagro et al., Humanization of Antibodies; Frontier's in Bioscience, 2008, vol. 13, pp. 1619-1633.
Al-Iazikani et al., Standard Conformations for the Canonical Structures of Immunoglobulins; J. Mol Biol., 1997, vol. 273, pp. 927-948.
CAS Reg.. No. 946414-94-4, Accessed Jun. 4, 2021.
Chen et al., PLGA-nanoparticle mediated delivery of anti-OX40 monoclonal antibody enhances anti-tumor cytotoxic T sell responses; Cellular Immunology, 2014, vol. 287, pp. 91-99.
Clothia et al., Conformations of immunoglobulin hypervariable regions; Nature, 1989, vol. 342, pp. 21-28.
Clackson et al., Making antibody fragments using phage display libraries; Nature, 1991, vol. 352, 5-pages.
Clynes et al., Fc receptors are required n passive and active immunity to melanoma; Proc. Natl. Acad. Sci., 1998, vol. 95, pp. 652-656.
Estep et al., High throughput solution-based measurement of antibody-antigen affinity and epitope binning; MAbs, 2013, vol. 5, No. 2, pp. 270-278.

Fellhouse et al., Synthetic antibodies from a four-amino-acid code: A dominant role for tyrosine in antigen recognition; PNAS, 2004, vol. 101, No. 34, pp. 12467-12472.
Flatman et al., Process analytics for purification of monoclonal antibodies; Journal of Chromatography B., 2007, vol. 348, pp. 79-87.
Gemgross, Advances in the production of human therapeutic proteins in yeasts and filamentous fungi; Nature biotechnology; 2004, vol. 22, No. 11, 6-pages.
Graham et al., Characteristics of a Human Cell Line Transformed by DNA from Human Adenovirus Type 5; J. gen. Viorol., 1977, vol. 36, pp. 59-72.
Gramaglia et al., Ox-040 Ligand: A potent Costimulatory Molecule for Sustaining Primary CD4T Cell Responses; 1998, J. Immunol., vol. 161, pp. 6510-6517.
Gramaglia et al., The OX40 Costimulatory Receptor Determines the Development of CD4 Memory by Regulating Primary Clonal Expansion; J Immunol, 2000, vol. 165, pp. 3043-3050.
Hirschhorn-Cymerman et al., OX40 engagement and chemotherapy combination provides potent antitumor immunity with concomitant regulatory T cell apoptosis; J. Exp. Med. vol., 2009, 206(5):1103-1116.
Holliger et al., "Diabodies": Small bivalent and bispecific antibody fragments; Proc. Natl. Acad. Sci, 1993, vol. 90, pp. 6444-6448.
Lee et al., High-affinity Human Antibodies from Phage-displayed Synthetic Fab Libraries with a Single Framework Scaffold; J. Mol. Biol., 2004, pp. 1073-1093.
Li et al., Optimization of humanized IgGs in glycoengineered Pichia pastoris; Nature Biotechnology, 2005, vol. 24(2), pp. 210-215.
Lonberg, Fully human antibodies from transgenic mouse and phage display platforms; Current Opinion in Immunology; 2008, vol. 20, pp. 450-459.
Mallett et al., Characterization of the MRC OX40 antigen of activated CD4 positive T lymphocytes-a molecule related to nerve growth factor receptor; The EMBO Journal, 1990, vol. 9, No. 4, pp. 1063-1068.
Marks et al., By-passing Immunization Human Antibodies from V-gene Libraries Displayed on Phage; J. Mol Biol., 1991, vol. 222, pp. 581-597.
McCafferty et al., Phage antibodies: filamentous phage displaying antibody variable domains; Nature, 1990, vol. 348, 552-654.
Morris et al., Development and Characterization of Recombinant Human Fc:OX40L fusion protein linked via a coiled-coil trimerization domain; Mol Immunol., 2007, vol. 44, No. 12, pp. 3112-3121.
Murata et al., Constitutive OX40/OX40 Ligand Interaction Induces Autoimmune-Like Diseases; J. Immunol, 2002, vol. 169, pp. 4628-4636.
Paterson et al., Antigens of Activated Rat T Lymphocytes Including a Molecule of 50,000 Mr Detected Only on CD4 Positive T Blasts; Molecular Immunology, 1987, vol. 24, No. 12, pp. 1281-1290.
Portolano et al., Lack of promiscuity in autoantigen-specific H and L chain combinations as revealed by human H and L chain "roulette"; J Immunol, 1993, vol. 150, pp. 880-887.
Ravetch et al., Fc Receptors; Annu. Rev. Immunol, 1991, vol. 9, pp. 457-492.
Sato et al., Consequences of OX40-OX40 ligand interactions in Langerhans cell function: enhanced contact hypersensitivity responses in OX40L-transgenic mice; Eur. J. Immunol., 2002, vol. 32, pp. 33326-3335.
Shields et al., Lack of Fucose on Human IgG1 N-Linked Oligosaccharide Improves Binding to Human FcRIII and Antibody-dependent Cellular Toxicity*; The Journal of Biological Chemistry, 2002, vol. 277, No. 30, pp. 2673-26740.
Sidhu et al., Phage-displayed Antibody Libraries of Synthetic Heavy Chain Complementarity Determining Regions; J. Mol. Biol., 2004, vol. 338, pp. 299-310.
Stahli et al., [20] Distinction of Epitopes by Monoclonal Antibodies; Methods in Enzymology, 1983, vol. 92, 12-pages.
Sugamura et al., Therapeutic Targeting of the Effector T-Cell Co-Stimulatory Molecule OX40; Nature, 2004, vol. 4, 12-pages.
Tutt et al., Trispecific F(ab')3 derivatives that use cooperative signaling via the TCR/CD3 resting cytotoxic T cells. complex and CD2 to activate and redirect; J Immunol, 1991, vol. 147, pp. 60-69.

(56) References Cited

OTHER PUBLICATIONS

Urlaub et al., Isolation of Chinese hamster cell mutants deficient in dihydrofolate reductase activity; Proc. Natl. Acad. Sci, 1980, vol. 77, No. 7, pp. 4216-4220.
WHO Drug Information, International nonproprietary names for pharmaceutical substances (INN) vol. 30, No. 2, 2016, pp. 241-357.
Xu et al., Addressing polyspecificity of antibodies selected from an in vitro yeast presentation system: a FACS-based, high-throughput selection and analytical tool; Protein Engineering, Design & Selection, 2013, vol. 26, No. 10, pp. 663-670.
Yazaki et al., Expression of Recombinant Antibodies in Mammalian Cell Lines; Methods in Molecular Biology, vol. 248: pp. 255-268, 2004.
Bremer, "Targeting of the Tumor Necrosis Factor Receptor Superfamily for Cancer Immunotherapy," ISRN Oncology, 2013, 1-25 (Article ID 371854.
Chen et al., PLGA-nanoparticle mediated delivery of anti-OX40 monoclonal antibody enhances anti-tumor cytotoxic T cell responses, Cellular Immunology, 2014, 287:91-99.
Zhang et al., Fc engineering approaches to enhance the agonist and effector function of an anti-OC40 antibody J. Biol. Chem., Dec. 30, 2016, 291(53): 27134-27146.
EPO Form 1707 04.17 Provisional Opinion Accompanying The Partial Search Result, European Patent Application No. 18 77 6775.1, sheets 1-13, dated Dec. 10, 2020.
Supplemental Partial European Search Report European Patent Application No. 18 77 6775.1, dated Dec. 10, 2020.
Moran et al., The TNFRs OX40, 4-1BB, and CD40 as targets for cancer immunotherapy, Curr Opin Immunol., Apr. 2013; 25(2):1-12.
Jensen et al., Signaling tarough OX40 enhances antitumor immunity, Seminars in Oncology, Oct. 2010, 37(5):524-532.
Charlton, Keith A.; Expression and Isolation of Recombinant Antibody Fragments in E. coli; From: Methods in Molecular Biology, vol. 248: Antibody Engineering: Methods and Protocols Edited by: B. K. C. Lo © Humana Press Inc., Totowa, NJ; pp. 245-255, 2004.
Hirschhorn-Cymerman et al., OX40 engagement and chemotherapy combination provides potent antitumor mmunity with concomitant regulatory T cell apoptosis; JEM (Journal of Experimental Medicine) vol. 206, No. 5, pp. 1103-1116, 2009.
Hoogenboom, Hennie R.; Overview of Antibody Phage-Display Technology and its Applications; From: Methods in Molecular Biology, vol. 178: Antibody Phage Display: Methods and Protocols Edited by: P. M. O'Brien and R. Aitken © Humana Press Inc., Totowa, NJ; pp. 1-37, 2002.
Hudson et al., Engineered antibodies: Nature Medicine, 2003, vol. 9, No. 1, pp. 129-134.
Li et al., Optimization of humanized IgGs in glycoengineered Pichia pastoris, Nature Biotechnology, 2005, vol. 24, No. 2, pp. 210-215.
Marks et al., Selection of Human Antibodies from Phage Display Libraries; From: Methods in Molecular Biology, vol. 248: Antibody Engineering: Methods and Protocols Edited by: B. K. C. Lo © Humana Press Inc., Totowa, NJ; pp. 161-175, 2004.
International non-proprietary names for pharmaceutical substances (INN) WHO Drug Information, vol. 30, No. 2, 2016, pp. 241-357.
McCafferty, et al., Phage antibodies: filamentous phage displaying antibody variable domains; Letters to Nature, vol. 348, No. 6, 1990, pp. 552-554, 1990.
Van Dijk et al., Human antibodies as next generation therapeutics; Genmab* and Immunotherapy laboratory†, Dept Immunology, University Medical Center Utrecht, PO Box 85090, 3508 GA Utrecht, The Netherlands *e-mail: M.A.vandijk@med.uu.nl †e-mail: J.vandewinkel@azu.nl Current Opinion in Chemical Biology 2001, vol. 5, pp. 368-374.
Yazaki et al., Expression of Recombinant Antibodies in Mammalian Cell Lines; From: Methods in Molecular Biology, vol. 248: Antibody Engineering: Methods and Protocols Edited by: B. K. C. Lo © Humana Press Inc., Totowa, NJ; pp. 255-268, 2004.

* cited by examiner

ANTI-OX40 ANTIBODY AND USE THEREOF

CROSS REFERENCE TO RELATED APPLICATIONS

This application is a U.S. national stage application of PCT Application No. PCT/CN2018/080315, filed Mar. 23, 2018 and claims priority to Chinese Application No. 201710185400.8, filed Mar. 25, 2017. Each of the above-cited applications is incorporated herein by reference in its entirety.

INCORPORATION OF SEQUENCE LISTING

A paper copy of the Sequence Listing and a computer readable form of the Sequence Listing containing the file named "SEQLISTING.TXT", created Nov. 21, 2019 which is 217,603 bytes in size (as measured in MICROSOFT WINDOWS® EXPLORER), are provided herein and are herein incorporated by reference. This Sequence Listing consists of SEQ ID NOs: 1-189.

FIELD OF THE INVENTION

The present invention relates to a novel antibody and antibody fragment that specifically binds to OX40 and to a composition comprising said antibody or antibody fragment. In addition, the present invention relates to a nucleic acid encoding the antibody or an antibody fragment thereof and a host cell comprising the same, and to a related use thereof. In addition, the present invention relates to the use of the antibody and antibody fragment for treatment and diagnosis.

BACKGROUND OF THE INVENTION

OX40 (also known as CD134, TNFRSF4 and ACT35) was originally described as T cell activation markers on rat CD4 T cells (Paterson D J, Jefferies W A, Green J R, Brandon M R, Corthesy P, Puklavec M, Williams A F. Antigens of activated rat T lymphocytes including a molecule of 50,000 Mr detected only on CD4 positive T blasts. Mol Immunol. 1987; 24: 1281-1290) and subsequently shown to be upregulated in TCR recruitment (Mallett S, Fossum S, Barclay A N. Characterization of the MRC OX40 antigen of activated CD4 positive T lymphocytes—a molecule related to nerve growth factor receptor. EMBO J. 1990; 9: 1063-1068). OX40 was identified on CD4+ T cells, CD8+ T cells, NK cells, NKT cells and neutrophils (D. J. Paterson, W. A. Jefferies, J. R. Green et al., "Antigens of activated Rat T lymphocytes including a molecule of 50,000 M(r) detected only on CD4 positive T blasts," Molecular Immunology, vol. 24, no. 12, pp. 1281-1290, 1987). OX40 signaling can promote costimulatory signals to T cells, leading to enhanced cell proliferation, survival, effector function and migration (Gramaglia I, Weinberg A D, Lemon M, Croft M. Ox-40 ligand: a potent costimulatory molecule for sustaining primary CD4 T cell responses. J Immunol. 1998; 161: 6510-6517; Gramaglia I, Jember A, Pippig S D, Weinberg A D, Killeen N, Croft M. The OX40 costimulatory receptor determines the development of CD4 memory by regulating primary clonal expansion. J Immunol. 2000; 165: 3043-3050).

OX40L, the ligand for OX40, is mainly expressed on antigen presenting cells (APCs) and its expression can be induced by CD40 and mast cell signaling, toll-like receptors (TLR), and inflammatory cytokines. In addition to APC, non-hematopoietic cells such as smooth muscle and vascular endothelial cells can also express OX40L. In transgenic mice overexpressing OX40L, T-cell activation was increased and, when immunized, these mice produced enhanced T cell responses (Murata K, Nose M, Ndhlovu L C, Sato T, Sugamura K, Ishii N. Constitutive OX40/OX40 ligand interaction induces autoimmune-like diseases. J Immunol. 2002; 169: 4628-4636, and Sato T, Ishii N, Murata K, Kikuchi K, Nakagawa S, Ndhlovu L C, Sugamura K. Consequences of OX40-OX40 ligand interactions in langerhans cell function: enhanced contact hypersensitivity responses in OX40L-transgenic mice. Eur J Immunol. 2002; 32:3326-3335). This data suggests that OX40L expression is a limiting factor for OX40 signaling in T cells.

In mice bearing tumors, the in vivo ligation of mouse OX40 (by soluble mouse OX40L-immunoglobulin fusion protein or mouse OX40L mimetic, such as anti-mouse CD134 specific antibody) enhances anti-tumor immunity, resulting in no tumor survival in the mouse models of various mouse malignant tumor cell lines such as lymphoma, melanoma, sarcoma, colon cancer, breast cancer and neuroglioma (Sugamura et al. Nature Rev Imm. 2004; 4: 420-431).

It has been suggested that the immune response of the mammal to the antigen is enhanced by the use of OX40 binding agent in combination with OX40 (WO99/42585; Weinberg, 2000). Although the literature generally refers to the OX40 binding agent, the emphasis is on the use of OX40L or a portion thereof; the anti-OX40 antibody is disclosed as an equivalent of OX40L. In fact, when the Weinberg group used the study in nonhuman primate studies, they again intentionally selected antibodies that bind OX40L binding sites and generally mimic OX40L.

Al-Shamkhani et al. (Eur J Chem. 1996; 26: 1695-1699) used an anti-OX40 antibody called OX86 that did not block OX40L binding, to explore the differential expression of OX40 on activated mouse T cells; Hirschhorn-Cymerman et al. (J Exp Med. 2009; 206: 1103-1116) used OX86 and cyclophosphamide as potential chemo-immunotherapy in the mouse model. However, OX86 is expected not to bind to human OX40, and when selecting an antibody that is effective in humans, an antibody that binds to the OX40L binding site will be selected according to Weinberg's study.

In severe combined immunodeficiency (SCID) mice, the in vivo ligation of human OX40 (by anti-human OX40-specific antibodies that interact with the OX40L binding domain on human OX40; US2009/0214560A1) enhances anti-tumor immunity, which results in tumor growth inhibition in a variety of human malignant tumor cell lines such as lymphoma, prostate cancer, colon cancer and breast cancer.

In humans, the exact mechanism of human OX40 ligation-mediated anti-tumor immune response has not been confirmed, but is thought to be mediated by OX40 transmembrane signaling pathway, which is stimulated by interaction with OX40L. This interaction is mediated by the binding of trimeric OX40L and OX40. In the current anti-cancer treatment, it is recommended to use trimerized OX40 ligands as a more potent drug than the anti-OX40 antibody (Morris et al. Mol Immunol. 2007; 44: 3112-3121).

In addition, a single anti-OX40 treatment does not provide sufficient anti-tumor immunogenicity in immunologically poor tumors, and it is also desirable to develop a combination of OX40 and other strategies. It has been found that regulating the combination of OX40 signaling and other signaling pathways (such as the angiogenesis pathway, PD-1 pathway) that is dysregulated in tumor cells can further enhance therapeutic efficacy.

However, there remains a need to develop a new anti-OX40 antibody that blocks the binding of OX40 to OX40L less than the anti-OX40 antibodies known in the art to better treat or delay various cancers, immune related diseases and T cell dysfunction diseases.

SUMMARY OF THE INVENTION

Applicants have surprisingly found that in order to activate T cells and to induce T cell mediated antitumor activity, an antibody or fragment thereof (e,g, antigen-binding fragment) bound to human OX40 is used, wherein the antibody or fragment thereof is capable of binding to human OX40 better while less blocking the binding of human OX40 to OX40 ligand (OX40L) and producing an enhanced immune response.

Preferably, the anti-OX40 antibody or fragment thereof of the present invention is capable of activating T cells, for example enhancing the immunostimulatory/effector function of T-effect cells and/or allowing these cells to proliferate and/or down-regulate the immunosuppressive function of T-regulated cells. More preferably, the antibody is capable of eliciting antibody-dependent cell-mediated cytotoxicity (ADCC). In some embodiments, the OX40 antibody of the present invention can be used to treat or delay various cancers, immune-related diseases and T-cell dysfunction disorders.

The invention thus provides an antibody or fragment thereof (preferably an antigen-binding fragment) that binds human OX40 or cynomolgus monkey OX40, wherein the antibody or fragment thereof less blocks binding of human or cynomolgus OX40 to its ligand OX40L. In some embodiments, the antibody or the fragment thereof of the present invention can bind human OX40, while less blocks binding of human OX40 to its ligand (OX40L)(for example, in comparison to the known OX40 antibody or OX40L), and produce enhanced immune response.

Preferably, the blocking of the antibody or fragment thereof of the present invention on the binding between human or cynomolgus OX40 and its ligand OX40L is lower than that of OX40L ligand or other anti-OX40 antibody known in the art (e.g., pogalizumab). More preferably, the anti-OX40 antibody or the fragment thereof maintain its strong binding to human or cynomolgus OX40 (e.g., comparable to the known anti-OX40 antibody, e.g., pogalizumab), while less block the binding between human or cynomolgus OX40 and its ligand OX40L (e.g., less than the blocking of OX40L or less than the blocking of pogalizumab).

In some embodiments, the antibody or fragment thereof of the present invention binds to human OX40 or cynomolgus monkey OX40. In some preferable embodiments, the antibody or fragment thereof of the present invention does not bind to murine OX40 or bind to murine OX40 less than binding to human or cynomolgus OX40, the murine OX40 is e.g., rat OX40 or mouse OX40.

In some embodiments, the anti-OX40 antibody of the present invention has agonist activity.

In some embodiments, the anti-OX40 antibody of the present invention or a fragment thereof binds to human OX40 or cynomolgus monkey OX40 with a $K_D$ of less than about 200 nM, preferably less than or equal to about 100 nM, about 50 nM, about 40 nM, about 30 nM, about 20 nM, about 10 nM, more preferably less than or equal to about 9 nM, more preferably less than or equal to about 8 nM, more preferably less than or equal to about 7 nM, 6 nM, 5 nM, 4 nM, 3 nM or 2 nM, and most preferably, the $K_D$ is less than or equal to about 1 nM or 0.8 nM or 0.4 nM or 0.3 nM or 0.2 nM or 0.1 nM. In some embodiments, the antibody binding affinity is determined using a Bio-light interferometry (e.g., Fortebio affinity measurement) or an MSD assay.

In some embodiments, the binding to human OX40 or cynomolgus monkey OX40 by the antibodies of the present invention or the fragment thereof is determined using the flow cytometry (e.g., FACS) assay. In some embodiments, the binding to human OX40 or cynomolgus OX40 in a cell has an EC50 of less than or equal to about 10 nM, 9 nm or 8 nm. In some embodiments, the binding to human OX40 or cynomolgus monkey OX40 has an EC50 of less than or equal to about 7 nM or about 6 nM or about 5 nm or about 4 nm or about 3 nM. In some embodiments, in an assay performed by flow cytometry, the antibodies or the antibody fragments bind to OX40 expressed on the cells with a MFI>1000× fold difference, preferably >1100 fold difference, 1200 fold difference, 1300 fold difference, 1400 fold difference, 1500 fold difference, 1600 fold difference, 1700 fold difference, 1800 fold difference, 1900 fold difference, 2000 fold difference, 2100 fold difference, 2200 fold difference, 2300 fold difference, 2400 fold difference or 2500 fold difference compared with corresponding control cells that do not express OX40.

In another aspect, the present invention provides an anti-OX40 antibody or fragment thereof having agonist activity capable of activating T cells (e.g., CD4+ T cells). Therefore, in some embodiments, the anti-OX40 antibody or fragment thereof can activate T cells.

In some embodiments, the anti-OX40 antibody or fragment thereof of the present invention enhances CD4+ effector T cell function, for example by increasing CD4+ effector T cell proliferation and/or increasing gamma-interferon production of CD4+ effector T cells (e.g., compared to the proliferation and/or cytokine production prior to the treatment of the anti-OX40 antibody or fragment thereof of the present invention, or compared to the proliferation and/or cytokine production of CD4+ effector T cell treated by the control antibody (e.g., IgG antibody). In some embodiments, the cytokine is a γ-interferon, such as IFNg or an interleukin, such as IL-2.

In some embodiments, the anti-OX40 antibody or fragment thereof of the present invention increases the number of intratumoral (invasive) CD4+ effector T cells (e.g., the total number of CD4+ effector T cells, or the percentage of CD4+ cells in CD45+ cells, for example), for example, compared to the number of intratumoral (invasive) CD4+ T cells prior to treatment with the anti-OX40 antibody or fragment thereof of the present invention (or after treatment with a control antibody (e.g., an IgG antibody). In some embodiments, the anti-OX40 antibody or fragment thereof of the present invention increases the number of intratumoral (invasive) CD4+ effector T cells expressing γ-interferon (e.g., the total number of CD4+ cells expressing γ-interferon, or a percentage of CD4+ cells expressing γ-interferon in total CD4+ cells), for example, compared to the number of intratumoral (invasive) CD4+ effector T cells expressing γ-interferon prior to treatment with the anti-OX40 antibody or fragment thereof of the present invention (or after treatment with a control antibody (e.g., an IgG antibody).

In some embodiments, the agonist activity of the anti-OX40 antibody is assessed by the level of cytokines released after T cell activation. Accordingly, the present invention provides an anti-OX40 antibody or fragment thereof that can enhance cytokine production of CD4+ T cells as compared to cytokine production of CD4+ T cells treated with IgG control. In some embodiments, the cytokine is an inflammatory cytokine, such as γ-interferon (e.g., IFNg) or an interleukin (e.g., IL-2).

Preferably, the anti-OX40 antibody or fragment thereof of the present invention is capable of increasing the level of IL-2 secreted by CD4+ T cells up to about 1, 2, 3, 4, 5, 6, 7, 8, 9, 10, 20, 30, 40, 50, 60, 70, 80, 90, 100, 110, 120, 130, 140, 150, 160 fold or higher as compared to the corresponding control IgG. In some embodiments, the anti-OX40 antibody or fragment thereof of the present invention is capable of increasing the level of IL-2 secreted by CD4+ T cells up to about 1, 2, 3, 4, 5, 6, 7, 8, 9, 10, 11, 12, 13, 14, 15, 16, 17, 18, 19, 20, 21, 22, 23, 24, 25, 26, 27 fold or higher as compared to the corresponding control IgG antibody. In some embodiments, an anti-OX40 antibody or fragment thereof of the invention is capable of increasing IFNg levels secreted by CD4+ T cells by a factor of 1, 2, 3 or more compared to a corresponding control IgG antibody. In some embodiments, the cytokine secretion levels of T cells are determined by ELISA.

In some embodiments, the agonist activity of the anti-OX40 antibody is assessed by OX40 signaling (e.g., monitoring of NF K B downstream signaling). In some embodiments, the anti-OX40 antibody or fragment thereof of the present invention enhances OX40 signal transduction in target cells expressing OX40. In some embodiments, OX40 signal transduction is detected by monitoring NFkB downstream signaling.

Accordingly, the present invention provides an anti-OX40 antibody or fragment thereof that enhances NFKB-mediated transcriptional activity levels as compared to an control IgG antibody. Preferably, the anti-OX40 antibody or fragment thereof of the present invention is capable of increasing the level of NFκB-mediated transcriptional activity by about 1, 2, 3, 4, 5, 6, 7 fold or higher as compared to the corresponding control IgG antibody.

In some embodiments, the anti-OX40 antibody or fragment thereof of the present invention increases the number of intratumoral (invasive) CD8+ effector T cells (e.g., the total number of CD8+ effector T cells, or the percentage of CD8+ in CD45+ cells, for example), for example, compared to the number of intratumoral (invasive) CD8+ effector T cells prior to treatment with the anti-OX40 antibody or fragment thereof of the present invention (or after treatment with a control antibody (e.g., an IgG antibody). In some embodiments, the anti-OX40 antibody or fragment thereof of the present invention increases the number of intratumoral (invasive) CD8+ effector T cells expressing γ-interferon (e.g., the percentage of CD8+ cells expressing γ-interferon in total CD8+ cells), for example, compared to the number of intratumoral (invasive) CD8+T effector cells expressing γ-interferon prior to treatment with the anti-OX40 antibody or fragment thereof of the present invention (or after treatment with a control antibody e.g., an IgG antibody).

In some embodiments, the anti-OX40 antibody or fragment thereof of the present invention enhances memory T cell function, for example by increasing memory T cell proliferation and/or increasing cytokine production in memory cells. In some embodiments, the cytokine is γ-interferon (e.g., IFNg) or interleukin (e.g., IL-2).

In some preferred embodiments, the anti-OX40 antibody or fragment thereof of the present invention is capable of eliciting antibody-dependent cell-mediated cytotoxicity (ADCC). In some embodiments, the anti-OX40 antibody or fragment thereof of the present invention binds to human effector cells, e.g., binds to FcγR (e.g., activated FcγR) expressed in human effector cells. In some embodiments, the human effector cells perform (are capable of performing) the ADCC effector function.

In some embodiments, the function of the anti-OX40 antibody or fragment thereof of the present invention requires antibody cross-linking. In some embodiments, the functions of the anti-OX40 antibody or fragment thereof of the present invention are as one or more of the following: increasing CD4+ effector T cell proliferation and/or cytokine production, enhancing CD4+ memory T cell proliferation and/or cytokines generation, and/or reduce the cells by ADCC. In some embodiments, antibody cross-linking is determined by providing anti-human OX40 agonistic antibodies that adhere to a solid surface, such as a cell culture plate. In some embodiments, antibody cross-linking is determined by introducing a mutation (e.g., amino acid mutation) into the IgG Fc portion of the antibody and testing the function of the mutant antibody. In some embodiments, antibody cross-linking is achieved by FcgRIIb. In some embodiments, the anti-OX40 antibody or the fragment thereof of the present invention can achieve its function without antibody cross-linking.

In some embodiments, the anti-OX40 antibody or the fragment thereof of the present invention can achieve its function in absence of FcgRIIb.

In some embodiments, the anti-OX40 antibody or the fragment thereof of the present invention have better anti-tumor activity. For example, compared to control IgG or known anti-OX40 antibody, the anti-OX40 antibody or the fragment thereof of the present invention can reduce the tumor volume in a subject, preferably do not influence the body weight of the subject in the meantime.

The IgG antibody as a control described herein includes an IgG1 antibody, or an IgG4 antibody or an IgG2 antibody, for example, an IgG1, IgG2 or IgG4 antibody having a light chain and a heavy chain as shown in Table 7.

In a preferred embodiment, the invention provides an anti-OX40 antibody or fragment thereof having one or more of the properties of an anti-OX40 antibody described above.

In some embodiments, an anti-OX40 antibody or antigen-binding fragment thereof of the invention comprises a heavy chain variable region (HCVR), wherein the HCVR comprises
(i) three complementarity determining regions (CDRs) HCDR1, HCDR2 and HCDR3 contained in the HCVR of any one of the antibodies listed in Table B, or
(ii) a sequence comprising at least one and no more than 10 or 5 amino acid changes (preferably amino acid substitutions, preferably conservative substitutions) in totalin the three CDR regions relative to the sequence of (i).

In some embodiments, an anti-OX40 antibody or antigen-binding fragment thereof of the invention comprises a light chain variable region (LCVR), wherein the LCVR comprises:
(i) the LCDR1, LCDR2 and LCDR3 sequences contained in the LCVR of anyone of the antibodies listed in Table B; or
(ii) a sequence comprising at least one and no more than 10 or 5 amino acid changes (preferably amino acid substitutions, preferably conservative substitutions) in totalin the three CDR regions relative to the sequence of (i).

In some embodiments, an anti-OX40 antibody or antigen-binding fragment thereof of the invention comprises a heavy chain variable region HCVR and a light chain variable region LCVR, wherein (a) the HCVR contains (i) three complementarity determining regions (CDRs) HCDR1, HCDR2 and HCDR3 contained in the HCVR of anyone of the antibodies listed in Table B, or (ii) a sequence comprising at least one and no more than 10 or 5 amino acid changes (preferably amino acid substitutions, preferably conservative substitutions) in total in said three CDR regions relative to the sequence of (i); and/or (b) The LCVR contains:

(i) the LCDR1, LCDR2 and LCDR3 sequences contained in the LCVR of anyone of the antibodies listed in Table B; or (ii) a sequence comprising at least one and no more than 10 or 5 amino acid changes (preferably amino acid substitutions, preferably conservative substitutions) in total in the three CDR regions relative to the sequence of (i).

In a preferred embodiment, the HCVR comprises an amino acid sequence selected from the group consisting of SEQ ID NO: 106, 107, 108, 109, 110, 111, 112, 113, 114, 115, 116, 117, 118, 119 or 120, or consists of the amino acid sequence.

In a preferred embodiment, the LCVR comprises or consists of an amino acid sequence selected from the group consisting of SEQ ID NO: 130, 131, 132, 133, 134, 135, 136, 137 or 138.

In some embodiments, an anti-OX40 antibody or antigen-binding fragment thereof of the invention comprises a heavy chain variable region (HCVR) and/or a light chain variable region (LCVR), wherein (i) the HCVR comprises a complementarity determining region (CDR) HCDR1, HCDR2 and HCDR3, wherein HCDR1 comprises or consists of an amino acid sequence selected from the group consisting of SEQ ID NO: 1, 2, 3, 4, 5, 6, 7, 8, 9, 10, 11, 12, 13, 14, 15 and 16, or HCDR1 comprises an amino acid sequence having one, two or three changes (preferably amino acid substitutions, preferably conservative substitutions) compared to the amino acid sequence selected from the group consisting of SEQ ID NO: 1, 2, 3, 4, 5, 6, 7, 8, 9, 10, 11, 12, 13, 14, 15 and 16; HCDR2 comprises or consists of an amino acid sequence selected from the group consisting of SEQ ID NO: 17, 18, 19, 20, 21, 22, 23, 24, 25, 26, 27, 28, 29, 30, 31, 32 and 33, or HCDR2 comprises an amino acid sequence having one, two or three changes (preferably amino acid substitutions, preferably conservative substitutions) compared to the amino acid sequence selected from the group consisting of SEQ ID NO: 17, 18, 19, 20, 21, 22, 23, 24, 25, 26, 27, 28, 29, 30, 31, 32 and 33; HCDR3 comprises or consists of an amino acid sequence selected from the group consisting of SEQ ID NO: 34, 35, 36, 37, 38, 39 and 40, or HCDR3 comprises an amino acid sequence having one, two or three changes (preferably amino acid substitutions, preferably conservative substitutions) compared to the amino acid sequence selected from the group consisting of SEQ ID NO: 34, 35, 36, 37, 38, 39 and 40;

and/or (ii) wherein the LCVR comprises complementarity determining regions (CDRs) LCDR1, LCDR2 and LCDR3, wherein LCDR1 comprises or consists of an amino acid sequence selected from the group consisting of SEQ ID NOs: 41, 42, 43, 44, 45 and 46, or LCDR1 comprises an amino acid sequence having one, two or three changes (preferably amino acid substitutions, preferably conservative substitutions) compared to an amino acid sequence selected from the group consisting of SEQ ID NO: 41, 42, 43, 44, 45 and 46; LCDR2 comprises or consists of an amino acid sequence selected from the group consisting of SEQ ID NOS: 47, 48, 49, 50, 51, and 52, or LCDR2 comprises an amino acid sequence having one, two or three changes (preferably amino acid substitutions, preferably conservative substitutions) compared to an amino acid sequence selected from the group consisting of SEQ ID NO: 47, 48, 49, 50, 51, and 52; LCDR3 comprises or consists of the amino acid sequence selected from the group consisting of SEQ ID NOs: 53, 54, 55, 56, 57, 58, 59, 60 and 61, or LCDR3 comprises an amino acid sequence having one, two or three changes (preferably amino acid substitutions, preferably conservative substitutions) compared to an amino acid sequence selected from the group consisting of SEQ ID NOs: 53, 54, 55, 56, 57, 58, 59, 60 and 61.

In a preferred embodiment, the invention provides an anti-OX40 antibody or antigen-binding fragment thereof comprising a heavy chain variable region (HCVR) and a light chain variable region (LCVR), wherein (a) the HCVR contains (i) a combination of HCDR1, HCDR2 and HCDR3 as shown in Table A; or (ii) a variant of the HCDR combination of (i) comprising at least one and no more than 10 or 5 amino acid changes (preferably amino acid substitutions, preferably conservative substitutions) in total in said three CDR regions;

and/or (b) the LCVR contains (i) a combination of LCDR1, LCDR2 and LCDR3 as shown in Table A; or (ii) a variant of the LCDR combination of (i), said variant comprising at least one and no more than 10 or 5 amino acid changes (preferably amino acid substitutions, preferably conservative substitutions) in total in said three CDR regions.

In a preferred embodiment, the present invention provides anti-OX40 antibody or antigen-binding fragment thereof comprising a heavy chain variable region (HCVR) and a light chain variable region (LCVR), wherein the HCVR comprises a complementarity determining region (CDR) HCDR1, HCDR2 and HCDR3 and the LCVR comprises (CDR) LCDR1, LCDR2 and LCDR3, wherein the combinations of the HCDR1, HCDR2, HCDR3, LCDR1, LCDR2 and LCDR3 comprised in said antibody or its antigen-binding fragment are represented as follows (Table A):

TABLE A

Exemplary combinations of HCDR1, HCDR2, HCDR3, LCDR1, LCDR2 and LCDR3 in the antibody or antigen-binding fragment thereof of the present invention:

| combination | HCDR1, which comprises or consists of the amino acid sequence as represented in the following SEQ ID NO | HCDR2, which comprises or consists of the amino acid sequence as represented in the following SEQ ID NO | HCDR3, which comprises or consists of the amino acid sequence as represented in the following SEQ ID NO | LCDR1, which comprises or consists of the amino acid sequence as represented in the following SEQ ID NO | LCDR2, which comprises or consists of the amino acid sequence as represented in the following SEQ ID NO | LCDR3, which comprises or consists of the amino acid sequence as represented in the following SEQ ID NO |
|---|---|---|---|---|---|---|
| (1) | SEQ ID NO: 1 | SEQ ID NO: 17 | SEQ ID NO: 34 | SEQ ID NO: 41 | SEQ ID NO: 47 | SEQ ID NO: 53 |
| (2) | SEQ ID NO: 1 | SEQ ID NO: 17 | SEQ ID NO: 34 | SEQ ID NO: 42 | SEQ ID NO: 48 | SEQ ID NO: 54 |
| (3) | SEQ ID NO: 2 | SEQ ID NO: 18 | SEQ ID NO: 34 | SEQ ID NO: 41 | SEQ ID NO: 47 | SEQ ID NO: 53 |
| (4) | SEQ ID NO: 3 | SEQ ID NO: 19 | SEQ ID NO: 34 | SEQ ID NO: 41 | SEQ ID NO: 47 | SEQ ID NO: 53 |
| (5) | SEQ ID NO: 4 | SEQ ID NO: 20 | SEQ ID NO: 34 | SEQ ID NO: 41 | SEQ ID NO: 47 | SEQ ID NO: 53 |
| (6) | SEQ ID NO: 4 | SEQ ID NO: 21 | SEQ ID NO: 34 | SEQ ID NO: 41 | SEQ ID NO: 47 | SEQ ID NO: 53 |
| (7) | SEQ ID NO: 5 | SEQ ID NO: 22 | SEQ ID NO: 34 | SEQ ID NO: 41 | SEQ ID NO: 47 | SEQ ID NO: 53 |
| (8) | SEQ ID NO: 6 | SEQ ID NO: 23 | SEQ ID NO: 34 | SEQ ID NO: 41 | SEQ ID NO: 47 | SEQ ID NO: 53 |
| (9) | SEQ ID NO: 7 | SEQ ID NO: 24 | SEQ ID NO: 35 | SEQ ID NO: 43 | SEQ ID NO: 49 | SEQ ID NO: 55 |
| (10) | SEQ ID NO: 8 | SEQ ID NO: 25 | SEQ ID NO: 35 | SEQ ID NO: 43 | SEQ ID NO: 49 | SEQ ID NO: 55 |
| (11) | SEQ ID NO: 9 | SEQ ID NO: 26 | SEQ ID NO: 35 | SEQ ID NO: 43 | SEQ ID NO: 49 | SEQ ID NO: 55 |
| (12) | SEQ ID NO: 10 | SEQ ID NO: 27 | SEQ ID NO: 35 | SEQ ID NO: 43 | SEQ ID NO: 49 | SEQ ID NO: 55 |
| (13) | SEQ ID NO: 11 | SEQ ID NO: 28 | SEQ ID NO: 35 | SEQ ID NO: 43 | SEQ ID NO: 49 | SEQ ID NO: 55 |
| (14) | SEQ ID NO: 12 | SEQ ID NO: 29 | SEQ ID NO: 36 | SEQ ID NO: 44 | SEQ ID NO: 50 | SEQ ID NO: 56 |
| (15) | SEQ ID NO: 13 | SEQ ID NO: 30 | SEQ ID NO: 37 | SEQ ID NO: 45 | SEQ ID NO: 51 | SEQ ID NO: 57 |
| (16) | SEQ ID NO: 14 | SEQ ID NO: 31 | SEQ ID NO: 38 | SEQ ID NO: 42 | SEQ ID NO: 52 | SEQ ID NO: 58 |
| (17) | SEQ ID NO: 15 | SEQ ID NO: 32 | SEQ ID NO: 39 | SEQ ID NO: 43 | SEQ ID NO: 49 | SEQ ID NO: 59 |
| (18) | SEQ ID NO: 15 | SEQ ID NO: 32 | SEQ ID NO: 39 | SEQ ID NO: 46 | SEQ ID NO: 49 | SEQ ID NO: 60 |
| (19) | SEQ ID NO: 16 | SEQ ID NO: 33 | SEQ ID NO: 40 | SEQ ID NO: 41 | SEQ ID NO: 47 | SEQ ID NO: 61 |

In some embodiments, an anti-OX40 antibody or antigen-binding fragment thereof of the invention comprises a heavy chain variable region HCVR and/or a light chain variable region LCVR, wherein (a) heavy chain variable region HCVR (i) comprising or consisting of an amino acid sequence having at least 90%, 91%, 92%, 93%, 94%, 95%, 96%, 97%, 98% or 99% identity with the amino acid sequence selected from the group consisting of SEQ ID NO: 106, 107, 108, 109, 110, 111, 112, 113, 114, 115, 116, 117, 118, 119 and 120; or (ii) comprising or consisting of an amino acid sequence selected from the group consisting of SEQ ID NOs: 106, 107, 108, 109, 110, 111, 112, 113, 114, 115, 116, 117, 118, 119 and 120; or (iii) comprising an amino acid sequence having one or more (preferably no more than 10, more preferably no more than 5) amino acid changes (preferably amino acid substitutions, more preferably conservative substitutions) compared to an amino acid sequence selected from the group consisting of SEQ ID NOs: 106, 107, 108, 109, 110, 111, 112, 113, 114, 115, 116, 117, 118, 119 and 120, preferably, said amino acid changes do not occur in the CDR regions; and/or (b) light chain variable region LCVR (i) comprising or consisting of an amino acid sequence having at least 90%, 91%, 92%, 93%, 94%, 95%, 96%, 97%, 98% or 99% identity with the amino acid sequence selected from the group consisting of SEQ ID NO: 130, 131, 132, 133, 134, 135, 136, 137 and 138;

(ii) comprising or consisting of an amino acid sequence selected from the group consisting of SEQ ID NOs: 130, 131, 132, 133, 134, 135, 136, 137 and 138; or (iii) comprising an amino acid sequence having one or more (preferably no more than 10, more preferably no more than 5) amino acid changes (preferably amino acid substitutions, more preferably conservative substitutions) compared to an amino acid sequence selected from the group consisting of SEQ ID NOs: 130, 131, 132, 133, 134, 135, 136, 137 and 138, preferably, said amino acid changes do not occur in the CDR regions.

In a preferred embodiment, the present invention provides anti-OX40 antibody or antigen-binding fragment thereof comprising a heavy chain variable region (HCVR) and a light chain variable region (LCVR), wherein the combinations of the heavy chain variable region HCVR and light chain variable region LCVR comprised in said antibody or its antigen-binding fragment are represented as follows (Table B):

TABLE B

Exemplary combinations of the heavy chain variable region HCVR and light chain variable region LCVR in the antibody or antigen-binding fragment thereof of the present invention:

| combination | HCVR, which comprises or consists of the amino acid sequence as represented in the following SEQ ID NO | LCVR, which comprises or consists of the amino acid sequence as represented in the following SEQ ID NO |
|---|---|---|
| (1) | SEQ ID NO: 106 | SEQ ID NO: 130 |
| (2) | SEQ ID NO: 106 | SEQ ID NO: 131 |
| (3) | SEQ ID NO: 107 | SEQ ID NO: 130 |
| (4) | SEQ ID NO: 108 | SEQ ID NO: 130 |
| (5) | SEQ ID NO: 109 | SEQ ID NO: 130 |
| (6) | SEQ ID NO: 110 | SEQ ID NO: 130 |
| (7) | SEQ ID NO: 111 | SEQ ID NO: 130 |
| (8) | SEQ ID NO: 112 | SEQ ID NO: 132 |
| (9) | SEQ ID NO: 113 | SEQ ID NO: 132 |
| (10) | SEQ ID NO: 114 | SEQ ID NO: 132 |
| (11) | SEQ ID NO: 115 | SEQ ID NO: 132 |
| (12) | SEQ ID NO: 116 | SEQ ID NO: 133 |
| (13) | SEQ ID NO: 117 | SEQ ID NO: 134 |
| (14) | SEQ ID NO: 118 | SEQ ID NO: 135 |
| (15) | SEQ ID NO: 119 | SEQ ID NO: 136 |
| (16) | SEQ ID NO: 119 | SEQ ID NO: 137 |
| (17) | SEQ ID NO: 120 | SEQ ID NO: 138 |

In some embodiments, the anti-OX40 antibody or antigen-binding fragment thereof of the present invention comprises a heavy chain and/or light chain, wherein
 (a) heavy chain
  (i) comprising or consisting of an amino acid sequence having at least 90%, 91%, 92%, 93%, 94%, 95%, 96%, 97%, 98% or 99% identity with the amino acid sequence selected from the group consisting of SEQ ID NO: 189, 139, 140, 141, 142, 143, 144, 145, 146, 147, 148, 149, 150, 151, 152, 153, 154, 155, 156, 157, 158, 159, 160, 161, 162, 163, 164, 165, 166 or 167;
  (ii) comprising or consisting of an amino acid sequence selected from the group consisting of SEQ ID NOs: 189, 139, 140, 141, 142, 143, 144, 145, 146, 147, 148, 149, 150, 151, 152, 153, 154, 155, 156, 157, 158, 159, 160, 161, 162, 163, 164, 165, 166 or 167; or
  (iii) comprising an amino acid sequence having one or more (preferably no more than 20 or 10, more preferably no more than 5) amino acid changes (preferably amino acid substitutions, more preferably conservative substitutions) compared to an amino acid sequence selected from the group consisting of SEQ ID NOs: 189, 139, 140, 141, 142, 143, 144, 145, 146, 147, 148, 149, 150, 151, 152, 153, 154, 155, 156, 157, 158, 159, 160, 161, 162, 163, 164, 165, 166 or 167, preferably, said amino acid changes do not occur in the CDR regions, more preferably, said amino acid changes do not occur in the heavy chain variable region;
 and/or
 (b) light chain
  (i) comprising or consisting of an amino acid sequence having at least 90%, 91%, 92%, 93%, 94%, 95%, 96%, 97%, 98% or 99% identity with the amino acid sequence selected from the group consisting of SEQ ID NO: 168, 169, 170, 171, 172, 173, 174, 175 or 176;
  (ii) comprising or consisting of an amino acid sequence selected from the group consisting of SEQ ID NOs: 168, 169, 170, 171, 172, 173, 174, 175 or 176; or
  (iii) comprising an amino acid sequence having one or more (preferably no more than 20 or 10, more preferably no more than 5) amino acid changes (preferably amino acid substitutions, more preferably conservative substitutions) compared to an amino acid sequence selected from the group consisting of SEQ ID NOs: 168, 169, 170, 171, 172, 173, 174, 175 or 176, preferably, said amino acid changes do not occur in the CDR regions, more preferably, said amino acid changes do not occur in the light chain variable region.

In a preferred embodiment, the anti-OX40 antibody or antigen-binding fragment thereof of the present invention comprises a heavy and a light chain, wherein the combinations of the heavy chain and light chain comprised in said antibody or its antigen-binding fragment are as follows (Table C):

TABLE C exemplary combinations of the heavy chain and light chain in the antibody or antigen-binding fragment thereof of the present invention:

| combination | Heavy chain, which comprises or consists of the amino acid sequence represented by the following SEQ ID NO | Light chain, , which comprises or consists of the amino acid sequence represented by the following SEQ ID NO |
| --- | --- | --- |
| (1) | SEQ ID NO: 189 | SEQ ID NO: 168 |
| (2) | SEQ ID NO: 139 | SEQ ID NO: 168 |
| (3) | SEQ ID NO: 140 | SEQ ID NO: 168 |
| (4) | SEQ ID NO: 141 | SEQ ID NO: 168 |
| (5) | SEQ ID NO: 142 | SEQ ID NO: 168 |
| (6) | SEQ ID NO: 143 | SEQ ID NO: 168 |
| (7) | SEQ ID NO: 144 | SEQ ID NO: 168 |
| (8) | SEQ ID NO: 145 | SEQ ID NO: 168 |
| (9) | SEQ ID NO: 146 | SEQ ID NO: 168 |
| (10) | SEQ ID NO: 147 | SEQ ID NO: 168 |
| (11) | SEQ ID NO: 148 | SEQ ID NO: 168 |
| (12) | SEQ ID NO: 149 | SEQ ID NO: 168 |
| (13) | SEQ ID NO: 150 | SEQ ID NO: 169 |
| (14) | SEQ ID NO: 151 | SEQ ID NO: 169 |
| (15) | SEQ ID NO: 152 | SEQ ID NO: 169 |
| (16) | SEQ ID NO: 153 | SEQ ID NO: 169 |
| (17) | SEQ ID NO: 154 | SEQ ID NO: 169 |
| (18) | SEQ ID NO: 155 | SEQ ID NO: 169 |
| (19) | SEQ ID NO: 156 | SEQ ID NO: 169 |
| (20) | SEQ ID NO: 157 | SEQ ID NO: 169 |
| (21) | SEQ ID NO: 158 | SEQ ID NO: 170 |
| (22) | SEQ ID NO: 159 | SEQ ID NO: 170 |
| (23) | SEQ ID NO: 160 | SEQ ID NO: 171 |
| (24) | SEQ ID NO: 161 | SEQ ID NO: 171 |
| (25) | SEQ ID NO: 162 | SEQ ID NO: 172 |
| (26) | SEQ ID NO: 163 | SEQ ID NO: 172 |
| (27) | SEQ ID NO: 164 | SEQ ID NO: 173 |
| (28) | SEQ ID NO: 165 | SEQ ID NO: 173 |
| (29) | SEQ ID NO: 164 | SEQ ID NO: 174 |
| (30) | SEQ ID NO: 165 | SEQ ID NO: 174 |
| (31) | SEQ ID NO: 166 | SEQ ID NO: 175 |
| (32) | SEQ ID NO: 167 | SEQ ID NO: 175 |
| (33) | SEQ ID NO: 189 | SEQ ID NO: 176 |
| (34) | SEQ ID NO: 139 | SEQ ID NO: 176 |

In some embodiments, the heavy chain of the anti-OX40 antibody or fragment thereof of the present invention further comprises a signal peptide sequence, such as (SEQ ID NO: 182)
METDTLLLWVLLLLVPGSTG.

In one embodiment of the invention, the amino acid changes described herein include substitutions, insertions or deletions of amino acids. Preferably, the amino acid changes described herein are amino acid substitutions, preferably conservative substitutions.

In some embodiments, an antibody of the invention is capable of binding OX40 and less blocking the binding of OX40 to its ligand OX40L. In some embodiments, an anti-OX40 antibody or fragment thereof of the invention has a functional Fc region. In some embodiments, the effector function of the functional Fc region is ADCC. In some embodiments, the Fc region is the Fc region of human IgG1 or the Fc region of human IgG2.

In some embodiments, an anti-OX40 antibody or fragment thereof of the invention has one or more of the following characteristics:
 (i) showing the same or similar binding affinity and/or specificity as anyone of the antibodies listed in Table 5 for OX40 (particularly human OX40);
 (ii) inhibiting (e.g, competitive inhibiting) the binding of anyone of the antibodies listed in Table 5 to OX40 (particularly human OX40);
 (iii) binding to an epitope that is the same or overlaps with that bound by anyone of the antibodies shown in Table 5;

(iv) competing with anyone of the antibodies shown in Table 5 to bind OX40 (particularly human OX40);

(v) having one or more of the biological properties of anyone of the antibodies listed in Table 5.

In some embodiments, the anti-OX40 antibody of the present invention is an antibody in the form of IgG1 or antibody in IgG2 form or antibody in IgG4 form. In some embodiments, the anti-OX40 antibody is a monoclonal antibody. In some embodiments, the anti-OX40 antibody is humanized. In some embodiments, the anti-OX40 antibody is a human antibody. In some embodiments, at least a portion of the anti-OX40 antibody's framework sequence is a human consensus framework sequence. In one embodiment, the anti-OX40 antibody of the present invention also encompasses an antibody fragment thereof, preferably an antibody fragment selected from the group consisting of Fab, Fab', Fab'-SH, Fv, single chain antibody (e.g., scFv) or (Fab')$_2$, single domain antibody, diabodies (dAb) or linear antibody.

In certain embodiments, the anti-OX40 antibody molecule is in the form of a bispecific or multispecific antibody molecule. In one embodiment, the bispecific antibody molecule has a first binding specificity for OX40 and a second binding specificity for PD-1, TIM-3, CEACAM (eg, CEACAM-1 and/or CEACAM-5), PD-L1 or PD-L2. In one embodiment, the bispecific antibody molecule binds to OX40 and PD-1. In another embodiment, the bispecific antibody molecule binds to OX40 and PD-L1. In yet another embodiment, the bispecific antibody molecule binds to OX40 and PD-L2. The multispecific antibody molecule can have any combination of binding specificities for the aforementioned molecules. The multispecific antibody molecule can be, for example, a trispecific antibody molecule comprising a first binding specificity for OX40 and a second and third binding specificity for one or more of the following molecules: PD-1, TIM-3, CEACAM (e.g., CEACAM-1 or CEACAM-5), PD-L1 or PD-L2.

In one aspect, the present invention provides nucleic acids encoding any of the above anti-OX40 antibodies or fragments thereof. In one embodiment, a vector comprising said nucleic acid is provided. In one embodiment, the vector is an expression vector. In one embodiment, a host cell comprising said vector is provided. In one embodiment, the host cell is eukaryotic. In another embodiment, the host cell is selected from yeast cells, mammalian cells (e.g., CHO cells or 293 cells), or other cells suitable for the preparation of antibodies or antigen-binding fragments thereof. In another embodiment, the host cell is prokaryotic.

In one embodiment, the present invention provides a method of preparing an anti-OX40 antibody or fragment thereof (preferably an antigen-binding fragment), wherein the method comprises culturing the host cell under conditions suitable for expression of a nucleic acid encoding the antibody or fragment thereof (preferably an antigen-binding fragment), and optionally isolating the antibody or fragment thereof (preferably an antigen-binding fragment). In an embodiment, the method further comprises recovering an anti-OX40 antibody or fragment thereof (preferably an antigen-binding fragment) from the host cell.

In some embodiments, the invention provides an immunoconjugate comprising any of the anti-OX40 antibodies provided herein and other agents, such as a cytotoxic agent. In some embodiments, the immunoconjugate is used to treat cancer, preferably lung cancer (e.g., non-small cell lung cancer), liver cancer, gastric cancer, colon cancer, and the like.

In some embodiments, the present invention provides a composition comprising any of the anti-OX40 antibodies or fragments thereof, preferably an antigen-binding fragment thereof, or immunoconjugate as described herein, preferably the composition is a pharmaceutical composition. In one embodiment, the composition further comprises a pharmaceutically acceptable adjuvants. In one embodiment, a composition, e.g., a pharmaceutical composition, comprises a combination of an anti-OX40 antibody or a fragment thereof, or an immunoconjugate thereof, of the invention, and one or more other therapeutic agents (e.g., a chemotherapeutic agent, an anti-angiogenic agent, an anti-PD-1 antibody, an anti-PD-L1 antibody, or an anti-PD-L2 antibody). In some embodiments, the pharmaceutical composition is used for the treatment of cancer, preferably lung cancer (e.g., non-small cell lung cancer), liver cancer, gastric cancer, colon cancer, and the like.

In one aspect, the present invention relates to a method of activating T cells or inducing T cell mediated antitumor activity or enhancing body immune response in a subject, which comprises administering to said subject an effective amount of any of the anti-OX40 antibodies or fragments thereof, immunoconjugate or pharmaceutical composition as described herein. The present invention also relates to the use of any anti-OX40 antibodies or a fragment thereof described herein for the preparation of a composition or medicament for activating T cells or inducing T cell mediated antitumor activity or enhancing the body immune response of in a subject.

In another aspect, the present invention relates to a method of treating cancer in a subject comprising administering to said subject an effective amount of any anti-OX40 antibody or fragment thereof, immunoconjugate or pharmaceutical composition as described herein. In one embodiment, the cancer is lung cancer (e.g., non-small cell lung cancer), liver cancer, gastric cancer, colon cancer, and the like. In another aspect, the invention also relates to the use of any anti-OX40 antibodies or a fragment thereof described herein for the manufacture of a medicament for the treatment of cancer in a subject. In one embodiment, the cancer is lung cancer (e.g., non-small cell lung cancer), liver cancer, gastric cancer, colon cancer, and the like.

In some embodiments, the methods described herein further comprise administering to the subject one or more therapies (e.g., a therapeutic manner and/or other therapeutic agent). In some embodiments, the therapeutic manner includes surgery and/or radiation therapy. In some embodiments, the other therapeutic agent is selected from the group consisting of a chemotherapeutic agent, a PD-1 axis binding antagonist (e.g., an anti-PD-1 antibody or an anti-PD-L1 antibody or an anti-PD-L2 antibody), or an anti-angiogenic agent (e.g., bevacizumab).

In another aspect, the invention relates to use of the anti-OX40 antibodies or fragments thereof described herein in combination with a PD-1 axis binding antagonist (e.g., an anti-PD-1 antibody or an anti-PD-L1 antibody or an anti-PD-L2 antibody) in the manufacture of a medicament for treating cancer in a subject. In one embodiment, the cancer is lung cancer (eg, non-small cell lung cancer), liver cancer, gastric cancer, colon cancer, and the like.

In some embodiments, the subject or individual is a mammal, preferably a human.

In one aspect, the present invention relates to a method of detecting OX40 in a sample comprising (a) contacting a sample with any anti-OX40 antibody or fragment thereof described herein; and (b) detecting the formation of a complex between anti-OX40 antibody or fragment thereof and OX40. In one embodiment, the anti-OX40 antibody is detectably labeled.

In some embodiments, the present invention relates to a kit or a manufacture articles comprising any of the anti-OX40 antibodies or fragments thereof described herein. In some embodiments, the kit or product comprises an anti-OX40 antibody or fragment thereof as described herein and optionally a pharmaceutically acceptable adjuvants, and optionally one or more additional therapeutic agent (such as a chemotherapeutic agent, a PD-1 axis binding antagonist (e.g., an anti-PD-1 antibody or an anti-PD-L1 antibody or an anti-PD-L2 antibody), or an anti-angiogenic agent (e.g., bevacizumab). In some embodiments, the kit or manufacture article further comprises instructions for administering a medicament for the treatment of cancer.

The invention also encompasses any combination of any of the embodiments described herein. Any of the embodiments described herein, or any combination thereof, are applicable to any and all of the anti-OX40 antibodies or fragments of the invention as described herein and methods and uses thereof.

DESCRIPTION OF THE INVENTION

Definitions

Figure 1:
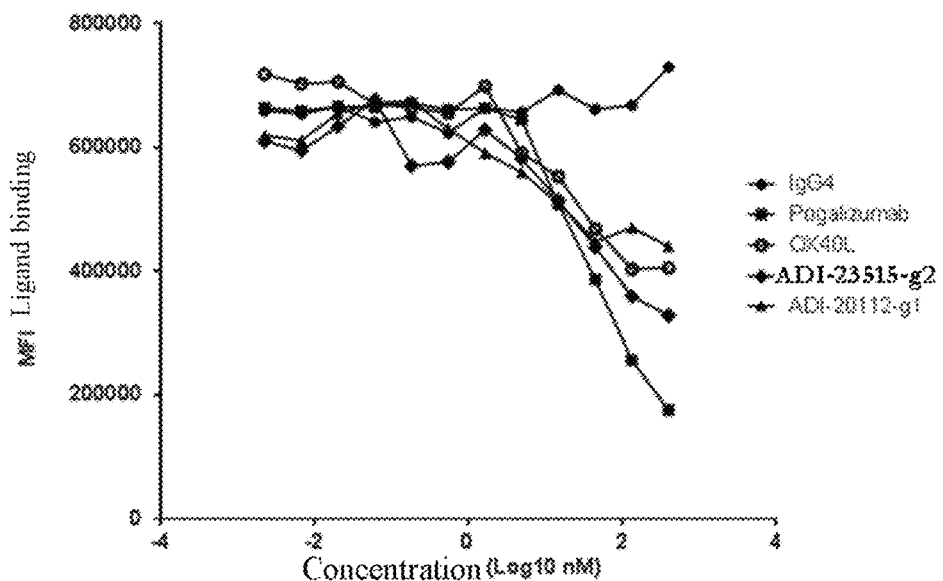
FIG. 1 shows the blocking of the binding of OX40L to OX40 expressed on CHO cells by the antibody of the present invention produced in CHO cells along with increasing concentration measured by flow cytometry.

Before the present invention is described in detail below, it is to be understood that the invention is not limited to the particular methodology, solutions, and reagents described herein, as these may vary. It is also understood that the terminology used herein is for the purpose of describing the particular embodiments and is not intended to limit the scope of the invention, which will only be restricted by the appended claims. All technical and scientific terms used herein have the same meaning as commonly understood by those skilled in the art to which this invention belongs, unless otherwise defined.

For the purpose of interpreting the specification, the following definitions will be used, and the terms used in the singular may also include the plural, vice versa, if appropriate. It is understood that the terminology used herein is for the purpose of describing particular embodiments and is not intended to be restrictive.

The term "about" when used in connection with a numerical value is meant to encompass numerical values within the range between the lower limit of 5% less than the specified numerical value and the upper limit of 5% greater than the specified numerical value.

"Affinity" refers to the strength of the sum of all non-covalent interactions between a single binding site of a molecule (e.g., an antibody) and its binding partner (e.g., an antigen). As used herein, "binding affinity" refers to the intrinsic binding affinity that reflects a 1:1 interaction between members of a binding pair (e.g., an antibody and an antigen), unless otherwise indicated. The affinity of molecule X for its partner Y is generally expressed by the equilibrium dissociation constant ($K_D$). Affinity can be measured by conventional methods known in the art, including those known in the art and described herein.

The term "anti-OX40 antibody", "anti-OX40", "OX40 antibody" or "antibody binding to OX40" as used herein refers to an antibody which is capable of binding to (human or Cynomolgus)OX40 protein or a fragment thereof with sufficient affinity such that the antibody can be used as diagnostic and/or therapeutic agent targeting (human or Cynomolgus)OX40. In one embodiment, the anti-OX40 antibody binds to non-(human or Cynomolgus)OX40 protein to an extent lesser than about 10%, about 20%, about 30%, about 40%, about 50%, about 60%, about 70%, about 80% or about 90% or above of the binding of the antibody to (human or Cynomolgus)OX40, as measured, for example, by radioimmunoassay (MA) or Bio-light interferometry or MSD assay. In some embodiments, the anti-OX40 antibody binds to human or Cynomolgus OX40 with an equilibrium dissociation constant ($K_D$) of ≤200 nM, ≤100 nM, ≤10 nM or ≤1 nM (e.g., below $10^{-7}$M, e.g., $10^{-7}$M to $10^{-10}$ M, e.g., $10^{-8}$M to $10^{-9}$M).

As used herein, "monoclonal antibody" or "mAb" refers to a single copy or cloned antibody derived from, for example, a eukaryotic, a prokaryotic, or a phage clone, while does not refer to a method of producing the same. Monoclonal antibodies or antigen-binding fragments thereof can be produced, for example, by hybridoma technology, recombinant technique, phage display technique, synthetic technique such as CDR grafting, or a combination of such or other techniques known in the art.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain. A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); single domain antibody; and multispecific antibodies formed from antibody fragments.

As used herein, the term "epitope" refers to a portion of an antigen (e.g., OX40) that specifically interacts with an antibody molecule. This portion (referred to herein as an epitope determinant) typically comprises an element such as an amino acid side chain or a sugar side chain or a component thereof. Epitope determinants can be defined according to methods known in the art or disclosed herein (e.g., by crystallography or by hydrogen-deuterium exchange). At least one or some portion of the antibody molecule that specifically interacts with an epitope determinant is generally located within the CDR. Typically, epitopes have specific three dimensional structural characteristics. Typically, epitopes have specific charge characteristics. Some epitopes are linear epitopes, while others are conformational epitopes.

An "antibody that binds to the same or overlapping epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

An antibody that competes with a reference antibody for binding to its antigen refers to an antibody that blocks 50%, 60%, 70%, 80%, 90% or 95% or more of the binding of the reference antibody to its antigen in a competition assay. In other words, the reference antibody blocks 50%, 60%, 70%, 80%, 90% or 95% or more of the binding of the antibody to its antigen in a competition assay. Numerous types of competitive binding assays can be used to determine whether an antigen binding protein competes with another assay such as solid phase direct or indirect radioimmunoassay (MA), solid phase direct or indirect enzyme immunoassay (EIA), Sandwich competition assays (see, e.g., Stahli et al, 1983, Methods in Enzymology 9: 242-253).

An antibody that inhibits (e.g., competitively inhibits) binding of a reference antibody to its antigen refers to an antibody that inhibits binding of 50%, 60%, 70%, 80%, 90%, or 95% or more of the reference antibody to its antigen. Conversely, the reference antibody inhibits binding of the antibody to its antigen by 50%, 60%, 70%, 80%, 90% or 95% or more. The binding of an antibody to its antigen can be measured by affinity (eg, equilibrium dissociation constant). Methods for determining affinity are known in the art.

An antibody that exhibits the same or similar binding affinity and/or specificity as a reference antibody refers to an antibody that has at least 50%, 60%, 70%, 80%, 90% or 95% or more of the binding affinity and/or specificity of the reference antibody. This can be determined by any method known in the art for determining binding affinity and/or specificity.

There are five major classes of antibodies known in the art: IgA, IgD, IgE, IgG and IgM, and several of these antibodies can be further divided into subclasses (isotypes), for example, $IgG_1$, $IgG_2$, $IgG_3$, $IgG_4$, $IgA_1$ and $IgA_2$. The heavy chain constant domains corresponding to different classes of immunoglobulins are referred to as α, δ, ε, γ, and μ, respectively. A person skilled in the art can select and obtain the antibody in an appropriate class of the present invention according to the practical desire.

"Antibody in IgG form" refers to the IgG form to which the heavy chain constant region of an antibody belongs. The heavy chain constant regions of all antibodies of the same type are identical, and the heavy chain constant regions differ between different types of antibodies. For example, an antibody in the IgG1 form refers to an Ig domain whose heavy chain constant region Ig domain is IgG1.

The term "dysfunction" in the context of immune dysfunction, refers to a state of reduced immune responsiveness to antigenic stimulation. The term "dysfunctional", as used herein, also includes refractory or unresponsive to antigen recognition, specifically, impaired capacity to translate antigen recognition into downstream T-cell effector functions, such as proliferation, cytokine production (e.g., gamma interferon) and/or target cell killing.

The expression "lower blocking of human OX40 binding to OX40 ligand/OX40L" as used herein means that the antibody of the present invention block the binding of OX40 to OX40L with less extent, compared to the known OX40 antibody (e.g., pogalizumab) or OX40L. In some embodiments, the extent of binding of OX40 to OX40L is reduced less in the presence of an anti-OX40 antibody of the invention compared to the extent of binding of OX40 to OX40L in the presence of a known OX40 antibody (e.g., pogalizumab) or OX40L. In some embodiments, the reduction in the extent of binding of OX40 to OX40L in the presence of an anti-OX40 antibody of the invention is less than about 50%, 40%, 30%, 20%, 10% or less compared to the extent of binding of OX40 to OX40L in the presence of a negative control (e.g., an IgG antibody). In some embodiments, the extent of binding of OX40 to OX40L is determined by a luciferase reporter gene. In some embodiments, the extent of binding of OX40 to OX40L is determined by flow cytometry.

"Activating T cell" means to induce, cause or stimulate an effector or memory T cell to have a renewed, sustained or amplified biological function. Examples of enhancing T-cell function include: increased secretion of γ-interferon (e.g., IFNg) or interleukin (e.g., IL-2) from $CD8^+$ effector T cells, increased secretion of γ-interferon (e.g., IFNg) or interleukin (e.g., IL-2) from CD4+ memory and/or effector T-cells, increased proliferation of $CD4^+$ effector and/or memory T cells, increased proliferation of $CD8^+$ effector T-cells, increased antigen responsiveness (e.g., clearance), relative to such levels before the intervention. In one embodiment, the level of enhancement is at least 50%, alternatively 60%, 70%, 80%, 90%, 100%, 120%, 150%, 2, 3, 4, 5, 6, 7, 8, 9, 10, 20, 30, 40, 50, 60, 70, 80, 90, 100, 110, 120, 130, 140, 150, 160 folds or more. The manner of measuring this enhancement is known to one of ordinary skill in the art.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenicity" refers to the ability of a particular substance to provoke an immune response. Tumors are immunogenic and enhancing tumor immunogenicity aids in the clearance of the tumor cells by the immune response.

An "agonist activity of an antibody," as used herein, is the activity with which an antibody can activate a biological activity of the antigen it binds.

An "anti-angiogenic agent" refers to a compound which blocks, or interferes with to some degree, the development of blood vessels. An anti-angiogenic agent may, for instance, be a small molecule or antibody that binds to a growth factor or growth factor receptor involved in promoting angiogenesis. In one embodiment, an anti-angiogenic agent is an antibody that binds to vascular endothelial growth factor (VEGF), such as bevacizumab (AVASTIN).

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist (e.g., PD-1 antibody), a PD-L1 binding antagonist (e.g., PD-L1 antibody) and a PD-L2 binding antagonist (e.g., PD-L2 antibody).

The term "PD-1 binding antagonists" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is, as disclosed in WO2015/095423, MDX-1106 (nivolumab), MK-3475 (pembrolizumab), CT-011 (pidilizumab) or AMP-224.

The term "PD-L1 binding antagonists" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is, as disclosed in WO2015/095423, YW243.55.S70, MDX-1105, MPDL3280A or MEDI4736

The term "PD-L2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

"Antibody-dependent cell-mediated cytotoxicity" or "ADCC" refers to a form of cytotoxicity in which secreted immunoglobulin bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRT, FcγRII, and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. PNAS (USA) 95:652-656 (1998). An exemplary assay for assessing ADCC activity is provided in the examples herein.

As used herein, the term "OX40" refers to any natural OX40 from any vertebrate source, including mammals such as primates (eg, humans, cynomolgus monkeys) and rodents (eg, mice and rats), unless otherwise specified. The term encompasses "full length", unprocessed OX40 and any form of OX40 due to processing in the cell. The term also encompasses naturally occurring variants of OX40, such as splice variants or allelic variants.

"OX40 activation" refers to the activation of the OX40 receptor. Typically, OX40 activation results in signal transduction.

The term "cytotoxic agent" as used in the present invention refers to a substance which inhibits or prevents cell function and/or causes cell death or destruction. For examples of cytotoxic agents, see those disclosed in WO 2015/153513.

"Chemotherapeutic agents" include chemical compounds that are useful in the treatment of cancer. For examples of chemotherapeutic agents, see those disclosed in WO 2015/153513, including erlotinib (TARCEVA®, Genentech/OSI Pharm.), bortezomib (VELCADE®, Millennium Pharm.), disulfiram, alkylating agents, such as thiotepa; alkyl sulfonates; aziridines; and the like; and pharmaceutically acceptable salts, acids, or derivatives of any of the above. Chemotherapeutic agents also include dexamethasone, hydrocortisone, interferon, bevacuzimab, bexarotene, and the like, and pharmaceutically acceptable salts thereof. Chemotherapeutic agents also include non-steroidal anti-inflammatory drugs with analgesic, antipyretic and anti-inflammatory effects. For a detailed illustration and introduction of various chemotherapeutic agents that can be used in the present invention, reference is made to those disclosed in PCT International Application WO2015/153513, which is incorporated herein by reference in its entirety.

The term "cytokine" is a generic term for proteins released by one cell population that act on another cell as intercellular mediators. Examples of such cytokines are lymphokines, monokines; interleukins (ILs) such as IL-1, IL-la, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL) and gamma interferon. As used herein, the term cytokine includes proteins from natural sources or from recombinant cell culture and biologically active equivalents of the native-sequence cytokines, including synthetically produced small-molecule entities and pharmaceutically acceptable derivatives and salts thereof.

The term "diabody" refers to an antibody fragment having two antigen binding sites, and said antibody fragment comprises a heavy chain variable domain (VH) linked to a light chain variable domain (VL) in the same polypeptide chain (VH-VL). The domains are forced to pair with the complementary domains on the other chain to create two antigen binding sites, by using a linker that is too short to make the two domains on the same chain be paired with each other. A diabody can be bivalent or bispecific. Diabodies are more fully described, for example, in EP 404,097; WO 1993/01161; Hudson et al, Nat. Med. 9: 129-134 (2003); and Hollinger et al., Proc. Natl. Acad. Sci. USA 90:6444-6448 (1993). Triabodies and tetrabodies are also described in Hudson et al, Nat. Med. 9: 129-134 (2003).

A "functional Fc region" possesses an "effector function" of a native sequence Fc region. Exemplary "effector functions" include Clq binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed herein.

"Effector function" refers to those biological activities attributable to the Fc region of an antibody, which vary with the antibody isotopes. Examples of antibody effector's functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Human effector cells" refer to leukocytes that express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

The term "effective amount" refers to an amount or dose of an antibody or fragment of the invention that produces the desired effect in a patient to be treated, when administered to the patient in single or multiple doses. An effective amount can be readily determined by the attending physician as a person skilled in the art by considering various factors such as the species of the mammal; its size, age and general health; the particular disease involved; the extent or severity of the disease; the response of an individual patient; the specific antibody to be administered; mode of administration; bioavailability characteristics of the formulation to be administered; selected dosing regimen; and use of any concomitant therapy.

"Antibodies and antigen-binding fragments thereof" suitable for use in the present invention include, but are not limited to, polyclonal, monoclonal, monovalent, bispecific, heteroconjugate, multispecific, recombinant, heterologous, heterozygous, chimeric, humanized (especially grafted with CDRs), deimmunized, or human antibody, Fab fragments, Fab' fragments, F(ab')2 fragments, fragments produced by Fab expression library, Fd, Fv, disulfide-linked Fv (dsFv), single-chain antibody (e.g., scFv), diabody or tetrabody (Holliger P. et al. (1993) Proc. Natl. Acad. Sci. USA 90 (14), 6444-6448), nanobody (also referred to as a single domain antibody), anti-idiotypic (anti-Id) antibody (including, for example, an anti-Id antibody against the antibody of the invention), and epitope-binding fragments of any of the above.

The term "Fc region" is used herein to define a C-terminal region of an immunoglobulin heavy chain, and the Fc region comprises at least a portion of the constant region. The term includes native Fc region sequence and Fc region variants. In certain embodiments, the human IgG heavy chain Fc region extends from Cys226 or Pro230 to the carbonyl terminus of the heavy chain. However, the C-terminal lysine (Lys447) of Fc region may or may not be present. Unless otherwise indicated, the amino acid residues in Fc region or constant region are numbered according to the EU numbering system, which is also referred to as the EU index, as described in Kabat et al., Sequences of Proteins of Immunological Interest, 5th Ed. Public Health Service, National. Institutes of Health, Bethesda, Md., 1991.

The term "variable region" or "variable domain" refers to the domain of an antibody heavy or light chain that is involved in binding the antibody to antigen. The variable domains of the heavy chain and light chain of a native antibody generally have similar structures, with each domain comprising four conserved framework regions (FRs) and three complementary determinant region (CDR). (See, e.g., Kindt et al. Kuby Immunology, 6$^{th}$ ed., W.H. Freeman and Co., page 91 (2007).) A single VH or VL domain may be sufficient to confer antigen-binding specificity. Furthermore, antibodies that bind to a particular antigen may be isolated using a VH or VL domain from an antibody that binds to the antigen to screen a library of complementary VL or VH domains, respectively. See, e.g., Portolano et al., J. Immunol. 150:880-887 (1993); Clarkson et al., Nature 352:624-628 (1991).

"Framework" or "FR" refers to variable domain residues other than hypervariable region (HVR) (e.g., complementarity determining region) residues. The FR of a variable domain typically consists of four FR domains: FR1, FR2, FR3 and FR4. Accordingly, the HVR and FR sequences generally appear in the following sequence in the heavy chain variable domain (VH) (or the light chain variable domain (VL)): FR1-H1(L1)-FR2-H2(L2)-FR3-H3(L3)-FR4.

A "complementarity determining region" or "CDR region" or "CDR" is an area that is hypervariable in sequence in an antibody variable domain and that forms a structurally defined loop ("hypervariable loop") and/or contains an antigen contact residue ("antigen contact point"). The CDR is primarily responsible for binding to an epitope. The CDRs of the heavy and light chains are commonly referred to as CDR1, CDR2 and CDR3, numbered sequentially from the N-terminus. The CDRs located within the antibody heavy chain variable domain are referred to as HCDR1, HCDR2 and HCDR3, while the CDRs located within the antibody light chain variable domain are referred to as LCDR1, LCDR2 and LCDR3. In a given light chain variable region or heavy chain variable region amino acid sequence, the exact amino acid sequence boundaries of each CDR can be determined using any one or combination of a number of well-known antibody CDR assignment systems, including for example: Chothia based on the three-dimensional structure of antibodies and the topology of CDR loops (Chothia et al. (1989) Nature 342: 877-883, Al-Lazikani et al., "Standard conformations for the canonical structures of immunoglobulins", Journal of Molecular Biology, 273, 927-948 (1997)), Kabat based on antibody sequence variability (Kabat et al, Sequences of Proteins of Immunological Interest, 4th edition, US Department of Health and Human Services, National Institutes of Health (1987)), AbM (University of Bath), Contact (University College London), International ImMunoGeneTics database (IMGT) (imgt.cines.fr/ on the World Wide Web), and North CDR definition based on affinity propagation clustering using a large number of crystal structures. The boundaries of CDRs of the antibodies of the invention can be determined by one of skill in the art in accordance with any aspect of the art, such as different assignment systems or combinations.

However, it should be noted that the boundaries of the CDRs of the variable regions of the same antibody obtained based on different assignment systems may vary. That is, the CDR sequences of the same antibody variable region defined under different assignment systems are different. Thus, where an antibody is defined by a particular CDR sequence as defined by the present invention, the scope of the antibody also encompasses an antibody whose variable region sequence comprises the particular CDR sequence, but due to the application of a different protocol (eg different assignment systems or combinations) have different claimed CDR boundaries than the specific CDR boundaries defined by the present invention.

Antibodies with different specificities (i.e., different binding sites for different antigens) have different CDRs. However, although the CDRs differ among antibodies, only a limited number of amino acid positions within the CDRs are directly involved in antigen binding. Using at least two of the Kabat, Chothia, AbM, Contact, and North methods, the minimal overlapping region can be determined to provide a "minimum binding unit" for antigen binding. The minimum binding unit can be a sub-portion of the CDR. As will be apparent to those skilled in the art, residues of the remaining part of the CDR sequences can be determined by the structure of the antibody and protein folding. Accordingly, the invention also contemplates variants of any of the CDRs presented herein. For example, in a variant of one CDR, the amino acid residues of the minimum binding unit may remain unchanged, while the other CDR residues defined by Kabat or Chothia may be replaced by conservative amino acid residues.

The terms "host cell" refers to cells into which exogenous nucleic acid has been introduced, including the progeny of such cells. Host cells include "transformants" and "transformed cells", which include the primary transformed cell and progeny derived therefrom regardless of the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subtype of variable domain sequences. Generally, the subtype of the sequences is a subtype as disclosed in Kabat et al., Sequences of Proteins of Immunological Interest, Fifth Edition, NIH Publication 91-3242, Bethesda Md. (1991), vols. 1-3. In a embodiment, for the VL, the subtype is subtype kappa I as in Kabat et al., supra. In some embodiments, for the VH, the subtype is subtype III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include lung cancer (e.g., non-small cell lung cancer), liver cancer, gastric cancer or colon cancer, including metastatic forms of those cancers.

The terms "cell proliferative disorder" and "proliferative disorder" refer to disorders that are associated with some degree of abnormal cell proliferation. In one embodiment, the cell proliferative disorder is cancer.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

An "immunoconjugate" is an antibody conjugated to one or more other agents, including but not limited to a cytotoxic agent.

An "individual" or "subject" includes a mammal. Mammals include, but are not limited to, domestic animals (e.g., cows, sheep, cats, dogs, and horses), primates (e.g., humans and non-human primates such as monkeys), rabbits, and rodents (e.g., mice and rats). In certain embodiments of the present invention, the individual or subject is a human.

An "isolated antibody" is one which has been separated from a component of its natural environment. In some embodiments, an antibody is purified to greater than 95% or 99% purity, for example, as determined by, e.g., electrophoresis (e.g., SDS-PAGE, isoelectric focusing (IEF), capillary electrophoresis) or chromatography (e.g., ion exchange or reverse phase HPLC). For a review of methods for assessment of antibody purity, see, e.g., Flatman et al., J. Chromatogr. B 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present outside the chromosomes or at a chromosomal location that is different from its natural chromosomal location.

An "isolated nucleic acid encoding an anti-OX40 antibody or fragment thereof" refers to one or more nucleic acid molecules encoding the heavy and light chain of an antibody or antigen-binding fragment thereof, including such nucleic acid molecules contained in a single vector or in separate vectors, as well as such nucleic acid molecules present at one or more locations within a host cell.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways in the art, for instance, using publicly available computer software such as BLAST, BLAST-2, ALIGN or MEGALIGN (DNASTAR) software. Those skilled in the art can determine appropriate parameters for aligning sequences, including any algorithm needed to achieve maximal alignment over the full length of the sequences being compared.

When percentages of sequence identity are referred to in this application, these percentages are calculated relative to the full length of the longer sequence, unless otherwise specifically indicated. The calculation relative to the full length of the longer sequence applies to both the nucleic acid sequence and the polypeptide sequence.

The term "pharmaceutical composition" refers to a formulation which is in such form as to permit the biological activity of an active ingredient contained therein to be effective, and which contains no additional components which are unacceptably toxic to a subject to which the formulation would be administered.

The term "pharmaceutically acceptable adjuvants" refers to a diluent, adjuvant (e.g., Freund's adjuvant (complete and incomplete)), excipient or vehicle co-administered with the therapeutic agent.

As used herein, "treating" refers to slowing, interrupting, arresting, ameliorating, stopping, reducing, or reversing the progression or severity of an existing symptom, condition, disorder, or disease.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

By "subject/patient sample" is meant a collection of cells or fluids obtained from a cancer patient or cancer subject. The source of the tissue or cell sample may be solid tissue as from a fresh, frozen and/or preserved organ or tissue sample or biopsy or aspirate; blood or any blood constituents; bodily fluids such as cerebrospinal fluid, amniotic fluid, peritoneal fluid, or interstitial fluid; cells from any time in gestation or development of the subject. The tissue sample may contain compounds which are not naturally intermixed with the tissue in nature such as preservatives, anticoagulants, buffers, fixatives, nutrients, antibiotics, or the like. Examples of tumor samples herein include, but are not limited to, tumor biopsy, fine needle aspirate, bronchiolar lavage, pleural fluid, sputum, urine, a surgical specimen, circulating tumor cells, serum, plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

The "instructions" contained in a kit or article as defined herein are used to refer to instructions generally included in commercial packages of therapeutic products containing information on indications, usage, dosage, administration, combination therapy, contraindications and/or warnings for applications involving such therapeutic products.

The Antibody of the Present Invention

The invention thus provides anti-OX40 antibodies as well as fragments thereof.

In one embodiment of the invention, the amino acid changes described herein include substitutions, insertions or deletions of amino acids. Preferably, the amino acid changes described herein are amino acid substitutions, preferably conservative substitutions.

In a preferred embodiment, the amino acid changes described herein occur in regions outside the CDRs (e.g., in FR). More preferably, the amino acid changes described herein occur in regions outside the heavy chain variable region and/or outside the light chain variable region.

In some embodiments, the substitution is conservative substitution. Conservative substitution means that one amino acid is replaced by another amino acid within the same class, for example, one acidic amino acid is replaced by another acidic amino acid, one basic amino acid is replaced by another basic amino acid, or one neutral amino acid is replaced by another neutral amino acid. Exemplary substitutions are shown in Table D below:

TABLE D

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

In some embodiments, an anti-OX40 antibody or fragment thereof of the invention encompasses an antibody or fragment thereof having a post-translational modification on a light chain variable region, a heavy chain variable region, a light chain or a heavy chain.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed. In some applications, modifications that remove unwanted glycosylation sites may be useful, for example, modifications that remove fucose modules so as to enhance the antibody-dependent cellular cytotoxicity (ADCC) function (see Shield et al. (2002) JBC 277: 26733). In other applications, galactosylation modification may be performed to modify complement-dependent cytotoxicity (CDC).

In certain embodiments, one or more amino acid modifications may be introduced into the Fc region of an antibody provided herein, thereby generating an Fc region variant, so as to enhance the efficiency of the antibody, for example, in the treatment of cancer or cell proliferation disease. The Fc region variant may comprise human Fc region sequence (e.g., human IgG1, IgG2, IgG3 or IgG4 Fc region) comprising an amino acid modification (e.g. a substitution) at one or more amino acid positions.

In certain embodiments, it may be desirable to create cysteine engineered antibodies, e.g., "thioMAbs," in which one or more residues of an antibody are substituted with cysteine residues.

In certain embodiments, an antibody provided herein may be further modified to contain additional non-proteinous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, poly-amino acids (either homopolymers or random copolymers), and glucan or poly(n-vinyl pyrrolidone) polyethylene glycol, propylene glycol homopolymers, polypropylene oxide/ethylene oxide co-polymers, polyoxyethylated polyols (e.g., glycerol), polyvinyl alcohol, and mixtures thereof.

In some embodiments, the invention encompasses fragments of an anti-OX40 antibody. Examples of antibody fragments include, but are not limited to, Fv, Fab, Fab', Fab'-SH, F(ab')$_2$, diabody, linear antibody, single chain antibody molecule (e.g., scFv); and multispecific antibody formed by antibody fragments. Two identical antigen-binding fragments produced by papain digestion on antibody are termed "Fab" fragments, in which each has a single antigen-binding site and a residual "Fc" fragment. Its name reflects the ability susceptible to crystallize. F(ab')$_2$ fragment is produced by pepsin treatment, and it has two antigen binding sites and is still capable of cross-linking antigen.

In some embodiments, an anti-OX40 antibody of the present invention is a humanized antibody. Different methods for humanizing antibodies are known to those skilled in the art, as reviewed by Almagro & Fransson, the contents of which are incorporated herein by reference in its entirety (Almagro J C and Fransson J (2008) Frontiers in Bioscience 13: 1619-1633).

In some embodiments, an anti-OX40 antibody of the invention is a human antibody. Human antibodies may be prepared using a variety of techniques known in the art.

Human antibodies are generally described in van Dijk and van de Winkel, Curr. Opin. Pharmacol 5: 368-74 (2001) and Lonberg, Curr. Opin. Immunol 20: 450-459 (2008).

Antibodies of the present invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In some embodiments, the invention also encompasses an anti-OX40 monoclonal antibody conjugated to other agent, e.g., a therapeutic moiety, such as a cytotoxic agent or an immunosuppressive agent ("immunoconjugates"). Cytotoxic agents include any agent that is harmful to cells. Examples of cytotoxic agents (e.g., chemotherapeutic agents) suitable for forming immunoconjugates are known in the art, see for example WO05/103081. For example, cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleic acid hydrolase; antibiotics; toxins such as small molecule toxins or enzymatically active toxins of bacterial, fungal, plant or animal origin, including fragments and/or variants thereof; and various well-known antitumor or anticancer agents. In one embodiment, the cytotoxic agent is a PD-1 axis binding antagonist. In one embodiment, the cytotoxic agent is an antibody, such as an anti-PD-1 antibody or an anti-PD-L1 antibody or an anti-PD-L2 antibody. In one embodiment, the cytotoxic agent is an anti-angiogenic agent, such as bevacizumab.

In some embodiments, an antibody of the invention may be monospecific, bispecific or multispecific. A multispecific monoclonal antibody may be specific for various epitopes of a target polypeptide or may contain antigen binding domains specific for more than one target polypeptides. See, for example, Tutt et al. (1991) J. Immunol. 147: 60-69. An anti-OX40 monoclonal antibody may be linked to or coexpressed with another functional molecule, such as another peptide or protein. For example, an antibody or fragments thereof may be functionally linked to one or more other molecules, such as another antibody or antibody fragment (e.g., anti-PD-1 antibody, anti-PD-L1 antibody or anti-PD-L2 antibody or fragments of said antibodies) (e.g., by chemical coupling, genetic fusion, non-covalent association, or otherwise) to produce a bispecific or multispecific antibody with a second or more binding specificities.

The Nucleic Acid Antibodies of the Present Invention and the Host Cell Comprising the Same In one aspect, the present invention provides nucleic acids encoding any of the above anti-OX40 antibodies or fragments thereof. The nucleic acid may comprise a nucleic acid encoding an amino acid sequence comprising a light chain variable region and/or a heavy chain variable region of an antibody, or a nucleic acid encoding an amino acid sequence comprising a light and/or heavy chain of an antibody. An exemplary nucleic acid sequence encoding a heavy chain variable region of an antibody comprises a nucleic acid sequence which is at least 90%, 91%, 92%, 93%, 94% 95%, 96%, 97%, 98% or 99% identity to the nucleic acid sequence selected from SEQ ID NOs: 91, 92, 93, 94, 95, 96, 97, 98, 99, 100, 101, 102, 103, 104 or 105, or comprises the nucleic acid sequence selected from SEQ ID NOs: 91, 92, 93, 94, 95, 96, 97, 98, 99, 100, 101, 102, 103, 104 or 105. An exemplary nucleic acid sequence encoding a light chain variable region of an antibody comprises a nucleic acid sequence which is at least 90%, 91%, 92%, 93%, 94% 95%, 96%, 97%, 98% or 99% identity to the nucleic acid sequence selected from SEQ ID NOs: 121, 122, 123, 124, 125, 126, 127, 128 or 129, or comprises the nucleic acid sequence selected from SEQ ID NO: 121, 122, 123, 124, 125, 126, 127, 128 or 129.

In one embodiment, one or more vectors comprising the nucleic acid are provided. In one embodiment, the vector is an expression vector, for example, eukaryotic expression vectors. Vectors include, but are not limited to, viruses, plasmids, cosmids, lambda phage, or yeast artificial chromosomes (YAC). In a preferred embodiment, the expression vector of the invention is a pTT5 expression vector.

In one embodiment, a host cell comprising the vector is provided. Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. See also Charlton, Methods in Molecular Biology, Vol. 248 (B. K. C. Lo, ed., Humana Press, Totowa, N.J., 2003, pp. 245-254, describing expression of antibody fragments in *E. coli*. After expression, the antibody may be isolated from the bacterial cell paste in a soluble fraction and can be further purified.

In one embodiment, the host cell is eukaryotic. In another embodiment, the host cell is selected from the group consisting of a yeast cell, a mammalian cell, or other cells suitable for use in the preparation of an antibody or antigen-binding fragments thereof. For example, eukaryotic microorganisms such as filamentous fungi or yeast are cloning or expression hosts suitable for vectors encoding antibodies. For example, fungi and yeast strains, glycosylation pathways of which have been "humanized", result in the production of antibodies with partial or complete human glycosylation pattern. See Gerngross, Nat. Biotech. 22: 1409-1414 (2004), and Li et al, Nat. Biotech. 24: 210-215 (2006). Host cells suitable for expression of glycosylated antibodies are also derived from multicellular organisms (invertebrates and vertebrates). Vertebrate cells can also be used as hosts. For example, mammalian cell lines which have been engineered to be suitable for suspension growth may be used. Other examples of useful mammalian host cell lines are the monkey kidney CV1 line (COS-7) transformed with SV40; human embryonic kidney line (293HEK or 293 cells, e.g., as described in such as Graham et al, J. Gen Virol. 36:59 (1977)), and so on. Other useful mammalian host cell lines include Chinese hamster ovary (CHO) cells, including DHFR-CHO cells (Urlaub et al, Proc. Natl. Acad. Sci. USA 77: 216 (1980)); and myeloma cell lines such as Y0, NS0 and Sp2/0. For a review of certain mammalian host cell lines suitable for producing antibodies, see, for example, Yazaki and Wu, Methods in Molecular Biology, Vol. 248 (B. K. C. Lo, ed., Humana Press, Totowa, N.J.), pp. 255-268 (2003).

In one embodiment, there is provided a method of preparing an anti-OX40 antibody, wherein the method comprises culturing a host cell comprising a nucleic acid encoding the antibody under conditions suitable for antibody expression, as provided above, and optionally recovering the antibody from the host cell (or host cell culture medium). To recombine to produce an anti-OX40 antibody, a nucleic acid encoding an antibody (e.g., an antibody as described above) is isolated and inserted into one or more vectors for further cloning and/or expression in a host cell. Such nucleic acids are readily isolated and sequenced using conventional procedures (e.g., by using oligonucleotide probes capable of specifically binding to genes encoding heavy and light chains of antibodies).

Determination Method

The anti-OX40 antibodies provided herein can be identified, screened, or characterized for their physical/chemical properties and/or biological activity by a variety of assays known in the art. In one aspect, the antibody of the present invention is tested for its antigen binding activity, for example, by known methods such as ELISA, Western blot, and the like. Binding to OX40 can be determined using methods known in the art, and exemplary methods are disclosed herein. In some embodiments, Bio-light interferometry (eg, Fortebio affinity measurement) or MSD assay is used.

In another aspect, a competition assay can be used to identify antibodies that compete with any of the anti-OX40 antibodies disclosed herein for binding to OX40. In certain embodiments, such a competitive antibody binds to an epitope (eg, a linear or conformational epitope) that is identical or overlapping with an epitope to which any of the anti-OX40 antibodies disclosed herein bind. A detailed exemplary method for locating epitopes bound by antibodies is found in Morris (1996) "Epitope Mapping Protocols", Methods in Molecular Biology vol. 66 (Humana Press, Totowa, N.J.).

The invention also provides assays for identifying biologically active anti-OX40 antibodies. Biological activity can include, for example, binding to OX40 (e.g., binding to human and/or cynomolgus OX40), increasing OX40-mediated signal transduction (e.g., increasing NFkB-mediated transcription), attenuating cells expressing human OX40 by ADCC, enhancing T Effector cell function (e.g., CD4+ effector T cells) (eg, by enhancing effector T cell proliferation and/or increasing cytokine production of effector T cells (e.g., gamma interferon or interleukin)), enhancing memory T cell function (e.g., CD4+ memory T cells) (eg, by increasing memory T cell proliferation and/or increasing cytokine production of memory T cells (eg, gamma interferon or interleukin)), binding to human effector cells. Antibodies having such biological activity in vivo and/or in vitro are also provided.

In certain embodiments, the antibodies of the invention are tested for such biological activity.

T cell activation can be assayed using methods known in the art. For example, it is determined by the level of a cytokine released after T cell activation, such as gamma interferon or interleukin. OX40 signaling can also be determined using methods well known in the art to determine activation of T cells. In one embodiment, a transgenic cell expressing human OX40 and a reporter gene comprising an NFkB promoter fused to a reporter gene (eg, beta luciferase) is generated. Addition of anti-OX40 antibodies to cells results in elevated NFkB transcription, which is detected using an assay for the reporter gene (eg, a luciferase reporter assay).

Cells for use in any of the above in vitro assays include cells or cell lines that naturally express OX40 or that are engineered to express OX40. Such cells include activated T cells that naturally express OX40, Treg cells, and activated memory T cells. Such cells also include cell lines that express OX40 and cell lines that do not normally express OX40 but have been transfected with a nucleic acid encoding OX40.

It will be appreciated that any of the above assays can be performed by replacing or supplementing the anti-OX40 antibody with an immunoconjugate of the invention.

It will be appreciated that any of the above assays can be performed using an anti-OX40 antibody and other active agents.

Pharmaceutical Compositions and Pharmaceutical Preparations

The invention also includes a composition (including pharmaceutical compositions or pharmaceutical preparations) comprising anti-OX40 antibody or immunoconjugate thereof and a composition comprising polynucleotides encoding the anti-OX40 antibody. In certain embodiments, the composition comprises one or more antibodies or fragments thereof that bind to OX40 or one or more polynucleotides encoding one or more antibodies or fragments thereof that bind to OX40. These compositions may also contain suitable pharmaceutically acceptable adjuvants, such as pharmaceutically acceptable carrier, pharmaceutically acceptable excipients known in the art, including buffers.

Pharmaceutically acceptable carriers suitable for use in the present invention may be sterile liquids such as water and oils, including those from petroleum, animal, plant or synthetic origin, such as peanut oil, soybean oil, mineral oil, sesame oil and the like. Water is a preferred carrier when the pharmaceutical composition is administered intravenously. Saline solution and aqueous dextrose and glycerol solution can also be used as liquid carriers, especially used as injectable solutions. Suitable pharmaceutical excipients include starch, glucose, lactose, sucrose, gelatin, malt, rice, flour, chalk, silica gel, sodium stearate, glyceryl monostearate, talc, sodium chloride, dried skim milk, glycerin, propylene, glycol, water, ethanol, etc. For excipients and the uses thereof, see also "Handbook of Pharmaceutical Excipients", Fifth Edition, R. C. Rowe, P. J. Seskey and S. C. Owen, Pharmaceutical Press, London, Chicago. If desired, the composition may also contain minor amounts of wetting or emulsifying agents, or pH buffer. These compositions may be in the form of solutions, suspensions, emulsions, tablets, pills, capsules, powders, sustained release preparations and the like. Oral formulations may contain standard carriers such as pharmaceutical grades of mannitol, lactose, starch, magnesium stearate, saccharin.

A pharmaceutical formulation comprising an anti-OX40 antibody of the invention can be prepared by mixing the anti-OX40 antibody of the present invention having desired purity with one or more optional pharmaceutically acceptable adjuvants (Remington's Pharmaceutical Sciences, 16th Ed., Osol, A., ed. (1980)), preferably in the form of a lyophilized preparation or an aqueous solution.

Exemplary lyophilized antibody formulations are described in U.S. Pat. No. 6,267,958. Aqueous antibody formulations include those described in U.S. Pat. No. 6,171,586 and WO2006/044908, and the latter includes histidine-acetate buffer.

The pharmaceutical compositions or formulations of the present invention may also contain one or more active ingredient which is required for a particular indication to be treated, preferably those active ingredients which do not adversely affect each other's complementary activities. For example, it is desirable to further provide other anti-cancer active ingredients, such as chemotherapeutic agents, PD-1 axis binding antagonists (such as anti-PD-1 antibodies or anti-PD-L1 antibodies or anti-PD-L2 antibodies) or anti-angiogenic agents (such as bevacizumab). The active ingredient is suitably present in combination in an amount effective for the intended use.

Sustained release formulations can be prepared. Suitable examples of the sustained release formulations include semipermeable matrices of solid hydrophobic polymers containing antibodies, the matrices are in the form of shaped articles, such as films or microcapsules.

With regard to other components of the pharmaceutical formulation comprising the antibody of the invention, reference is also made to those disclosed in WO2015/153513.

Antibody Treatment and Use

In one aspect, the invention relates to a method of activating T cell or inducing T cell mediated antitumor activity or enhancing an immune response of the body in a subject comprising administering to said subject an effective amount of any of the anti-OX40 antibody or fragment thereof, or immunoconjugates or pharmaceutical compositions comprising said antibody or fragments.

In another aspect, the invention relates to a method of treating tumor, e.g., cancer, in a subject comprising administering to said subject an effective amount of any anti-OX40 antibody or fragment thereof as described herein, or immunoconjugates or pharmaceutical compositions comprising said antibody or fragments. In one embodiment, the cancer is lung cancer (e.g., non-small cell lung cancer), liver cancer, gastric cancer, colon cancer, and the like.

In another aspect, the invention relates to a method of causing antibody-dependent cell-mediated cytotoxicity in a subject comprising administering to said subject an effective amount of any anti-OX40 antibody or fragment thereof described herein, or immunoconjugates or pharmaceutical compositions comprising said antibody or fragments.

In another aspect, the invention relates to a method of treating or delaying various cancers, immune-related diseases, and T-cell dysfunction diseases in a subject, comprising administering to said subject an effective amount of any anti-OX40 antibody or fragment thereof described herein, or immunoconjugates or pharmaceutical compositions comprising said antibody or fragments.

In some embodiments, the methods described herein further comprise administering to the subject one or more therapies (e.g., a therapeutic manner and/or other therapeutic agent). In some embodiments, the treatment manner includes surgery and/or radiation therapy. In some embodiments, the other therapeutic agent is selected from the group consisting of a chemotherapeutic agent, a PD-1 axis binding antagonist (eg, an anti-PD-1 antibody or an anti-PD-L1 antibody or an anti-PD-L2 antibody), or an anti-angiogenic agent (eg, bevacate) Bead monoclonal antibody).

In some embodiments, the subject or individual is a mammal, preferably a human.

In other aspects, the invention provides the use of an anti-OX40 antibody or fragment thereof in the manufacture or preparation of a medicament for the treatment of a related disease or condition mentioned above.

In some embodiments, an antibody or antibody fragment thereof of the invention may delay the onset of conditions and/or symptoms associated with the condition.

In some embodiments, the cancer suitable for the present invention is selected from the group consisting of lung cancer (eg, non-small cell lung cancer), liver cancer, gastric cancer, colon cancer, and the like.

In some embodiments, examples of cancer further include, but are not limited to, B-cell proliferative disorders, which further include, but are not limited to, lymphomas (e.g., B-Cell Non-Hodgkin's lymphomas (NHL)) and lymphocytic leukemias.

In some embodiments of any of the methods of the invention, the cancer as described herein displays human effector cells (e.g., is infiltrated by human effector cells). Methods for detecting human effector cells are well known in the art, including, e.g., by IHC. In some embodiments, the cancer display high levels of human effector cells. In some embodiments, human effector cells are one or more of NK cells, macrophages, monocytes.

In some embodiments of any of the methods of the invention, the cancer as described herein displays cells expressing FcR (e.g., is infiltrated by cells expressing FcR). Methods for detecting FcR are well known in the art, including, e.g., by IHC. In some embodiments, the cancer display high levels of cells expressing FcR. In some embodiments, FcR is FcγR. In some embodiments, FcR is activating FcγR. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma.

In some embodiments of any of the methods of the invention, administration of an anti-OX40 antibody or fragment thereof of the invention having agonist activity is combined with administration of a tumor antigen. In some embodiments, the tumor antigen comprises a protein. In some embodiments, the tumor antigen comprises a nucleic acid. In some embodiments, the tumor antigen is a tumor cell.

In certain embodiments, the methods and uses described herein further comprise administering to the subject one or more therapies (e.g., therapeutical manner and/or other therapeutical agents). Antibodies of the invention can be used either alone or in combination with other agents in a therapy. For instance, an antibody of the invention may be co-administered with at least one additional therapeutic agent.

Such combination therapies encompass combined administration (for example, two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-OX40 antibody and administration of an additional therapeutic agent occur within about one month, or within about one, two or three weeks, or within about one, two, three, four, five, or six days, of each other. Antibodies of the invention can also be used in combination with surgery or radiation therapy.

In some embodiments, the therapeutic manner includes surgery (e.g., tumor resection); radiation therapy (e.g., external particle beam therapy, which involves three-dimensional conformal radiation therapy in which the illumination region is designed), local irradiation (e.g., irradiation pointing to a pre-selected target or organs) or focused irradiation) and the like.

In some embodiments, an anti-OX40 antibody or fragment thereof of the invention may be administered in combination with a chemotherapy or chemotherapeutic agent. In some embodiments, an anti-OX40 antibody or fragment thereof of the invention may be administered in combination with a radiotherapy or radiotherapy agent. In some embodiments, an anti-OX40 antibody or fragment thereof of the invention may be administered in combination with a targeted therapy or a targeted therapeutic agent. In some embodiments, the anti-OX40 antibody or fragment thereof of the invention may be administered in combination with an immunotherapy or immunotherapeutic agent, such as a monoclonal antibody.

In some embodiments, the anti-OX40 antibody or fragment thereof of the invention may be administered in combination with a PARP inhibitor (e.g., Olaparanib, Rucaparib, Niraparib, Cediranib, BMN673, Veliparib)

In some embodiments, the anti-OX40 antibody or fragment thereof of the invention may be administered in combination with a PD-1 axis binding antagonist. A PD-1 axis binding antagonist includes but is not limited to a PD-1 binding antagonist, a PD-L1 binding antagonist and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2. In some embodiments, the PD-1 binding antagonist is a molecule that inhibits the binding of PD-1 to its ligand or binding partners. In a specific aspect the PD-1 ligandare PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide. In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of MDX-1106 (nivolumab, OPDIVO), Merck 3475 (MK-3475, pembrolizumab, KEYTRUDA) and CT-011 (Pidilizumab). In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. In some embodiments, the PD-L1 binding antagonist is anti-PD-L1 antibody. In some embodiments, the anti-PD-L1 binding antagonist is selected from the group consisting of YW243.55.S70, MPDL3280A, MEDI4736 and MDX-1105. MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO2010/077634 A1. MDX-1106, also known as MDX-1106-04, ONO-4538, BMS-936558 or nivolumab, is an anti-PD-1 antibody described in WO2006/121168. Merck 3475, also known as MK-3475, SCH-900475 or pembrolizumab, is an anti-PD-1 antibody described in WO2009/114335. CT-011, also known as hBAT, hBAT-1 or pidilizumab, is an anti-PD-1 antibody described in WO2009/101611. AMP-224, also known as B7-DCIg, is a PD-L2-Fc fusion soluble receptor described in WO2010/027827 and WO2011/066342. In some embodiments, the anti-PD-1 antibody is MDX-1106. Alternative names for "MDX-1106" include MDX-1106-04, ONO-4538, BMS-936558 or nivolumab. In some embodiments, the anti-PD-1 antibody is nivolumab (CAS Registry Number: 946414-94-4).

In some embodiments, an anti-OX40 antibody or fragment thereof of the invention may be administered in combination with an agonist directed against an activating co-stimulatory molecule. In some embodiments, an activating co-stimulatory molecule may include CD40, CD226, CD28, GITR, CD137, CD27, HVEM, or CD127. In some embodiments, the agonist directed against an activating co-stimulatory molecule is an agonist antibody that binds to CD40, CD226, CD28, OX40, GITR, CD137, CD27, HVEM, or CD127. In some embodiments, an anti-OX40 antibody or fragment thereof of the invention may be administered in combination with an antagonist directed against an inhibitory co-stimulatory molecule. In some embodiments, an inhibitory co-stimulatory molecule may include CTLA-4 (also known as CD152), PD-1, TIM-3, BTLA, VISTA, LAG-3, B7-H3, B7-H4, IDO, TIGIT, MICA/B, or arginase. In some embodiments, the antagonist directed against an inhibitory co-stimulatory molecule is an antagonist antibody that binds to CTLA-4, PD-1, TIM-3, BTLA, VISTA, LAG-3 (e.g., LAG-3-IgG fusion protein (IMP321)), B7-H3, B7-H4, IDO, TIGIT, MICA/B, or arginase.

In some embodiments, an anti-OX40 antibody or fragment thereof of the invention may be administered in combination with a treatment comprising adoptive transfer of a T cell (e.g., a cytotoxic T cell or CTL) expressing a chimeric antigen receptor (CAR).

In some embodiments, an anti-OX40 antibody or fragment thereof of the invention may be administered in combination with an angiogenesis inhibitor. In some embodiments, an anti-OX40 antibody or fragment thereof of the invention can be administered in combination with bevacizumab (also known as AVASTIN®, Genentech).

In some embodiments, the anti-OX40 antibody or fragment thereof of the invention may be administered in combination with an angiogenesis inhibitor and in combination with a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody). In some embodiments, the anti-OX40 antibody or fragment thereof of the invention may be administered in combination with bevacizumab and a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody). In some embodiments, the anti-OX40 antibody or fragment thereof of the invention may be administered in combination with bevacizumab and MDX-1106 (nivolumab, OPDIVO). In some embodiments, the anti-OX40 antibody or fragment thereof of the invention may be administered in combination with bevacizumab and Merck 3475 (MK-3475, pembrolizumab, KEYTRUDA). In some embodiments, the anti-OX40 antibody or fragment thereof of the invention may be administered in combination with bevacizumab and CT-011 (Pidilizumab). In some embodiments, the anti-OX40 antibody or fragment thereof of the invention may be administered in combination with bevacizumab and YW243.55.570. In some embodiments, the anti-OX40 antibody or fragment thereof of the invention may be administered in combination with bevacizumab and MPDL3280A. In some embodiments, the anti-OX40 antibody or fragment thereof of the invention may be administered in combination with bevacizumab and MEDI4736. In some embodiments, the anti-OX40 antibody or fragment thereof of the invention may be administered in combination with bevacizumab and MDX-1105.

In some embodiments, the anti-OX40 antibody or fragment thereof of the invention may be administered in combination with an anti-tumor agent. In some embodiments, the anti-OX40 antibody or fragment thereof of the invention may be administered in combination with an inhibitor of Bruton's tyrosine kinase (BTK).

In some embodiments, the anti-OX40 antibody or fragment thereof of the invention may be administered in combination with obinutuzumab and a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody).

In some embodiments, an anti-OX40 antibody or fragment thereof of the invention may be administered in combination with a cancer vaccine. In some embodiments, the cancer vaccine is a peptide cancer vaccine, which in some embodiments is a personalized peptide vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci, 104: 14-21, 2013).

In some embodiments, an anti-OX40 antibody or fragment thereof of the invention may be administered in combination with an adjuvant. In some embodiments, an anti-OX40 antibody or fragment thereof of the invention may be administered in combination with a treatment comprising a TLR agonist, e.g., Poly-ICLC (also known as Hiltonol®), LPS, MPL, or CpG ODN.

In some embodiments, an anti-OX40 antibody or fragment thereof of the invention may be administered in combination with a tumor necrosis factor (TNF) a. In some embodiments, the anti-OX40 antibody or fragment thereof of the invention may be administered in combination with interleukins (e.g., IL-1, IL-10, IL-4, IL-13, IL-17, etc.). In some embodiments, the anti-OX40 antibody or fragment thereof of the invention may be administered in combination with the treatment of targeting CXCL10. In some embodiments, the anti-OX40 antibody or fragment thereof of the invention may be administered in combination with the treatment of targeting CCLS. In some embodiments, the anti-OX40 antibody or fragment thereof of the invention may be administered in combination with an LFA-1 or ICAM1 agonist. In some embodiments, an anti-OX40 antibody or fragment thereof of the invention may be administered in combination with a Selectin agonist.

In some embodiments, an anti-OX40 antibody or fragment thereof of the invention may be administered in combination with an inhibitor of B-Raf.

In some embodiments, the anti-OX40 antibody or fragment thereof of the invention may be administered in combination with an inhibitor of B-Raf (e.g., vemurafenib or dabrafenib) and an inhibitor of MEK (e.g., MEK1 and/or MEK2), (e.g., cobimetinib or trametinib).

In some embodiments, the anti-OX40 antibody or fragment thereof of the invention may be administered in combination with an inhibitor of c-Met.

In some embodiments, an anti-OX40 antibody or fragment thereof of the invention may be administered in combination with an agent that selectively degrades the estrogen receptor.

In some embodiments, the anti-OX40 antibody or fragment thereof of the invention may be administered in combination with radiation therapy.

In some embodiments, an anti-OX40 antibody or fragment thereof of the invention may be administered in combination with an oncolytic virus.

More therapies or therapeutic agents or pharmaceuticals or active ingredients that can be combined with the anti-OX40 antibody or fragment thereof of the invention are described in WO2015/153513.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Methods and Compositions for Diagnosis and Detection

In certain embodiments, any anti-OX40 antibody or antigen-binding fragment thereof provided herein may be used to detect the presence of OX40 in a biological sample. The term "detection" is used herein to include quantitative or qualitative detection. In certain embodiments, the biological sample is another liquid sample of blood, serum, or biological origin. In certain embodiments, the biological sample comprises cells or tissues.

In one embodiment, an anti-OX40 antibody is provided for a diagnostic or detection method. In another aspect, a method is provided for detecting the presence of OX40 in a biological sample. In certain embodiments, the method comprises detecting the presence of the OX40 protein in a biological sample. In certain embodiments, the OX40 is human OX40. In certain embodiments, the method comprises contacting a biological sample with an anti-OX40 antibody as described herein under conditions that allow binding of the anti-OX40 antibody to OX40 and detecting whether a complex is formed between the anti-OX40 antibody and the OX40. The method may be in vitro or in vivo. In one embodiment, the anti-OX40 antibody is used to select a subject suitable for treatment with an anti-OX40 antibody, for example wherein the OX40 is a biomarker for selecting a patient.

In one embodiment, the antibody of the present invention may be used to diagnose cancer or tumors.

In certain embodiments, a labeled anti-OX40 antibody is provided. The marker includes, but is not limited to, directly detected markers or portions (such as fluorescent labels, chromophore labels, electronically dense labels, chemiluminescent labels and radiolabeled labels), as well as indirectly detected moieties such as enzymes or ligands, e.g., through enzymatic reactions or molecular interactions. Exemplary markers include, but are not limited to, radioisotopes 32P, 14C, 125I, 3H and 131I, fluorophores such as rare earth chelates or fluorescein and its derivatives, rhodamine and its derivatives, dansyl, umbelliferone, luceriferase, for example, firefly luciferase and bacterial luciferase (U.S. Pat. No. 4,737,456), fluorescein, 2,3-dihydrophthalazinedione, horseradish peroxidase (HR), alkaline phosphatase, β-galactosidase, glucoamylase, lyase, carbohydrate oxidase, for example, glucose oxidase, galactose oxidase, and glucose-6-phosphate dehydrogenase, heterocyclic oxidases such as uricase and xanthine oxidase, as well as enzymes that oxidize dye precursors using hydrogen peroxide, such as HR, lactoperoxidase, microperoxidase, biotin/avidin, spin label, phage label, stable free radicals, and the like.

In one aspect, the present invention provides diagnostic methods, such as for identifying cancer patients who are likely to respond to anti-OX40 antibody therapy.

In some embodiments, provided is a method for identifying a patient likely to respond to an anti-OX40 antibody treatment or a method for diagnosing cancer, the method comprising (i) determining the presence or absence or amount (e.g., number of each given size of the samples) of FcR-expressing cells from a cancer sample of the patient; (ii) if the sample contains cells expressing FcR (e.g., a high number of cells expressing FcR), the patient is identified as being likely to respond, or diagnose said patient as having cancers comprising FcR (e.g., high FcR). Methods for detecting cells expressing FcR are well known in the art and include, for example, IHC. In some embodiments, FcR is FcγR. In some embodiments, FcR is activating FcγR. In some embodiments, the cancer is any of the cancers described herein. In some embodiments, the cancer is non-small cell lung cancer (NSCLC), glioblastoma, neuroblastoma, melanoma, breast cancer (e.g., triple negative breast cancer), gastric cancer, colorectal cancer (CRC) or hepatocellular carcinoma. In some embodiments, the method is an in vitro method.

In some embodiments, provided is a method for identifying a patient likely to respond to an anti-OX40 antibody treatment or a method for diagnosing cancer, the method comprising (i) determining the presence or absence or amount (e.g., number of each given size of the samples) of human effector cells (e.g., invasive effector cells) from the patient's cancer sample, and (ii) if the sample comprises effector cells (e.g., a high number of effector cells), the patient is identified as being likely to respond, or diagnosed as having cancer comprising human effector cell. Methods for detecting invasive human effector cells are well known in the art and include, for example, IHC. In some embodiments, the human effector cells are one or more of NK cells, macrophages, monocytes. In some embodiments, the effector cells express the activating FcγR. In some embodiments, the method is an in vitro method. In some embodiments, the cancer is any of the cancers described herein. In some embodiments, the cancer is non-small cell lung cancer (NSCLC), glioblastoma, neuroblastoma, melanoma, breast cancer (e.g., triple negative breast cancer), gastric cancer, colorectal cancer (CRC) or hepatocellular carcinoma.

In some embodiments, a method is provided for recommending treatment to a cancer patient comprising the steps of a method for identifying a patient likely to respond to an anti-OX40 antibody treatment or a method for diagnosing cancer as described above, and (iii) when the sample has cells expressing FcR or has human effector cells, it is recommended an anti-OX40 antibody (e.g., anti-OX40 antibody or the fragment thereof of the present invention) treatment.

In some embodiments, a method is provided for treating a cancer patient comprising the steps a method for identifying a patient likely to respond to an anti-OX40 antibody treatment or a method for diagnosing cancer as described above, and (iii) when the sample has cells expressing FcR or has human effector cells, the patient is treated with an anti-OX40 antibody (e.g., an anti-OX40 antibody or the fragment thereof of the present invention).

In some embodiments of any invention provided herein, the sample is obtained prior to treatment with anti-OX40 antibody. In some embodiments, the sample is obtained prior to treatment with the cancer drug. In some embodiments, the sample is obtained after cancer metastasis. In some embodiments, the sample is fixed with formalin and coated with paraffin (FFPE). In some embodiments, the sample is a biopsy (e.g., a core biopsy), a surgical specimen (e.g., from a surgically resected specimen), or a fine needle aspirate.

Sequences of the Exemplary Anti-OX40 Antibody of the Present Invention

TABLE 1

FR and CDR sequences of heavy chain variable domain (VH, or heavy chain variable region (HCVR)) of the exemplary antibody of the present invention

| Antibody Name | optimized linkage | VH FR1 | VH CDR1/HCDR1 | VH FR2 | VH CDR2/HCDR2 |
|---|---|---|---|---|---|
| ADI-20112 | Parent antibody | QVQLVESGGGVVQPG RSLRLSCAASG(SEQ ID NO: 62) | FTFSSYGMH (SEQ ID NO: 1) | WVRQAPGKGLEW VA (SEQ ID NO: 183) | VISYDGSNKYYADS VKG(SEQ ID NO: 17) |
| ADI-20113 | Parent antibody | QVQLVESGGGVVQPG RSLRLSCAASG(SEQ ID NO: 62) | FTFSSYGMH (SEQ ID NO: 1) | WVRQAPGKGLEW VA (SEQ ID NO: 183) | VISYDGSNKYYADS VKG(SEQ ID NO: 17) |
| ADI-25650 | ADI-20112 | QVQLVESGGGVVQPG RSLRLSCAASG(SEQ ID NO: 62) | FTFSVYNMH (SEQ ID NO: 2) | WVRQAPGKGLEW VA (SEQ ID NO: 183) | VIAYDGSAKYYADS VKG(SEQ ID NO: 18) |

TABLE 1-continued

FR and CDR sequences of heavy chain variable domain (VH, or heavy chain variable region (HCVR))
of the exemplary antibody of the present invention

| | | | | | |
|---|---|---|---|---|---|
| ADI-25651 | ADI-20112 | QVQLVESGGGVVQPGRSLRLSCAASG(SEQ ID NO: 62) | FTFSSRNMH (SEQ ID NO: 3) | WVRQAPGKGLEWVA (SEQ ID NO: 183) | VIAYDGSLKYYADSVKG(SEQ ID NO: 19) |
| ADI-25652 | ADI-20112 | QVQLVESGGGVVQPGRSLRLSCAASG(SEQ ID NO: 62) | FTFVSYNMH (SEQID NO: 4) | WVRQAPGKGLEWVA (SEQ ID NO: 183) | VIAYDGSVKYYADSVKG(SEQ ID NO: 20) |
| ADI-25653 | ADI-20112 | QVQLVESGGGVVQPGRSLRLSCAASG(SEQ ID NO: 62) | FTFVSYNMH (SEQID NO: 4) | WVRQAPGKGLEWVA (SEQ ID NO: 183) | VIMYDGSAKYYADSVKG(SEQ ID NO: 21) |
| ADI-25654 | ADI-20112 | QVQLVESGGGVVQPGRSLRLSCAASG(SEQ ID NO: 62) | FTFRSYDMH (SEQID NO: 5) | WVRQAPGKGLEWVA (SEQ ID NO: 183) | YIAYDGSNKYYADSVKG(SEQ ID NO: 22) |
| consensus seqeunce | | | FTFX1X2X3X4MH(wherein X1 is selected from S, V, R; X2 is selected from V, S; X3 is selected from Y, R; X4 is selected from G, N, D)(SEQ ID NO: 6) | | X1IX2YDGSX3KYYADSVKG(wherein X1 is selected from V, Y; X2 is selected from S, A, M; X3 is selected from N, A, L, V)(SEQ ID NO: 23) |
| ADI-20078 | Parent antibody | QVQLQESGPGLVKPSQTLSLTCTVSG(SEQ ID NO: 63) | GSISSGSYYWS(SEQ ID NO: 7) | WIRQHPGKGLEWIG (SEQ ID NO: 184) | YIYYSGSTYYNPSLKS(SEQ ID NO: 24) |
| ADI-23515 | ADI-20078 | QVQLQESGPGLVKPSQTLSLTCTVSG(SEQ ID NO: 63) | GSIRSGAYYWS(SEQ ID NO: 8) | WIRQHPGKGLEWIG (SEQ ID NO: 184) | YIYYDGQTYYNPSLKS(SEQ ID NO: 25) |
| ADI-23518 | ADI-20078 | QVQLQESGPGLVKPSQTLSLTCTVSG(SEQ ID NO: 63) | GSISSGASYWS(SEQ ID NO: 9) | WIRQHPGKGLEWIG (SEQ ID NO: 184) | YIYYSGETYYNPSLKS(SEQ ID NO: 26) |
| ADI-23519 | ADI-20078 | QVQLQESGPGLVKPSQTLSLTCTVSG(SEQ ID NO: 63) | GSISSGSSYWS(SEQ ID NO: 10) | WIRQHPGKGLEWIG (SEQ ID NO: 184) | YIYMSGETYYNPSLKS(SEQ ID NO: 27) |
| consensus seqeunce | | | GSIX1SGX2X3 (X1 is selected from S, R; X2 is selected from S, A; X3 is selected from Y, S)(SEQ ID NO: 11) | | YIYX1X2GX3TYYNPSLKS(其中 X1 is selected from Y, M; X2 is selected from D, S; X3 is selected from S, Q, E)(SEQ ID NO: 28) |
| ADI-20048 | Parent antibody | QVQLQESGPGLVKPSETLSLTCTVSG(SEQ ID NO: 64) | GSISSYYWS(SEQ ID NO: 12) | WIRQPPGKGLEWIG (SEQ ID NO: 185) | YIYSSGSTNYNPSLKS(SEQ ID NO: 29) |
| ADI-20096 | Parent antibody | EVQLVESGGGLVKPGGSLRLSCAASG(SEQ ID NO: 65) | FTFSSYSMN (SEQ ID NO: 13) | WVRQAPGKGLEWVS (SEQ ID NO: 186) | SISSSSNYIYYADSVKG(SEQ ID NO: 30) |
| ADI-20051 | Parent antibody | QVQLQQWGAGLLKPSETLSLTCAVYG(SEQ ID NO: 66) | GSFSGYYWS(SEQ ID NO: 14) | WIRQPPGKGLEWIG (SEQ ID NO: 185) | EIDHSGSTNYNPSLKS(SEQ ID NO: 31) |
| ADI-20065 | Parent antibody | QLQLQESGPGLVKPSETLSLTCTVSG(SEQ ID NO: 188) | GSISSSSYWG(SEQ ID NO: 15) | WIRQPPGKGLEWIG (SEQ ID NO: 185) | SIYYSGSTYYNPSLKS(SEQ ID NO: 32) |
| ADI-20066 | Parent antibody | QLQLQESGPGLVKPSETLSLTCTVSG(SEQ ID NO: 188) | GSISSSSYWG(SEQ ID NO: 15) | WIRQPPGKGLEWIG (SEQ ID NO: 185) | SIYYSGSTYYNPSLKS(SEQ ID NO: 32) |
| ADI-20118 | Parent antibody | QVQLVQSGAEVKKPGASVKVSCKASG(SEQ ID NO: 67) | YTFTSYAIS (SEQ ID NO: 16) | WVRQAPGQGLEWMG(SEQ ID NO: 187) | WISAYNGNTNYAQKLQG(SEQ ID NO: 33) |

TABLE 1-continued

FR and CDR sequences of heavy chain variable domain (VH, or heavy chain variable region (HCVR)) of the exemplary antibody of the present invention

| Antibody Name | VH FR3 | VH CDR3/HCDR3 | VH FR4 |
|---|---|---|---|
| ADI-20112 | RFTISRDNSKNTLYLQMNSLRAEDTAVYYC (SEQ ID NO: 68) | ARGRPWYSETGTSAFDI (SEQ ID NO: 34) | WGQGTMVTVSS (SEQ ID NO: 86) |
| ADI-20113 | RFTISRDNSKNTLYLQMNSLRAEDTAVYYC (SEQ ID NO: 68) | ARGRPWYSETGTSAFDI (SEQ ID NO: 34) | WGQGTMVTVSS (SEQ ID NO: 86) |
| ADI-25650 | RFTISRDNSKNTLYLQMNSLRAEDTAVYYC (SEQ ID NO: 68) | ARGRPWYSETGTSAFDI (SEQ ID NO: 34) | WGQGTMVTVSS (SEQ ID NO: 86) |
| ADI-25651 | RFTISRDNSKNTLYLQMNSLRAEDTAVYYC (SEQ ID NO: 68) | ARGRPWYSETGTSAFDI (SEQ ID NO: 34) | WGQGTMVTVSS (SEQ ID NO: 86) |
| ADI-25652 | RFTISRDNSKNTLYLQMNSLRAEDTAVYYC (SEQ ID NO: 68) | ARGRPWYSETGTSAFDI (SEQ ID NO: 34) | WGQGTMVTVSS (SEQ ID NO: 86) |
| ADI-25653 | RFTISRDNSKNTLYLQMNSLRAEDTAVYYC (SEQ ID NO: 68) | ARGRPWYSETGTSAFDI (SEQ ID NO: 34) | WGQGTMVTVSS (SEQ ID NO: 86) |
| ADI-25654 | RFTISRDNSKNTLYLQMNSLRAEDTAVYYC (SEQ ID NO: 68) | ARGRPWYSETGTSAFDI (SEQ ID NO: 34) | WGQGTMVTVSS (SEQ ID NO: 86) |
| consensus seqeunce | | | |
| ADI-20078 | RVTISVDTSKNQFSLKLSSVTAADTAVYYC (SEQ ID NO: 69) | ARDVGYPHYYGMDV (SEQ ID NO: 35) | WGQGTTVTVSS (SEQ ID NO: 87) |
| ADI-23515 | RVTISVDTSKNQFSLKLSSVTAADTAVYYC (SEQ ID NO: 69) | ARDVGYPHYYGMDV (SEQ ID NO: 35) | WGQGTTVTVSS (SEQ ID NO: 87) |
| ADI-23518 | RVTISVDTSKNQFSLKLSSVTAADTAVYYC (SEQ ID NO: 69) | ARDVGYPHYYGMDV (SEQ ID NO: 35) | WGQGTTVTVSS (SEQ ID NO: 87) |
| ADI-23519 | RVTISVDTSKNQFSLKLSSVTAADTAVYYC (SEQ ID NO: 69) | ARDVGYPHYYGMDV (SEQ ID NO: 35) | WGQGTTVTVSS (SEQ ID NO: 87) |
| consensus seqeunce | | | |
| ADI-20048 | RVTISVDTSKNQFSLKLSSVTAADTAVYYC (SEQ ID NO: 69) | ARDAPGGSSYQDYYMDV (SEQ ID NO: 36) | WGKGTTVTVSS (SEQ ID NO: 88) |

TABLE 1-continued

FR and CDR sequences of heavy chain variable domain (VH, or heavy chain variable region (HCVR))
of the exemplary antibody of the present invention

| | | | |
|---|---|---|---|
| ADI-20096 | RFTISRDNAKN SLYLQMNSLR AEDTAVYYC (SEQ ID NO: 70) | ARGAPLG YSWEYFD L(SEQ ID NO: 37) | WGRGT LVTVSS (SEQ ID NO: 89) |
| ADI-20051 | RVTISVDTSKN QFSLKLSSVTA ADTAVYYC(SEQ ID NO: 69) | ARDGGGG YASPFDY (SEQ ID NO: 38) | WGQGT LVTVSS (SEQ ID NO: 90) |
| ADI-20065 | RVTISVDTSKN QFSLKLSSVTA ADTAVYYC(SEQ ID NO: 69) | ARDPGYS ASPNVVFD P(SEQ ID NO: 39) | WGQGT LVTVSS (SEQ ID NO: 90) |
| ADI-20066 | RVTISVDTSKN QFSLKLSSVTA ADTAVYYC(SEQ ID NO: 69) | ARDPGYS ASPNVVFD P(SEQ ID NO: 39) | WGQGT LVTVSS (SEQ ID NO: 90) |
| ADI-20118 | RVTMTTDTSTS TAYMELRSLRS DDTAVYYC(SEQ ID NO: 71) | ARSGGGS GPNWFDP (SEQ ID NO: 40) | WGQGT LVTVSS (SEQ ID NO: 90) |

TABLE 2

FR and CDR sequences of light chain variable domain(VL)(or light variable region(LCVR))
of the exemplary antibody of the present invention

| Antibody Name | optimized linkage | VL FR1 | VL CDR1/ LCDR1 | VL FR2 | CDR2/ LCDR2 | VL FR3 | VL CDR3/LCDR3 | VL FR4 |
|---|---|---|---|---|---|---|---|---|
| ADI-20112 | Parent antibody | DIQMTQSPSSL SASVGDRVTIT C(SEQ ID NO: 72) | QASQDISN YLN(SEQ ID NO: 41) | WYQQKPGKA PKLLIY(SEQ ID NO: 77) | DASNLET (SEQ ID NO: 47) | GVPSRFSGSGSGTD FTFTISSLQPEDIAT YYC(SEQ ID NO: 80) | QQSDHYPT (SEQ ID NO: 53) | FGGGTKVEIK (SEQ ID NO: 85) |
| ADI-20113 | Parent antibody | EIVMTQSPATL SVSPGERATLS C(SEQ ID NO: 73) | RASQSVSS NLA(SEQ ID NO: 42) | WYQQKPGQA PRLLIY(SEQ ID NO: 78) | SASTRAT (SEQ ID NO: 48) | GIPARFSGSGSGTEF TLTISSLQSEDFAVY YC(SEQ ID NO: 81) | QQHNVYPPY T(SEQ ID NO: 54) | FGGGTKVEIK (SEQ ID NO: 85) |
| ADI-25650 | ADI-20112 | DIQMTQSPSSL SASVGDRVTIT C(SEQ ID NO: 72) | QASQDISN YLN(SEQ ID NO: 41) | WYQQKPGKA PKLLIY(SEQ ID NO: 77) | DASNLET (SEQ ID NO: 47) | GVPSRFSGSGSGTD FTFTISSLQPEDIAT YYC(SEQ ID NO: 80) | QQSDHYPT (SEQ ID NO: 53) | FGGGTKVEIK (SEQ ID NO: 85) |
| ADI-25651 | ADI-20112 | DIQMTQSPSSL SASVGDRVTIT C(SEQ ID NO: 72) | QASQDISN YLN(SEQ ID NO: 41) | WYQQKPGKA PKLLIY(SEQ ID NO: 77) | DASNLET (SEQ ID NO: 47) | GVPSRFSGSGSGTD FTFTISSLQPEDIAT YYC(SEQ ID NO: 80) | QQSDHYPT (SEQ ID NO: 53) | FGGGTKVEIK (SEQ ID NO: 85) |
| ADI-25652 | ADI-20112 | DIQMTQSPSSL SASVGDRVTIT C(SEQ ID NO: 72) | QASQDISN YLN(SEQ ID NO: 41) | WYQQKPGKA PKLLIY(SEQ ID NO: 77) | DASNLET (SEQ ID NO: 47) | GVPSRFSGSGSGTD FTFTISSLQPEDIAT YYC(SEQ ID NO: 80) | QQSDHYPT (SEQ ID NO: 53) | FGGGTKVEIK (SEQ ID NO: 85) |
| ADI-25653 | ADI-20112 | DIQMTQSPSSL SASVGDRVTIT C(SEQ ID NO: 72) | QASQDISN YLN(SEQ ID NO: 41) | WYQQKPGKA PKLLIY(SEQ ID NO: 77) | DASNLET (SEQ ID NO: 47) | GVPSRFSGSGSGTD FTFTISSLQPEDIAT YYC(SEQ ID NO: 80) | QQSDHYPT (SEQ ID NO: 53) | FGGGTKVEIK (SEQ ID NO: 85) |
| ADI-25654 | ADI-20112 | DIQMTQSPSSL SASVGDRVTIT C(SEQ ID NO: 72) | QASQDISN YLN(SEQ ID NO: 41) | WYQQKPGKA PKLLIY(SEQ ID NO: 77) | DASNLET (SEQ ID NO: 47) | GVPSRFSGSGSGTD FTFTISSLQPEDIAT YYC(SEQ ID NO: 80) | QQSDHYPT (SEQ ID NO: 53) | FGGGTKVEIK (SEQ ID NO: 85) |
| ADI-20078 | Parent antibody | EIVLTQSPGTL SLSPGERATLS C(SEQ ID NO: 74) | RASQSVSSS YLA(SEQ ID NO: 43) | WYQQKPGQA PRLLIY(SEQ ID NO: 78) | GASSRAT (SEQ ID NO: 49) | GIPDRFSGSGSGTD FTLTISRLEPEDFAV YYC(SEQ ID NO: 82) | QQSERSPFT (SEQ ID NO: 55) | FGGGTKVEIK (SEQ ID NO: 85) |

TABLE 2-continued

FR and CDR sequences of light chain variable domain(VL)(or light variable region(LCVR))
of the exemplary antibody of the present invention

| Antibody Name | optimized linkage | VL FR1 | VL CDR1/LCDR1 | VL FR2 | CDR2/LCDR2 | VL FR3 | VL CDR3/LCDR3 | VL FR4 |
|---|---|---|---|---|---|---|---|---|
| ADI-23515 | ADI-20078 | EIVLTQSPGTL SLSPGERATLS C(SEQ ID NO: 74) | RASQSVSSS YLA(SEQ ID NO: 43) | WYQQKPGQA PRLLIY(SEQ ID NO: 78) | GASSRAT (SEQ ID NO: 49) | GIPDRFSGSGSGTD FTLTISRLEPEDFAV YYC(SEQ ID NO: 82) | QQSERSPFT (SEQ ID NO: 55) | FGGGTKVEIK (SEQ ID NO: 85) |
| ADI-23518 | ADI-20078 | EIVLTQSPGTL SLSPGERATLS C(SEQ ID NO: 74) | RASQSVSSS YLA(SEQ ID NO: 43) | WYQQKPGQA PRLLIY(SEQ ID NO: 78) | GASSRAT (SEQ ID NO: 49) | GIPDRFSGSGSGTD FTLTISRLEPEDFAV YYC(SEQ ID NO: 82) | QQSERSPFT (SEQ ID NO: 55) | FGGGTKVEIK (SEQ ID NO: 85) |
| ADI-23519 | ADI-20078 | EIVLTQSPGTL SLSPGERATLS C(SEQ ID NO: 74) | RASQSVSSS YLA(SEQ ID NO: 43) | WYQQKPGQA PRLLIY(SEQ ID NO: 78) | GASSRAT (SEQ ID NO: 49) | GIPDRFSGSGSGTD FTLTISRLEPEDFAV YYC(SEQ ID NO: 82) | QQSERSPFT (SEQ ID NO: 55) | FGGGTKVEIK (SEQ ID NO: 85) |
| ADI-20048 | Parent antibody | EIVLTQSPATL SLSPGERATLS C(SEQ ID NO: 75) | RASQSVSS YLA(SEQ ID NO: 44) | WFQQKPGQAP RLLIY(SEQ ID NO: 79) | DASNRAT (SEQ ID NO: 50) | GIPARFSGSGSGTDF TLTISSLEPEDFAVY C(SEQ ID NO: 83) | QQAFSMPPT (SEQ ID NO: 56) | FGGGTKVEIK (SEQ ID NO: 85) |
| ADI-20096 | Parent antibody | DIQMTQSPSTL SASVGDRVTIT C(SEQ ID NO: 76) | RASQSISSW LA(SEQ ID NO: 45) | WYQQKPGKA PKLLIY(SEQ ID NO: 77) | DASSLES (SEQ ID NO: 51) | GVPSRFSGSGSGTE FTLTISSLQPDDFAT YYC(SEQ ID NO: 84) | QQFQSYSYT (SEQ ID NO: 57) | FGGGTKVEIK (SEQ ID NO: 85) |
| ADI-20051 | Parent antibody | EIVMTQSPATL SVSPGERATLS C(SEQ ID NO: 73) | RASQSVSS NLA(SEQ ID NO: 42) | WYQQKPGQA PRLLIY(SEQ ID NO: 78) | GASTRAT (SEQ ID NO: 52) | GIPARFSGSGSGTEF TLTISSLQSEDFAVY C(SEQ ID NO: 81) | QQYHAWPP T(SEQ ID NO: 58) | FGGGTKVEIK (SEQ ID NO: 85) |
| ADI-20065 | Parent antibody | EIVLTQSPGTL SLSPGERATLS C(SEQ ID NO: 74) | RASQSVSSS YLA(SEQ ID NO: 43) | WYQQKPGQA PRLLIY(SEQ ID NO: 78) | GASSRAT (SEQ ID NO: 49) | GIPDRFSGSGSGTD FTLTISRLEPEDFAV YYC(SEQ ID NO: 82) | QQFDSSPT (SEQ ID NO: 59) | FGGGTKVEIK (SEQ ID NO: 85) |
| ADI-20066 | Parent antibody | EIVLTQSPGTL SLSPGERATLS C(SEQ ID NO: 74) | RASQSVSSS FLA(SEQ ID NO: 46) | WYQQKPGQA PRLLIY(SEQ ID NO: 78) | GASSRAT (SEQ ID NO: 49) | GIPDRFSGSGSGTD FTLTISRLEPEDFAV YYC(SEQ ID NO: 82) | QQYDVFPIT (SEQ ID NO: 60) | FGGGTKVEIK (SEQ ID NO: 85) |
| ADI-20118 | Parent antibody | DIQMTQSPSSL SASVGDRVTIT C(SEQ ID NO: 72) | QASQDISN YLN(SEQ ID NO: 41) | WYQQKPGKA PKLLIY(SEQ ID NO: 77) | DASNLET (SEQ ID NO: 47) | GVPSRFSGSGSGTD FTFTISSLQPEDIAT YYC(SEQ ID NO: 80) | QQPATLPWT (SEQ ID NO: 61) | FGGGTKVEIK (SEQ ID NO: 85) |

TABLE 3

DNA and amino acid sequences of heavy chain variable domain (VH)(or heavy chain variable region (HCVR)) of the exemplary antibody of the present invention

| Antibody Name | optimized linkage | VH DNA sequence | VH amino acid sequence |
|---|---|---|---|
| ADI-20112 | Parent antibody | CAGGTGCAGCTGGTGGAGTCTGGGGGAGGCGTGGTCCAGCCTGGGAGGTC CCTGAGACTCTCCTGTGCAGCGTCTGGATTCACCTTCAGTAGCTATGGCATG CACTGGGTCCGCCAGGCTCCAGGCAAGGGGCTGGAGTGGGTGGCAGTTATA TCGTATGATGGAAGTAATAAATACTATGCAGACTCCGTGAAGGGCCGATTCA CCATCTCCAGAGACAATTCCAAGAACACGCTGTATCTGCAAATGAACAGCC TGAGAGCCGAGGACACGGCGGTGTACTACTGCGCCAGAGGCCGTCCTTGGT ACAGCGAAACTGGTACCTCAGCTTTCGACATATGGGGTCAGGGTACAATGG TCACCGTCTCCTCA(SEQ ID NO: 91) | QVQLVESGGGVVQPGRSLRLSCAASGFT FSSYGMHWVRQAPGKGLEWVAVISYDG SNKYYADSVKGRFTISRDNSKNTLYLQM NSLRAEDTAVYYCARGRPWYSETGTSAF DIWGQGTMVTVSS(SEQ ID NO: 106) |
| ADI-20113 | Parent antibody | CAGGTGCAGCTGGTGGAGTCTGGGGGAGGCGTGGTCCAGCCTGGGAGGTC CCTGAGACTCTCCTGTGCAGCGTCTGGATTCACCTTCAGTAGCTATGGCATG CACTGGGTCCGCCAGGCTCCAGGCAAGGGGCTGGAGTGGGTGGCAGTTATA TCGTATGATGGAAGTAATAAATACTATGCAGACTCCGTGAAGGGCCGATTCA CCATCTCCAGAGACAATTCCAAGAACACGCTGTATCTGCAAATGAACAGCC TGAGAGCCGAGGACACGGCGGTGTACTACTGCGCCAGAGGCCGTCCTTGGT | QVQLVESGGGVVQPGRSLRLSCAASGFT FSSYGMHWVRQAPGKGLEWVAVISYDG SNKYYADSVKGRFTISRDNSKNTLYLQM NSLRAEDTAVYYCARGRPWYSETGTSAF DIWGQGTMVTVSS(SEQ ID NO: 106) |

TABLE 3-continued

DNA and amino acid sequences of heavy chain variable domain (VH)(or heavy chain variable region (HCVR)) of the exemplary antibody of the present invention

| Antibody Name | optimized linkage | VH DNA sequence | VH amino acid sequence |
|---|---|---|---|
| | | ACAGCGAAACTGGTACCTCAGCTTTCGACATATGGGGTCAGGGTACAATGG TCACCGTCTCCTCA(SEQ ID NO: 91) | |
| ADI-25650 | ADI-20112 | CAGGTGCAGCTGGTGGAGTCTGGGGGAGGCGTGGTCCAGCCTGGGAGGTC CCTGAGACTCTCCTGTGCAGCGTCTGGATTCACCTTCAGTGTGTATAATATG CACTGGGTCCGCCAGGCTCCAGGCAAGGGGCTGGAGTGGGTGGCAGTTATA GCGTATGATGGAAGTGCGAAATACTATGCAGACTCCGTGAAGGGCCGATTC ACCATCTCCAGAGACAATTCCAAGAACACGCTGTATCTGCAAATGAACAGC CTGAGAGCCGAGGACACGGCGGTGTACTACTGCGCCAGAGGCCGTCCTTG GTACAGCGAAACTGGTACCTCAGCTTTCGACATATGGGGTCAGGGTACAAT GGTCACCGTCTCCTCA(SEQ ID NO: 92) | QVQLVESGGGVVQPGRSLRLSCAASGFT FSVYNMHWVRQAPGKGLEWVAVIAYD GSAKYYADSVKGRFTISRDNSKNTLYLQ MNSLRAEDTAVYYCARGRPWYSETGTS AFDIWGQGTMVTVSS(SEQ ID NO: 107) |
| ADI-25651 | ADI-20112 | CAGGTGCAGCTGGTGGAGTCTGGGGGAGGCGTGGTCCAGCCTGGGAGGTC CCTGAGACTCTCCTGTGCAGCGTCTGGATTCAGCTCAGTAGCCGGAATATG CACTGGGTCCGCCAGGCTCCAGGCAAGGGGCTGGAGTGGGTGGCAGTTATA GCGTATGATGGAAGTCTTAAATACTATGCAGACTCCGTGAAGGGCCGATTCA CCATCTCCAGAGACAATTCCAAGAACACGCTGTATCTGCAAATGAACAGCC TGAGAGCCGAGGACACGGCGGTGTACTACTGCGCCAGAGGCCGTCCTTGGT ACAGCGAAACTGGTACCTCAGCTTTCGACATATGGGGTCAGGGTACAATGG TCACCGTCTCCTCA(SEQ ID NO: 93) | QVQLVESGGGVVQPGRSLRLSCAASGFT FSSRNMHWVRQAPGKGLEWVAVIAYD SLKYYADSVKGRFTISRDNSKNTLYLQM NSLRAEDTAVYYCARGRPWYSETGTSAF DIWGQGTMVTVSS(SEQ ID NO: 108) |
| ADI-25652 | ADI-20112 | CAGGTGCAGCTGGTGGAGTCTGGGGGAGGCGTGGTCCAGCCTGGGAGGTC CCTGAGACTCTCCTGTGCAGCGTCTGGATTCACCTTCGTGAGCTATAATATG CACTGGGTCCGCCAGGCTCCAGGCAAGGGGCTGGAGTGGGTGGCAGTTATA GCGTATGATGGAAGTGTTAAATACTATGCAGACTCCGTGAAGGGCCGATTCA CCATCTCCAGAGACAATTCCAAGAACACGCTGTATCTGCAAATGAACAGCC TGAGAGCCGAGGACACGGCGGTGTACTACTGCGCCAGAGGCCGTCCTTGGT ACAGCGAAACTGGTACCTCAGCTTTCGACATATGGGGTCAGGGTACAATGG TCACCGTCTCCTCA(SEQ ID NO: 94) | QVQLVESGGGVVQPGRSLRLSCAASGFT FVSYNMHWVRQAPGKGLEWVAVIAYD GSVKYYADSVKGRFTISRDNSKNTLYLQ MNSLRAEDTAVYYCARGRPWYSETGTS AFDIWGQGTMVTVSS(SEQ ID NO: 109) |
| ADI-25653 | ADI-20112 | CAGGTGCAGCTGGTGGAGTCTGGGGGAGGCGTGGTCCAGCCTGGGAGGTC CCTGAGACTCTCCTGTGCAGCGTCTGGATTCACCTTCGTGAGCTATAATATG CACTGGGTCCGCCAGGCTCCAGGCAAGGGGCTGGAGTGGGTGGCAGTTATA ATGTATGATGGAAGTGCTAAATACTATGCAGACTCCGTGAAGGGCCGATTCA CCATCTCCAGAGACAATTCCAAGAACACGCTGTATCTGCAAATGAACAGCC TGAGAGCCGAGGACACGGCGGTGTACTACTGCGCCAGAGGCCGTCCTTGGT ACAGCGAAACTGGTACCTCAGCTTTCGACATATGGGGTCAGGGTACAATGG TCACCGTCTCCTCA(SEQ ID NO: 95) | QVQLVESGGGVVQPGRSLRLSCAASGFT FVSYNMHWVRQAPGKGLEWVAVIMYD GSAKYYADSVKGRFTISRDNSKNTLYLQ MNSLRAEDTAVYYCARGRPWYSETGTS AFDIWGQGTMVTVSS(SEQ ID NO: 110) |
| ADI-25654 | ADI-20112 | CAGGTGCAGCTGGTGGAGTCTGGGGGAGGCGTGGTCCAGCCTGGGAGGTC CCTGAGACTCTCCTGTGCAGCGTCTGGATTCACCTTCAGGAGCTATGATATG CACTGGGTCCGCCAGGCTCCAGGCAAGGGGCTGGAGTGGGTGGCATATATA GCGTATGATGGAAGTAATAAATACTATGCAGACTCCGTGAAGGGCCGATTCA CCATCTCCAGAGACAATTCCAAGAACACGCTGTATCTGCAAATGAACAGCC TGAGAGCCGAGGACACGGCGGTGTACTACTGCGCCAGAGGCCGTCCTTGGT ACAGCGAAACTGGTACCTCAGCTTTCGACATATGGGGTCAGGGTACAATGG TCACCGTCTCCTCA(SEQ ID NO: 96) | QVQLVESGGGVVQPGRSLRLSCAASGFT FRSYDMHWVRQAPGKGLEWVAVIAYD GSNKYYADSVKGRFTISRDNSKNTLYLQ MNSLRAEDTAVYYCARGRPWYSETGTS AFDIWGQGTMVTVSS(SEQ ID NO: 111) |
| ADI-20078 | Parent antibody | CAGGTGCAGCTGCAGGAGTCGGGCCCAGGACTGGTGAAGCCTTCACAGAC CCTGTCCCTCACCTGTACTGTCTCTGGTGGCTCCATCAGCAGTGGTAGCTAC TACTGGAGCTGGATCCGCCAGCACCCAGGGAAGGGCCTGGAGTGGATTGG GTACATCTATTACAGTGGGAGCACCTACTACAACCCGTCCCTCAAGAGTCGA GTTACCATATCAGTAGACACGTCTAAGAACCAGTTCTCCCTGAAGCTGAGTT CTGTGACCGCCGCAGACACGGCGGTGTACTACTGCGCCAGAGATGTAGGAT ACCCACACTACTACGGAATGGACGTATGGGGCCAGGGAACAACTGTCACCG TCTCCTCA(SEQ ID NO: 97) | QVQLQESGPGLVKPSQTLSLTCTVSGGSI SSGSYYWSWIRQHPGKGLEWIGYIYYSG STYYNPSLKSRVTISVDTSKNQFSLKLSS VTAADTAVYYCARDVGYPHYYGMDVW GQGTTVTVSS(SEQ ID NO: 112) |
| ADI-23515 | ADI-20078 | CAGGTGCAGCTGCAGGAGTCGGGCCCAGGACTGGTGAAGCCTTCACAGAC CCTGTCCCTCACCTGTACTGTCTCTGGTGGCTCCATCCGTAGTGGTGCTTACT ACTGGAGCTGGATCCGCCAGCACCCAGGGAAGGGCCTGGAGTGGATTGGG TACATCTATTACGATGGGCAGACCTACTACAACCCGTCCCTCAAGAGTCGAG TTACCATATCAGTAGACACGTCTAAGAACCAGTTCTCCCTGAAGCTGAGTTC TGTGACCGCCGCAGACACGGCGGTGTACTACTGCGCCAGAGATGTAGGATA CCCACACTACTACGGAATGGACGTATGGGGCCAGGGAACAACTGTCACCGT CTCCTCA(SEQ ID NO: 98) | QVQLQESGPGLVKPSQTLSLTCTVSGGSI RSGAYYWSWIRQHPGKGLEWIGYIYYD GQTYYNPSLKSRVTISVDTSKNQFSLKLS SVTAADTAVYYCARDVGYPHYYGMDV WGQGTTVTVSS(SEQ ID NO: 113) |
| ADI-23518 | ADI-20078 | CAGGTGCAGCTGCAGGAGTCGGGCCCAGGACTGGTGAAGCCTTCACAGAC CCTGTCCCTCACCTGTACTGTCTCTGGTGGCTCCATCAGCAGTGGTGCTAGT TACTGGAGCTGGATCCGCCAGCACCCAGGGAAGGGCCTGGAGTGGATTGG GTACATCTATTACAGTGGGGAGACCTACTACAACCCGTCCCTCAAGAGTCGA GTTACCATATCAGTAGACACGTCTAAGAACCAGTTCTCCCTGAAGCTGAGTT CTGTGACCGCCGCAGACACGGCGGTGTACTACTGCGCCAGAGATGTAGGAT | QVQLQESGPGLVKPSQTLSLTCTVSGGSI SSGASYWSWIRQHPGKGLEWIGYIYYSG ETYYNPSLKSRVTISVDTSKNQFSLKLSS VTAADTAVYYCARDVGYPHYYGMDVW GQGTTVTVSS(SEQ ID NO: 114) |

TABLE 3-continued

DNA and amino acid sequences of heavy chain variable domain (VH)(or heavy chain variable region (HCVR)) of the exemplary antibody of the present invention

| Antibody Name | optimized linkage | VH DNA sequence | VH amino acid sequence |
|---|---|---|---|
| | | ACCCACACTACTACGGAATGGACGTATGGGGCCAGGGAACAACTGTCACCG TCTCCTCA(SEQ ID NO: 99) | |
| ADI-23519 | ADI-20078 | CAGGTGCAGCTGCAGGAGTCGGGCCCAGGACTGGTGAAGCCTTCACAGAC CCTGTCCCTCACCTGTACTGTCTCTGGTGGCTCCATCAGCAGTGGTTCGTCC TACTGGAGCTGGATCCGCCAGCACCCAGGGAAGGGCCTGGAGTGGATTGG GTACATCTATATGAGTGGGGAGACCTACTACAACCCGTCCCTCAAGAGTCGA GTTACCATATCAGTAGACACGTCTAAGAACCAGTTCTCCCTGAAGCTGAGTT CTGTGACCGCCGCAGACACGGCGGTGTACTACTGCGCCAGAGATGTAGGAT ACCCACACTACTACGGAATGGACGTATGGGGCCAGGGAACAACTGTCACCG TCTCCTCA(SEQ ID NO: 100) | QVQLQESGPGLVKPSQTLSLTCTVSGGSI SSGSSYWSWIRQHPGKGLEWIGYIYMSG ETYYNPSLKSRVTISVDTSKNQFSLKLS VTAADTAVYYCARDVGYPHYYGMDVW GQGTTVTVSS(SEQ ID NO: 115) |
| ADI-20048 | Parent antibody | CAGGTGCAGCTGCAGGAGTCGGGCCCAGGACTGGTGAAGCCTTCGGAGAC CCTGTCCCTCACCTGCACTGTCTCTGGTGGCTCCATCAGTAGTAGTTACTACTGG AGCTGGATCCGGCAGCCCCCAGGGAAGGGACTGGAGTGGATTGGGTATATC TATAGTAGTGGGAGCACCAACTACAACCCCTCCCTCAAGAGTCGAGTCACC ATATCAGTAGACACGTCCAAGAACCAGTTCTCCCTGAAGCTGAGTTCTGTG ACCGCCGCAGACACGGCGGTGTACTACTGCGCCAGAGATGCTCCTGGCGGA TCCTCCTACCAGGACTACATGGACGTATGGGGCAAGGGTACAACTGTC ACCGTCTCCTCA(SEQ ID NO: 101) | QVQLQESGPGLVKPSETLSLTCTVSGGSI SSYYWSWIRQPPGKGLEWIGYIYSSGST NYNPSLKSRVTISVDTSKNQFSLKLSSVT AADTAVYYCARDAPGSSYQDYYMDV WGKGTTVTVSS(SEQ ID NO: 116) |
| ADI-20096 | Parent antibody | GAGGTGCAGCTGGTGGAGTCTGGGGGAGGCCTGGTCAAGCCTGGGGGGTC CCTGAGACTCTCCTGTGCAGCCTCTGGATTCACCTTCAGTAGCTATAGCATG AACTGGGTCCGCCAGGCTCCAGGGAAGGGGCTGGAGTGGGTCTCATCCATT AGTAGTAGTAATTACATATACTACGCAGACTCAGTGAAGGGCCGATTCA CCATCTCCAGAGACAACGCCAAGAACTCACTGTATCTGCAAATGAACAGCC TGAGAGCCGAGGACACGGCGGTGTACTACTGCGCCAGAGGGGCCCCTCTG GGATACAGCTGGGAGTACTTCGACCTATGGGGAGAGGTACCTTGGTCACC GTCTCCTCA(SEQ ID NO: 102) | EVQLVESGGGLVKPGGSLRLSCAASGFT FSSYSMNWVRQAPGKGLEWVSSISSSSN YIYYADSVKGRFTISRDNAKNSLYLQMN SLRAEDTAVYYCARGAPLGYSWEYFDL WGRGTLVTVSS(SEQ ID NO: 117) |
| ADI-20051 | Parent antibody | CAAGTACAATTACAACAGTGGGGAGCTGGTTTATTAAAGCCTTCAGAAACT TTAAGTTTGACCTGTGCTGTTTACGGTGGATCATTTTCTGGTTATTACTGGAG TTGGATTCGTCAACCACCAGGCAAAGGATTGGAGTGGATCGGTGAGATAGA CCATTCAGGCTCCACTAACTACAATCCAAGTTTAAAATCCAGGGTTACTATC TCCGTAGACACGTCCAAGAACCAGTTCTCCCTGAAGCTGAGTTCTGTGACC GCCGCAGACACGGCGGTGTACTACTGCGCCAGAGATGGTGGCGGAGGATAC GCTTCCCCCTTCGACTATTGGGGACAGGGTACATTGGTCACCGTCTCCTCA (SEQ ID NO: 103) | QVQLQQWGAGLLKPSETLSLTCAVYGG SFSGYYWSWIRQPPGKGLEWIGEIDHSG STNYNPSLKSRVTISVDTSKNQFSLKLSS VTAADTAVYYCARDGGGGYASPFDYWG QGTLVTVSS(SEQ ID NO: 118) |
| ADI-20065 | Parent antibody | CAGCTGCAGCTGCAGGAGTCGGGCCCAGGACTGGTGAAGCCTTCGGAGAC CCTGTCCCTCACCTGCACTGTCTCTGGTGGCTCCATCAGCAGTAGTAGTTAC TACTGGGGCTGGATCCGCCAGCCCCCAGGGAAGGGGCTGGAGTGGATTGG GAGTATCTATTATAGTGGGAGCACCTACTACAACCCGTCCCTCAAGAGTCGA GTCACCATATCCGTAGACACGTCCAAGAACCAGTTCTCCCTGAAGCTGAGT TCTGTGACCGCCGCAGACACGGCGGTGTACTACTGCGCGCAGAGATCCAGGA TACAGCGCTTCCCCCAATTGGTTTGATCCATGGGGACAGGGTACATTGGTCA CCGTCTCCTCA(SEQ ID NO: 104) | QLQLQESGPGLVKPSETLSLTCTVSGGSI SSSSYYWGWIRQPPGKGLEWIGSIYYSG STYYNPSLKSRVTISVDTSKNQFSLKLSS VTAADTAVYYCARDPGYSASPNWFDPW GQGTLVTVSS(SEQ ID NO: 119) |
| ADI-20066 | Parent antibody | CAGCTGCAGCTGCAGGAGTCGGGCCCAGGACTGGTGAAGCCTTCGGAGAC CCTGTCCCTCACCTGCACTGTCTCTGGTGGCTCCATCAGCAGTAGTAGTTAC TACTGGGGCTGGATCCGCCAGCCCCCAGGGAAGGGGCTGGAGTGGATTGG GAGTATCTATTATAGTGGGAGCACCTACTACAACCCGTCCCTCAAGAGTCGA GTCACCATATCCGTAGACACGTCCAAGAACCAGTTCTCCCTGAAGCTGAGT TCTGTGACCGCCGCAGACACGGCGGTGTACTACTGCGCCAGAGATCCAGGA TACAGCGCTTCCCCCAATTGGTTTGATCCATGGGGACAGGGTACATTGGTCA CCGTCTCCTCA(SEQ ID NO: 104) | QLQLQESGPGLVKPSETLSLTCTVSGGSI SSSSYYWGWIRQPPGKGLEWIGSIYYSG STYYNPSLKSRVTISVDTSKNQFSLKLSS VTAADTAVYYCARDPGYSASPNWFDPW GQGTLVTVSS(SEQ ID NO: 119) |
| ADI-20118 | Parent antibody | CAGGTTCAGCTGGTGCAGTCTGGAGCTGAGGTGAAGAAGCCTGGGGCCTC AGTGAAGGTCTCCTGCAAGGCTTCTGGTTACACCTTTACCAGCTATGCCATC AGCTGGGTGCGACAGGCCCCTGGACAAGGGCTTGAGTGGATGGGATGGAT CAGCGCTTACAATGGTAACACAAACTATGCACAGAAGCTCCAGGGCAGAGT CACCATGACCACAGACACATCCACGAGCACAGCCTACATGGAGCTGAGGAG CCTGAGATCTGACGACACGGCGGTGTACTACTGCGCCAGATCAGGAGGCGG CAGCGGACCCAATTGGTTTGATCCATGGGGACAGGGTACATTGGTCACCGT CTCCTCA(SEQ ID NO: 105) | QVQLVQSGAEVKKPGASVKVSCKASGY TFTSYAISWVRQAPGQGLEWMGWISAY NGNTNYAQKLQGRVTMTTDTSTSTAYM ELRSLRSDDTAVYYCARSGGGSGPNWF DPWGQGTLVTVSS(SEQ ID NO: 120) |

TABLE 4

DNA and amino acid sequences of light chain variable domain (VL)(or light chain variable region (LCVR)) of the exemplary of the present invention

| Antibody Name | optimized linkage | VL DNA sequence | VL amino acid sequence |
|---|---|---|---|
| ADI-20112 | Parent antibody | GACATCCAGATGACCCAGTCTCCATCCTCCCTGTCTGCATCTGTAG GAGACAGAGTCACCATCACTTGCCAGGCGAGTCAGGACATTAGCA ACTATTTAAATTGGTATCAGCAGAAACCAGGGAAAGCCCCTAAGCT CCTGATCTACGATGCATCCAATTTGGAAACAGGGGTCCCATCAAGG TTCAGTGGAAGTGGATCTGGGACAGATTTTACTTTCACCATCAGCA GCCTGCAGCCTGAAGATATTGCAACATATTACTGTCAGCAGTCCGA TCACTACCCTACTTTTGGCGGAGGGACCAAGGTTGAGATCAAA (SEQ ID NO: 121) | DIQMTQSPSSLSASVGDRVTITCQASQD ISNYLNWYQQKPGKAPKLLIYDASNLE TGVPSRFSGSGSGTDFTFTISSLQPEDIA TYYCQQSDHYPTFGGGTKVEIK(SEQ ID NO: 130) |
| ADI-20113 | Parent antibody | GAAATAGTGATGACGCAGTCTCCAGCCACCCTGTCTGTGTCTCCAG GGGAAAGAGCCACCCTCTCCTGCAGGGCCAGTCAGAGTGTTAGCA GCAACTTAGCCTGGTACCAGCAGAAACCTGGCCAGGCTCCCAGGC TCCTCATCTATAGCGCATCCACCAGGGCCACTGGTATCCCAGCCAG GTTCAGTGGCAGTGGGTCTGGGACAGAGTTCACTCTCACCATCAG CAGCCTGCAGTCTGAAGATTTTGCAGTTTATTACTGTCAGCAGCAC AATGTCTACCCTCCTTACACTTTTGGCGGAGGGACCAAGGTTGAGA TCAAA(SEQ ID NO: 122) | EIVMTQSPATLSVSPGERATLSCRASQS VSSNLAWYQQKPGQAPRLLIYSASTRA TGIPARFSGSGSGTEFTLTISSLQSEDFAV YYCQQHNVYPPYTFGGGTKVEIK(SEQ ID NO: 131) |
| ADI-25650 | ADI-20112 | GACATCCAGATGACCCAGTCTCCATCCTCCCTGTCTGCATCTGTAG GAGACAGAGTCACCATCACTTGCCAGGCGAGTCAGGACATTAGCA ACTATTTAAATTGGTATCAGCAGAAACCAGGGAAAGCCCCTAAGCT CCTGATCTACGATGCATCCAATTTGGAAACAGGGGTCCCATCAAGG TTCAGTGGAAGTGGATCTGGGACAGATTTTACTTTCACCATCAGCA GCCTGCAGCCTGAAGATATTGCAACATATTACTGTCAGCAGTCCGA TCACTACCCTACTTTTGGCGGAGGGACCAAGGTTGAGATCAAA (SEQ ID NO: 121) | DIQMTQSPSSLSASVGDRVTITCQASQD ISNYLNWYQQKPGKAPKLLIYDASNLE TGVPSRFSGSGSGTDFTFTISSLQPEDIA TYYCQQSDHYPTFGGGTKVEIK(SEQ ID NO: 130) |
| ADI-25651 | ADI-20112 | GACATCCAGATGACCCAGTCTCCATCCTCCCTGTCTGCATCTGTAG GAGACAGAGTCACCATCACTTGCCAGGCGAGTCAGGACATTAGCA ACTATTTAAATTGGTATCAGCAGAAACCAGGGAAAGCCCCTAAGCT CCTGATCTACGATGCATCCAATTTGGAAACAGGGGTCCCATCAAGG TTCAGTGGAAGTGGATCTGGGACAGATTTTACTTTCACCATCAGCA GCCTGCAGCCTGAAGATATTGCAACATATTACTGTCAGCAGTCCGA TCACTACCCTACTTTTGGCGGAGGGACCAAGGTTGAGATCAAA (SEQ ID NO: 121) | DIQMTQSPSSLSASVGDRVTITCQASQD ISNYLNWYQQKPGKAPKLLIYDASNLE TGVPSRFSGSGSGTDFTFTISSLQPEDIA TYYCQQSDHYPTFGGGTKVEIK(SEQ ID NO: 130) |
| ADI-25652 | ADI-20112 | GACATCCAGATGACCCAGTCTCCATCCTCCCTGTCTGCATCTGTAG GAGACAGAGTCACCATCACTTGCCAGGCGAGTCAGGACATTAGCA ACTATTTAAATTGGTATCAGCAGAAACCAGGGAAAGCCCCTAAGCT CCTGATCTACGATGCATCCAATTTGGAAACAGGGGTCCCATCAAGG TTCAGTGGAAGTGGATCTGGGACAGATTTTACTTTCACCATCAGCA GCCTGCAGCCTGAAGATATTGCAACATATTACTGTCAGCAGTCCGA TCACTACCCTACTTTTGGCGGAGGGACCAAGGTTGAGATCAAA (SEQ ID NO: 121) | DIQMTQSPSSLSASVGDRVTITCQASQD ISNYLNWYQQKPGKAPKLLIYDASNLE TGVPSRFSGSGSGTDFTFTISSLQPEDIA TYYCQQSDHYPTFGGGTKVEIK(SEQ ID NO: 130) |
| ADI-25653 | ADI-20112 | GACATCCAGATGACCCAGTCTCCATCCTCCCTGTCTGCATCTGTAG GAGACAGAGTCACCATCACTTGCCAGGCGAGTCAGGACATTAGCA ACTATTTAAATTGGTATCAGCAGAAACCAGGGAAAGCCCCTAAGCT CCTGATCTACGATGCATCCAATTTGGAAACAGGGGTCCCATCAAGG TTCAGTGGAAGTGGATCTGGGACAGATTTTACTTTCACCATCAGCA GCCTGCAGCCTGAAGATATTGCAACATATTACTGTCAGCAGTCCGA TCACTACCCTACTTTTGGCGGAGGGACCAAGGTTGAGATCAAA (SEQ ID NO: 121) | DIQMTQSPSSLSASVGDRVTITCQASQD ISNYLNWYQQKPGKAPKLLIYDASNLE TGVPSRFSGSGSGTDFTFTISSLQPEDIA TYYCQQSDHYPTFGGGTKVEIK(SEQ ID NO: 130) |
| ADI-25654 | ADI-20112 | GACATCCAGATGACCCAGTCTCCATCCTCCCTGTCTGCATCTGTAG GAGACAGAGTCACCATCACTTGCCAGGCGAGTCAGGACATTAGCA ACTATTTAAATTGGTATCAGCAGAAACCAGGGAAAGCCCCTAAGCT CCTGATCTACGATGCATCCAATTTGGAAACAGGGGTCCCATCAAGG TTCAGTGGAAGTGGATCTGGGACAGATTTTACTTTCACCATCAGCA GCCTGCAGCCTGAAGATATTGCAACATATTACTGTCAGCAGTCCGA TCACTACCCTACTTTTGGCGGAGGGACCAAGGTTGAGATCAAA (SEQ ID NO: 121) | DIQMTQSPSSLSASVGDRVTITCQASQD ISNYLNWYQQKPGKAPKLLIYDASNLE TGVPSRFSGSGSGTDFTFTISSLQPEDIA TYYCQQSDHYPTFGGGTKVEIK(SEQ ID NO: 130) |
| ADI-20078 | Parent antibody | GAAATTGTGTTGACGCAGTCTCCAGGCACCCTGTCTTTGTCTCCAG GGGAAAGAGCCACCCTCTCCTGCAGGGCCAGTCAGAGTGTTAGCA GCAGCTACTTAGCCTGGTACCAGCAGAAACCTGGCCAGGCTCCCA GGCTCCTCATCTATGGTGCATCCAGCAGGGCCACTGGCATCCCAGA CAGGTTCAGTGGCAGTGGGTCTGGGACAGACTTCACTCTCACCAT CAGCAGACTGGAGCCTGAAGATTTTGCAGTGTATTACTGTCAGCAG TCCGAACGAAGCCCTTTCACTTTTGGCGGAGGGACCAAGGTTGAG ATCAAA(SEQ ID NO: 123) | EIVLTQSPGTLSLSPGERATLSCRASQSV SSSYLAWYQQKPGQAPRLLIYGASSRA TGIPDRFSGSGSGTDFTLTISRLEPEDFA VYYCQQSERSPFTFGGGTKVEIK(SEQ ID NO: 132) |

TABLE 4-continued

DNA and amino acid sequences of light chain variable domain (VL)(or light chain variable region (LCVR)) of the exemplary of the present invention

| Antibody Name | optimized linkage | VL DNA sequence | VL amino acid sequence |
|---|---|---|---|
| ADI-23515 | ADI-20078 | GAAATTGTGTTGACGCAGTCTCCAGGCACCCTGTCTTTGTCTCCAG GGGAAAGAGCCACCCTCTCCTGCAGGGCCAGTCAGAGTGTTAGCA GCAGCTACTTAGCCTGGTACCAGCAGAAAACCTGGCCAGGCTCCCA GGCTCCTCATCTATGGTGCATCCAGCAGGGCCACTGGCATCCCAGA CAGGTTCAGTGGCAGTGGGTCTGGGACAGACTTCACTCTCACCAT CAGCAGACTGGAGCCTGAAGATTTTGCAGTGTATTACTGTCAGCAG TCCGAACGAAGCCCTTTCACTTTTGGCGGAGGGACCAAGGTTGAG ATCAAA(SEQ ID NO: 123) | EIVLTQSPGTLSLSPGERATLSCRASQSV SSSYLAWYQQKPGQAPRLLIYGASSRA TGIPDRFSGSGSGTDFTLTISRLEPEDFA VYYCQQSERSPFTFGGGTKVEIK(SEQ ID NO: 132) |
| ADI-23518 | ADI-20078 | GAAATTGTGTTGACGCAGTCTCCAGGCACCCTGTCTTTGTCTCCAG GGGAAAGAGCCACCCTCTCCTGCAGGGCCAGTCAGAGTGTTAGCA GCAGCTACTTAGCCTGGTACCAGCAGAAAACCTGGCCAGGCTCCCA GGCTCCTCATCTATGGTGCATCCAGCAGGGCCACTGGCATCCCAGA CAGGTTCAGTGGCAGTGGGTCTGGGACAGACTTCACTCTCACCAT CAGCAGACTGGAGCCTGAAGATTTTGCAGTGTATTACTGTCAGCAG TCCGAACGAAGCCCTTTCACTTTTGGCGGAGGGACCAAGGTTGAG ATCAAA(SEQ ID NO: 123) | EIVLTQSPGTLSLSPGERATLSCRASQSV SSSYLAWYQQKPGQAPRLLIYGASSRA TGIPDRFSGSGSGTDFTLTISRLEPEDFA VYYCQQSERSPFTFGGGTKVEIK(SEQ ID NO: 132) |
| ADI-23519 | ADI-20078 | GAAATTGTGTTGACGCAGTCTCCAGGCACCCTGTCTTTGTCTCCAG GGGAAAGAGCCACCCTCTCCTGCAGGGCCAGTCAGAGTGTTAGCA GCAGCTACTTAGCCTGGTACCAGCAGAAAACCTGGCCAGGCTCCCA GGCTCCTCATCTATGGTGCATCCAGCAGGGCCACTGGCATCCCAGA CAGGTTCAGTGGCAGTGGGTCTGGGACAGACTTCACTCTCACCAT CAGCAGACTGGAGCCTGAAGATTTTGCAGTGTATTACTGTCAGCAG TCCGAACGAAGCCCTTTCACTTTTGGCGGAGGGACCAAGGTTGAG ATCAAA(SEQ ID NO: 123) | EIVLTQSPGTLSLSPGERATLSCRASQSV SSSYLAWYQQKPGQAPRLLIYGASSRA TGIPDRFSGSGSGTDFTLTISRLEPEDFA VYYCQQSERSPFTFGGGTKVEIK(SEQ ID NO: 132) |
| ADI-20048 | Parent antibody | GAAATTGTGTTGACACAGTCTCCAGCCACCCTGTCTTTGTCTCCAG GGGAAAGAGCCACCCTCTCCTGCAGGGCCAGTCAGAGTGTTAGCA GCTACTTAGCCTGGTTCCAACAGAAACCTGGCCAGGCTCCCAGGC TCCTCATCTATGATGCATCCAACAGGGCCACTGGCATCCCAGCCAG GTTCAGTGGCAGTGGGTCTGGGACAGACTTCACTCTCACCATCAG CAGCCTAGAGCCTGAAGATTTTGCAGTTTATTACTGTCAGCAGGCA TTCTCCATGCCTCCTACTTTTGGCGGAGGGACCAAGGTTGAGATCA AA(SEQ ID NO: 124) | EIVLTQSPATLSLSPGERATLSCRASQSV SSYLAWYQQKPGQAPRLLIYDASNRAT GIPARFSGSGSGTDFTLTISSLEPEDFAV YYCQQAFSMPPTFGGGTKVEIK(SEQ ID NO: 133) |
| ADI-20096 | Parent antibody | GACATCCAGATGACCCAGTCTCCTTCCACCCTGTCTGCATCTGTAG GAGACAGAGTCACCATCACTTGCCGGGCCAGTCAGAGTATTAGTA GCTGGTTAGCCTGGTATCAGCAGAAACCAGGGAAAGCCCCTAAGC TCCTGATCTATGATGCCTCCAGTTTGGAAAGTGGGGTCCCATCAAG GTTCAGCGGCAGTGGATCTGGGACAGAATTCACTCTCACCATCAGC AGCCTGCAGCCTGATGATTTTGCAACTTATTACTGCCAGCAGTTCC AAAGTTACTCTTACACTTTTGGCGGAGGGACCAAGGTTGAGATCA AA(SEQ ID NO: 125) | DIQMTQSPSTLSASVGDRVTITCRASQS ISSWLAWYQQKPGKAPKLLIYDASSLE SGVPSRFSGSGSGTEFTLTISSLQPDDFA TYYCQQFQSYSYTFGGGTKVEIK(SEQ ID NO: 134) |
| ADI-20051 | Parent antibody | GAAATAGTGATGACGCAGTCTCCAGCCACCCTGTCTGTGTCTCCAG GGGAAAGAGCCACCCTCTCCTGCAGGGCCAGTCAGAGTGTTAGCA GCAACTTAGCCTGGTACCAGCAGAAACCTGGCCAGGCTCCCAGGC TCCTCATCTATGGTGCATCCACCAGGGCCACTGGTATCCCAGCCAG GTTCAGTGGCAGTGGGTCTGGGACAGAGTTCACTCTCACCATCAG CAGCCTGCAGTCTGAAGATTTTGCAGTTTATTACTGTCAGCAGTAC CACGCCTGGCCTCCTACTTTTGGCGGAGGGACCAAGGTTGAGATC AAA(SEQ ID NO: 126) | EIVMTQSPATLSVSPGERATLSCRASQS VSSNLAWYQQKPGQAPRLLIYGASTRA TGIPARFSGSGSGTEFTLTISSLQSEDFAV YYCQQYHAWPPTFGGGTKVEIK(SEQ ID NO: 135) |
| ADI-20065 | Parent antibody | GAAATTGTGTTGACGCAGTCTCCAGGCACCCTGTCTTTGTCTCCAG GGGAAAGAGCCACCCTCTCCTGCAGGGCCAGTCAGAGTGTTAGCA GCAGCTACTTAGCCTGGTACCAGCAGAAAACCTGGCCAGGCTCCCA GGCTCCTCATCTATGGTGCATCCAGCAGGGCCACTGGCATCCCAGA CAGGTTCAGTGGCAGTGGGTCTGGGACAGACTTCACTCTCACCAT CAGCAGACTGGAGCCTGAAGATTTTGCAGTGTATTACTGTCAGCAG TTCGACAGCAGTCCTACTTTTGGCGGAGGGACCAAGGTTGAGATC AAA(SEQ ID NO: 127) | EIVLTQSPGTLSLSPGERATLSCRASQSV SSSYLAWYQQKPGQAPRLLIYGASSRA TGIPDRFSGSGSGTDFTLTISRLEPEDFA VYYCQQFDSSPTFGGGTKVEIK(SEQ ID NO: 136) |
| ADI-20066 | Parent antibody | GAAATTGTGTTGACGCAGTCTCCAGGCACCCTGTCTTTGTCTCCAG GGGAAAGAGCCACCCTCTCCTGCAGGGCCAGTCAGAGTGTTAGCA GCAGCTTCTTAGCCTGGTACCAGCAGAAAACCTGGCCAGGCTCCCA GGCTCCTCATCTATGGTGCATCCAGCAGGGCCACTGGCATCCCAGA CAGGTTCAGTGGCAGTGGGTCTGGGACAGACTTCACTCTCACCAT CAGCAGACTGGAGCCTGAAGATTTTGCAGTGTATTACTGTCAGCAG TACGACGTCTTCCCTATCACTTTTGGCGGAGGGACCAAGGTTGAGA TCAAA(SEQ ID NO: 128) | EIVLTQSPGTLSLSPGERATLSCRASQSV SSSFLAWYQQKPGQAPRLLIYGASSRA TGIPDRFSGSGSGTDFTLTISRLEPEDFA VYYCQQYDVFPITFGGGTKVEIK(SEQ ID NO: 137) |
| ADI-20118 | Parent antibody | GACATCCAGATGACCCAGTCTCCATCCTCCCTGTCTGCATCTGTAG GAGACAGAGTCACCATCACTTGCCAGGCGAGTCAGGACATTAGCA ACTATTTAAATTGGTATCAGCAGAAACCAGGGAAAGCCCCTAAGCT CCTGATCTACGATGCATCCAATTTGGAAACAGGGGTCCCATCAAGG TTCAGTGGAAGTGGATCTGGGACAGATTTTACTTTCACCATCAGCA | DIQMTQSPSSLSASVGDRVTITCQASQD ISNYLNWYQQKPGKAPKLLIYDASNLE TGVPSRFSGSGSGTDFTFTISSLQPEDIA TYYCQQPATLPWTFGGGTKVEIK(SEQ ID NO: 138) |

TABLE 4-continued

DNA and amino acid sequences of light chain variable domain (VL)(or light chain variable region (LCVR)) of the exemplary of the present invention

| Antibody Name | optimized linkage | VL DNA sequence | VL amino acid sequence |
|---|---|---|---|
| | | GCCTGCAGCCTGAAGATATTGCAACATATTACTGTCAGCAGCCCGC CACCCTACCTTGGACTTTTGGCGGAGGGACCAAGGTTGAGATCAA A(SEQ ID NO: 129) | |

TABLE 5

Sequences of heavy chain and light chain of the exemplary antibody of the present invention

| Antibody Name | IgG Format | Amino acid sequence of heavy chain | Amino acid sequence of light chain |
|---|---|---|---|
| ADI-20112 | IgG1 format; ADI-20112 | QVQLVESGGGVVQPGRSLRLSCAASGFTFSSYGMHWVRQAPGKGL EWVAVISYDGSNKYYADSVKGRFTISRDNSKNTLYLQMNSLRAEDTA VYYCARGRPWYSETGTSAFDIWGQGTMVTVSSASTKGPSVFPLAPS SKSTSGGTAALGCLVKDYFPEPVTVSWNSGALTSGVHTFPAVLQSSG LYSLSSVVTVPSSSLGTQTYICNVNHKPSNTKVDKKAEPKSCDKTHT CPPCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSRDELTKNQVSL TCLVKGFYPSDIAVEWESNGQPENNYKTTPPVLDSDGSFFLYSKLTV DKSRWQQGNVFSCSVMHEALHNHYTQKSLSLSPGK(SEQ ID NO: 189) | DIQMTQSPSSLSASVGDRVTITCQASQDISNYLNW YQQKPGKAPKLLIYDASNLETGVPSRFSGSGSGTD FTFTISSLQPEDIATYYCQQSDHYPTFGGGTKVEIK RTVAAPSVFIFPPSDEQLKSGTASVVCLLNNFYPRE AKVQWKVDNALQSGNSQESVTEQDSKDSTYSLS STLTLSKADYEKHKVYACEVTHQGLSSPVTKSFN RGEC(SEQ ID NO: 168) |
| ADI-20112 | IgG2 format; ADI-20112 | QVQLVESGGGVVQPGRSLRLSCAASGFTFSSYGMHWVRQAPGKGL EWVAVISYDGSNKYYADSVKGRFTISRDNSKNTLYLQMNSLRAEDTA VYYCARGRPWYSETGTSAFDIWGQGTMVTVSSASTKGPSVFPLAPC SRSTSESTAALGCLVKDYFPEPVTVSWNSGALTSGVHTFPAVLQSSGL YSLSSVVTVPSSNFGTQTYTCNVDHKPSNTKVDKTVERKCCVECPPC PAPPVAGPSVFLFPPKPKDTLMISRTPEVTCVVVDVSHEDPEVQFNW YVDGVEVHNAKTKPREEQFNSTFRVVSVLTVVHQDWLNGKEYKCK VSNKGLPAPIEKTISKTKGQPREPQVYTLPPSREEMTKNQVSLTCLVK GFYPSDIAVEWESNGQPENNYKTTPPMLDSDGSFFLYSKLTVDKSRW QQGNVFSCSVMHEALHNHYTQKSLSLSPG(SEQ ID NO: 139) | |
| ADI-25650 | IgG1 format; ADI-25650 | QVQLVESGGGVVQPGRSLRLSCAASGFTFSVYNMHWVRQAPGKGL EWVAVIAYDGSAKYYADSVKGRFTISRDNSKNTLYLQMNSLRAEDTA VYYCARGRPWYSETGTSAFDIWGQGTMVTVSSASTKGPSVFPLAPS SKSTSGGTAALGCLVKDYFPEPVTVSWNSGALTSGVHTFPAVLQSSG LYSLSSVVTVPSSSLGTQTYICNVNHKPSNTKVDKKAEPKSCDKTHT CPPCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSRDELTKNQVSL TCLVKGFYPSDIAVEWESNGQPENNYKTTPPVLDSDGSFFLYSKLTV DKSRWQQGNVFSCSVMHEALHNHYTQKSLSLSPGK(SEQ ID NO: 140) | |
| | IgG2 format; ADI-25650 | QVQLVESGGGVVQPGRSLRLSCAASGFTFSVYNMHWVRQAPGKGL EWVAVIAYDGSAKYYADSVKGRFTISRDNSKNTLYLQMNSLRAEDTA VYYCARGRPWYSETGTSAFDIWGQGTMVTVSSASTKGPSVFPLAPC SRSTSESTAALGCLVKDYFPEPVTVSWNSGALTSGVHTFPAVLQSSGL YSLSSVVTVPSSNFGTQTYTCNVDHKPSNTKVDKTVERKCCVECPPC PAPPVAGPSVFLFPPKPKDTLMISRTPEVTCVVVDVSHEDPEVQFNW YVDGVEVHNAKTKPREEQFNSTFRVVSVLTVVHQDWLNGKEYKCK VSNKGLPAPIEKTISKTKGQPREPQVYTLPPSREEMTKNQVSLTCLVK GFYPSDIAVEWESNGQPENNYKTTPPMLDSDGSFFLYSKLTVDKSRW QQGNVFSCSVMHEALHNHYTQKSLSLSPG(SEQ ID NO: 141) | |
| ADI-25651 | IgG1 format; ADI-25651 | QVQLVESGGGVVQPGRSLRLSCAASGFTFSSRNMHWVRQAPGKGL EWVAVIAYDGSLKYYADSVKGRFTISRDNSKNTLYLQMNSLRAEDTA VYYCARGRPWYSETGTSAFDIWGQGTMVTVSSASTKGPSVFPLAPS SKSTSGGTAALGCLVKDYFPEPVTVSWNSGALTSGVHTFPAVLQSSG LYSLSSVVTVPSSSLGTQTYICNVNHKPSNTKVDKKAEPKSCDKTHT CPPCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSRDELTKNQVSL TCLVKGFYPSDIAVEWESNGQPENNYKTTPPVLDSDGSFFLYSKLTV DKSRWQQGNVFSCSVMHEALHNHYTQKSLSLSPGK(SEQ ID NO: 142) | |

TABLE 5-continued

Sequences of heavy chain and light chain of the exemplary antibody of the present invention

| Antibody Name | IgG Format | Amino acid sequence of heavy chain | Amino acid sequence of light chain |
|---|---|---|---|
| | IgG2 format; ADI-25651 | QVQLVESGGGVVQPGRSLRLSCAASGFTFSSRNMHWVRQAPGKGL EWVAVIAYDGSLKYYADSVKGRFTISRDNSKNTLYLQMNSLRAEDTA VYYCARGRPWYSETGTSAFDIWGQGTMVTVSSASTKGPSVFPLAPC SRSTSESTAALGCLVKDYFPEPVTVSWNSGALTSGVHTFPAVLQSSGL YSLSSVVTVPSSNFGTQTYTCNVDHKPSNTKVDKTVERKCCVECPPC PAPPVAGPSVFLFPPKPKDTLMISRTPEVTCVVVDVSHEDPEVQFNW YVDGVEVHNAKTKPREEQFNSTFRVVSVLTVVHQDWLNGKEYKCK VSNKGLPAPIEKTISKTKGQPREPQVYTLPPSREEMTKNQVSLTCLVK GFYPSDIAVEWESNGQPENNYKTTPPMLDSDGSFFLYSKLTVDKSRW QQGNVFSCSVMHEALHNHYTQKSLSLSPG(SEQ ID NO: 143) | |
| ADI-25652 | IgG1 format; ADI-25652 | QVQLVESGGGVVQPGRSLRLSCAASGFTFVSYNMHWVRQAPGKGL EWVAVIAYDGSVKYYADSVKGRFTISRDNSKNTLYLQMNSLRAEDTA VYYCARGRPWYSETGTSAFDIWGQGTMVTVSSASTKGPSVFPLAPS SKSTSGGTAALGCLVKDYFPEPVTVSWNSGALTSGVHTFPAVLQSS GLYSLSSVVTVPSSSLGTQTYICNVNHKPSNTKVDKKAEPKSCDKTHT CPPCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSRDELTKNQVSL TCLVKGFYPSDIAVEWESNGQPENNYKTTPPVLDSDGSFFLYSKLTV DKSRWQQGNVFSCSVMHEALHNHYTQKSLSLSPGK(SEQ ID NO: 144) | |
| | IgG2 format; ADI-25652 | QVQLVESGGGVVQPGRSLRLSCAASGFTFVSYNMHWVRQAPGKGL EWVAVIAYDGSVKYYADSVKGRFTISRDNSKNTLYLQMNSLRAEDTA VYYCARGRPWYSETGTSAFDIWGQGTMVTVSSASTKGPSVFPLAPC SRSTSESTAALGCLVKDYFPEPVTVSWNSGALTSGVHTFPAVLQSSGL YSLSSVVTVPSSNFGTQTYTCNVDHKPSNTKVDKTVERKCCVECPPC PAPPVAGPSVFLFPPKPKDTLMISRTPEVTCVVVDVSHEDPEVQFNW YVDGVEVHNAKTKPREEQFNSTFRVVSVLTVVHQDWLNGKEYKCK VSNKGLPAPIEKTISKTKGQPREPQVYTLPPSREEMTKNQVSLTCLVK GFYPSDIAVEWESNGQPENNYKTTPPMLDSDGSFFLYSKLTVDKSRW QQGNVFSCSVMHEALHNHYTQKSLSLSPG(SEQ ID NO: 145) | |
| ADI-25653 | IgG1 format; ADI-25653 | QVQLVESGGGVVQPGRSLRLSCAASGFTFVSYNMHWVRQAPGKGL EWVAVIMYDGSAKYYADSVKGRFTISRDNSKNTLYLQMNSLRAEDT AVYYCARGRPWYSETGTSAFDIWGQGTMVTVSSASTKGPSVFPLAP SSKSTSGGTAALGCLVKDYFPEPVTVSWNSGALTSGVHTFPAVLQSS GLYSLSSVVTVPSSSLGTQTYICNVNHKPSNTKVDKKAEPKSCDKTH TCPPCPAPELLGGPSVFLFPPKPKDTLMISRTPEVTCVVVDVSHEDPE VKFNWYVDGVEVHNAKTKPREEQYNSTYRVVSVLTVLHQDWLNG KEYKCKVSNKALPAPIEKTISKAKGQPREPQVYTLPPSRDELTKNQVS LTCLVKGFYPSDIAVEWESNGQPENNYKTTPPVLDSDGSFFLYSKLTV DKSRWQQGNVFSCSVMHEALHNHYTQKSLSLSPGK(SEQ ID NO: 146) | |
| | IgG2 format; ADI-25653 | QVQLVESGGGVVQPGRSLRLSCAASGFTFVSYNMHWVRQAPGKGL EWVAVIMYDGSAKYYADSVKGRFTISRDNSKNTLYLQMNSLRAEDT AVYYCARGRPWYSETGTSAFDIWGQGTMVTVSSASTKGPSVFPLAP CSRSTSESTAALGCLVKDYFPEPVTVSWNSGALTSGVHTFPAVLQSSG LYSLSSVVTVPSSNFGTQTYTCNVDHKPSNTKVDKTVERKCCVECPP CPAPPVAGPSVFLFPPKPKDTLMISRTPEVTCVVVDVSHEDPEVQFN WYVDGVEVHNAKTKPREEQFNSTFRVVSVLTVVHQDWLNGKEYKC KVSNKGLPAPIEKTISKTKGQPREPQVYTLPPSREEMTKNQVSLTCLV KGFYPSDIAVEWESNGQPENNYKTTPPMLDSDGSFFLYSKLTVDKSR WQQGNVFSCSVMHEALHNHYTQKSLSLSPG(SEQ ID NO: 147) | |
| ADI-25654 | IgG1 format; ADI-25654 | QVQLVESGGGVVQPGRSLRLSCAASGFTFRSYDMHWVRQAPGKGL EWVAYIAYDGSNKYYADSVKGRFTISRDNSKNTLYLQMNSLRAEDTA VYYCARGRPWYSETGTSAFDIWGQGTMVTVSSASTKGPSVFPLAPS SKSTSGGTAALGCLVKDYFPEPVTVSWNSGALTSGVHTFPAVLQSS GLYSLSSVVTVPSSSLGTQTYICNVNHKPSNTKVDKKAEPKSCDKTHT CPPCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSRDELTKNQVSL TCLVKGFYPSDIAVEWESNGQPENNYKTTPPVLDSDGSFFLYSKLTV DKSRWQQGNVFSCSVMHEALHNHYTQKSLSLSPGK(SEQ ID NO: 148) | |
| | IgG2 format; ADI-25654 | QVQLVESGGGVVQPGRSLRLSCAASGFTFRSYDMHWVRQAPGKGL EWVAYIAYDGSNKYYADSVKGRFTISRDNSKNTLYLQMNSLRAEDTA VYYCARGRPWYSETGTSAFDIWGQGTMVTVSSASTKGPSVFPLAPC SRSTSESTAALGCLVKDYFPEPVTVSWNSGALTSGVHTFPAVLQSSGL YSLSSVVTVPSSNFGTQTYTCNVDHKPSNTKVDKTVERKCCVECPPC | |

TABLE 5-continued

Sequences of heavy chain and light chain of the exemplary antibody of the present invention

| Antibody Name | IgG Format | Amino acid sequence of heavy chain | Amino acid sequence of light chain |
|---|---|---|---|
| | | PAPPVAGPSVFLFPPKPKDTLMISRTPEVTCVVVDVSHEDPEVQFNW YVDGVEVHNAKTKPREEQFNSTFRVVSVLTVVHQDWLNGKEYKCK VSNKGLPAPIEKTISKTKGQPREPQVYTLPPSREEMTKNQVSLTCLVK GFYPSDIAVEWESNGQPENNYKTTPPMLDSDGSFFLYSKLTVDKSRW QQGNVFSCSVMHEALHNHYTQKSLSLSPG(SEQ ID NO: 149) | |
| ADI-20078 | IgG1 format; ADI-20078 | QVQLQESGPGLVKPSQTLSLTCTVSGGSISSGSYYWSWIRQHPGKGL EWIGYIYYSGSTYYNPSLKSRVTISVDTSKNQFSLKLSSVTAADTAVY YCARDVGYPHYYGMDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKKAEPKSCDKTHTCPPCP APELLGGPSVFLFPPKPKDTLMISRTPEVTCVVVDVSHEDPEVKFNW YVDGVEVHNAKTKPREEQYNSTYRVVSVLTVLHQDWLNGKEYKCK VSNKALPAPIEKTISKAKGQPREPQVYTLPPSRDELTKNQVSLTCLVK GFYPSDIAVEWESNGQPENNYKTTPPVLDSDGSFFLYSKLTVDKSRW QQGNVFSCSVMHEALHNHYTQKSLSLSPGK(SEQ ID NO: 150) | EIVLTQSPGTLSLSPGERATLSCRASQSVSSSYLAW YQQKPGQAPRLLIYGASSRATGIPDRFSGSGSGTD FTLTISRLEPEDFAVYYCQQSERSPFTFGGGTKVEI KRTVAAPSVFIFPPSDEQLKSGTASVVCLLNNFYPR EAKVQWKVDNALQSGNSQESVTEQDSKDSTYSL SSTLTLSKADYEKHKVYACEVTHQGLSSPVTKSFN RGEC (SEQ ID NO: 169) |
| | IgG2 format; ADI-20078 | QVQLQESGPGLVKPSQTLSLTCTVSGGSISSGSYYWSWIRQHPGKGL EWIGYIYYSGSTYYNPSLKSRVTISVDTSKNQFSLKLSSVTAADTAVY YCARDVGYPHYYGMDVWGQGTTVTVSSASTKGPSVFPLAPCSRSTS ESTAALGCLVKDYFPEPVTVSWNSGALTSGVHTFPAVLQSSGLYSLSS VVTVPSSNFGTQTYTCNVDHKPSNTKVDKTVERKCCVECPPCPAPPV AGPSVFLFPPKPKDTLMISRTPEVTCVVVDVSHEDPEVQFNWYVDG VEVHNAKTKPREEQFNSTFRVVSVLTVVHQDWLNGKEYKCKVSNK GLPAPIEKTISKTKGQPREPQVYTLPPSREEMTKNQVSLTCLVKGFYP SDIAVEWESNGQPENNYKTTPPMLDSDGSFFLYSKLTVDKSRWQQG NVFSCSVMHEALHNHYTQKSLSLSPG(SEQ ID NO: 151) | |
| ADI-23515 | IgG1 format; ADI-23515 | QVQLQESGPGLVKPSQTLSLTCTVSGGSIRSGAYYWSWIRQHPGKGL EWIGYIYYDGQTYYNPSLKSRVTISVDTSKNQFSLKLSSVTAADTAV YYCARDVGYPHYYGMDVWGQGTTVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKKAEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSRDELTKNQVSLTCL VKGFYPSDIAVEWESNGQPENNYKTTPPVLDSDGSFFLYSKLTVDKS RWQQGNVFSCSVMHEALHNHYTQKSLSLSPGK(SEQ ID NO: 152) | |
| | IgG2 format; ADI-23515 | QVQLQESGPGLVKPSQTLSLTCTVSGGSIRSGAYYWSWIRQHPGKGL EWIGYIYYDGQTYYNPSLKSRVTISVDTSKNQFSLKLSSVTAADTAV YYCARDVGYPHYYGMDVWGQGTTVTVSSASTKGPSVFPLAPCSRS TSESTAALGCLVKDYFPEPVTVSWNSGALTSGVHTFPAVLQSSGLYSL SSVVTVPSSNFGTQTYTCNVDHKPSNTKVDKTVERKCCVECPPCPAP PVAGPSVFLFPPKPKDTLMISRTPEVTCVVVDVSHEDPEVQFNWYVD GVEVHNAKTKPREEQFNSTFRVVSVLTVVHQDWLNGKEYKCKVSN KGLPAPIEKTISKTKGQPREPQVYTLPPSREEMTKNQVSLTCLVKGFY PSDIAVEWESNGQPENNYKTTPPMLDSDGSFFLYSKLTVDKSRWQQG NVFSCSVMHEALHNHYTQKSLSLSPG(SEQ ID NO: 153) | |
| ADI-23518 | IgG1 format; ADI-23518 | QVQLQESGPGLVKPSQTLSLTCTVSGGSISSGASYWSWIRQHPGKGL EWIGYIYYSGETYYNPSLKSRVTISVDTSKNQFSLKLSSVTAADTAVY YCARDVGYPHYYGMDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKKAEPKSCDKTHTCPPCP APELLGGPSVFLFPPKPKDTLMISRTPEVTCVVVDVSHEDPEVKFNW YVDGVEVHNAKTKPREEQYNSTYRVVSVLTVLHQDWLNGKEYKCK VSNKALPAPIEKTISKAKGQPREPQVYTLPPSRDELTKNQVSLTCLVK GFYPSDIAVEWESNGQPENNYKTTPPVLDSDGSFFLYSKLTVDKSRW QQGNVFSCSVMHEALHNHYTQKSLSLSPGK(SEQ ID NO: 154) | |
| | IgG2 format; ADI-23518 | QVQLQESGPGLVKPSQTLSLTCTVSGGSISSGASYWSWIRQHPGKGL EWIGYIYYSGETYYNPSLKSRVTISVDTSKNQFSLKLSSVTAADTAVY YCARDVGYPHYYGMDVWGQGTTVTVSSASTKGPSVFPLAPCSRSTS ESTAALGCLVKDYFPEPVTVSWNSGALTSGVHTFPAVLQSSGLYSLSS VVTVPSSNFGTQTYTCNVDHKPSNTKVDKTVERKCCVECPPCPAPPV AGPSVFLFPPKPKDTLMISRTPEVTCVVVDVSHEDPEVQFNWYVDG VEVHNAKTKPREEQFNSTFRVVSVLTVVHQDWLNGKEYKCKVSNK GLPAPIEKTISKTKGQPREPQVYTLPPSREEMTKNQVSLTCLVKGFYP SDIAVEWESNGQPENNYKTTPPMLDSDGSFFLYSKLTVDKSRWQQG NVFSCSVMHEALHNHYTQKSLSLSPG(SEQ ID NO: 155) | |
| ADI-23519 | IgG1 format; | QVQLQESGPGLVKPSQTLSLTCTVSGGSISSGSSYWSWIRQHPGKGLE WIGYIYMSGETYYNPSLKSRVTISVDTSKNQFSLKLSSVTAADTAVY | |

TABLE 5-continued

Sequences of heavy chain and light chain of the exemplary antibody of the present invention

| Antibody Name | IgG Format | Amino acid sequence of heavy chain | Amino acid sequence of light chain |
|---|---|---|---|
| | ADI-23519 | YCARDVGYPHYYGMDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKKAEPKSCDKTHTCPPCP APELLGGPSVFLFPPKPKDTLMISRTPEVTCVVVDVSHEDPEVKFNW YVDGVEVHNAKTKPREEQYNSTYRVVSVLTVLHQDWLNGKEYKCK VSNKALPAPIEKTISKAKGQPREPQVYTLPPSRDELTKNQVSLTCLVK GFYPSDIAVEWESNGQPENNYKTTPPVLDSDGSFFLYSKLTVDKSRW QQGNVFSCSVMHEALHNHYTQKSLSLSPGK(SEQ ID NO: 156) | |
| | IgG2 format; ADI-23519 | QVQLQESGPGLVKPSQTLSLTCTVSGGSISSGSSYWSWIRQHPGKGLE WIGYIYMSGETYYNPSLKSRVTISVDTSKNQFSLKLSSVTAADTAVY YCARDVGYPHYYGMDVWGQGTTVTVSSASTKGPSVFPLAPCSRSTS ESTAALGCLVKDYFPEPVTVSWNSGALTSGVHTFPAVLQSSGLYSLSS VVTVPSSNFGTQTYTCNVDHKPSNTKVDKTVERKCCVECPPCPAPPV AGPSVFLFPPKPKDTLMISRTPEVTCVVVDVSHEDPEVQFNWYVDG VEVHNAKTKPREEQFNSTFRVVSVLTVVHQDWLNGKEYKCKVSNK GLPAPIEKTISKTKGQPREPQVYTLPPSREEMTKNQVSLTCLVKGFYP SDIAVEWESNGQPENNYKTTPPMLDSDGSFFLYSKLTVDKSRWQQG NVFSCSVMHEALHNHYTQKSLSLSPG(SEQ ID NO: 157) | |
| ADI-20048 | IgG1 format; ADI-20048 | QVQLQESGPGLVKPSETLSLTCTVSGGSISSYYWSWIRQPPGKGLEWI GYIYSSGSTNYNPSLKSRVTISVDTSKNQFSLKLSSVTAADTAVYYCA RDAPGGSSYQDYYMDVWGKGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKKAEPKSCDKTHTCPPCP APELLGGPSVFLFPPKPKDTLMISRTPEVTCVVVDVSHEDPEVKFNW YVDGVEVHNAKTKPREEQYNSTYRVVSVLTVLHQDWLNGKEYKCK VSNKALPAPIEKTISKAKGQPREPQVYTLPPSRDELTKNQVSLTCLVK GFYPSDIAVEWESNGQPENNYKTTPPVLDSDGSFFLYSKLTVDKSRW QQGNVFSCSVMHEALHNHYTQKSLSLSPGK(SEQ ID NO: 158) | EIVLTQSPATLSLSPGERATLSCRASQSVSSYLAWF QQKPGQAPRLLIYDASNRATGIPARFSGSGSGTDF TLTISSLEPEDFAVYYCQQAFSMPPTFGGGTKVEIK RTVAAPSVFIFPPSDEQLKSGTASVVCLLNNFYPRE AKVQWKVDNALQSGNSQESVTEQDSKDSTYSLS STLTLSKADYEKHKVYACEVTHQGLSSPVTKSFN RGEC (SEQ ID NO: 170) |
| | IgG2 format; ADI-20048 | QVQLQESGPGLVKPSETLSLTCTVSGGSISSYYWSWIRQPPGKGLEWI GYIYSSGSTNYNPSLKSRVTISVDTSKNQFSLKLSSVTAADTAVYYCA RDAPGGSSYQDYYMDVWGKGTTVTVSSASTKGPSVFPLAPCSRSTS ESTAALGCLVKDYFPEPVTVSWNSGALTSGVHTFPAVLQSSGLYSLSS VVTVPSSNFGTQTYTCNVDHKPSNTKVDKTVERKCCVECPPCPAPPV AGPSVFLFPPKPKDTLMISRTPEVTCVVVDVSHEDPEVQFNWYVDG VEVHNAKTKPREEQFNSTFRVVSVLTVVHQDWLNGKEYKCKVSNK GLPAPIEKTISKTKGQPREPQVYTLPPSREEMTKNQVSLTCLVKGFYP SDIAVEWESNGQPENNYKTTPPMLDSDGSFFLYSKLTVDKSRWQQG NVFSCSVMHEALHNHYTQKSLSLSPG(SEQ ID NO: 159) | |
| ADI-20096 | IgG1 format; ADI-20096 | EVQLVESGGGLVKPGGSLRLSCAASGFTFSSYSMNWVRQAPGKGLE WVSSISSSSNYIYYADSVKGRFTISRDNKNSLYLQMNSLRAEDTAV YYCARGAPLGYSWEYFDLWGRGTLVTVSSASTKGPSVFPLAPSSKST SGGTAALGCLVKDYFPEPVTVSWNSGALTSGVHTFPAVLQSSGLYSL SSVVTVPSSSLGTQTYICNVNHKPSNTKVDKKAEPKSCDKTHTCPPC PAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSRDELTKNQVSLTCL VKGFYPSDIAVEWESNGQPENNYKTTPPVLDSDGSFFLYSKLTVDKS RWQQGNVFSCSVMHEALHNHYTQKSLSLSPGK(SEQ ID NO: 160) | DIQMTQSPSTLSASVGDRVTITCRASQSISSWLAW YQQKPGKAPKLLIYDASSLESGVPSRFSGSGSGTE FTLTISSLQPDDFATYYCQQFQSYSYTFGGGTKVEI KRTVAAPSVFIFPPSDEQLKSGTASVVCLLNNFYPR EAKVQWKVDNALQSGNSQESVTEQDSKDSTYSL SSTLTLSKADYEKHKVYACEVTHQGLSSPVTKSFN RGEC (SEQ ID NO: 171 ) |
| | IgG2 format; ADI-20096 | EVQLVESGGGLVKPGGSLRLSCAASGFTFSSYSMNWVRQAPGKGLE WVSSISSSSNYIYYADSVKGRFTISRDNAKNSLYLQMNSLRAEDTAV YYCARGAPLGYSWEYFDLWGRGTLVTVSSASTKGPSVFPLAPCSRST SESTAALGCLVKDYFPEPVTVSWNSGALTSGVHTFPAVLQSSGLYSLS SVVTVPSSNFGTQTYTCNVDHKPSNTKVDKTVERKCCVECPPCPAPP VAGPSVFLFPPKPKDTLMISRTPEVTCVVVDVSHEDPEVQFNWYVDG VEVHNAKTKPREEQFNSTFRVVSVLTVVHQDWLNGKEYKCKVSNK GLPAPIEKTISKTKGQPREPQVYTLPPSREEMTKNQVSLTCLVKGFYP SDIAVEWESNGQPENNYKTTPPMLDSDGSFFLYSKLTVDKSRWQQG NVFSCSVMHEALHNHYTQKSLSLSPG(SEQ ID NO: 161) | |
| ADI-20051 | IgG1 format; ADI-20051 | QVQLQQWGAGLLKPSETLSLTCAVYGGSFSGYYWSWIRQPPGKGLE WIGEIDHSGSTNYNPSLKSRVTISVDTSKNQFSLKLSSVTAADTAVYY CARDGGGGYASPFDYWGQGTLVTVSSASTKGPSVFPLAPSSKSTSGG TAALGCLVKDYFPEPVTVSWNSGALTSGVHTFPAVLQSSGLYSLSSV VTVPSSSLGTQTYICNVNHKPSNTKVDKKAEPKSCDKTHTCPPCPAP ELLGGPSVFLFPPKPKDTLMISRTPEVTCVVVDVSHEDPEVKFNWYV DGVEVHNAKTKPREEQYNSTYRVVSVLTVLHQDWLNGKEYKCVS NKALPAPIEKTISKAKGQPREPQVYTLPPSRDELTKNQVSLTCLVKGF YPSDIAVEWESNGQPENNYKTTPPVLDSDGSFFLYSKLTVDKSRWQQ GNVFSCSVMHEALHNHYTQKSLSLSPGK(SEQ ID NO: 162) | EIVMTQSPATLSVSPGERATLSCRASQSVSSNLAW YQQKPGQAPRLLIYGASTRATGIPARFSGSGSGTEF TLTISSLQSEDFAVYYCQQYHAWPPTFGGGTKVEI KRTVAAPSVFIFPPSDEQLKSGTASVVCLLNNFYPR EAKVQWKVDNALQSGNSQESVTEQDSKDSTYSL SSTLTLSKADYEKHKVYACEVTHQGLSSPVTKSFN RGEC(SEQ ID NO: 172) |

TABLE 5-continued

Sequences of heavy chain and light chain of the exemplary antibody of the present invention

| Antibody Name | IgG Format | Amino acid sequence of heavy chain | Amino acid sequence of light chain |
|---|---|---|---|
| | IgG2 format; ADI-20051 | QVQLQQWGAGLLKPSETLSLTCAVYGGSFSGYYWSWIRQPPGKGLE WIGEIDHSGSTNYNPSLKSRVTISVDTSKNQFSLKLSSVTAADTAVYY CARDGGGGYASPFDYWGQGTLVTVSSASTKGPSVFPLAPCSRSTSES TAALGCLVKDYFPEPVTVSWNSGALTSGVHTFPAVLQSSGLYSLSSV VTVPSSNFGTQTYTCNVDHKPSNTKVDKTVERKCCVECPPCPAPPVA GPSVFLFPPKPKDTLMISRTPEVTCVVVDVSHEDPEVQFNWYVDGVE VHNAKTKPREEQFNSTFRVVSVLTVVHQDWLNGKEYKCKVSNKGL PAPIEKTISKTKGQPREPQVYTLPPSREEMTKNQVSLTCLVKGFYPSD IAVEWESNGQPENNYKTTPPMLDSDGSFFLYSKLTVDKSRWQQGNVF SCSVMHEALHNHYTQKSLSLSPG (SEQ ID NO: 163) | |
| ADI-20065 | IgG1 format; ADI-20065 | QLQLQESGPGLVKPSETLSLTCTVSGGSISSSSYYWGWIRQPPGKGLE WIGSIYYSGSTYYNPSLKSRVTISVDTSKNQFSLKLSSVTAADTAVYY CARDPGYSASPNWFDPWGQGTLVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKKAEPKSCDKTHTCPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKV SNKALPAPIEKTISKAKGQPREPQVYTLPPSRDELTKNQVSLTCLVKG FYPSDIAVEWESNGQPENNYKTTPPVLDSDGSFFLYSKLTVDKSRWQ QGNVFSCSVMHEALHNHYTQKSLSLSPGK (SEQ ID NO: 164) | EIVLTQSPGTLSLSPGERATLSCRASQSVSSSYLAW YQQKPGQAPRLLIYGASSRATGIPDRFSGSGSGTD FTLTISRLEPEDFAVYYCQQFDSSPTFGGGTKVEIK RTVAAPSVFIFPPSDEQLKSGTASVVCLLNNFYPRE AKVQWKVDNALQSGNSQESVTEQDSKDSTYSLS STLTLSKADYEKHKVYACEVTHQGLSSPVTKSFN RGEC (SEQ ID NO: 173) |
| | IgG2 format; ADI-20065 | QLQLQESGPGLVKPSETLSLTCTVSGGSISSSSYYWGWIRQPPGKGLE WIGSIYYSGSTYYNPSLKSRVTISVDTSKNQFSLKLSSVTAADTAVYY CARDPGYSASPNWFDPWGQGTLVTVSSASTKGPSVFPLAPCSRSTSE STAALGCLVKDYFPEPVTVSWNSGALTSGVHTFPAVLQSSGLYSLSSV VTVPSSNFGTQTYTCNVDHKPSNTKVDKTVERKCCVECPPCPAPPVA GPSVFLFPPKPKDTLMISRTPEVTCVVVDVSHEDPEVQFNWYVDGVE VHNAKTKPREEQFNSTFRVVSVLTVVHQDWLNGKEYKCKVSNKGL PAPIEKTISKTKGQPREPQVYTLPPSREEMTKNQVSLTCLVKGFYPSD IAVEWESNGQPENNYKTTPPMLDSDGSFFLYSKLTVDKSRWQQGNVF SCSVMHEALHNHYTQKSLSLSPG (SEQ ID NO: 165) | |
| ADI-20066 | IgG1 format; ADI-20066 | QLQLQESGPGLVKPSETLSLTCTVSGGSISSSSYYWGWIRQPPGKGLE WIGSIYYSGSTYYNPSLKSRVTISVDTSKNQFSLKLSSVTAADTAVYY CARDPGYSASPNWFDPWGQGTLVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKKAEPKSCDKTHTCPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKV SNKALPAPIEKTISKAKGQPREPQVYTLPPSRDELTKNQVSLTCLVKG FYPSDIAVEWESNGQPENNYKTTPPVLDSDGSFFLYSKLTVDKSRWQ QGNVFSCSVMHEALHNHYTQKSLSLSPGK (SEQ ID NO: 164) | EIVLTQSPGTLSLSPGERATLSCRASQSVSSSFLAW YQQKPGQAPRLLIYGASSRATGIPDRFSGSGSGTD FTLTISRLEPEDFAVYYCQQYDVFPITFGGGTKVEI KRTVAAPSVFIFPPSDEQLKSGTASVVCLLNNFYPR EAKVQWKVDNALQSGNSQESVTEQDSKDSTYSL SSTLTLSKADYEKHKVYACEVTHQGLSSPVTKSFN RGEC (SEQ ID NO: 174) |
| | IgG2 format; ADI-20066 | QLQLQESGPGLVKPSETLSLTCTVSGGSISSSSYYWGWIRQPPGKGLE WIGSIYYSGSTYYNPSLKSRVTISVDTSKNQFSLKLSSVTAADTAVYY CARDPGYSASPNWFDPWGQGTLVTVSSASTKGPSVFPLAPCSRSTSE STAALGCLVKDYFPEPVTVSWNSGALTSGVHTFPAVLQSSGLYSLSSV VTVPSSNFGTQTYTCNVDHKPSNTKVDKTVERKCCVECPPCPAPPVA GPSVFLFPPKPKDTLMISRTPEVTCVVVDVSHEDPEVQFNWYVDGVE VHNAKTKPREEQFNSTFRVVSVLTVVHQDWLNGKEYKCKVSNKGL PAPIEKTISKTKGQPREPQVYTLPPSREEMTKNQVSLTCLVKGFYPSD IAVEWESNGQPENNYKTTPPMLDSDGSFFLYSKLTVDKSRWQQGNVF SCSVMHEALHNHYTQKSLSLSPG (SEQ ID NO: 165) | |
| ADI-20118 | IgG1 format; ADI-20118 | QVQLVQSGAEVKKPGASVKVSCKASGYTFTSYAISWVRQAPGQGLE WMGWISAYNGNTNYAQKLQGRVTMTTDTSTSTAYMELRSLRSDDTA VYYCARSGGGSGPNWFDPWGQGTLVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKKAEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSRDELTKNQVSLTCL VKGFYPSDIAVEWESNGQPENNYKTTPPVLDSDGSFFLYSKLTVDKS RWQQGNVFSCSVMHEALHNHYTQKSLSLSPGK (SEQ ID NO: 166) | DIQMTQSPSSLSASVGDRVTITCQASQDISNYLNW YQQKPGKAPKLLIYDASNLETGVPSRFSGSGSGTD FTFTISSLQPEDIATYYCQQPATLPWTFGGGTKVEI KRTVAAPSVFIFPPSDEQLKSGTASVVCLLNNFYPR EAKVQWKVDNALQSGNSQESVTEQDSKDSTYSL SSTLTLSKADYEKHKVYACEVTHQGLSSPVTKSFN RGEC (SEQ ID NO: 175) |
| | IgG2 format; ADI-20118 | QVQLVQSGAEVKKPGASVKVSCKASGYTFTSYAISWVRQAPGQGLE WMGWISAYNGNTNYAQKLQGRVTMTTDTSTSTAYMELRSLRSDDTA VYYCARSGGGSGPNWFDPWGQGTLVTVSSASTKGPSVFPLAPCSRS TSESTAALGCLVKDYFPEPVTVSWNSGALTSGVHTFPAVLQSSGLYSL SSVVTVPSSNFGTQTYTCNVDHKPSNTKVDKTVERKCCVECPPCPAP PVAGPSVFLFPPKPKDTLMISRTPEVTCVVVDVSHEDPEVQFNWYVD GVEVHNAKTKPREEQFNSTFRVVSVLTVVHQDWLNGKEYKCKVSN | |

TABLE 5-continued

Sequences of heavy chain and light chain of the exemplary antibody of the present invention

| Antibody Name | IgG Format | Amino acid sequence of heavy chain | Amino acid sequence of light chain |
|---|---|---|---|
| | | KGLPAPIEKTISKTKGQPREPQVYTLPPSREEMTKNQVSLTCLVKGFY PSDIAVEWESNGQPENNYKTTPPMLDSDGSFFLYSKLTVDKSRWQQG NVFSCSVMHEALHNHYTQKSLSLSPG(SEQ ID NO: 167) | |
| ADI-20113 | IgG1 format; ADI-20113 | QVQLVESGGGVVQPGRSLRLSCAASGFTFSSYGMHWVRQAPGKGL EWVAVISYDGSNKYYADSVKGRFTISRDNSKNTLYLQMNSLRAEDTA VYYCARGRPWYSETGTSAFDIWGQGTMVTVSSASTKGPSVFPLAPS SKSTSGGTAALGCLVKDYFPEPVTVSWNSGALTSGVHTFPAVLQSSG LYSLSSVVTVPSSSLGTQTYICNVNHKPSNTKVDKKAEPKSCDKTHT CPPCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSRDELTKNQVSL TCLVKGFYPSDIAVEWESNGQPENNYKTTPPVLDSDGSFFLYSKLTV DKSRWQQGNVFSCSVMHEALHNHYTQKSLSLSPGK(SEQ ID NO: 189) | EIVMTQSPATLSVSPGERATLSCRASQSVSSNLAW YQQKPGQAPRLLIYSASTRATGIPARFSGSGSGTEF TLTISSLQSEDFAVYYCQQHNVYPPYTFGGGTKVE IKRTVAAPSVFIFPPSDEQLKSGTASVVCLLNNFYP REAKVQWKVDNALQSGNSQESVTEQDSKDSTYS LSSTLTLSKADYEKHKVYACEVTHQGLSSPVTKSF NRGEC(SEQ ID NO: 176) |
| | IgG2 format; ADI-20113 | QVQLVESGGGVVQPGRSLRLSCAASGFTFSSYGMHWVRQAPGKGL EWVAVISYDGSNKYYADSVKGRFTISRDNSKNTLYLQMNSLRAEDTA VYYCARGRPWYSETGTSAFDIWGQGTMVTVSSASTKGPSVFPLAPC SRSTSESTAALGCLVKDYFPEPVTVSWNSGALTSGVHTFPAVLQSSGL YSLSSVVTVPSSNFGTQTYTCNVDHKPSNTKVDKTVERKCCVECPPC PAPPVAGPSVFLFPPKPKDTLMISRTPEVTCVVVDVSHEDPEVQFNW YVDGVEVHNAKTKPREEQFNSTFRVVSVLTVVHQDWLNGKEYKCK VSNKGLPAPIEKTISKTKGQPREPQVYTLPPSREEMTKNQVSLTCLVK GFYPSDIAVEWESNGQPENNYKTTPPMLDSDGSFFLYSKLTVDKSRW QQGNVFSCSVMHEALHNHYTQKSLSLSPG(SEQ ID NO: 139) | |

TABLE 6

Exemplary signal peptide sequence of the present invention

METDTLLLWVLLLWVPGSTG (SEQ ID NO: 182)

These and other aspects and embodiments of the present invention are described in the drawings (hereinafter briefly described) and the detailed description of the invention and are illustrated in the following examples. Any or all of the features discussed above and throughout this application may be combined in various embodiments of the invention. The invention is further illustrated by the following

TABLE 7

Heavy chain and light chain sequence of some of antibody control used in the examples of the present invention

| IgG1 heavy chain | MGWSLILLFLVAVATRVLSEVRLLESGGGLVQPGGSLRLSCAASGFTFSNYAMGWVRQAPGKGLEWVSAISGSGGSTYYADSVKG RFTTSRDDSKNALYLQMNSLRAEDTAVYYCARGGPGWYAADVWGQGTTVTVSSASTKGPSVFPLAPSSKSTSGGTAALGCLVKD YFPEPVTVSWNSGALTSGVHTFPAVLQSSGLYSLSSVVTVPSSSLGTQTYICNVNHKPSNTKVDKKAEPKSCDKTHTCPPCPAPELLG GPSVFLFPPKPKDTLMISRTPEVTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIAVEWESNGQPENNYKTTPPVLDSDGSFFLYSK LTVDKSRWQQGNVFSCSVMHEALHNHYTQKSLSLSPGK(SEQ ID NO: 177) |
|---|---|
| IgG4 heavy chain | MGWSLILLFLVAVATRVLSEVRLLESGGGLVQPGGSLRLSCAASGFTFSNYAMGWVRQAPGKGLEWVS AISGSGGSTYYADSVKGRFTTSRDDSKNALYLQMNSLRAEDTAVYYCARGGPGWYAADVWGQGTTVTVSSASTKGPSVFPLAPCS RSTSESTAALGCLVKDYFPEPVTVSWNSGALTSGVHTFPAVLQSSGLYSLSSVVTVPSSSLGTKTYTCNVDHKPSNTKVDKRVESKY GPPCPPCPAPEFLGGPSVFLFPPKPKDTLMISRTPEVTCVVVDVSQEDPEVQFNWYVDGVEVHNAKTKPREEQFNSTYRVVSVLTVL HQDWLNGKEYKCKVSNKGLPSSIEKTISKAKGQPREPQVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLSLGK(SEQ ID NO: 178) |
| IgG1 & IgG4 light chain | MDFQVQIIISFLLISASVIMSRGDIQMTQSPSSLSASVGDRVTITCRASQSISSYLNWYQQKPGKAPKLLIYAASSLQSGVPSRFSGSGSG TDFTLTISSLQPEDFATYYCQQADLPAFAFGGGTKVEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSFNRGEC(SEQ ID NO: 179) |
| IgG2 heavy chain | MGWSLILLFLVAVATRVLSQLQLQKSGPGLVKPSETLSLTCTVSGFTFSNYAMGWIRQPPGKGLEWIGAISGSGGSTYYADSVKGR VTISVDTSKNQFSLKLSSVTAADTAVYYCARGGPGWYAADVWGQGTLVTVSSASTKGPSVFPLAPCSRSTSESTAALGCLVKDYFP EPVTVSWNSGALTSGVHTFPAVLQSSGLYSLSSVVTVPSSNFGTQTYTCNVDHKPSNTKVDKTVERKCCVECPPCPAPPVAGPSVFL FPPKPKDTLMISRTPEVTCVVVDVSHEDPEVQFNWYVDGVEVHNAKTKPREEQFNSTFRVVSVLTVVHQDWLNGKEYKCKVSNK GLPAPIEKTISKTKGQPREPQVYTLPPSREEMTKNQVSLTCLVKGFYPSDIAVEWESNGQPENNYKTTPPMLDSDGSFFLYSKLTVDK SRWQQGNVFSCSVMHEALHNHYTQKSLSLSPG(SEQ ID NO: 180) |
| IgG2 light chain | MDFQVQIISFLLISASVIMSRGEIVLTQSPATLSLSPGERATLSCRASQSISSYLNWYQQKPGQAPRLLIYAASSLQSGIPARFSGSGSGT DFTLTISSLEPEDFAVYYCQQADLPAFAFGGGTKVEIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKSFNRGEC(SEQ ID NO: 181) | examples, which are to be understood by way of illustration and not limitation, and the skilled person in the art can make various modifications.

EXAMPLES

Example 1. Production and Purification of Anti-OX40 Antibody and Control Antibody Anti-OX40 antibodies were identified by the Adimab antibody platform. Libraries and their use in screening procedures are described, for example, in Xu et al, 2013; WO2009036379; WO2010105256; WO2012009568.

The following anti-OX40 antibodies of the present invention were expressed in yeast or CHO-S cell or 293 HEK cells and then purified:

| Antibody Name |
|---|
| ADI-20112 |
| ADI-25650 (ADI-20112progeny) |
| ADI-25651 (ADI-20112progeny) |
| ADI-25652 (ADI-20112progeny) |
| ADI-25653 (ADI-20112progeny) |
| ADI-25654 (ADI-20112progeny) |
| ADI-20078 |
| ADI-23515 (ADI-20078progeny) |
| ADI-23518 (ADI-20078progeny) |
| ADI-23519 (ADI-20078progeny) |
| ADI-20048 |
| ADI-20096 |
| ADI-20051 |
| ADI-20065 |
| ADI-20066 |
| ADI-20118 |
| ADI-20113 |

The following control antibodies were expressed in 293HEK cells and then purified:

| Control Antibody |
|---|
| pogalizumab |
| Hu106-222 |
| 11D4 |
| tavolixizumab |

As used herein, pogalizumab is a human IgG1 OX40 antibody transiently expressed in 293 HEK cells that utilizes the heavy chain and light chain sequences from Proposed INN: List 114 (c.f, WHO Drug Information, Vo. 29, No. 4, pg. 503-602, 2015. As used herein, Hu106-222 is a humanized IgG1 OX40 antibody transiently expressed in 293 HEK cells that utilizes the heavy chain and light chain sequences from U.S. Pat. No. 9,006,399. As used herein, 11D4 is a humanized IgG1 OX40 antibody transiently expressed in 293 HEK cells that utilizes the heavy chain and light chain sequences from U.S. Pat. No. 8,236,930. As used herein, tavolixizumab is a humanized IgG1 OX40 antibody transiently expressed in 293 HEK cells that utilizes the heavy chain and light chain sequences from Proposed INN: List 115 (c.f, WHO Drug Information, Vol. 30, No. 2, pg. 241-357, 2016.

For the Treatment of Yeast Material:

Yeast clones were grown to saturation and then induced for 48 h at 30° C. with shaking. After induction, yeast cells were pelleted and the supernatants were harvested for purification. IgGs were purified using a Protein A column and eluted with acetic acid, PH 2.0. Fab fragments were generated by papain digestion and purified over KappaSelect (GE Healtheare LifeSciences).

For the Treatment of CHO-S Cells:

Expression CHO-S cell lines were generated according to the manufacturer's instructions using the Freedom® CHO-S® Kit (Invitrogen). For mAb expression, DNA sequences of heavy and light chains were inserted into the pCHO 1.0 plasmid with the heavy chain upstream of the light chain. Full length human OX40 CDS sequences (purchased from Sino Biological) were inserted into the pCHO 1.0 vector for the generation of stable overexpression cell lines.

For the Treatment of 293HEK Cells:

For transient expression of proteins in 293HEK cells, the vector pTT5 was used with heavy and light chains of the antibodies cloned into a standalone vector. Transfection into 293HEK cells was carried out using standard procedures with PEI; supernatants were collected after 7 days of culture and purified on an AKTA system (GE).

Example 2: Binding Kinetics and Affinity Assay on Anti-OX40 Antibodies

The kinetics and equilibrium dissociation constant ($K_D$) for human OX40 is determined for antibodies of the present invention using MSD and bio-light interferometry (ForteBio) assay methods.

1. ForteBio KD Assay (Bio-Light Interferometry)

ForteBio affinity measurements were performed generally as previously described (Estep, P., et al., High throughput solution-based measurement of antibody-antigen affinity and epitope binning. MAbs, 2013. 5(2): p. 270-8.). Briefly, ForteBio affinity measurements were performed by equilibrating sensors off-line in assay buffer for 30 min, and then monitoring on-line for 60 seconds for baseline establishmen, loading the purified antibodies obtained as described above online onto AHQ sensors (ForteBio). Sensors with loaded antibodies were exposed to 100 nM OX40 antigens for 5 min, afterwards they were transferred to assay buffer for dissociation of 5 min for off-rate measurement. Kinetics was analysed using the 1:1 binding model.

In experiments performed as described in the above assay, ADI-20051. ADI-20065, ADI-20066, ADI-20078, ADI-20112, ADI-20113 and ADI-20118 (Fab format of anti-OX40 antibody in the form of IgG1 expressed in yeast), bind human OX40_Fc (human OX40 binding to antibody Fc moiety, purchased from R&D Systems) with a monovalent $K_D$ in sub micromolar range. When the antibody was on the sensor tip, ADI-20048, ADI-20051, ADI-20065, ADI-20066, ADI-20078, ADI-20096, ADI-20112, ADI-20113 and ADI-20118 (anti-OX40 antibody in an IgG1 format and expressed in yeast), bind human OX40 Fc (purchased from R&D Systems) with an avid $K_D$ value at a single digit nanomolar to lower range; and bind cyno OX40 Fc (purchased from Acro Biosystems) at double single digit nanomolar or lower range. When the antibody was on the sensor tip, ADI-20048, ADI-20078 and ADI-20096 (anti-OX40 antibodies in an IgG1 format and expressed in yeast), bind mouse OX40_Fc (purchased from Acro Biosystems) at single digit nanomolar values (Table 8).

TABLE 8

Binding by Bio-light interferometry of antibodies of the invention in IgG1 format

| Antibody | ForteBio Image: Human OX40-Fc on AHQ tip, antibody in the form of Fab in solution (200 nM) [Monovalent] | ForteBio Image: Antibodies in the form of IgG1 on AHQ tip, Human OX40-Fc in solution (50 nM) [Avid] | ForteBio Image: Antibodies in the form of IgG1 on AHQ tip, Cyno OX40-Fc in solution (100 nM) [Avid] | ForteBio Image: Antibodies in the form of IgG1 on AHQ tip, Mouse OX40-Fc in solution (100 nM) [Avid] |
|---|---|---|---|---|
| Hu106-222 | 1.53E−08 | 2.50E−10 | 4.96E−09 | N.B. |
| ADI-20048 | N.B. | 3.68E−09 | 9.86E−09 | 3.76E−09 |
| ADI-20051 | 2.58E−08 | 7.40E−10 | 1.18E−08 | N.B. |
| ADI-20065 | 1.08E−08 | 3.52E−10 | 5.77E−09 | N.B. |
| ADI-20066 | 2.18E−08 | 9.10E−10 | 1.43E−08 | N.B. |
| ADI-20078 | 1.99E−07 | 1.08E−09 | 3.35E−09 | 9.17E−09 |
| ADI-20096 | N.B. | 3.36E−09 | N.B. | 5.41E−09 |
| ADI-20112 | 7.06E−08 | 7.35E−10 | 5.98E−09 | N.B. |
| ADI-20113 | 1.82E−07 | 1.22E−09 | 5.52E−09 | N.B. |
| ADI-20118 | 1.37E−07 | 5.10E−10 | 1.14E−08 | N.B. |

After affinity maturation of ADI-20112 and ADI-20078, its progenies ADI-25650, ADI-25651, ADI-25652, ADI-25653, ADI-25654, ADI-23515, ADI-23518, and ADI-23519 show improved monovalent binding shown by $K_D$ values of the antibodies in Fab format produced from IgG1 expressed in yeast when binding to human OX40 Fc on a sensor chip; improvement of avid binding affinity when the antibody was on the sensor tip, in an IgG1 format and expressed in yeast, binding to human OX40 Fc in solution; and improvement of binding affinity when the antibody was on the sensor tip, in an IgG1 format and expressed in yeast, binding to cyno OX40 Fc in solution (Table 9).

TABLE 9

Binding by Bio-light interferometry of affinity matured antibodies of the invention in IgG1 format

| Antibody | ForteBio Image: Human OX40-Fc on AHQ tip, Antibody in the form of Fab in solution (200 nM) [Monovalent] | ForteBio Image: Antibodies in the form of IgG1 on AHQ tip, Human OX40-Fc in solution (50 nM) [Avid] | ForteBio Image: Antibodies in the form of IgG1 on AHQ tip, Cyno OX40-Fc in solution (100 nM) [Avid] | ForteBio Image: Antibodies in the form of IgG1 on AHQ tip, Mouse OX40-Fc in solution (100 nM) [Avid] |
|---|---|---|---|---|
| 11D4 | 2.80E−08 | 6.13E−10 | 5.95E−09 | N.B. |
| Hu106-222 | 1.30E−08 | 4.75E−10 | 5.17E−09 | N.B. |
| ADI-20112 | 6.39E−08 | 7.75E−10 | 6.82E−09 | N.B. |
| ADI-25650 | 1.04E−09 | 2.30E−10 | 1.60E−09 | N.B. |
| ADI-25651 | 2.32E−09 | 2.68E−10 | 1.37E−09 | N.B. |
| ADI-25652 | 1.31E−09 | 2.61E−10 | 2.11E−09 | N.B. |
| ADI-25653 | 1.63E−09 | 2.23E−10 | 1.15E−09 | N.B. |
| ADI-25654 | 1.80E−09 | 2.83E−10 | 1.53E−09 | N.B. |
| ADI-20078 | 9.80E−08 | 1.49E−09 | 2.85E−09 | 8.06E−09 |
| ADI-23515 | 3.79E−09 | 2.73E−10 | 1.09E−09 | 8.98E−09 |
| ADI-23518 | 7.16E−09 | 2.97E−10 | 1.08E−09 | P.F. |
| ADI-23519 | 5.36E−09 | 2.55E−10 | 1.10E−09 | P.F. |

MSD-SET Kinetic Assay

Equilibrium affinity measurements see Estep, P., et al., MAbs, 2013. 5(2): p. 270-8. Solution equilibrium titrations (SET) are performed in PBS+0.1% IgG-Free BSA (PBSF) where antigen (biotin-OX-40 monomer (biotinylated OX40, purchased from Acro Biosystems) is held constant at 10-100 pM and is incubated with 3- to 5-fold serial dilutions of Fab or mAbs starting at 5-100 nM (experimental condition is sample dependent). Antibodies diluted at 20 nM in PBS are coated onto standard bind MSD-ECL plates (Multi-array 96-well plate, Cat #: L15XA-3, MSD) overnight at 4° C. or at room temperature for 30 min. Plates are blocked with BSA for 30 min whilst shaking at 700 rpm. Plates are then washed 3× with wash buffer (PBSF+0.05% Tween 20). SET samples are applied and incubated on the plates for 150 s with shaking at 700 rpm followed by one wash. Antigen captured on a plate is detected with 250 ng/mL sulfo tag-labeled streptavidin in PBSF by incubation on the plate for 3 min. The plates are washed three times with wash buffer and are then read on the MSD Sector Imager 2400 instrument using 1× Read Buffer T (Cat #R92TC-1, MSD) with surfactant. The percentage free antigen is plotted as a function of titrated antibody in Prism and fit to a quadratic equation to extract the KD. To improve throughput, liquid handling robots are used throughout MSD-SET experiments, including for SET sample preparation.

In experiments performed as described in the above assay, Fab form of ADI-25650, ADI-25651, ADI-25652, ADI-25653, ADI-25654, ADI-23515 and ADI-23519, in an IgG1 format and expressed in yeast, bind human OX40 with detectable sub-nanomolar monovalent $K_D$ values (Table 10).

TABLE 10

Binding by MSD of antibodies of the invention in IgG1 format

| Antibody | MSD KD (M) Human biotinylated OX40-His monomer incubated with Antibody Fab |
|---|---|
| 11D4 | N.D. |
| Hu106-222 | N.D. |
| ADI-20112 | N.D. |
| ADI-25650 | 1.40E−10 |
| ADI-25651 | 1.70E−10 |
| ADI-25652 | 1.50E−10 |
| ADI-25653 | 8.60E−11 |
| ADI-25654 | 1.80E−10 |
| ADI-20078 | N.D. |
| ADI-23515 | 1.60E−10 |
| ADI-23518 | N.D. |

Example 3: Binding Between the Anti-OX40 Antibody of the Present Invention and Human OX40

The binding of an antibody of the present invention to human OX40 may be measured in a flow cytometry-based assay.

1. Binding to Human OX40 on CHO Cells

CHO cells overexpressing human OX40 (CHO-hOX40 cells) were generated by transfecting pCHO1.0 vector (Invitrogen) with human OX40 cDNA (Sino Biological, HG10481-G) cloned into the MCS. CHO-hOX40 cells (0.2× $10^6$ cells) are incubated with the experimental antibody at 100 nM for 30 min in PBS 0.1% BSA on ice. Cells are then washed at least twice, and are incubated with a secondary antibody (PE-labelled, SouthernBiotech, at final concentration of 5 μg/ml) in PBS 0.1% BSA for 30 min on ice (protected from light). Cells are washed at least twice and analysed via flow cytometry. Flow cytometry is performed on a Canto II system (BD Biosciences) and MFIs are calculated accordingly.

In experiments performed as described in the above assay, ADI-20048, ADI-20051, ADI-20065, ADI-20066, ADI-20078, ADI-20096, ADI-20112, ADI-20113 and ADI-20118 (IgG1 format, expressed in yeast) binds OX40 overexpressed on CHO cells with MFI values >1000 fold difference compared with stained wild-type CHO cells (Table 11).

TABLE 11

Binding of antibodies of the invention in IgG1 format generated in yeast to CHO cells expression human OX40 by flow cytometry

| Antibody | CHO binding intensity (MFI) | CHO-OX40 binding intensity (MFI) | Fold difference |
|---|---|---|---|
| Hu106-222 | 62.48 | 164239.15 | 2628.66757362356 |
| ADI-20048 | 97.8 | 143461.23 | 1466.88374233129 |
| ADI-20051 | 96.17 | 151191.75 | 1572.1300821462 |
| ADI-20065 | 70.1 | 157294.81 | 2243.86319543509 |
| ADI-20066 | 58.39 | 160635.77 | 2751.08357595479 |
| ADI-20078 | 122.4 | 141543.26 | 1156.39918300654 |
| ADI-20096 | 67.67 | 133399.72 | 1971.32732377715 |
| ADI-20112 | 63.68 | 153432.17 | 2409.42478015075 |
| ADI-20113 | 61.79 | 151897.05 | 2458.27884770999 |
| ADI-20118 | 77.18 | 143967.03 | 1865.34115055714 |

In experiments performed as described in the above assay, after affinity maturation of ADI-20112 and ADI-20078, its progenies ADI-25650, ADI-25651, ADI-25652, ADI-25653, ADI-25654, ADI-23515, ADI-23518, and ADI-23519 retain binding strength to CHO cells overexpressing human OX40 (Table 12).

TABLE 12

Binding of affinity matured antibodies of the invention in IgG1 format generated in yeast to CHO cells expression human OX40 by flow cytometry

| Antibody | CHO binding intensity (MFI) | CHO-OX40 binding intensity (MFI) | Fold difference |
|---|---|---|---|
| 11D4 | 103.8 | 169078.52 | 1628.88747591522 |
| Hu106-222 | 107.91 | 183487.48 | 1700.375127421 |
| ADI-20112 | 117.48 | 244141.56 | 2078.15423901941 |
| ADI-25650 | 123.52 | 251531.8 | 2036.3649611399 |
| ADI-25651 | 108.09 | 252745.63 | 2338.28874086409 |
| ADI-25652 | 105.37 | 252663.66 | 2397.87093100503 |
| ADI-25653 | 108.47 | 251842.51 | 2321.77108878031 |
| ADI-25654 | 111.57 | 251911.27 | 2257.87640046608 |
| ADI-20078 | 103.2 | 140889.45 | 1365.20784883721 |
| ADI-23515 | 117.12 | 181008.63 | 1545.49718237705 |
| ADI-23518 | 117.02 | 173107.61 | 1479.29935053837 |
| ADI-23519 | 113.95 | 177986.07 | 1561.966388767 |

In experiments performed as described in the above assay, ADI-20051, ADI-20078, ADI-20112 and ADI-20118, in IgG1 format, expressed in 293HEK cells, bind OX40 overexpressed on CHO cells with EC50 values of 2.734, 2.874, 2.799, and 6.71 nM, respectively (Table 13).

TABLE 13

Binding of antibodies of the invention in IgG1 format generated in 293HEK cells to CHO cells expressing human OX40 by flow cytometry(MFI)

| mAb concentration (nM) | ADI-20051 | ADI-20078 | ADI-20112 | ADI-20118 | IgG1* | Hu106-222 | OX40L |
|---|---|---|---|---|---|---|---|
| 200 | 3,892,625 | 4,331,942.5 | 3,968,422.5 | 3,887,261 | 2,823 | 2,641,566.5 | 2,676,466 |
| 100 | 4,353,622 | 3,749,820 | 3,821,556 | 3,829,764.5 | 1,724.5 | 2,501,123 | 2,566,729.5 |
| 50 | 3,797,245.5 | 4,177,968 | 4,041,423 | 3,347,599.5 | 1,697 | 2,337,112 | 2,718,729.5 |
| 25 | 3,888,215.5 | 4,044,853.5 | 3,863,618 | 3,402,198 | 1,564 | 2,243,315 | 2,800,686.5 |
| 12.5 | 3,519,989.5 | 3,086,415 | 3,642,910 | 2,426,690 | 1,629 | 2,177,780 | 1,990,551.5 |
| 6.25 | 3,058,740 | 2,909,226 | 2,635,481.5 | 1,905,832 | 1,599.5 | 2,020,453.5 | 1,475,888.5 |
| 3.125 | 2,820,887 | 2,260,563.5 | 1,984,982 | 1,424,275 | 1,745.5 | 1,769,950 | 932,206 |
| 1.5625 | 976,540.5 | 1,278,333 | 1,535,375 | 834,045 | 1,930 | 1,253,256 | 553,849 |
| 0.78125 | 603,919 | 684,834 | 655,291 | 529,956 | 1,681 | 600,191.5 | 316,826 |
| 0.390625 | 493,981 | 432,702 | 302,819 | 191,627 | 1,710 | 474,061 | 118,773.5 |
| 0.1953125 | 293,798 | 267,094.5 | 225,752.5 | 131,627.5 | 1,505.5 | 181,238.5 | 83,150 |
| 0.09765625 | 124,618 | 101,394.5 | 80,628.5 | 75,465 | 2,383.5 | 77,551 | 35,188.5 |
| 0.048828125 | 63,925 | 54,087.5 | 56,293.5 | 42,682.5 | 2,016 | 49,775.5 | 33,965 |

TABLE 13-continued

Binding of antibodies of the invention in IgG1 format generated in 293HEK cells to CHO cells expressing human OX40 by flow cytometry(MFI)

| mAb concentration (nM) | ADI-20051 | ADI-20078 | ADI-20112 | ADI-20118 | IgG1* | Hu106-222 | OX40L |
|---|---|---|---|---|---|---|---|
| 0.024414063 | 43,228.5 | 35,991.5 | 36,783.5 | 18,963.5 | 2,072 | 26,693 | 12,831 |
| EC50 | 2.734 | 2.874 | 2.799 | 6.71 | N/A | 1.939 | 5.325 |

*IgG1 comprises the heavy chain of SEQ ID NO: 177 and the light chain of SEQ ID NO: 179, and the same for the IgG1 control in the following content.

In experiments performed as described in the above assay, ADI-20051, ADI-20078, ADI-20112 and ADI-20118, in IgG2 format, expressed in 293HEK cells, bind OX40 overexpressed on CHO cells with EC50 values of 5.49, 4.022, 2.777, and 5.838 nM, respectively (Table 14).

TABLE 14

Binding of antibodies of the invention in IgG2 format generated in 293HEK cells to CHO cells expressing human OX40 by flow cytometry (MFI)

| mAb concentration (nM) | ADI-20051 | ADI-20078 | ADI-20112 | ADI-20118 | IgG2* | Hu106-222 (IgG2) | OX40L |
|---|---|---|---|---|---|---|---|
| 200 | 2,505,571.5 | 2,340,461.5 | 1,794,440.5 | 1,721,947.5 | 216,463 | 2,547,473.5 | 2,079,671.5 |
| 100 | 2,352,269.5 | 2,302,557.5 | 1,781,267 | 1,530,379 | 93,016.5 | 2,390,473.5 | 2,509,891 |
| 50 | 2,097,152 | 1,845,269.5 | 1,552,003 | 1,376,523.5 | 44,135 | 1,586,637 | 1,075,813 |
| 25 | 2,328,715 | 2,331,766 | 1,825,143.5 | 1,500,387 | 22,093.5 | 2,158,051.5 | 1,842,256 |
| 12.5 | 1,620,692 | 1,504,606 | 1,342,114 | 1,128,280.5 | 11,883 | 1,524,125.5 | 1,107,920.5 |
| 6.25 | 1,331,847.5 | 1,510,032.5 | 1,427,757.5 | 889,093 | 6,395 | 1,058,626 | 599,830.5 |
| 3.125 | 912,960 | 1,155,515.5 | 985,181 | 600,036.5 | 4,151.5 | 660,113 | 341,966 |
| 1.5625 | 610,550.5 | 679,365.5 | 602,131.5 | 351,749 | 2,898 | 333,812 | 172,319 |
| 0.78125 | 315,041 | 344,013 | 313,831 | 207,156 | 2,249 | 188,470 | 86,024.5 |
| 0.390625 | 155,997.5 | 191,290 | 188,741 | 119,907 | 1,892 | 100,782 | 49,659.5 |
| 0.1953125 | 80,545.5 | 91,837.5 | 94,230 | 60,444.5 | 1,685 | 49,458.5 | 24,816 |
| 0.09765625 | 40,673.5 | 44,953.5 | 48,522 | 36,842 | 1,590.5 | 28,207.5 | 14,492 |
| 0.048828125 | 19,401.00 | 26,640.00 | 25,653.00 | 18,428.00 | 1,562.00 | 15,366 | 8,354.50 |
| 0.024414063 | 20,873.50 | 25,589.00 | 24,560.50 | 16,484.00 | 1,511.50 | 14,635.5 | 7,974.00 |
| EC50 | 5.49 | 4.022 | 2.777 | 5.838 | N/A | 8.367 | 12.4 |

*IgG2 comprises the heavy chain of SEQ ID NO: 180 and the light chain of SEQ ID NO: 181, and the same for the IgG1 control in the following content.

2. Binding to Human OX40 on 293HEK Cells

The binding of an antibody of the present invention to human OX40 may be measured in a flow cytometry assay. 293HEK cells overexpressing human OX40 (0.2×10$^6$ cells, prepared by the similar method for CHO cells as described above) are incubated with the experimental antibody at 100 nM for 30 min in PBS 0.1% BSA on ice. Cells are then washed at least twice, and are incubated with a secondary antibody (PE-labelled, SouthernBiotech, at final concentration of 5 μg/ml) in PBS 0.1% BSA for 30 min on ice (protected from light). Cells are washed at least twice and analysed via flow cytometry. Flow cytometry is performed on an Accuri C6 system (BD Biosciences) and MFIs are calculated accordingly.

In experiments performed as described in the above assay, ADI-20048, ADI-20051, ADI-20065, ADI-20066, ADI-20078, ADI-20096, ADI-20112, ADI-20113 and ADI-20118 (IgG1 format, expressed in yeast) binds OX40 in a dose-dependent manner, compared to the negative control IgG1 control (Table 15).

TABLE 15

Binding of antibodies of the invention in IgG1 format generated in yeast cells to 293HEK cells expressing human OX40 by flow cytometry (MFI)

| | Concentration | | | |
|---|---|---|---|---|
| Antibody | 200 nM | 40 nM | 8 nM | 1.6 nM |
| IgG1 control | 11,089.00 | 25,186.50 | 5,311.00 | 5,625.50 |
| 11D4 | 2,405,701.00 | 2,755,335.00 | 2,060,113.00 | 613,085.00 |
| Hu106-222 | 1,787,941.00 | 1,798,292.50 | 1,737,822.00 | 650,133.50 |
| ADI-20048 | 1,703,707.00 | 1,851,598.50 | 1,726,793.50 | 976,743.50 |
| ADI-20051 | 2,465,528.00 | 2,394,265.00 | 2,328,569.50 | 788,317.00 |
| ADI-20065 | 3,031,816.50 | 2,424,762.50 | 2,458,475.00 | 807,629.00 |
| ADI-20066 | 2,552,042.00 | 2,388,745.00 | 2,823,986.00 | 625,539.50 |
| ADI-20078 | 1,943,603.50 | 1,565,973.00 | 1,575,529.00 | 541,760.00 |
| ADI-20096 | 1,842,613.00 | 1,816,164.50 | 1,100,745.50 | 416,902.00 |
| ADI-20112 | 2,305,931.00 | 1,923,515.00 | 1,975,220.00 | 894,984.00 |
| ADI-20113 | 2,409,755.50 | 2,181,506.00 | 1,997,251.00 | 734,281.00 |
| ADI-20118 | 1,730,309.00 | 1,979,720.00 | 1,962,026.00 | 848,675.50 |

3. Binding to Human OX40 on Activated Primary CD4+ T Cells

The binding of an antibody of the present invention to human OX40 on primary T cells may be measured in a flow cytometry assay.

Primary CD4+ T cells from healthy donors are activated with anti-CD3/CD28 DynaBeads (Invitrogen) for 48 hours and 0.2×10⁶ cells are incubated with the experimental antibody at 100 nM for 30 min in PBS 0.1% BSA on ice. Cells are then washed at least twice, and are incubated with a secondary antibody (PE-labelled, SouthernBiotech, at final concentration of 5 µg/ml) in PBS 0.1% BSA for 30 min on ice (protected from light). Cells are washed at least twice and analysed via flow cytometry. Flow cytometry is performed on an Accuri C6 system (BD Biosciences) and MFIs are calculated accordingly.

In experiments performed as described in the above assay, ADI-20048, ADI-20051, ADI-20065, ADI-20066, ADI-20078, ADI-20096, ADI-20112, ADI-20113 and ADI-20118 (IgG1 format, expressed in yeast) binds OX40 with a high MFI signal compared to the negative control IgG1 control (Table 16).

TABLE 16

Binding of antibodies of the invention in IgG1 format generated in yeast cells to activated CD4+ T cells by flow cytometry (MFI)

| Antibody | Human OX40 on primary CD4+ T cells derived from healthy Donor 1 | Human OX40 on primary CD4+ T cells derived from healthy Donor 2 |
|---|---|---|
| IgG1 control | 6,309.00 | 1,707.00 |
| Hu106-222 | 114,899.50 | 136,049.50 |
| 11D4 | 196,478.50 | 242,033.50 |
| ADI-20048 | 43,129.00 | 62,592.00 |
| ADI-20051 | 140,903.50 | 172,241.50 |
| ADI-20065 | 152,901.00 | 208,500.50 |
| ADI-20066 | 134,167.00 | 193,030.00 |
| ADI-20078 | 60,318.50 | 80,891.00 |
| ADI-20096 | 54,618.00 | 75,446.00 |
| ADI-20112 | 100,101.50 | 125,179.00 |
| ADI-20113 | 84,378.50 | 114,677.00 |
| ADI-20118 | 78,556.50 | 107,498.50 |

Example 4. Blocking of the Antibody of the Present Invention on the Interaction Between Human OX40L and OX40 on CHO Cells The ability of an antibody of the present invention to block binding of human OX40 to OX40L may be measured by flow cytometry.

Method 1:

0.2×10⁶ CHO cells expressing human OX40 prepared as described in the above Example 3 are incubated with the experimental antibody (100 nM) for 30 min in PBS 0.1% BSA on ice. Cells are then washed 3×, and are incubated with OX40L-hFc (obtained form AcroBiosystems) (~10 µg/ml) linked with NHS-Fluorescein (Promega) in PBS 0.1% BSA for 30 min on ice (protected from light). Cells are washed 3×. Flow cytometry is performed on an Accuri C6 system (BD Biosciences) and MFIs are calculated on the C6 software.

In the experiment performed by the above assay, ADI-20048, ADI-20051, ADI-20065, ADI-20066, ADI-20078, ADI-20096, ADI-20112, ADI-20113 and ADI-20118 (IgG1 format expressed in yeast) blocked human OX40L-FITC binding to different levels, with only the FITC signal blocking of ADI-20051 is slightly stronger than that of OX40L, with an MFI value of 17,225, compared with 19,344. ADI-20048, ADI-20065, ADI-20066, ADI-20078, ADI-20096, ADI-20112, ADI-20113 and ADI-20118, show higher MFI values than OX40L, at 34,342, 33,687, 32,813, 28,112, 31,917, 22,525, 24,020.5, and 26,580.5, respectively (Table 17).

TABLE 17

Blocking of OX40L binding to OX40 expressed on CHO cells by flow cytometry of antibodies of the invention in IgG1 format generated in yeast cells

| Antibody | MFI of OX40L signal on CHO-OX40 cells |
|---|---|
| Blank | 5,006 |
| IgG1 control | 35090 |
| Hu106-222 | 25,807 |
| 11D4 | 35,963 |
| OX40L | 19,344 |
| ADI-20048 | 34,342 |
| ADI-20051 | 17,225 |
| ADI-20065 | 33,687 |
| ADI-20066 | 32,813 |
| ADI-20078 | 28,112 |
| ADI-20096 | 31,917 |
| ADI-20112 | 22,525 |
| ADI-20113 | 24,020.5 |
| ADI-20118 | 26,580.5 |

Method 2:

OX40L fused to murine Fc (OX40L-mFc, obtained from AcroBiosystems) was also used followed by anti-murine FC-FITC secondary antibody (Biolegend), using the staining methods, as described in Method 1. Flow cytometry is performed on an Accuri C6 system (BD Biosciences) and MFIs are calculated on the C6 software.

In experiments performed as described in the above assay, ADI-23515-g2 and ADI-20112-g1 (in IgG2 and IgG1 isoforms, respectively, and expressed in CHO cells) although blocked human OX40L fused to mouse Fc (60 µg/ml) binding to OX40 on CHO cells, showing lower blocking activity compared to Pogalizumab, and at similar levels to OX40L (FIG. 1), wherein control IgG4 comprises the heavy chain of SEQ ID NO:178 and the light chain of SEQ ID NO:179 (the same for the IgG4 control in the following content).

Example 5. Agonist Activity of Anti-OX40 Antibody of the Present Invention

1. Plate Bound Antibody T Cell Activation Assay

T cell Isolation is performed as per manufacturer's instructions in the Untouched CD4+ T cell isolation kit (Invitrogen). A magnet fitted with a 1.5 ml tube rack is used to remove unwanted magnetic beads (QIAGEN).

The agonist activity of anti-OX40 antibodies of the present invention may be evaluated by measuring the release of inflammatory cytokines by T cells after T cell activation. 96-well flat-bottom plates (Corning) were coated with suboptimal anti-CD3 (0.25 µg/ml) antibody (Biolegend), and anti-OX40 (6 µg/ml) test antibodies at 37 degrees Celsius for 2 hours or overnight at 4 degrees Celsius. After washing, 100,000 CD4+ primary T cells were added into each well in a total of 200 µl media with 2 µg/ml anti-CD28 antibody (Biolegend) in solution. After 5 days, IL-2 secretion levels were tested by ELISA (Ready-SET-Go!; eBioscience).

In experiments performed as described in the above assay, ADI-20048, ADI-20051, ADI-20065, ADI-20066, ADI-20078, ADI-20096, ADI-20112, ADI-20113 and ADI-20118 in IgG1 format generated in yeast cells, increased IL-2 and IFNg secretion over the IgG4 control, with up to 100-fold increase in IL-2 levels and ~3-fold difference in IFNg levels in the T cells from two different healthy donors (Table 18).

TABLE 18

IL-2 and IFNg secretion upon T cell activation with suboptimal anti-CD3 activation plus antibody of the invention in IgG1 format generated in yeast cells

| | Fold change in IL-2 or IFNg secretion over control | | | |
|---|---|---|---|---|
| Antibody | IL-2 secretion of T cells of Donor 1 | IFNg secretion of T cells of Donor 1 | IL-2 secretion of T cells of Donor 1 | IFNg secretion of T cells of Donor 2 |
| IgG4 control | 1 | 1 | 1 | 1 |
| Hu106-222 | 98.799087 | 3.372629843 | 27.14136126 | 2.238952537 |
| 11D4 | 143.68493 | 3.570898599 | 150.6753927 | 2.481314785 |
| OX40L | 130.30594 | 2.25329761 | 97.4869 | 1.67649 |
| ADI-20048 | 143.34703 | 2.91117065 | 160.581 | 2.03546 |
| ADI-20051 | 157.44292 | 2.87448475 | 165.681 | 1.47095 |
| ADI-20065 | 142.56621 | 2.83099753 | 159.277 | 1.58129 |
| ADI-20066 | 142.39269 | 2.47650453 | 163.351 | 1.52032 |
| ADI-20078 | 152.08219 | 3.4641385 | 148.649 | 2.34984 |
| ADI-20096 | 143.35616 | 3.49443528 | 147.89 | 2.3868 |
| ADI-20112 | 150.83562 | 3.1417972 | 159.66 | 2.98882 |
| ADI-20113 | 141.73059 | 3.32914262 | 143.806 | 1.71399 |
| ADI-20118 | 147.88128 | 2.69579555 | 147.529 | 1.80742 |

2. Soluble Antibody T Cell Activation Assay

Assay 1:

The agonist activity of anti-OX40 antibodies of the present invention may be evaluated by measuring the release of inflammatory cytokines by T cells after T cell activation. 100,000 CD4+ T cells are stimulated by PHA (10 µg/ml, Sigma) and 200 nM anti-OX40 candidate antibodies for 5 days. IL-2 secretion is tested by ELISA (Ready-SET-Go!; eBioscience).

In experiments performed as described in the above assay, ADI-20048, ADI-20051, ADI-20065, ADI-20066, ADI-20078, ADI-20096, ADI-20112, ADI-20113 and ADI-20118 in IgG1 format generated in yeast cells, increased IL-2 secretion over the IgG4 control, with up to 10-fold increases in IL-2 levels from six different healthy donors (Table 19).

TABLE 19

IL-2 secretion upon T cell activation with PHA activation plus antibodies of the invention in IgG1 format generated in yeast cells

| | Fold change in IL-2 secretion over control | | | | | |
|---|---|---|---|---|---|---|
| Antibody | IL-2 secretion of T cells of Donor 1 | IL-2 secretion of T cells of Donor 2 | IL-2 secretion of T cells of Donor 3 | IL-2 secretion of T cells of Donor 4 | IL-2 secretion of T cells of Donor 5 | IL-2 secretion of T cells of Donor 6 |
| IgG4 control | 1 | 1 | 1 | 1 | 1 | 1 |
| Hu106-222 | 0.6542 | 0.602241 | 0.745803 | 0.669903 | 0.541237 | 0.569652 |
| 11D4 | 1.1542 | 1.980392 | 1.551559 | 0.932039 | 2.025773 | 1.514925 |
| OX40L | 2.2757 | 9.509804 | 2.59952 | 2.558252 | 9.384021 | 3.159204 |
| ADI-20048 | 11.173 | 7.358543 | 4.678657 | 11.73301 | 8.515464 | 3.80597 |
| ADI-20051 | 2.229 | 2.515406 | 1.223022 | 1.757282 | 2.646907 | 1.41791 |
| ADI-20065 | 2.9626 | 3.2493 | 1.484412 | 2.684466 | 2.984536 | 1.679104 |
| ADI-20066 | 2.2617 | 2.495798 | 1.371703 | 2.495146 | 2.07732 | 1.350746 |
| ADI-20078 | 10.565 | 4.719888 | 6.429257 | 13.14078 | 5.10567 | 7.365672 |
| ADI-20096 | 1.8879 | 2.857143 | 2.64988 | 4.728155 | 2.430412 | 3.218905 |
| ADI-20112 | 4.2664 | 2.753501 | 2.472422 | 4.218447 | 2.780928 | 2.81592 |
| ADI-20113 | 4.0654 | 5.848739 | 2.285372 | 4.063107 | 5.742268 | 2.365672 |
| ADI-20118 | 7.0841 | 10.36975 | 7.105516 | 6.65534 | 10.15722 | 8.477612 |

Assay 2:

The agonist activity of anti-OX40 antibodies of the present invention may be evaluated by measuring the release of inflammatory cytokines by T cells after T cell activation. 100,000 CD4+ T cells were stimulated with anti-CD3 antibody (Biolegend) (at the concentration of 1 µg/ml), anti-CD28 antibodies (Biolegend) (at the concentration of 2 µg/ml) and 10 µg/ml, 20 µg/ml or 40 µg/ml anti-OX40 antibodies for 5 days. IL-2 secretion is tested by ELISA (Ready-SET-Go!; eBioscience).

In experiments performed as described in the above assay, anti-OX40 antibody ADI-2005720051, ADI-20078, ADI-20112 and ADI-20118, in IgG1 format expressed by HEK293 cells, increased IL-2 secretion over the IgG1 control at 20 ug/ml concentrations or above (Table 20), and also anti-OX40 antibody in IgG2 format expressed by HEK293 cells at all concentrations (Table 21).

reporter assay. Jurkat cells (US, ATCC) overexpressing human OX40 (purchased from Sino) and NFkB-luciferase constructs (NFkB promoter-luc, Promega) were activated with PHA (5 µg/ml; Sigma) or anti-CD3 (2 µg/ml; Biolegend) plus anti-CD28 (2 µg/ml; Biolegend) with anti-OX40 antibody in solution (100 nM) for 18 h, then tested after cell lysis and addition of substrate and bioluminescence measurement on a detection device (Molecular Devices) that indicates relative luciferase expression induction.

In experiments performed as described in the above assay, ADI-20048, ADI-20051, ADI-20065, ADI-20066, ADI-20078, ADI-20096, ADI-20112, ADI-20113 and ADI-20118 in IgG1 format generated in yeast cells increase luciferase expression greater than the IgG4 control, with up to 4-fold increases and 7-fold increases in signal using PHA (Sigma) or anti-CD3 (Biolegend) activation, respectively (Table 22).

TABLE 20

IL-2 secretion upon T cell activation with anti-CD3 antibody, anti-CD28 antibody in solution plus antibody of the invention in IgG1 format generated HEK293 cells

| mAb concentration (µg/ml) | ADI-20051 | ADI-20078 | ADI-200112 | ADI-200118 | IgG1 control | OX40L |
|---|---|---|---|---|---|---|
| 40 | 1.274526678 | 2.724612737 | 2.984509466 | 1.939759036 | 1 | 1.972461274 |
| 20 | 1.450503356 | 1.979026846 | 2.785234899 | 1.431208054 | 1 | 1.687919463 |
| 10 | 0.867399267 | 1.546520147 | 1.820512821 | 0.914285714 | 1 | 4.174358974 |

TABLE 21

IL-2 secretion upon T cell activation with anti-CD3 antibody, anti-CD28 antibody in solution plus antibody of the invention in IgG2 format generated in HEK293 cells

| mAb concentration (µg/ml) | ADI-20051 | ADI-20078 | ADI-200112 | ADI-200118 | IgG1 control | OX40L |
|---|---|---|---|---|---|---|
| 40 | 3.375075988 | 4.989361702 | 8.699088146 | 6.962006079 | 1 | 8.215805471 |
| 20 | 1.162091765 | 3.188539371 | 4.674013224 | 3.815267481 | 1 | 6.658585454 |
| 10 | 14.44130127 | 15.82602546 | 26.78925035 | 22.0466761 | 1 | 3.490806223 |

Assay 3:

The agonist activity of anti-OX40 antibodies of the present invention may be evaluated by measuring the release of inflammatory cytokines by T cells after T cell activation. 100,000 PBMC are stimulated with PHA (5 µg/ml; Sigma) and 5 µg/ml, 10 µg/ml or 20 µg/ml anti-OX40 antibodies for 5 days before testing IL-2 secretion by ELISA (Ready-SET-Go!; eBioscience).

Figure 2:
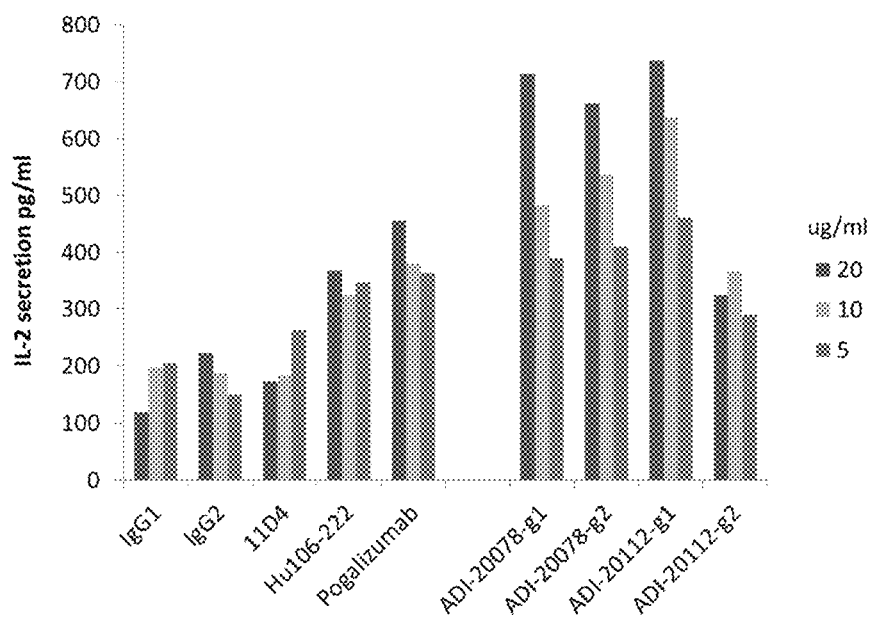
FIG. 2 shows IL-2 secretion upon T cell activation in PBMCs activated by PHA plus the antibody of the present invention in the form of IgG1 and IgG2 produced in CHO cells.

In experiments performed as described in the above assay, ADI-20078-g1 (IgG1 format), ADI-20078-g2 (IgG2 format), ADI-20112-g1 (IgG1 format), and ADI-20112-g2 (IgG2 format), expressed in CHO cells, increased IL-2 secretion over the IgG1 control and IgG2 controls at 5 µg/ml, 10 µg/ml, and 20 µg/ml, higher than control antibodies 11D4, Hu106-222, and pogalizumab benchmarks (FIG. 2).

3. Luciferase Reporter T Cell Activation Assay

The agonist activity of anti-OX40 antibodies of the present invention may be evaluated by measuring the promotion of NFkB-mediated transcriptional activation in a luciferase

TABLE 22

Luciferase reporter detection in Jurkat stably transfected with human OX40 and NFkB promoter-luc by PHA or anti-CD3 and anti-CD28 stimulation plus the stimulation of antibodies of the invention in IgG1 format generated in yeast cells

| Antibody | NFkB-Luc fold change in Jurkat stimulated by PHA+ anti-CD28 | NFkB-Luc fold change in Jurkat stimulated by anti-CD3+ anti-CD28 |
|---|---|---|
| IgG4 control | 1 | 1 |
| Hu106-222 | 1.929795 | 1.774336 |
| 11D4 | 1.955867 | 1.480546 |
| OX40L | 4.823335 | 4.049893 |
| ADI-20048 | 3.626118 | 5.76953 |
| ADI-20051 | 1.832293 | 1.289518 |
| ADI-20065 | 2.112869 | 1.19408 |
| ADI-20066 | 2.085514 | 1.959262 |
| ADI-20078 | 4.623152 | 7.455066 |
| ADI-20096 | 4.567301 | 5.122978 |
| ADI-20112 | 4.193475 | 3.972688 |
| ADI-20113 | 3.794002 | 3.97635 |
| ADI-20118 | 3.990324 | 5.265868 |

Figure 3:
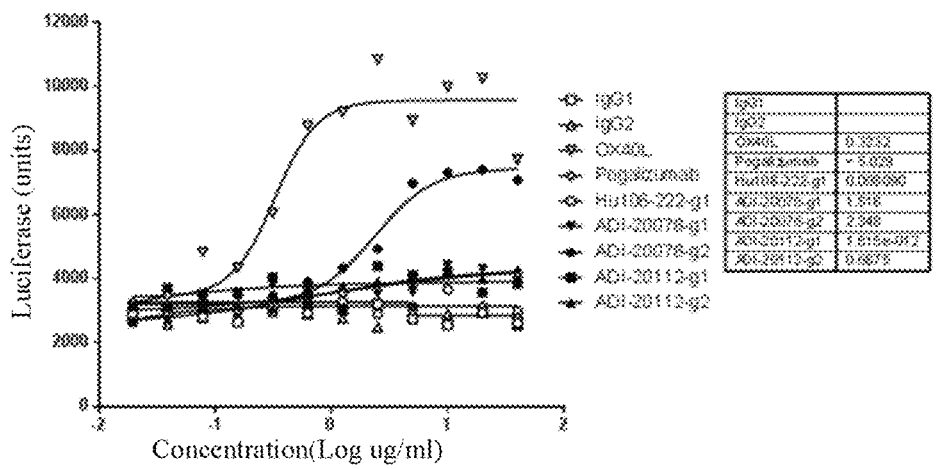
FIG. 3 shows luciferase reporter detection in Jurkat stably transfected with human OX40 and NFkB promoter-luc by anti-CD3 and anti-CD28 stimulation plus antibodies of the invention in IgG1 or IgG2 format generated in CHO cells.

In experiments performed as described in the above assay, using anti-CD3 and anti-CD28 dynabeads (Invitrogen) as an activator, ADI-20078-g2 is a human IgG2 OX40 antibody transiently expressed in CHO cells that increased luciferase expression greater than the IgG control (IgG1 and IgG2 control), ADI-20078-g1 (human IgG1 OX40 antibody expressed in CHO cells), ADI-20112-g1 (human IgG1 OX40 antibody expressed in CHO cells), ADI-20112-g2 (human IgG2 OX40 antibody expressed in CHO cells), pogalizumab and Hu106-222 (FIG. 3).

Figure 4:
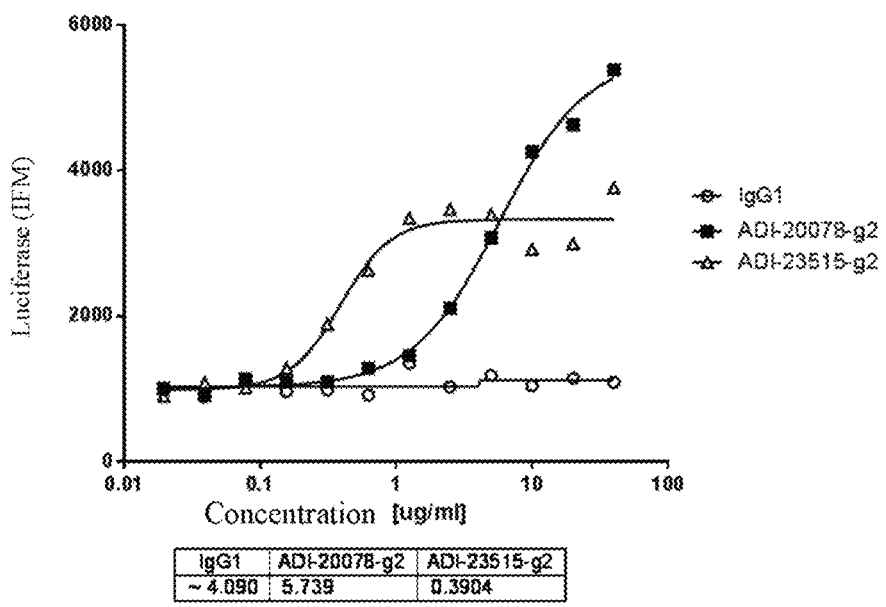
FIG. 4 shows luciferase reporter detection in Jurkat stably transfected with human OX40 and NFkB promoter-luc by anti-CD3 and anti-CD28 stimulation plus antibodies of the invention in IgG2 format generated in CHO cells.

In experiments performed as described in the above assay, ADI-20078-g2 is a human IgG2 OX40 antibody expressed in CHO cells that increases luciferase expression greater than the IgG control (IgG1 control), and ADI-23515-g2 is an affinity matured human IgG2 OX40 antibody expressed in CHO cells that has a lower EC50 value of 0.3904 nM compared to ADI-20078-g2 with an EC50 value of 5.739 nM (FIG. 4).

Figure 5:
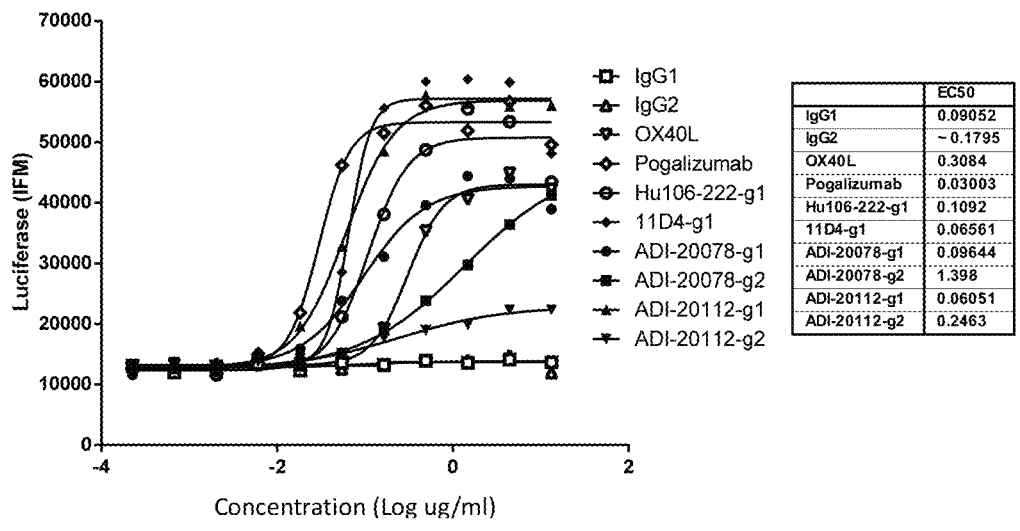
FIG. 5 shows luciferase reporter detection in Jurkat stably transfected with human OX40 and NFkB promoter-luc by anti-CD3 and anti-CD28 stimulation plus antibodies of the invention in IgG1 or IgG2 formats generated in CHO cells, wherein the Jurkat is mixed with Raji cells.

In experiments performed as described in the above assay, adding Raji cells (ATCC) to provide co-stimulation signals and FcgRIIb for IgG cross-linking, ADI-20112-g1 is a human IgG1 OX40 antibody, ADI-20112-g2 is a human IgG2 OX40 antibody, ADI-20078-g1 is a human IgG1 OX40 antibody, ADI-20078-g2 is a human IgG2 OX40 antibody, all expressed in CHO cells, increased luciferase expression through OX40 activation greater than the IgG control (IgG1 control and IgG2 control), with EC50 values of 0.06051 nM, 0.2463 nM, 0.09644 nM, and 1.398 nM, respectively. ADI-20112-g1 is equivalent to or a better agonist compared with pogalizumab, Hu106-222 and 11D4 (FIG. 5).

Figure 6:
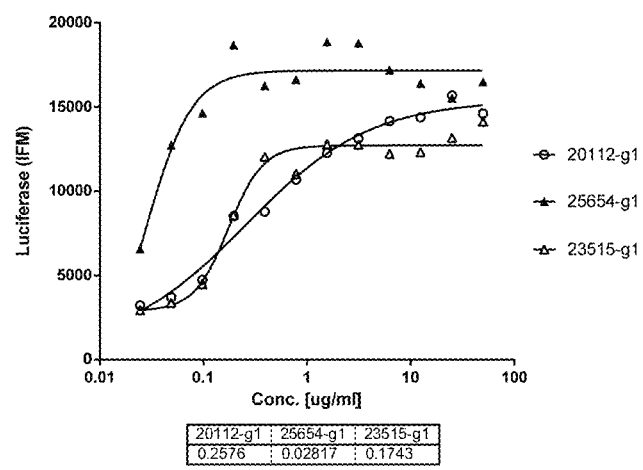
FIG. 6 shows the luciferase reporter detection in Jurkat stably transfected with human OX40 and NFkB promoter-luc by anti-CD3 and anti-CD28 stimulation plus antibodies of the invention in IgG1 formats generated in CHO cells, wherein the Jurkat is mixed with Raji cells.

In experiments performed as described in the above assay, ADI-25654-g1, a human IgG1 OX40 antibody generated in CHO cells, is an affinity matured form of ADI-20112-g1, a human IgG1 OX40 antibody generated in CHO cells; and ADI-23515-g1, a human IgG1 OX40 antibody generated in CHO cells, is an affinity matured form of ADI-20078-g1, a human IgG1 OX40 antibody generated in CHO cells. ADI-25654-g1 and ADI-23515-g1 show better agonist activity with EC50 values of 0.02817 nM, and 0.1743 nM respectively, compared with ADI-20112-g1 that has an EC50 of 0.2576 nM (FIG. 6).

4. Mixed Lymphocyte Reaction (MLR)/DC T Cell Co-Culture Assay

The agonist activity of OX40 signals by antibodies of the present invention may be evaluated by measuring the release of IL-2 during a mixed lymphocyte reaction or DC-T cell co-culture assays. $2 \times 10^6$ PBMC are plated per well in a 6 well tissue culture plate or T25 tissue culture flask. Cells are incubated for 2-3 hours, to allow for adherence of monocytes.

Immature myeloid moDCs are generated by culturing monocytes ($1 \times 10^6$ cells/ml) from PBMC in X-VIVO 15 media containing 1% AB serum, 10 mM HEPES, 50 µM β-Me, IL-4 (1000 U/ml) and GM-CSF (1000 U/ml), or 25-50 ng/ml of each. After 2 days fresh medium supplemented with IL-4 and GM-CSF is added. On Day 5, cells are either frozen or maturation is induced by adding a stimulation cocktail containing rTNFa (1000 U/ml), IL-1b (5 ng/ml), IL-6 (10 ng/ml) and 1 µM PGE$_2$ for 2 days at a cell density of $3 \times 10^5$ cells/ml. T cell Isolation is performed as per manufacturer's instructions in the Untouched CD4+ T cell isolation kit (Invitrogen). A magnet fitted with a 1.5 ml tube rack is used to remove unwanted magnetic beads (QIAGEN).

100,000-200,000 isolated T cells (from donor) are mixed with 10,000-20,000 allogeneic moDCs (as above) in a total volume of 200 µl in 96-round bottom tissue culture plates for 4-5 days at 37° C. SEE (1 ng/ml) was added to increase T cell activation. Test antibodies are added at the beginning of the MLR and incubated throughout the culture period. Detection of IL-2 is carried out as per manufacturer's instructions (eBioscience). OD measurements are determined on a Multiskan FC system (Thermo).

Figure 7:
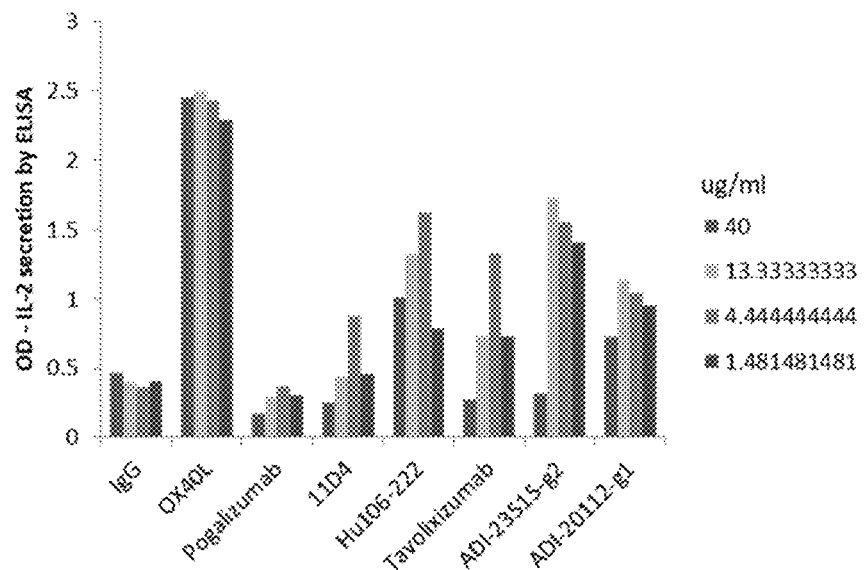
FIG. 7 shows a DC co-culture assay with SEE (1 ng/ml) and the OX40 antibody of the present invention in IgG1 or IgG2 format produced in CHO cells.

In experiments performed as described in the above assay, ADI-23515-g2, a human antibody in IgG2 format expressed in CHO cells, and ADI-20112-g1, a human IgG1 antibody expressed in CHO cells, increased IL-2 when using at ~13.3 µg/ml, ~4.4 µg/ml and ~1.48 µg/ml concentrations, equally or better than pogalizumab, 11D4, Hu106-222, and tavolixizumab. Pogalizumab had poor agonist activity at all concentrations, and 40 µg/ml of 11D4, Hu106-222, tavolixizumab, ADI-23515-g1, and ADI-20112-g1 showed lower agonist activity at the highest concentration of OX40 antibody of 40 µg/ml (FIG. 7, wherein IgG control is IgG1 control).

Example 6. Detection of T Cell Activation of OX40-Mediated by OX40L by the Antibodies of the Present Invention Based on Luciferase Reporter The blocking activity of anti-OX40 antibodies of the present invention may be evaluated by measuring the propensity of the antibody in blocking OX40L-mediated T cell activation of OX40. Activation property of T cells are evaluated by NFkB mediated transcription activity (c.f., Example 5). Jurkat cells (US ATCC) overexpressing human OX40 and NFkB-luciferase constructs (NFkB promoter-luc, US Promega) were activated with anti-CD3 (2 µg/ml; Biolegend), anti-CD28 (2 µg/ml (Biolegend) and recombinant OX40L (60 µg/ml; Acro Biosystems) plus increasing concentrations of anti-OX40 antibody (ADI-0112-g1 in IgG1 format expressed in CHO cells of the present invention, ADI-23515-G2 in IgG2 format expressed in CHO cells of the present invention) and IgG4 control, Pogalizumab, OX40L (obtained AcroBiosystems) in solution for 18 h, then tested after cell lysis and addition of substrate and absorbance measurement.

Figure 8:
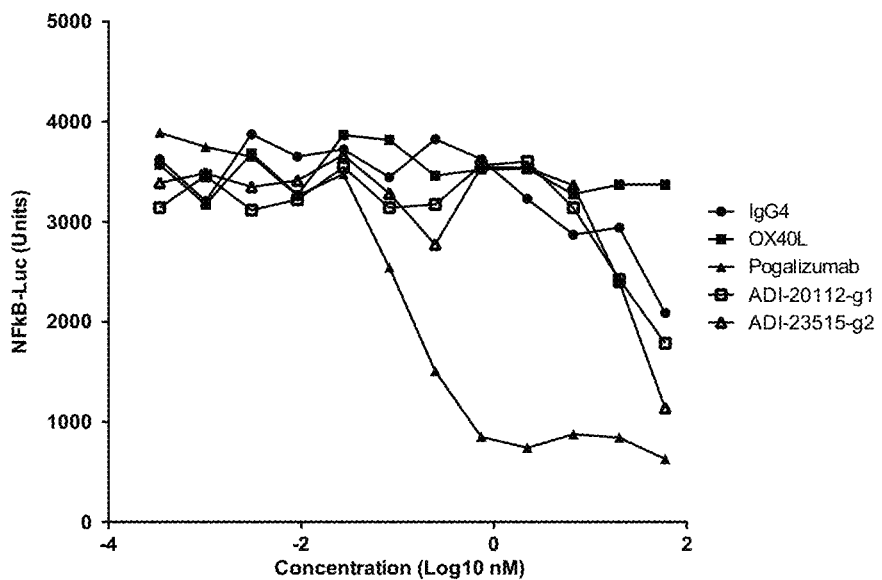
FIG. 8 shows the luciferase reporter detection in Jurkat cell stably transfected with human OX40 and NFkB promoter-luc by stimulation of anti-CD3 and anti-CD28 plus recombinant OX40L and antibodies of the invention in IgG1 or IgG2 formats generated in CHO cells or control (IgG4 Pogalizumab, OX40L), mixed with Raji cells.

Pogalizumab readily blocked OX40L-based activation at concentrations of more than about 0.08 nM or above, whereas ADI-20112-g1, a human IgG1 OX40 antibody generated in CHO cells, and ADI-23515-g2, a human IgG2 OX40 antibody generated in CHO cells, blocked OX40L-based activation at 20 nM and above (FIG. 8).

Example 7. Antibody Dependent Cell-Mediated Cytotoxicity of the Antibody of the Present Invention Luciferase Reporter Based Antibody Dependent Cell-Mediated Cytotoxicity Assays Antibody dependent cell-mediated cytotoxicity (ADCC) activity of OX40 antibodies can be measured using a luciferase reporter assay (Promega). Target cells (CHO cells expressing human OX40, prepared as above) are seeded at $1.2 \times 10^6$ cells/ml in 25 µl RPMI media (Gibco) containing 10% Ultra-Low IgG FBS(Sigma). 1:3 serial dilutions of 1 µg/ml antibody are made, adding 25 µL/well. $6 \times 10^6$ cells/ml ADCC effector cells (Promega) are seeded and incubated for 6 hours at 37° C. with 5% CO$_2$. 75 µl luciferase assay reagent (Promega) is added and the mixtures are brought to RT for 20 minutes. The plate is centrifuged for 2 minutes at 300 g/min. 120 µl of cell supernatant is carefully transferred to Optiplates. The plate is read in luminometer. Curves are fitting and EC50 of antibody response is determined using GraphPad Prism 6.0.

Figure 9:
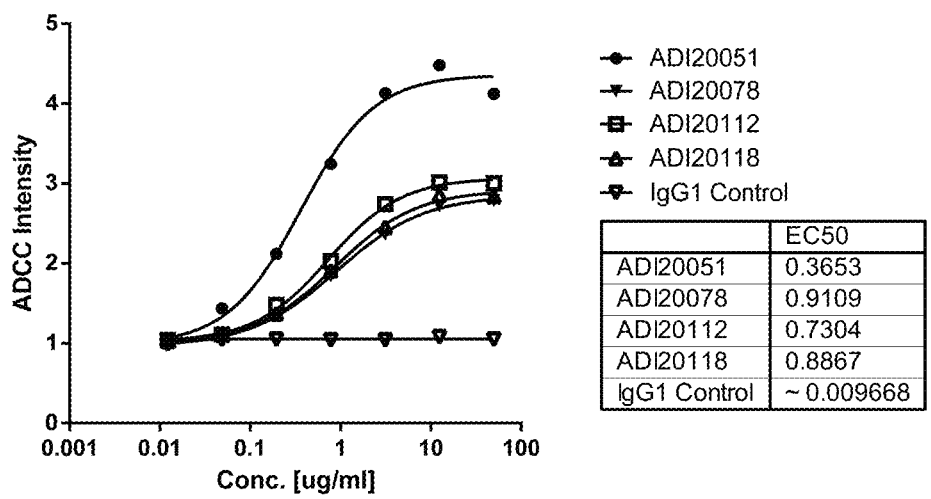
FIG. 9 shows the ADCC activity to CHO cells expressing human OX40 in luciferase reporter based system by the antibody of the invention in IgG1 format generated in HEK293 cells.
Figure 10:
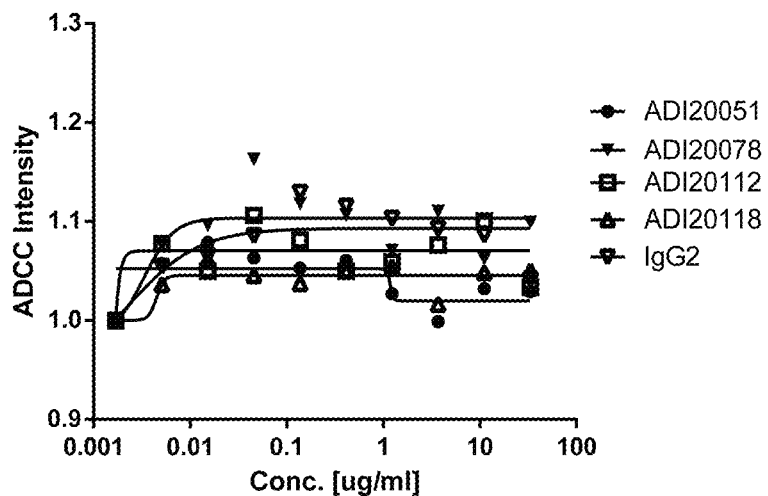
FIG. 10 shows ADCC activity to CHO cells expressing human OX40 in luciferase reporter based system by the antibody of the invention in IgG2 format generated in HEK293 cells.

In experiments performed as described in the above assay, ADI-20051, ADI-20078, ADI-20112, and ADI-20118, in IgG1 format expressed in HEK293 cells, increase luciferase expression with EC50 values of 0.3653, 0.9109, 0.7304, and 0.8867 nM, respectively (FIG. 9). ADI-20051, ADI-20078, ADI-20112, and ADI-20118, in IgG2 isotype expressed in HEK293 cells, did not elicit ADCC activity (FIG. 10).

Example 8. Anti-Tumor Activity of the Antibodies of the Present Invention

Anti-tumour efficacy of OX40 antibodies of the invention can be studied in humanized mouse models (NOG hu-PBMC LoVo tumour model).

LoVo human colon cancer cells (ATCC #CCL-229) were cultured according to ATCC instructions (F-12K). Two million LoVo cells suspended in 0.2 mL PBS contained with 0.66 million human PBMCs were implanted in the right flank of female NOG (Beijing Vital River Laboratory Animal Technology Co.).

Tumors and body weights were measured twice a week throughout the study, and mice were euthanized when the tumors reached endpoint or when mice had >20% body weight loss. At 3 days post implantation, mice were randomized into groups of 6-7 each that the mean tumor volume estimated with digital calipers, and tumor volume in mm$^3$ was calculated by the formula: (width)2×length/2 for each group was approximately 50 mm$^3$.

On day 3, 7, 11, and 14 (or 15) post implantation, mice were dosed intraperitoneally (IP) with PBS, 10 mg/kg of relevant IgG isotype control (equitech-Bio), or anti-OX40 antibodies (ADI-20112-g1, human OX40 antibody in IgG1 format expressed in CHO cells or ADI-23515-g2, human OX40 antibody in IgG1 format expressed in CHO cells).

Figure 11:
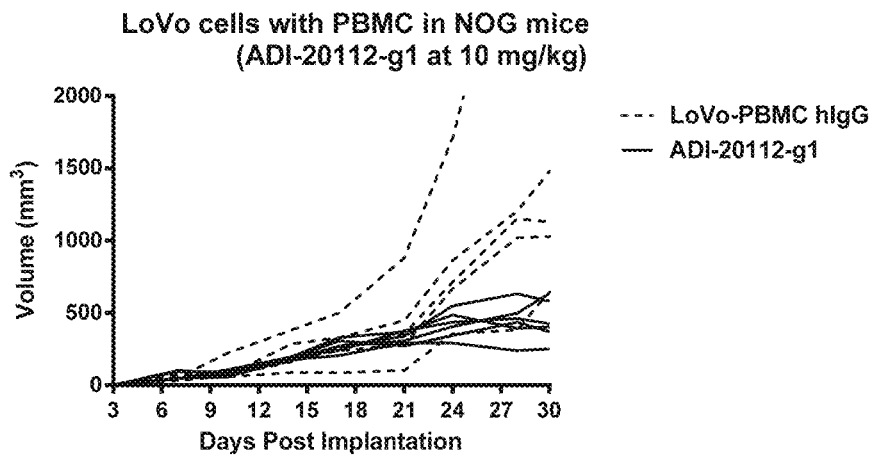
FIG. 11 shows the tumor growth curve of an individual mouse in the Hu-PBMC LoVo tumor mouse model by administering OX40 antibody ADI-20112-g1 antibodies of the present invention in IgG1 format generated in CHO cells to NOG mice (each curve represents the data of one mouse).
Figure 13:
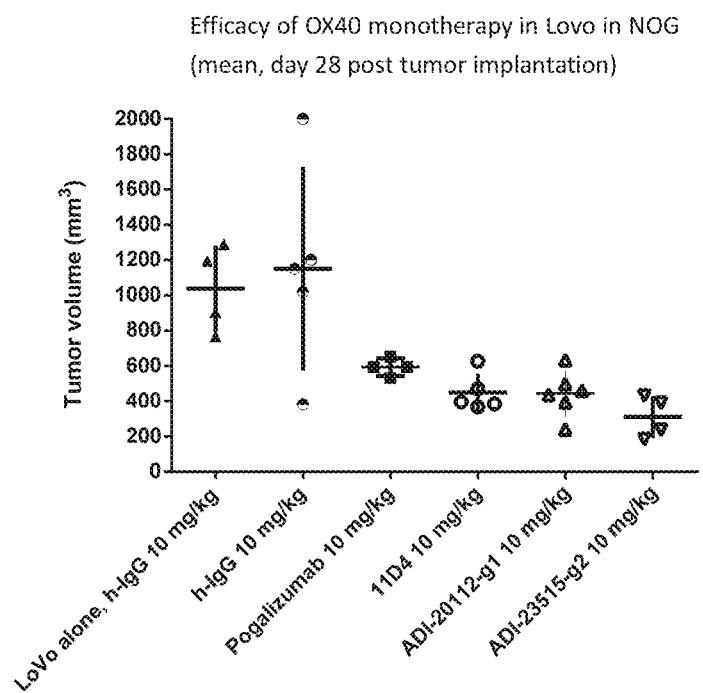
FIG. 13 shows a Hu-PBMC LoVo tumor mouse model by administering OX40 antibody ADI-20112-g1 and ADI-23515-g2 of the present invention in IgG1 and IgG2 format generated in CHO cells to NOG mice. It shows the final tumor volume measurement on day 28 after tumor implantation.

In experiments performed as described in the above assay, ADI-20112-g1, a human OX40 antibody in IgG1 format expressed in CHO cells reduces tumour volume growth compared with IgG control (equitech-Bio) (FIG. 11), and compared with pogalizumab and 11D4 (FIG. 13). In experiments performed as described in the above assay, ADI-23515-g2, a human OX40 antibody in IgG2 format expressed in CHO cells significantly reduces tumour volume 20112-IgG1 (IgG1 format, expressed in CHO cells), ADI-20112-IgG2 (IgG2 format, expressed in CHO cells) i.v. doses of 10 mg/kg antibodies to female Balb/C mice. The dose volume was injected into the mouse based on body weight.

Timing for blood collection begun at the beginning of dosing. For i.v. administration, timepoints included 0.083 hours (5 minutes) up to day 21. Blood was collected from three mice for each time point. Approximately 100 ul of blood was collected into microcentrifuge tubes. The blood samples were stored on ice for at least 10 minutes at a speed setting of 3000 RPM to obtain approximately 40-50 ul of serum.

Serum concentrations of antibodies dosed to mice were determined by immunoassay using either a plate-based sandwich ELISA method. Briefly, microtiter plate (Nunc, cat #442404) was coated with OX40 (ACRO, cat #1044-5CIS1-AF) at 1 ug/mL in 0.2 M CBS (PH9.4) at 4° C. overnight. After washing, the plate was then blocked with 5% non-fat milk for 1.5 h at ambient temperature, mice serum samples were applied to coated plates for 1.5 h at RT. Anti-OX40 antibody was used to prepare the standard curve in pooled normal mouse serum with a range of 0.315-80 ng/mL, and QC samples.

Bound anti-OX40 antibody was detected using a horseradish peroxidase-labeled goat anti-human Fc antibody (Bethyl, cat #A80-104P-84) diluted at 1:100,000 in 5% BSA in 0.05% PBST (0.05% Tween in PBS). After a wash step, the plate was developed with TMB for 10-15 min at room temperature, which was stopped after 5 min by the addition of 2 N sulfuric acid. The optical density was measured at 450 nm with a 620 nm reference wavelength subtraction, using a Thermo ELISA plate reader (Multiskan FC). Quantitation was based on a four-parameter logistic (1/Y2) regression of the prepared standard curves using Skanit Software3.1 (Thermo).

PK parameters (Cmax, AUC, $t_{1/2}$, Cl, and Vss) were analyzed by PKSolver software based on a non-compartmental model with means of concentration of each group (Table 23).

TABLE 23

PK summary of OX40 comparison in female Balb/C mice following a single 10 mg/kg bolus administration

Figure 12:
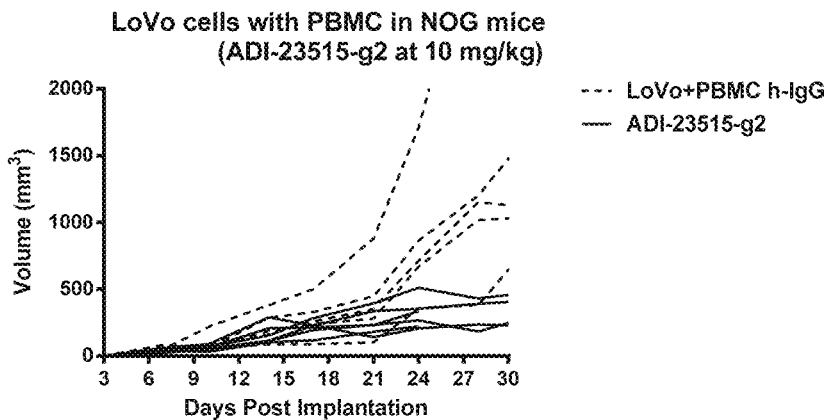
FIG. 12 shows the tumor growth curve of an individual mouse in the Hu-PBMC LoVo tumor mouse model by administering OX40 antibody ADI-23515-g2 antibodies of the present invention in IgG2 format generated in CHO cells to NOG mice (each curve represents the data of one mouse).
Figure 14:
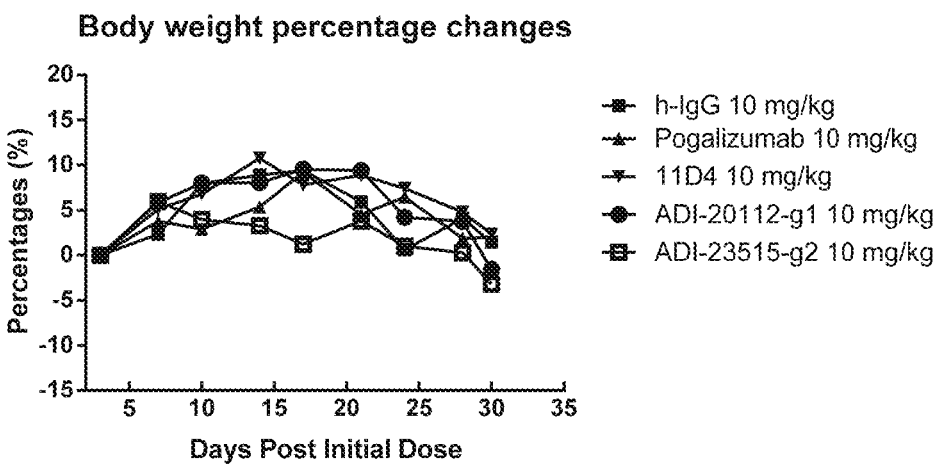
FIG. 14 shows a Hu-PBMC LoVo tumor mouse model by administering OX40 antibody ADI-20112-g1 and ADI-23515-g2 of the present invention in IgG1 and IgG2 format generated in CHO cells to NOG mice. It shows body weight change of the mouse after dosing.

| | | Parameters | | | | | |
|---|---|---|---|---|---|---|---|
| Study | Compound | $C_{max}$ (ug/mL) | $AUC_{0-t}$ (ug*hr/mL) | $AUC_{0-inf\_obs}$ (ug/mL*hr) | CL (mL/hr/kg) | $t_{1/2}$ (hr) | $V_{ss}$ (mg/kg)/(ug/mL) |
| PK of OX40 | ADI-20078-IgG1 | 135 | 24123 | 39579 | 0.00025 | 386 | 0.13 |
| | ADI-20078-IgG2 | 168 | 29502 | 47639 | 0.00021 | 365 | 0.11 |
| | ADI-20112-IgG1 | 184 | 27409 | 37486 | 0.00026 | 264 | 0.10 |
| | ADI-20112-IgG2 | 204 | 39175 | 55246 | 0.00018 | 310 | 0.07 | growth compared with IgG control (equitech-Bio) (FIG. 12), pogalizumab and 11D4 (FIG. 13). ADI-20112-g1 and ADI-23515-g2 do not significantly affect mouse body weight compared with IgG control, pogalizumab, and 11D4 (FIG. 14).

Example 9: Pharmacokinetic Assay

Pharmacokinetic data was assessed following ADI-20078-IgG1 (IgG1 format, expressed in CHO cells), ADI-20078-IgG2 (IgG2 format, expressed in CHO cells), ADI- Example 10. Study on Pharmaceutical Efficacy of Anti-OX40 Antibody in Combination with Anti-PD-1 Antibody on MC38 Tumor-Bearing OX40 Transgenic Mice In this study, MC38 (mouse intestinal cancer cells) tumor-bearing OX40 transgenic mice were used to study on the synergistic antitumor efficacy of anti-OX40 antibody ADI-20112-IgG1 (referred as ADI-20112 in this example and in FIG. 15) at different doses in combination with anti-PD1 antibody C. Antibody C is a monoclonal antibody against the programmed death receptor 1 (PD-1) (Patent application number: PCT/CN2017/072190).

Human OX40 Transgenic Mouse

Female human OX40 transgenic mice with C57Bl/6 background (approximately 8 weeks old) were purchased from Shanghai Southern Model Biotechnology Co., Ltd. The mice were domesticated for 7 days after arrival and then the study was started.

Cell

MC38 murine colon cancer cells were purchased from Heyuan Biotechnology (Shanghai) Co., Ltd. and routinely subcultured for subsequent in vivo experiments strictly according to the instructions. The cells were collected by centrifugation, resuspended in sterile PBS and adjusted to a cell density of 5×10e6/ml. On day 0, 0.2 ml of the cell suspension was subcutaneously inoculated (1×10 6 cells/mouse) into the right abdomen region of human OX40 transgenic mice to establish a MC38-hOX40 tumor-bearing mouse model.

Administration

Six days after tumor cell inoculation, the tumor volume of each mouse was measured, and mice with a tumor volume ranging from 87.4 mm$^3$ to 228.4 mm$^3$ were selected and grouped according to the tumor volume on average, so that the average initial volume of each group was about 110 mm$^3$.

The mice were divided into 7 groups (7 mice per group), and each group was intraperitoneally injected with the following doses of antibody:

Group 1 (control group): h-IgG (equitech-Bio), 10 mg/kg;
Group 2: anti-OX40 antibody (ADI-20112), 0.1 mg/kg;
Group 3: anti-OX40 antibody (ADI-20112), 1 mg/kg;
Group 4: anti-OX40 antibody (ADI-20112), 10 mg/kg;
Group 5: PD-1 antibody (Antibody C), 0.5 mg/kg;
Group 6: anti-OX40 antibody (ADI-20112) 1 mg/kg+ PD-1 antibody (Antibody C) 0.5 mg/kg;
Group 7: Anti-OX40 antibody (ADI-20112) 10 mg/kg+ PD-1 antibody (Antibody C) 0.5 mg/kg.

Reagent Injection

On the 6th day after inoculation, each group of mice was administered with the above 7 groups of reagents, respectively, by intraperitoneal injection at a frequency of 2 times/week for 2 weeks.

Analysis:

Tumors and body weight were measured twice a week from day 6 (before dosing) throughout the study and monitored continuously for 4 weeks. The maximum length axis (L) and the largest width axis (W) of the tumor were measured using a vernier caliper, and the tumor volume (V) was calculated as follows: $V=L \times W^2/2$. Tumor size from each group of mice was plotted against time. Analysis of variance (ANOVA) was used to determine statistical significance. P value of <0.05 was considered to be statistically significant in all analyses.

At the end of the experiment at Day 29, the mice were euthanized. The isolated tumor tissues were photographed and weighed, and the tumor weight and volume (tumor terminal volume) of each group were measured, and the relative tumor growth inhibition rate (TGI (%)) was calculated.

Result

The results of the experiment showed that after administration for 1 week, relative to group 1 (h-IgG-10 mg/kg), group 2-4 (ADI-20112-0.1 mg/kg, ADI-20112-1 mg/kg, ADI-20112-10 mg/kg) inhibited tumor growth in MC38-hOX40 tumor-bearing mice, and the tumor volume and tumor weight decreased, and tumor growth also slowed down, in a dose-dependent manner. The test results also showed that the anti-OX40 antibody ADI-20112 of the present invention exhibited a good synergistic antitumor effect with the anti-PD-1 mAb antibody C. The specific results are as follows.

Figure 15:
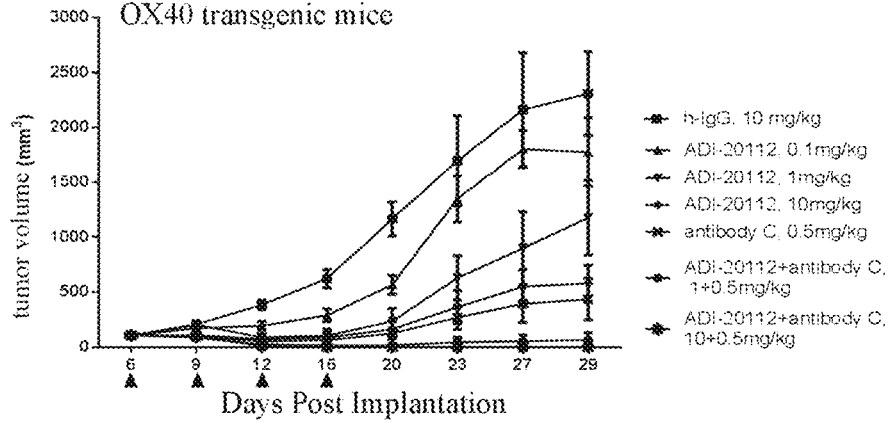
FIG. 15 shows the study on efficacy of anti-OX40 antibody in combination with anti-PD-1 antibody in MC38 tumor-bearing OX40 transgenic mice.

As shown in FIG. 15, after 1 week of administration, relative to group 1 (h-IgG-10 mg/kg group), group 2 (ADI-20112-0.1 mg/kg group) had a slower tumor growth while group 3-7 (ADI-20112-1 mg/kg group, ADI-20112-10 mg/kg group, antibody C-0.5 mg/kg group, ADI-20112-1 mg/kg+antibody C-0.5 mg/kg, ADI-20112-10 mg/kg+antibody C-0.5 mg/kg) showed significant anti-tumor effects. Tumor growth in mice of group 1 (h-IgG-10 mg/kg administration group) to 500 mm$^3$ required 14 days, whereas group 2 (ADI-20112-0.1 mg/kg administration group) required 19 days, group 3 (ADI-20112-1 mg/kg group) required 22 days, group 4 (ADI-20112-10 mg/kg group) required 26 days, group 5 (antibody C-0.5 mg/kg group), group 6 (ADI)-20112-1 mg/kg+antibody C-0.5 mg/kg group), group 7 (ADI-20112-10 mg/kg+antibody C-0.5 mg/kg group) had an average tumor volume of less than 500 mm$^3$ within 29 days.

When the experiment was terminated after 29 days, in some experimental groups, the mouse tumor completely disappeared. Table 24 below summarizes the number of mice in each group with complete tumor disappearance.

TABLE 24 the number of mice in each group with complete tumor disappearance

| Group | Administration(Antibody, dose) | The number of mice with complete tumor disappearance |
| --- | --- | --- |
| Group 1 | h-IgG, 10 mg/kg | 0/7 |
| Group 2 | ADI-20112, 0.1 mg/kg | 0/7 |
| Group 3 | ADI-20112, 1 mg/kg | 0/7 |
| Group 4 | ADI-20112, 10 mg/kg | 0/7 |
| Group 5 | Antibody C, 0.5 mg/kg | 3/7 |
| Group 6 | ADI-20112 + antibody C, 1 + 0.5 mg/kg | 6/7 |
| Group 7 | ADI-20112 + antibody C, 10 + 0.5 mg/kg | 7/7 |

As shown in the above table, in group 5 (antibody C-0.5 mg/kg group), 3 mice had complete tumor disappearance; 6 mice in group 6 (20112-1 mg/kg+antibody C-0.5 mg/kg group) had complete tumor disappearance; 7 mice in group 7 (20112-10 mg/kg+antibody C-0.5 mg/kg) had complete tumor disappearance.

In addition, the present invention also calculated the relative tumor growth inhibition rate in mice of each group at the end of the experiment on Day 29. The relative tumor growth inhibition rate is calculated as follows:

Relative tumor growth inhibition rate $TGI$ (%)=$100\% \times (Tvol_{control} - Tvol_{treated})/(Tvol_{control} - Tvol_{predose})$ wherein $Tvol_{control} - Tvol_{treated}$=tumor terminal volume after administration in the control group−tumor terminal volume after administration in the drug-administered group; $Tvol_{control} - Tvol_{predose}$=tumor terminal volume after administration in the control group−tumor volume before administration in the control group (Tumor volume before administration on Day 6).

The calculation results are shown in Table 25 below:

TABLE 25

Effect of anti-OX40 antibody, anti-PD1 antibody, anti-OX40 antibody + anti-PD1 antibody on tumor tissue growth of tumor-bearing mice (mm$^3$, Mean ± SD, n = 7;)

| Group | Administration(Antibody, dose) | tumor at the end of the experiment (tumor terminal volume) | TGI(%) |
|---|---|---|---|
| Group 1 | h-IgG, 10 mg/kg | 2531.83 ± 1037.94 | N/A |
| Group 2 | ADI-20112, 0.1 mg/kg | 1859.82 ± 508.64# | 28% |
| Group 3 | ADI-20112, 1 mg/kg | 1176.17 ± 897.65 | 56% |
| Group 4 | ADI-20112, 10 mg/kg | 579.38 ± 439.83 | 81% |
| Group 5 | Antibody C, 0.5 mg/kg | 435.07 ± 498.04 | 86% |
| Group 6 | ADI-20112 + antibody C, 1 + 0.5 mg/kg | 66.25 ± 175.27 | 102% |
| Group 7 | ADI-20112+antibody C, 10 + 0.5 mg/kg | 0.00 ± 0.00 | 104% | indicated in this statistic analysis, n = 6(20112-0.1 group, mice No. 3 died due to tumor rupture)

The results of the experiment showed in group 6 (ADI-20112-1 mg/kg+antibody C-0.5 mg/kg group) and group 7 (ADI-20112-10 mg/kg+antibody C-0.5 mg/kg group), tumor growth inhibition rate was 102% and 104%, respectively, and the anti-OX40 antibody showed synergistic anti-tumor effects in combination with the anti-PD1 antibody.

The invention claimed is:

1. An anti-OX40 antibody or antigen-binding fragment thereof comprising a heavy chain variable region (HCVR) and a light chain variable region (LCVR), wherein:
   1) The HCVR comprises three complementarity determining regions HCDR1, HCDR2 and HCDR3 contained in the HCVR as shown in SEQ ID NO:106, and the LCVR comprises the LCDR1, LCDR2 and LCDR3 sequences contained in the LCVR as shown in SEQ ID NO:130;
   2) The HCVR comprises three complementarity determining regions HCDR1, HCDR2 and HCDR3 contained in the HCVR as shown in SEQ ID NO:106, and the LCVR comprises the LCDR1, LCDR2 and LCDR3 sequences contained in the LCVR as shown in SEQ ID NO:131;
   3) The HCVR comprises three complementarity determining regions HCDR1, HCDR2 and HCDR3 contained in the HCVR as shown in SEQ ID NO:107, and the LCVR comprises the LCDR1, LCDR2 and LCDR3 sequences contained in the LCVR as shown in SEQ ID NO:130;
   4) The HCVR comprises three complementarity determining regions HCDR1, HCDR2 and HCDR3 contained in the HCVR as shown in SEQ ID NO:108, and the LCVR comprises the LCDR1, LCDR2 and LCDR3 sequences contained in the LCVR as shown in SEQ ID NO:130;
   5) The HCVR comprises three complementarity determining regions HCDR1, HCDR2 and HCDR3 contained in the HCVR as shown in SEQ ID NO:109, and the LCVR comprises the LCDR1, LCDR2 and LCDR3 sequences contained in the LCVR as shown in SEQ ID NO:130;
   6) The HCVR comprises three complementarity determining regions HCDR1, HCDR2 and HCDR3 contained in the HCVR as shown in SEQ ID NO:110, and the LCVR comprises the LCDR1, LCDR2 and LCDR3 sequences contained in the LCVR as shown in SEQ ID NO:130; and
   7) The HCVR comprises three complementarity determining regions HCDR1, HCDR2 and HCDR3 contained in the HCVR as shown in SEQ ID NO:111, and the LCVR comprises the LCDR1, LCDR2 and LCDR3 sequences contained in the LCVR as shown in SEQ ID NO:130.

2. An anti-OX40 antibody or antigen-binding fragment thereof, comprising a heavy chain variable region (HCVR) and a light chain variable region (LCVR), wherein the HCVR comprises a complementarity determining region HCDR1, HCDR2 and HCDR3 and the LCVR comprises LCDR1, LCDR2 and LCDR3, wherein the combinations of the HCDR1, HCDR2, HCDR3, LCDR1, LCDR2 and LCDR3 comprised in said antibody or its antigen-binding fragment are represented in the following table:

| combination | the amino acid sequence of HCDR1 | the amino acid sequence of HCDR2 | the amino acid sequence of HCDR3 | the amino acid sequence of LCDR1 | the amino acid sequence of LCDR2 | the amino acid sequence of LCDR3 |
|---|---|---|---|---|---|---|
| (1) | SEQ ID NO: 1 | SEQ ID NO: 17 | SEQ ID NO: 34 | SEQ ID NO: 41 | SEQ ID NO: 47 | SEQ ID NO: 53 |
| (2) | SEQ ID NO: 1 | SEQ ID NO: 17 | SEQ ID NO: 34 | SEQ ID NO: 42 | SEQ ID NO: 48 | SEQ ID NO: 54 |
| (3) | SEQ ID NO: 2 | SEQ ID NO: 18 | SEQ ID NO: 34 | SEQ ID NO: 41 | SEQ ID NO: 47 | SEQ ID NO: 53 |
| (4) | SEQ ID NO: 3 | SEQ ID NO: 19 | SEQ ID NO: 34 | SEQ ID NO: 41 | SEQ ID NO: 47 | SEQ ID NO: 53 |
| (5) | SEQ ID NO: 4 | SEQ ID NO: 20 | SEQ ID NO: 34 | SEQ ID NO: 41 | SEQ ID NO: 47 | SEQ ID NO: 53 |
| (6) | SEQ ID NO: 4 | SEQ ID NO: 21 | SEQ ID NO: 34 | SEQ ID NO: 41 | SEQ ID NO: 47 | SEQ ID NO: 53 |
| (7) | SEQ ID NO: 5 | SEQ ID NO: 22 | SEQ ID NO: 34 | SEQ ID NO: 41 | SEQ ID NO: 47 | SEQ ID NO: 53 |
| (8) | SEQ ID NO: 6 | SEQ ID NO: 23 | SEQ ID NO: 34 | SEQ ID NO: 41 | SEQ ID NO: 47 | SEQ ID NO: 53. |

3. An anti-OX40 antibody or antigen-binding fragment thereof, which comprises a heavy chain variable region HCVR and a light chain variable region LCVR, wherein the combinations of the heavy chain variable region HCVR and light chain variable region LCVR comprised in said antibody or its antigen-binding fragment are represented in the following table:

| combination | HCVR, which comprises or consists of the amino acid sequence as represented in the following SEQ ID NO | LCVR, which comprises or consists of the amino acid sequence as represented in the following SEQ ID NO |
|---|---|---|
| (1) | SEQ ID NO: 106 | SEQ ID ND: 130 |
| (2) | SEQ ID NO: 106 | SEQ ID NO: 131 |
| (3) | SEQ ID NO: 107 | SEQ ID NO: 130 |
| (4) | SEQ ID NO: 108 | SEQ ID NO: 130 |
| (5) | SEQ ID NO: 109 | SEQ ID NO: 130 |
| (6) | SEQ ID NO: 110 | SEQ ID NO: 130 |
| (7) | SEQ ID NO: 111 | SEQ ID NO: 130. |

4. An antibody or antigen-binding fragment thereof of claim 1, which comprises a heavy chain and a light chain, wherein the combinations of the heavy chain and light chain comprised in said antibody or its antigen-binding fragment are in the following table:

| combination | Heavy chain, which comprises or consists of the amino acid sequence represented by the following SEQ ID NO | Light chain,, which comprises or consists of the amino acid sequence represented by the following SEQ ID NO |
|---|---|---|
| (1) | SEQ ID NO: 189 | SEQ ID NO: 168 |
| (2) | SEQ ID NO: 139 | SEQ ID NO: 168 |
| (3) | SEQ ID NO: 140 | SEQ ID NO: 168 |
| (4) | SEQ ID NO: 141 | SEQ ID NO: 168 |
| (5) | SEQ ID NO: 142 | SEQ ID NO: 168 |
| (6) | SEQ ID NO: 143 | SEQ ID NO: 168 |
| (7) | SEQ ID NO: 144 | SEQ ID NO: 168 |
| (8) | SEQ ID NO: 145 | SEQ ID NO: 168 |
| (9) | SEQ ID NO: 146 | SEQ ID NO: 168 |
| (10) | SEQ ID NO: 147 | SEQ ID NO: 168 |
| (11) | SEQ ID NO: 148 | SEQ ID NO: 168 |
| (12) | SEQ ID NO: 149 | SEQ ID NO: 168. |

5. The anti-OX40 antibody or antigen-binding fragment thereof according to claim 1, wherein the antibody is an antibody in IgG1 format or an antibody in IgG2 format or an antibody in IgG4 format or antigen-binding fragment thereof.

6. The anti-OX40 antibody or antigen-binding fragment thereof according to claim 1, wherein the antibody is a monoclonal antibody.

7. The antibody or antigen-binding fragment thereof according to claim 1, wherein the antigen-binding fragment is an antibody fragment selected from the group consisting of Fab, Fab', Fab'-SH, Fv, single chain antibody (scFv) or (Fab')2, diabodies (dAb) or linear antibody.

8. The antibody or antigen-binding fragment thereof according to claim 1, wherein said antibody is a bispecific or multispecific antibody molecule.

9. An isolated nucleic acid encoding an anti-OX40 antibody or antigen-binding fragment thereof according to claim 1.

10. An expression vector comprising the nucleic acid according to claim 9.

11. A mammalian host cell comprising the nucleic acid according to claim 9.

12. A method of preparing an anti-OX40 antibody or antigen-binding fragment thereof comprising culturing the host cell according to claim 11 under conditions suitable for expression of a nucleic acid encoding an anti-OX40 antibody or antigen-binding fragment thereof, optionally isolating the antibody or antigen-binding fragment thereof, and optionally said method further comprises recovering the anti-OX40 antibody or antigen-binding fragment thereof from the host cell.

13. An immunoconjugate comprising the anti-OX40 antibody or antigen-binding fragment thereof according to claim 1 conjugated to a cytotoxic agent.

14. A pharmaceutical composition comprising the anti-OX40 antibody or antigen-binding fragment thereof according to claim 1, and optionally a pharmaceutically acceptable adjuvant, and optionally further comprising one or more other therapeutic agents.

15. A method of activating T cells or inducing T cell mediated antitumor activity or increasing T cell proliferation, survival, effector function, or migration in a subject comprising administering to said subject an effective amount of the anti-OX40 antibody or antigen-binding fragment thereof according to claim 1.

16. A method of treating cancer in a subject comprising administering to said subject an effective amount of the anti-OX40 antibody or antigen-binding fragment thereof according to claim 1.

17. The method of claim 16, further comprising administering to said subject in combination with one or more therapies.

18. The anti-OX40 antibody or antigen-binding fragment thereof according to claim 2, wherein the antibody is a monoclonal antibody.

19. The antibody or antigen-binding fragment thereof according to claim 2, wherein the antigen-binding fragment is an antibody fragment selected from the group consisting of Fab, Fab', Fab'-SH, Fv, single chain antibody (scFv) or (Fab')2, diabodies (dAb) or linear antibody.

20. The antibody or antigen-binding fragment thereof according to claim 8, wherein the bispecific antibody molecule binds to OX40 and PD-1.

21. A pharmaceutical composition according to claim 14, wherein the other therapeutic agent is an anti-PD-1 antibody.

22. The method according to claim 16, wherein said cancer is lung cancer, non-small cell lung cancer, liver cancer, stomach cancer, or colon cancer.

23. The method according to claim 17, wherein the therapies comprise surgery, radiation therapy, and/or administration of another therapeutic agent selected from the group consisting of a chemotherapeutic agent, an anti-angiogenic agent, an anti-PD-1 antibody, an anti-PD-L1 antibody, and an anti-PD-L2 antibody.

24. The method according to claim 23, wherein the anti-angiogenic agent is bevacizumab.

\* \* \* \* \*

```
                        SEQUENCE LISTING

<160> NUMBER OF SEQ ID NOS: 189

<210> SEQ ID NO 1
<211> LENGTH: 9
<212> TYPE: PRT
<213> ORGANISM: Artificial
<220> FEATURE:
<223> OTHER INFORMATION: Synthetic construct

<400> SEQUENCE: 1

Phe Thr Phe Ser Ser Tyr Gly Met His
1               5

<210> SEQ ID NO 2
<211> LENGTH: 9
<212> TYPE: PRT
<213> ORGANISM: Artificial
<220> FEATURE:
<223> OTHER INFORMATION: Synthetic construct

<400> SEQUENCE: 2

Phe Thr Phe Ser Val Tyr Asn Met His
1               5

<210> SEQ ID NO 3
<211> LENGTH: 9
<212> TYPE: PRT
<213> ORGANISM: Artificial
<220> FEATURE:
<223> OTHER INFORMATION: Synthetic construct

<400> SEQUENCE: 3

Phe Thr Phe Ser Ser Arg Asn Met His
1               5

<210> SEQ ID NO 4
<211> LENGTH: 9
<212> TYPE: PRT
<213> ORGANISM: Artificial
<220> FEATURE:
<223> OTHER INFORMATION: Synthetic construct

<400> SEQUENCE: 4

Phe Thr Phe Val Ser Tyr Asn Met His
1               5
```

```
<210> SEQ ID NO 5
<211> LENGTH: 9
<212> TYPE: PRT
<213> ORGANISM: Artificial
<220> FEATURE:
<223> OTHER INFORMATION: Synthetic construct

<400> SEQUENCE: 5

Phe Thr Phe Arg Ser Tyr Asp Met His
1               5

<210> SEQ ID NO 6
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be S, V or R
<220> FEATURE:
<221> NAME/KEY: misc_feature
<222> LOCATION: (5)..(5)
<223> OTHER INFORMATION: Xaa can be V or S
<220> FEATURE:
<221> NAME/KEY: misc_feature
<222> LOCATION: (6)..(6)
<223> OTHER INFORMATION: Xaa can be Y or R
<220> FEATURE:
<221> NAME/KEY: misc_feature
<222> LOCATION: (7)..(7)
<223> OTHER INFORMATION: Xaa can be G, N or D

<400> SEQUENCE: 6

Phe Thr Phe Xaa Xaa Xaa Xaa Met His
1               5

<210> SEQ ID NO 7
<211> LENGTH: 11
<212> TYPE: PRT
<213> ORGANISM: Artificial
<220> FEATURE:
<223> OTHER INFORMATION: Synthetic construct

<400> SEQUENCE: 7

Gly Ser Ile Ser Ser Gly Ser Tyr Tyr Trp Ser
1               5                   10

<210> SEQ ID NO 8
<211> LENGTH: 11
<212> TYPE: PRT
<213> ORGANISM: Artificial
<220> FEATURE:
<223> OTHER INFORMATION: Synthetic construct

<400> SEQUENCE: 8

Gly Ser Ile Arg Ser Gly Ala Tyr Tyr Trp Ser
1               5                   10

<210> SEQ ID NO 9
<211> LENGTH: 11
<212> TYPE: PRT
<213> ORGANISM: Artificial
<220> FEATURE:
<223> OTHER INFORMATION: Synthetic construct

<400> SEQUENCE: 9

Gly Ser Ile Ser Ser Gly Ala Ser Tyr Trp Ser
1               5                   10
```

```
<210> SEQ ID NO 10
<211> LENGTH: 11
<212> TYPE: PRT
<213> ORGANISM: Artificial
<220> FEATURE:
<223> OTHER INFORMATION: Synthetic construct

<400> SEQUENCE: 10

Gly Ser Ile Ser Ser Gly Ser Ser Tyr Trp Ser
1               5                   10

<210> SEQ ID NO 11
<211> LENGTH: 11
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be S or R
<220> FEATURE:
<221> NAME/KEY: misc_feature
<222> LOCATION: (7)
<223> OTHER INFORMATION: Xaa can be S or A
<220> FEATURE:
<221> NAME/KEY: misc_feature
<222> LOCATION: (8)
<223> OTHER INFORMATION: Xaa can be Y or S

<400> SEQUENCE: 11

Gly Ser Ile Xaa Ser Gly Xaa Xaa Tyr Trp Ser
1               5                   10

<210> SEQ ID NO 12
<211> LENGTH: 9
<212> TYPE: PRT
<213> ORGANISM: Artificial
<220> FEATURE:
<223> OTHER INFORMATION: Synthetic construct

<400> SEQUENCE: 12

Gly Ser Ile Ser Ser Tyr Tyr Trp Ser
1               5

<210> SEQ ID NO 13
<211> LENGTH: 9
<212> TYPE: PRT
<213> ORGANISM: Artificial
<220> FEATURE:
<223> OTHER INFORMATION: Synthetic construct

<400> SEQUENCE: 13

Phe Thr Phe Ser Ser Tyr Ser Met Asn
1               5

<210> SEQ ID NO 14
<211> LENGTH: 9
<212> TYPE: PRT
<213> ORGANISM: Artificial
<220> FEATURE:
<223> OTHER INFORMATION: Synthetic construct

<400> SEQUENCE: 14

Gly Ser Phe Ser Gly Tyr Tyr Trp Ser
1               5
```

```
<210> SEQ ID NO 15
<211> LENGTH: 11
<212> TYPE: PRT
<213> ORGANISM: Artificial
<220> FEATURE:
<223> OTHER INFORMATION: Synthetic construct

<400> SEQUENCE: 15

Gly Ser Ile Ser Ser Ser Ser Tyr Tyr Trp Gly
1               5                   10

<210> SEQ ID NO 16
<211> LENGTH: 9
<212> TYPE: PRT
<213> ORGANISM: Artificial
<220> FEATURE:
<223> OTHER INFORMATION: Synthetic construct

<400> SEQUENCE: 16

Tyr Thr Phe Thr Ser Tyr Ala Ile Ser
1               5

<210> SEQ ID NO 17
<211> LENGTH: 17
<212> TYPE: PRT
<213> ORGANISM: Artificial
<220> FEATURE:
<223> OTHER INFORMATION: Synthetic construct

<400> SEQUENCE: 17

Val Ile Ser Tyr Asp Gly Ser Asn Lys Tyr Tyr Ala Asp Ser Val Lys
1               5                   10                  15

Gly

<210> SEQ ID NO 18
<211> LENGTH: 17
<212> TYPE: PRT
<213> ORGANISM: Artificial
<220> FEATURE:
<223> OTHER INFORMATION: Synthetic construct

<400> SEQUENCE: 18

Val Ile Ala Tyr Asp Gly Ser Ala Lys Tyr Tyr Ala Asp Ser Val Lys
1               5                   10                  15

Gly

<210> SEQ ID NO 19
<211> LENGTH: 17
<212> TYPE: PRT
<213> ORGANISM: Artificial
<220> FEATURE:
<223> OTHER INFORMATION: Synthetic construct

<400> SEQUENCE: 19

Val Ile Ala Tyr Asp Gly Ser Leu Lys Tyr Tyr Ala Asp Ser Val Lys
1               5                   10                  15

Gly

<210> SEQ ID NO 20
<211> LENGTH: 17
<212> TYPE: PRT
<213> ORGANISM: Artificial
<220> FEATURE:
<223> OTHER INFORMATION: Synthetic construct

<400> SEQUENCE: 20
```

```
Val Ile Ala Tyr Asp Gly Ser Val Lys Tyr Tyr Ala Asp Ser Val Lys
1               5                   10                  15

Gly

<210> SEQ ID NO 21
<211> LENGTH: 17
<212> TYPE: PRT
<213> ORGANISM: Artificial
<220> FEATURE:
<223> OTHER INFORMATION: Synthetic construct

<400> SEQUENCE: 21

Val Ile Met Tyr Asp Gly Ser Ala Lys Tyr Tyr Ala Asp Ser Val Lys
1               5                   10                  15

Gly

<210> SEQ ID NO 22
<211> LENGTH: 17
<212> TYPE: PRT
<213> ORGANISM: Artificial
<220> FEATURE:
<223> OTHER INFORMATION: Synthetic construct

<400> SEQUENCE: 22

Tyr Ile Ala Tyr Asp Gly Ser Asn Lys Tyr Tyr Ala Asp Ser Val Lys
1               5                   10                  15

Gly

<210> SEQ ID NO 23
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be V or Y
<220> FEATURE:
<221> NAME/KEY: misc_feature
<222> LOCATION: (3)..(3)
<223> OTHER INFORMATION: Xaa can be S, A or M
<220> FEATURE:
<221> NAME/KEY: misc_feature
<222> LOCATION: (8)..(8)
<223> OTHER INFORMATION: Xaa can be N, A, L or V

<400> SEQUENCE: 23

Xaa Ile Xaa Tyr Asp Gly Ser Xaa Lys Tyr Tyr Ala Asp Ser Val Lys
1               5                   10                  15

Gly

<210> SEQ ID NO 24
<211> LENGTH: 16
<212> TYPE: PRT
<213> ORGANISM: Artificial
<220> FEATURE:
<223> OTHER INFORMATION: Synthetic construct

<400> SEQUENCE: 24

Tyr Ile Tyr Tyr Ser Gly Ser Thr Tyr Tyr Asn Pro Ser Leu Lys Ser
1               5                   10                  15

<210> SEQ ID NO 25
<211> LENGTH: 16
```

```
<212> TYPE: PRT
<213> ORGANISM: Artificial
<220> FEATURE:
<223> OTHER INFORMATION: Synthetic construct

<400> SEQUENCE: 25

Tyr Ile Tyr Tyr Asp Gly Gln Thr Tyr Tyr Asn Pro Ser Leu Lys Ser
1               5                   10                  15

<210> SEQ ID NO 26
<211> LENGTH: 16
<212> TYPE: PRT
<213> ORGANISM: Artificial
<220> FEATURE:
<223> OTHER INFORMATION: Synthetic construct

<400> SEQUENCE: 26

Tyr Ile Tyr Tyr Ser Gly Glu Thr Tyr Tyr Asn Pro Ser Leu Lys Ser
1               5                   10                  15

<210> SEQ ID NO 27
<211> LENGTH: 16
<212> TYPE: PRT
<213> ORGANISM: Artificial
<220> FEATURE:
<223> OTHER INFORMATION: Synthetic construct

<400> SEQUENCE: 27

Tyr Ile Tyr Met Ser Gly Glu Thr Tyr Tyr Asn Pro Ser Leu Lys Ser
1               5                   10                  15

<210> SEQ ID NO 28
<211> LENGTH: 16
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be Y or M
<220> FEATURE:
<221> NAME/KEY: misc_feature
<222> LOCATION: (5)..(5)
<223> OTHER INFORMATION: Xaa can be D or S
<220> FEATURE:
<221> NAME/KEY: misc_feature
<222> LOCATION: (7)..(7)
<223> OTHER INFORMATION: Xaa can be S, Q or E

<400> SEQUENCE: 28

Tyr Ile Tyr Xaa Xaa Gly Xaa Thr Tyr Tyr Asn Pro Ser Leu Lys Ser
1               5                   10                  15

<210> SEQ ID NO 29
<211> LENGTH: 16
<212> TYPE: PRT
<213> ORGANISM: Artificial
<220> FEATURE:
<223> OTHER INFORMATION: Synthetic construct

<400> SEQUENCE: 29

Tyr Ile Tyr Ser Ser Gly Ser Thr Asn Tyr Asn Pro Ser Leu Lys Ser
1               5                   10                  15

<210> SEQ ID NO 30
<211> LENGTH: 17
<212> TYPE: PRT
<213> ORGANISM: Artificial
```

```
<220> FEATURE:
<223> OTHER INFORMATION: Synthetic construct

<400> SEQUENCE: 30

Ser Ile Ser Ser Ser Ser Asn Tyr Ile Tyr Tyr Ala Asp Ser Val Lys
1               5                   10                  15

Gly

<210> SEQ ID NO 31
<211> LENGTH: 16
<212> TYPE: PRT
<213> ORGANISM: Artificial
<220> FEATURE:
<223> OTHER INFORMATION: Synthetic construct

<400> SEQUENCE: 31

Glu Ile Asp His Ser Gly Ser Thr Asn Tyr Asn Pro Ser Leu Lys Ser
1               5                   10                  15

<210> SEQ ID NO 32
<211> LENGTH: 16
<212> TYPE: PRT
<213> ORGANISM: Artificial
<220> FEATURE:
<223> OTHER INFORMATION: Synthetic construct

<400> SEQUENCE: 32

Ser Ile Tyr Tyr Ser Gly Ser Thr Tyr Tyr Asn Pro Ser Leu Lys Ser
1               5                   10                  15

<210> SEQ ID NO 33
<211> LENGTH: 17
<212> TYPE: PRT
<213> ORGANISM: Artificial
<220> FEATURE:
<223> OTHER INFORMATION: Synthetic construct

<400> SEQUENCE: 33

Trp Ile Ser Ala Tyr Asn Gly Asn Thr Asn Tyr Ala Gln Lys Leu Gln
1               5                   10                  15

Gly

<210> SEQ ID NO 34
<211> LENGTH: 17
<212> TYPE: PRT
<213> ORGANISM: Artificial
<220> FEATURE:
<223> OTHER INFORMATION: Synthetic construct

<400> SEQUENCE: 34

Ala Arg Gly Arg Pro Trp Tyr Ser Glu Thr Gly Thr Ser Ala Phe Asp
1               5                   10                  15

Ile

<210> SEQ ID NO 35
<211> LENGTH: 14
<212> TYPE: PRT
<213> ORGANISM: Artificial
<220> FEATURE:
<223> OTHER INFORMATION: Synthetic construct

<400> SEQUENCE: 35

Ala Arg Asp Val Gly Tyr Pro His Tyr Tyr Gly Met Asp Val
1               5                   10
```

<210> SEQ ID NO 36
<211> LENGTH: 17
<212> TYPE: PRT
<213> ORGANISM: Artificial
<220> FEATURE:
<223> OTHER INFORMATION: Synthetic construct

<400> SEQUENCE: 36

Ala Arg Asp Ala Pro Gly Gly Ser Ser Tyr Gln Asp Tyr Tyr Met Asp
1               5                   10                  15

Val

<210> SEQ ID NO 37
<211> LENGTH: 15
<212> TYPE: PRT
<213> ORGANISM: Artificial
<220> FEATURE:
<223> OTHER INFORMATION: Synthetic construct

<400> SEQUENCE: 37

Ala Arg Gly Ala Pro Leu Gly Tyr Ser Trp Glu Tyr Phe Asp Leu
1               5                   10                  15

<210> SEQ ID NO 38
<211> LENGTH: 14
<212> TYPE: PRT
<213> ORGANISM: Artificial
<220> FEATURE:
<223> OTHER INFORMATION: Synthetic construct

<400> SEQUENCE: 38

Ala Arg Asp Gly Gly Gly Gly Tyr Ala Ser Pro Phe Asp Tyr
1               5                   10

<210> SEQ ID NO 39
<211> LENGTH: 15
<212> TYPE: PRT
<213> ORGANISM: Artificial
<220> FEATURE:
<223> OTHER INFORMATION: Synthetic construct

<400> SEQUENCE: 39

Ala Arg Asp Pro Gly Tyr Ser Ala Ser Pro Asn Trp Phe Asp Pro
1               5                   10                  15

<210> SEQ ID NO 40
<211> LENGTH: 14
<212> TYPE: PRT
<213> ORGANISM: Artificial
<220> FEATURE:
<223> OTHER INFORMATION: Synthetic construct

<400> SEQUENCE: 40

Ala Arg Ser Gly Gly Gly Ser Gly Pro Asn Trp Phe Asp Pro
1               5                   10

<210> SEQ ID NO 41
<211> LENGTH: 11
<212> TYPE: PRT
<213> ORGANISM: Artificial
<220> FEATURE:
<223> OTHER INFORMATION: Synthetic construct

<400> SEQUENCE: 41

Gln Ala Ser Gln Asp Ile Ser Asn Tyr Leu Asn
1               5                   10

```
<210> SEQ ID NO 42
<211> LENGTH: 11
<212> TYPE: PRT
<213> ORGANISM: Artificial
<220> FEATURE:
<223> OTHER INFORMATION: Synthetic construct

<400> SEQUENCE: 42

Arg Ala Ser Gln Ser Val Ser Ser Asn Leu Ala
1               5                   10

<210> SEQ ID NO 43
<211> LENGTH: 12
<212> TYPE: PRT
<213> ORGANISM: Artificial
<220> FEATURE:
<223> OTHER INFORMATION: Synthetic construct

<400> SEQUENCE: 43

Arg Ala Ser Gln Ser Val Ser Ser Ser Tyr Leu Ala
1               5                   10

<210> SEQ ID NO 44
<211> LENGTH: 11
<212> TYPE: PRT
<213> ORGANISM: Artificial
<220> FEATURE:
<223> OTHER INFORMATION: Synthetic construct

<400> SEQUENCE: 44

Arg Ala Ser Gln Ser Val Ser Ser Tyr Leu Ala
1               5                   10

<210> SEQ ID NO 45
<211> LENGTH: 11
<212> TYPE: PRT
<213> ORGANISM: Artificial
<220> FEATURE:
<223> OTHER INFORMATION: Synthetic construct

<400> SEQUENCE: 45

Arg Ala Ser Gln Ser Ile Ser Ser Trp Leu Ala
1               5                   10

<210> SEQ ID NO 46
<211> LENGTH: 12
<212> TYPE: PRT
<213> ORGANISM: Artificial
<220> FEATURE:
<223> OTHER INFORMATION: Synthetic construct

<400> SEQUENCE: 46

Arg Ala Ser Gln Ser Val Ser Ser Ser Phe Leu Ala
1               5                   10

<210> SEQ ID NO 47
<211> LENGTH: 7
<212> TYPE: PRT
<213> ORGANISM: Artificial
<220> FEATURE:
<223> OTHER INFORMATION: Synthetic construct

<400> SEQUENCE: 47

Asp Ala Ser Asn Leu Glu Thr
1               5
```

<210> SEQ ID NO 48
<211> LENGTH: 7
<212> TYPE: PRT
<213> ORGANISM: Artificial
<220> FEATURE:
<223> OTHER INFORMATION: Synthetic construct

<400> SEQUENCE: 48

Ser Ala Ser Thr Arg Ala Thr
1               5

<210> SEQ ID NO 49
<211> LENGTH: 7
<212> TYPE: PRT
<213> ORGANISM: Artificial
<220> FEATURE:
<223> OTHER INFORMATION: Synthetic construct

<400> SEQUENCE: 49

Gly Ala Ser Ser Arg Ala Thr
1               5

<210> SEQ ID NO 50
<211> LENGTH: 7
<212> TYPE: PRT
<213> ORGANISM: Artificial
<220> FEATURE:
<223> OTHER INFORMATION: Synthetic construct

<400> SEQUENCE: 50

Asp Ala Ser Asn Arg Ala Thr
1               5

<210> SEQ ID NO 51
<211> LENGTH: 7
<212> TYPE: PRT
<213> ORGANISM: Artificial
<220> FEATURE:
<223> OTHER INFORMATION: Synthetic construct

<400> SEQUENCE: 51

Asp Ala Ser Ser Leu Glu Ser
1               5

<210> SEQ ID NO 52
<211> LENGTH: 7
<212> TYPE: PRT
<213> ORGANISM: Artificial
<220> FEATURE:
<223> OTHER INFORMATION: Synthetic construct

<400> SEQUENCE: 52

Gly Ala Ser Thr Arg Ala Thr
1               5

<210> SEQ ID NO 53
<211> LENGTH: 8
<212> TYPE: PRT
<213> ORGANISM: Artificial
<220> FEATURE:
<223> OTHER INFORMATION: Synthetic construct

<400> SEQUENCE: 53

Gln Gln Ser Asp His Tyr Pro Thr
1               5

```
<210> SEQ ID NO 54
<211> LENGTH: 10
<212> TYPE: PRT
<213> ORGANISM: Artificial
<220> FEATURE:
<223> OTHER INFORMATION: Synthetic construct

<400> SEQUENCE: 54

Gln Gln His Asn Val Tyr Pro Pro Tyr Thr
1               5                   10

<210> SEQ ID NO 55
<211> LENGTH: 9
<212> TYPE: PRT
<213> ORGANISM: Artificial
<220> FEATURE:
<223> OTHER INFORMATION: Synthetic construct

<400> SEQUENCE: 55

Gln Gln Ser Glu Arg Ser Pro Phe Thr
1               5

<210> SEQ ID NO 56
<211> LENGTH: 9
<212> TYPE: PRT
<213> ORGANISM: Artificial
<220> FEATURE:
<223> OTHER INFORMATION: Synthetic construct

<400> SEQUENCE: 56

Gln Gln Ala Phe Ser Met Pro Pro Thr
1               5

<210> SEQ ID NO 57
<211> LENGTH: 9
<212> TYPE: PRT
<213> ORGANISM: Artificial
<220> FEATURE:
<223> OTHER INFORMATION: Synthetic construct

<400> SEQUENCE: 57

Gln Gln Phe Gln Ser Tyr Ser Tyr Thr
1               5

<210> SEQ ID NO 58
<211> LENGTH: 9
<212> TYPE: PRT
<213> ORGANISM: Artificial
<220> FEATURE:
<223> OTHER INFORMATION: Synthetic construct

<400> SEQUENCE: 58

Gln Gln Tyr His Ala Trp Pro Pro Thr
1               5

<210> SEQ ID NO 59
<211> LENGTH: 8
<212> TYPE: PRT
<213> ORGANISM: Artificial
<220> FEATURE:
<223> OTHER INFORMATION: Synthetic construct

<400> SEQUENCE: 59

Gln Gln Phe Asp Ser Ser Pro Thr
1               5

<210> SEQ ID NO 60
```

```
<211> LENGTH: 9
<212> TYPE: PRT
<213> ORGANISM: Artificial
<220> FEATURE:
<223> OTHER INFORMATION: Synthetic construct

<400> SEQUENCE: 60

Gln Gln Tyr Asp Val Phe Pro Ile Thr
1               5

<210> SEQ ID NO 61
<211> LENGTH: 9
<212> TYPE: PRT
<213> ORGANISM: Artificial
<220> FEATURE:
<223> OTHER INFORMATION: Synthetic construct

<400> SEQUENCE: 61

Gln Gln Pro Ala Thr Leu Pro Trp Thr
1               5

<210> SEQ ID NO 62
<211> LENGTH: 26
<212> TYPE: PRT
<213> ORGANISM: Artificial
<220> FEATURE:
<223> OTHER INFORMATION: Synthetic construct

<400> SEQUENCE: 62

Gln Val Gln Leu Val Glu Ser Gly Gly Gly Val Val Gln Pro Gly Arg
1               5                   10                  15

Ser Leu Arg Leu Ser Cys Ala Ala Ser Gly
            20                  25

<210> SEQ ID NO 63
<211> LENGTH: 26
<212> TYPE: PRT
<213> ORGANISM: Artificial
<220> FEATURE:
<223> OTHER INFORMATION: Synthetic construct

<400> SEQUENCE: 63

Gln Val Gln Leu Gln Glu Ser Gly Pro Gly Leu Val Lys Pro Ser Gln
1               5                   10                  15

Thr Leu Ser Leu Thr Cys Thr Val Ser Gly
            20                  25

<210> SEQ ID NO 64
<211> LENGTH: 26
<212> TYPE: PRT
<213> ORGANISM: Artificial
<220> FEATURE:
<223> OTHER INFORMATION: Synthetic construct

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 65
<211> LENGTH: 26
<212> TYPE: PRT
<213> ORGANISM: Artificial
<220> FEATURE:
<223> OTHER INFORMATION: Synthetic construct
```

<400> SEQUENCE: 65

Glu Val Gln Leu Val Glu Ser Gly Gly Gly Leu Val Lys Pro Gly Gly
1               5                   10                  15

Ser Leu Arg Leu Ser Cys Ala Ala Ser Gly
            20                  25

<210> SEQ ID NO 66
<211> LENGTH: 26
<212> TYPE: PRT
<213> ORGANISM: Artificial
<220> FEATURE:
<223> OTHER INFORMATION: Synthetic construct

<400> SEQUENCE: 66

Gln Val Gln Leu Gln Gln Trp Gly Ala Gly Leu Leu Lys Pro Ser Glu
1               5                   10                  15

Thr Leu Ser Leu Thr Cys Ala Val Tyr Gly
            20                  25

<210> SEQ ID NO 67
<211> LENGTH: 26
<212> TYPE: PRT
<213> ORGANISM: Artificial
<220> FEATURE:
<223> OTHER INFORMATION: Synthetic construct

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 68
<211> LENGTH: 30
<212> TYPE: PRT
<213> ORGANISM: Artificial
<220> FEATURE:
<223> OTHER INFORMATION: Synthetic construct

<400> SEQUENCE: 68

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 69
<211> LENGTH: 30
<212> TYPE: PRT
<213> ORGANISM: Artificial
<220> FEATURE:
<223> OTHER INFORMATION: Synthetic construct

<400> SEQUENCE: 69

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 70
<211> LENGTH: 30
<212> TYPE: PRT
<213> ORGANISM: Artificial
<220> FEATURE:

<223> OTHER INFORMATION: Synthetic construct

<400> SEQUENCE: 70

Arg Phe Thr Ile Ser Arg Asp Asn Ala Lys Asn Ser Leu Tyr Leu Gln
1               5                   10                  15
Met Asn Ser Leu Arg Ala Glu Asp Thr Ala Val Tyr Tyr Cys
            20                  25                  30

<210> SEQ ID NO 71
<211> LENGTH: 30
<212> TYPE: PRT
<213> ORGANISM: Artificial
<220> FEATURE:
<223> OTHER INFORMATION: Synthetic construct

<400> SEQUENCE: 71

Arg Val Thr Met Thr Thr Asp Thr Ser Thr Ser Thr Ala Tyr Met Glu
1               5                   10                  15
Leu Arg Ser Leu Arg Ser Asp Asp Thr Ala Val Tyr Tyr Cys
            20                  25                  30

<210> SEQ ID NO 72
<211> LENGTH: 23
<212> TYPE: PRT
<213> ORGANISM: Artificial
<220> FEATURE:
<223> OTHER INFORMATION: Synthetic construct

<400> SEQUENCE: 72

Asp Ile Gln Met Thr Gln Ser Pro Ser Ser Leu Ser Ala Ser Val Gly
1               5                   10                  15
Asp Arg Val Thr Ile Thr Cys
            20

<210> SEQ ID NO 73
<211> LENGTH: 23
<212> TYPE: PRT
<213> ORGANISM: Artificial
<220> FEATURE:
<223> OTHER INFORMATION: Synthetic construct

<400> SEQUENCE: 73

Glu Ile Val Met Thr Gln Ser Pro Ala Thr Leu Ser Val Ser Pro Gly
1               5                   10                  15
Glu Arg Ala Thr Leu Ser Cys
            20

<210> SEQ ID NO 74
<211> LENGTH: 23
<212> TYPE: PRT
<213> ORGANISM: Artificial
<220> FEATURE:
<223> OTHER INFORMATION: Synthetic construct

<400> SEQUENCE: 74

Glu Ile Val Leu Thr Gln Ser Pro Gly Thr Leu Ser Leu Ser Pro Gly
1               5                   10                  15
Glu Arg Ala Thr Leu Ser Cys
            20

<210> SEQ ID NO 75
<211> LENGTH: 23
<212> TYPE: PRT
<213> ORGANISM: Artificial

```
<220> FEATURE:
<223> OTHER INFORMATION: Synthetic construct

<400> SEQUENCE: 75

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 76
<211> LENGTH: 23
<212> TYPE: PRT
<213> ORGANISM: Artificial
<220> FEATURE:
<223> OTHER INFORMATION: Synthetic construct

<400> SEQUENCE: 76

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 77
<211> LENGTH: 15
<212> TYPE: PRT
<213> ORGANISM: Artificial
<220> FEATURE:
<223> OTHER INFORMATION: Synthetic construct

<400> SEQUENCE: 77

Trp Tyr Gln Gln Lys Pro Gly Lys Ala Pro Lys Leu Leu Ile Tyr
1               5                   10                  15

<210> SEQ ID NO 78
<211> LENGTH: 15
<212> TYPE: PRT
<213> ORGANISM: Artificial
<220> FEATURE:
<223> OTHER INFORMATION: Synthetic construct

<400> SEQUENCE: 78

Trp Tyr Gln Gln Lys Pro Gly Gln Ala Pro Arg Leu Leu Ile Tyr
1               5                   10                  15

<210> SEQ ID NO 79
<211> LENGTH: 15
<212> TYPE: PRT
<213> ORGANISM: Artificial
<220> FEATURE:
<223> OTHER INFORMATION: Synthetic construct

<400> SEQUENCE: 79

Trp Phe Gln Gln Lys Pro Gly Gln Ala Pro Arg Leu Leu Ile Tyr
1               5                   10                  15

<210> SEQ ID NO 80
<211> LENGTH: 32
<212> TYPE: PRT
<213> ORGANISM: Artificial
<220> FEATURE:
<223> OTHER INFORMATION: Synthetic construct

<400> SEQUENCE: 80

Gly Val Pro Ser Arg Phe Ser Gly Ser Gly Ser Gly Thr Asp Phe Thr
1               5                   10                  15
```

Phe Thr Ile Ser Ser Leu Gln Pro Glu Asp Ile Ala Thr Tyr Tyr Cys
            20                  25                  30

<210> SEQ ID NO 81
<211> LENGTH: 32
<212> TYPE: PRT
<213> ORGANISM: Artificial
<220> FEATURE:
<223> OTHER INFORMATION: Synthetic construct

<400> SEQUENCE: 81

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 82
<211> LENGTH: 32
<212> TYPE: PRT
<213> ORGANISM: Artificial
<220> FEATURE:
<223> OTHER INFORMATION: Synthetic construct

<400> SEQUENCE: 82

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 83
<211> LENGTH: 32
<212> TYPE: PRT
<213> ORGANISM: Artificial
<220> FEATURE:
<223> OTHER INFORMATION: Synthetic construct

<400> SEQUENCE: 83

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 84
<211> LENGTH: 32
<212> TYPE: PRT
<213> ORGANISM: Artificial
<220> FEATURE:
<223> OTHER INFORMATION: Synthetic construct

<400> SEQUENCE: 84

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 85
<211> LENGTH: 10
<212> TYPE: PRT
<213> ORGANISM: Artificial
<220> FEATURE:
<223> OTHER INFORMATION: Synthetic construct

<400> SEQUENCE: 85

Phe Gly Gly Gly Thr Lys Val Glu Ile Lys
1               5                   10

<210> SEQ ID NO 86
<211> LENGTH: 11
<212> TYPE: PRT
<213> ORGANISM: Artificial
<220> FEATURE:
<223> OTHER INFORMATION: Synthetic construct

<400> SEQUENCE: 86

Trp Gly Gln Gly Thr Met Val Thr Val Ser Ser
1               5                   10

<210> SEQ ID NO 87
<211> LENGTH: 11
<212> TYPE: PRT
<213> ORGANISM: Artificial
<220> FEATURE:
<223> OTHER INFORMATION: Synthetic construct

<400> SEQUENCE: 87

Trp Gly Gln Gly Thr Thr Val Thr Val Ser Ser
1               5                   10

<210> SEQ ID NO 88
<211> LENGTH: 11
<212> TYPE: PRT
<213> ORGANISM: Artificial
<220> FEATURE:
<223> OTHER INFORMATION: Synthetic construct

<400> SEQUENCE: 88

Trp Gly Lys Gly Thr Thr Val Thr Val Ser Ser
1               5                   10

<210> SEQ ID NO 89
<211> LENGTH: 11
<212> TYPE: PRT
<213> ORGANISM: Artificial
<220> FEATURE:
<223> OTHER INFORMATION: Synthetic construct

<400> SEQUENCE: 89

Trp Gly Arg Gly Thr Leu Val Thr Val Ser Ser
1               5                   10

<210> SEQ ID NO 90
<211> LENGTH: 11
<212> TYPE: PRT
<213> ORGANISM: Artificial
<220> FEATURE:
<223> OTHER INFORMATION: Synthetic construct

<400> SEQUENCE: 90

Trp Gly Gln Gly Thr Leu Val Thr Val Ser Ser
1               5                   10

<210> SEQ ID NO 91
<211> LENGTH: 372
<212> TYPE: DNA
<213> ORGANISM: Artificial
<220> FEATURE:
<223> OTHER INFORMATION: Synthetic construct

<400> SEQUENCE: 91
caggtgcagc tggtggagtc tgggggaggc gtggtccagc ctggggaggtc cctgagactc      60 tcctgtgcag cgtctggatt caccttcagt agctatggca tgcactgggt ccgccaggct     120
ccaggcaagg ggctggagtg ggtggcagtt atatcgtatg atggaagtaa taaatactat    180
gcagactccg tgaagggccg attcaccatc tccagagaca attccaagaa cacgctgtat    240
ctgcaaatga acagcctgag agccgaggac acggcggtgt actactgcgc cagaggccgt    300
ccttggtaca gcgaaactgg tacctcagct ttcgacatat ggggtcaggg tacaatggtc    360
accgtctcct ca                                                        372

<210> SEQ ID NO 92
<211> LENGTH: 372
<212> TYPE: DNA
<213> ORGANISM: Artificial
<220> FEATURE:
<223> OTHER INFORMATION: Synthetic construct

<400> SEQUENCE: 92
caggtgcagc tggtggagtc tgggggaggc gtggtccagc ctggGaggtc cctgagactc     60
tcctgtgcag cgtctggatt caccttcagt gtgtataata tgcactgggt ccgccaggct    120
ccaggcaagg ggctggagtg ggtggcagtt atagcgtatg atggaagtgc gaaatactat    180
gcagactccg tgaagggccg attcaccatc tccagagaca attccaagaa cacgctgtat    240
ctgcaaatga acagcctgag agccgaggac acggcggtgt actactgcgc cagaggccgt    300
ccttggtaca gcgaaactgg tacctcagct ttcgacatat ggggtcaggg tacaatggtc    360
accgtctcct ca                                                        372

<210> SEQ ID NO 93
<211> LENGTH: 372
<212> TYPE: DNA
<213> ORGANISM: Artificial
<220> FEATURE:
<223> OTHER INFORMATION: Synthetic construct

<400> SEQUENCE: 93
caggtgcagc tggtggagtc tgggggaggc gtggtccagc ctgggaggtc cctgagactc     60
tcctgtgcag cgtctggatt caccttcagt agccggaata tgcactgggt ccgccaggct    120
ccaggcaagg ggctggagtg ggtggcagtt atagcgtatg atggaagtct taaatactat    180
gcagactccg tgaagggccg attcaccatc tccagagaca attccaagaa cacgctgtat    240
ctgcaaatga acagcctgag agccgaggac acggcggtgt actactgcgc cagaggccgt    300
ccttggtaca gcgaaactgg tacctcagct ttcgacatat ggggtcaggg tacaatggtc    360
accgtctcct ca                                                        372

<210> SEQ ID NO 94
<211> LENGTH: 372
<212> TYPE: DNA
<213> ORGANISM: Artificial
<220> FEATURE:
<223> OTHER INFORMATION: Synthetic construct

<400> SEQUENCE: 94
caggtgcagc tggtggagtc tgggggaggc gtggtccagc ctgggaggtc cctgagactc     60
tcctgtgcag cgtctggatt caccttcgtg agctataata tgcactgggt ccgccaggct    120
ccaggcaagg ggctggagtg ggtggcagtt atagcgtatg atggaagtgt taaatactat    180
gcagactccg tgaagggccg attcaccatc tccagagaca attccaagaa cacgctgtat    240
ctgcaaatga acagcctgag agccgaggac acggcggtgt actactgcgc cagaggccgt    300

```
ccttggtaca gcgaaactgg tacctcagct ttcgacatat ggggtcaggg tacaatggtc    360
accgtctcct ca                                                        372
```

<210> SEQ ID NO 95
<211> LENGTH: 372
<212> TYPE: DNA
<213> ORGANISM: Artificial
<220> FEATURE:
<223> OTHER INFORMATION: Synthetic construct

<400> SEQUENCE: 95

```
caggtgcagc tggtggagtc tgggggaggc gtggtccagc ctgggaggtc cctgagactc     60
tcctgtgcag cgtctggatt caccttcgtg agctataata tgcactgggt ccgccaggct    120
ccaggcaagg ggctggagtg ggtggcagtt ataatgtatg atggaagtgc taaatactat    180
gcagactccg tgaagggccg attcaccatc tccagagaca attccaagaa cacgctgtat    240
ctgcaaatga acagcctgag agccgaggac acggcggtgt actactgcgc cagaggccgt    300
ccttggtaca gcgaaactgg tacctcagct ttcgacatat ggggtcaggg tacaatggtc    360
accgtctcct ca                                                        372
```

<210> SEQ ID NO 96
<211> LENGTH: 372
<212> TYPE: DNA
<213> ORGANISM: Artificial
<220> FEATURE:
<223> OTHER INFORMATION: Synthetic construct

<400> SEQUENCE: 96

```
caggtgcagc tggtggagtc tgggggaggc gtggtccagc ctgggaggtc cctgagactc     60
tcctgtgcag cgtctggatt caccttcagg agctatgata tgcactgggt ccgccaggct    120
ccaggcaagg ggctggagtg ggtggcatat atagcgtatg atggaagtaa taaatactat    180
gcagactccg tgaagggccg attcaccatc tccagagaca attccaagaa cacgctgtat    240
ctgcaaatga acagcctgag agccgaggac acggcggtgt actactgcgc cagaggccgt    300
ccttggtaca gcgaaactgg tacctcagct ttcgacatat ggggtcaggg tacaatggtc    360
accgtctcct ca                                                        372
```

<210> SEQ ID NO 97
<211> LENGTH: 366
<212> TYPE: DNA
<213> ORGANISM: Artificial
<220> FEATURE:
<223> OTHER INFORMATION: Synthetic construct

<400> SEQUENCE: 97

```
caggtgcagc tgcaggagtc gggcccagga ctggtgaagc cttcacagac cctgtccctc     60
acctgtactg tctctggtgg ctccatcagc agtggtagct actactggag ctggatccgc    120
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagttctgt gaccgccgca gacacggcgg tgtactactg cgccagagat    300
gtaggatacc cacactacta cggaatggac gtatggggcc agggaacaac tgtcaccgtc    360
tcctca                                                              366
```

<210> SEQ ID NO 98
<211> LENGTH: 366

```
<212> TYPE: DNA
<213> ORGANISM: Artificial
<220> FEATURE:
<223> OTHER INFORMATION: Synthetic construct

<400> SEQUENCE: 98
caggtgcagc tgcaggagtc gggcccagga ctggtgaagc cttcacagac cctgtccctc    60
acctgtactg tctctggtgg ctccatccgt agtggtgctt actactggag ctggatccgc   120
cagcacccag ggaagggcct ggagtggatt gggtacatct attacgatgg cagacctac    180 tacaacccgt ccctcaagag tcgagttacc atatcagtag acacgtctaa gaaccagttc   240
tccctgaagc tgagttctgt gaccgccgca gacacggcgg tgtactactg cgccagagat   300
gtaggatacc cacactacta cggaatggac gtatggggcc agggaacaac tgtcaccgtc   360
tcctca                                                              366

<210> SEQ ID NO 99
<211> LENGTH: 366
<212> TYPE: DNA
<213> ORGANISM: Artificial
<220> FEATURE:
<223> OTHER INFORMATION: Synthetic construct

<400> SEQUENCE: 99
caggtgcagc tgcaggagtc gggcccagga ctggtgaagc cttcacagac cctgtccctc    60
acctgtactg tctctggtgg ctccatcagc agtggtgcta gttactggag ctggatccgc   120
cagcacccag ggaagggcct ggagtggatt gggtacatct attacagtgg ggagacctac   180
tacaacccgt ccctcaagag tcgagttacc atatcagtag acacgtctaa gaaccagttc   240
tccctgaagc tgagttctgt gaccgccgca gacacggcgg tgtactactg cgccagagat   300
gtaggatacc cacactacta cggaatggac gtatggggcc agggaacaac tgtcaccgtc   360
tcctca                                                              366

<210> SEQ ID NO 100
<211> LENGTH: 366
<212> TYPE: DNA
<213> ORGANISM: Artificial
<220> FEATURE:
<223> OTHER INFORMATION: Synthetic construct

<400> SEQUENCE: 100
caggtgcagc tgcaggagtc gggcccagga ctggtgaagc cttcacagac cctgtccctc    60
acctgtactg tctctggtgg ctccatcagc agtggttcgt cctactggag ctggatccgc   120
cagcacccag ggaagggcct ggagtggatt gggtacatct atatgagtgg ggagacctac   180
tacaacccgt ccctcaagag tcgagttacc atatcagtag acacgtctaa gaaccagttc   240
tccctgaagc tgagttctgt gaccgccgca gacacggcgg tgtactactg cgccagagat   300
gtaggatacc cacactacta cggaatggac gtatggggcc agggaacaac tgtcaccgtc   360
tcctca                                                              366

<210> SEQ ID NO 101
<211> LENGTH: 369
<212> TYPE: DNA
<213> ORGANISM: Artificial
<220> FEATURE:
<223> OTHER INFORMATION: Synthetic construct

<400> SEQUENCE: 101
```

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctatagta gtgggagcac caactacaac   180
ccctccctca agagtcgagt caccatatca gtagacacgt ccaagaacca gttctccctg   240
aagctgagtt ctgtgaccgc cgcagacacg gcggtgtact actgcgccag agatgctcct   300
ggcggatcct cctaccagga ctactacatg gacgtatggg gcaagggtac aactgtcacc   360
gtctcctca                                                           369

<210> SEQ ID NO 102
<211> LENGTH: 366
<212> TYPE: DNA
<213> ORGANISM: Artificial
<220> FEATURE:
<223> OTHER INFORMATION: Synthetic construct

<400> SEQUENCE: 102
gaggtgcagc tggtggagtc tgggggaggc ctggtcaagc ctgggggtc cctgagactc     60 tcctgtgcag cctctggatt caccttcagt agctatagca tgaactgggt ccgccaggct   120
ccagggaagg gctggagtg gtctcatcc attagtagta gtagtaatta catatactac    180
gcagactcag tgaagggccg attcaccatc tccagagaca acgccaagaa ctcactgtat   240
ctgcaaatga acagcctgag agccgaggac acggcggtgt actactgcgc cagaggggcc   300
cctctgggat acagctggga gtacttcgac ctatggggga ggtaccttt ggtcaccgtc   360 tcctca                                                              366

<210> SEQ ID NO 103
<211> LENGTH: 360
<212> TYPE: DNA
<213> ORGANISM: Artificial
<220> FEATURE:
<223> OTHER INFORMATION: Synthetic construct

<400> SEQUENCE: 103
caagtacaat tacaacagtg gggagctggt ttattaaagc cttcagaaac tttaagtttg     60
acctgtgctg tttacggtgg atcatttttct ggttattact ggagttggat tcgtcaacca  120
ccaggcaaag gattggagtg gatcggtgag atagaccatt caggctccac taactacaat   180
ccaagtttaa aatccagggt tactatctcc gtagacacgt ccaagaacca gttctccctg   240
aagctgagtt ctgtgaccgc cgcagacacg gcggtgtact actgcgccag agatggtggc   300
ggaggatacg cttccccctt cgactattgg ggacaggta cattggtcac cgtctcctca   360

<210> SEQ ID NO 104
<211> LENGTH: 369
<212> TYPE: DNA
<213> ORGANISM: Artificial
<220> FEATURE:
<223> OTHER INFORMATION: Synthetic construct

<400> SEQUENCE: 104
cagctgcagc tgcaggagtc gggcccagga ctggtgaagc cttcggagac cctgtccctc     60
acctgcactg tctctggtgg ctccatcagc agtagtagtt actactgggg ctggatccgc   120
cagcccccag ggaaggggct ggagtggatt gggagtatct attatagtgg gagcacctac   180
tacaacccgt ccctcaagag tcgagtcacc atatccgtag acacgtccaa gaaccagttc   240
tccctgaagc tgagttctgt gaccgccgca gacacggcgg tgtactactg cgccagagat   300
```

```
ccaggataca gcgcttcccc caattggttt gatccatggg gacagggtac attggtcacc    360
gtctcctca                                                            369
```

<210> SEQ ID NO 105
<211> LENGTH: 363
<212> TYPE: DNA
<213> ORGANISM: Artificial
<220> FEATURE:
<223> OTHER INFORMATION: Synthetic construct

<400> SEQUENCE: 105

```
caggttcagc tggtgcagtc tggagctgag gtgaagaagc ctggggcctc agtgaaggtc     60
tcctgcaagg cttctggtta cacctttacc agctatgcca tcagctgggt gcgacaggcc    120
cctggacaag gcttgagtg gatgggatgg atcagcgctt acaatggtaa cacaaactat     180
gcacagaagc tccagggcag agtcaccatg accacagaca catccacgag cacagcctac    240
atggagctga ggagcctgag atctgacgac acggcggtgt actactgcgc cagatcagga    300
ggcggcagcg gacccaattg gtttgatcca tggggacagg gtacattggt caccgtctcc    360
tca                                                                  363
```

<210> SEQ ID NO 106
<211> LENGTH: 124
<212> TYPE: PRT
<213> ORGANISM: Artificial
<220> FEATURE:
<223> OTHER INFORMATION: Synthetic construct

<400> SEQUENCE: 106

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser
        115                 120
```

<210> SEQ ID NO 107
<211> LENGTH: 124
<212> TYPE: PRT
<213> ORGANISM: Artificial
<220> FEATURE:
<223> OTHER INFORMATION: Synthetic construct

<400> SEQUENCE: 107

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30
```

Asn Met His Trp Val Arg Gln Ala Pro Gly Lys Gly Leu Glu Trp Val
            35                  40                  45

Ala Val Ile Ala Tyr Asp Gly Ser Ala Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser
            115                 120

<210> SEQ ID NO 108
<211> LENGTH: 124
<212> TYPE: PRT
<213> ORGANISM: Artificial
<220> FEATURE:
<223> OTHER INFORMATION: Synthetic construct

<400> SEQUENCE: 108

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Arg
            20                  25                  30

Asn Met His Trp Val Arg Gln Ala Pro Gly Lys Gly Leu Glu Trp Val
            35                  40                  45

Ala Val Ile Ala Tyr Asp Gly Ser Leu Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser
            115                 120

<210> SEQ ID NO 109
<211> LENGTH: 124
<212> TYPE: PRT
<213> ORGANISM: Artificial
<220> FEATURE:
<223> OTHER INFORMATION: Synthetic construct

<400> SEQUENCE: 109

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Val Ser Tyr
            20                  25                  30

Asn Met His Trp Val Arg Gln Ala Pro Gly Lys Gly Leu Glu Trp Val
            35                  40                  45

Ala Val Ile Ala Tyr Asp Gly Ser Val Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser
        115                 120

<210> SEQ ID NO 110
<211> LENGTH: 124
<212> TYPE: PRT
<213> ORGANISM: Artificial
<220> FEATURE:
<223> OTHER INFORMATION: Synthetic construct

<400> SEQUENCE: 110

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Val Ser Tyr
            20                  25                  30

Asn Met His Trp Val Arg Gln Ala Pro Gly Lys Gly Leu Glu Trp Val
        35                  40                  45

Ala Val Ile Met Tyr Asp Gly Ser Ala Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser
        115                 120

<210> SEQ ID NO 111
<211> LENGTH: 124
<212> TYPE: PRT
<213> ORGANISM: Artificial
<220> FEATURE:
<223> OTHER INFORMATION: Synthetic construct

<400> SEQUENCE: 111

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Asp Met His Trp Val Arg Gln Ala Pro Gly Lys Gly Leu Glu Trp Val
        35                  40                  45

Ala Tyr Ile Ala Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser
        115                 120

<210> SEQ ID NO 112
<211> LENGTH: 122
<212> TYPE: PRT

<213> ORGANISM: Artificial
<220> FEATURE:
<223> OTHER INFORMATION: Synthetic construct

<400> SEQUENCE: 112

```
Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Ser Ser Gly
            20                  25                  30
Ser Tyr Tyr Trp Ser Trp Ile Arg Gln His Pro Gly Lys Gly Leu Glu
        35                  40                  45
Trp Ile Gly Tyr Ile Tyr Tyr Ser Gly Ser Thr Tyr Tyr Asn Pro Ser
50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Asp Val Gly Tyr Pro His Tyr Tyr Gly Met Asp Val Trp
            100                 105                 110
Gly Gln Gly Thr Thr Val Thr Val Ser Ser
        115                 120
```

<210> SEQ ID NO 113
<211> LENGTH: 122
<212> TYPE: PRT
<213> ORGANISM: Artificial
<220> FEATURE:
<223> OTHER INFORMATION: Synthetic construct

<400> SEQUENCE: 113

```
Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Arg Ser Gly
            20                  25                  30
Ala Tyr Tyr Trp Ser Trp Ile Arg Gln His Pro Gly Lys Gly Leu Glu
        35                  40                  45
Trp Ile Gly Tyr Ile Tyr Tyr Asp Gly Gln Thr Tyr Tyr Asn Pro Ser
50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Asp Val Gly Tyr Pro His Tyr Tyr Gly Met Asp Val Trp
            100                 105                 110
Gly Gln Gly Thr Thr Val Thr Val Ser Ser
        115                 120
```

<210> SEQ ID NO 114
<211> LENGTH: 122
<212> TYPE: PRT
<213> ORGANISM: Artificial
<220> FEATURE:
<223> OTHER INFORMATION: Synthetic construct

<400> SEQUENCE: 114

```
Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Ser Ser Gly
            20                  25                  30
```

```
Ala Ser Tyr Trp Ser Trp Ile Arg Gln His Pro Gly Lys Gly Leu Glu
        35                  40                  45

Trp Ile Gly Tyr Ile Tyr Tyr Ser Gly Glu Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Asp Val Gly Tyr Pro His Tyr Tyr Gly Met Asp Val Trp
                100                 105                 110

Gly Gln Gly Thr Thr Val Thr Val Ser Ser
                115                 120

<210> SEQ ID NO 115
<211> LENGTH: 122
<212> TYPE: PRT
<213> ORGANISM: Artificial
<220> FEATURE:
<223> OTHER INFORMATION: Synthetic construct

<400> SEQUENCE: 115

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Ser Ser Tyr Trp Ser Trp Ile Arg Gln His Pro Gly Lys Gly Leu Glu
        35                  40                  45

Trp Ile Gly Tyr Ile Tyr Met Ser Gly Glu Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Asp Val Gly Tyr Pro His Tyr Tyr Gly Met Asp Val Trp
                100                 105                 110

Gly Gln Gly Thr Thr Val Thr Val Ser Ser
                115                 120

<210> SEQ ID NO 116
<211> LENGTH: 123
<212> TYPE: PRT
<213> ORGANISM: Artificial
<220> FEATURE:
<223> OTHER INFORMATION: Synthetic construct

<400> SEQUENCE: 116

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
        35                  40                  45

Gly Tyr Ile Tyr Ser Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
```

```
                85                  90                  95
Arg Asp Ala Pro Gly Gly Ser Ser Tyr Gln Asp Tyr Tyr Met Asp Val
            100                 105                 110

Trp Gly Lys Gly Thr Thr Val Thr Val Ser Ser
        115                 120

<210> SEQ ID NO 117
<211> LENGTH: 122
<212> TYPE: PRT
<213> ORGANISM: Artificial
<220> FEATURE:
<223> OTHER INFORMATION: Synthetic construct

<400> SEQUENCE: 117

Glu Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Asn Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Leu Gly Tyr Ser Trp Glu Tyr Phe Asp Leu Trp
            100                 105                 110

Gly Arg Gly Thr Leu Val Thr Val Ser Ser
        115                 120

<210> SEQ ID NO 118
<211> LENGTH: 120
<212> TYPE: PRT
<213> ORGANISM: Artificial
<220> FEATURE:
<223> OTHER INFORMATION: Synthetic construct

<400> SEQUENCE: 118

Gln Val Gln Leu Gln Gln Trp Gly Ala Gly Leu Leu Lys Pro Ser Glu
1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Gly Gly Gly Tyr Ala Ser Pro Phe Asp Tyr Trp Gly Gln
            100                 105                 110

Gly Thr Leu Val Thr Val Ser Ser
        115                 120

<210> SEQ ID NO 119
<211> LENGTH: 123
```

```
<212> TYPE: PRT
<213> ORGANISM: Artificial
<220> FEATURE:
<223> OTHER INFORMATION: Synthetic construct

<400> SEQUENCE: 119

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Gly Tyr Ser Ala Ser Pro Asn Trp Phe Asp Pro
            100                 105                 110

Trp Gly Gln Gly Thr Leu Val Thr Val Ser Ser
        115                 120

<210> SEQ ID NO 120
<211> LENGTH: 121
<212> TYPE: PRT
<213> ORGANISM: Artificial
<220> FEATURE:
<223> OTHER INFORMATION: Synthetic construct

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gly Gly Ser Gly Pro Asn Trp Phe Asp Pro Trp Gly
            100                 105                 110

Gln Gly Thr Leu Val Thr Val Ser Ser
        115                 120

<210> SEQ ID NO 121
<211> LENGTH: 318
<212> TYPE: DNA
<213> ORGANISM: Artificial
<220> FEATURE:
<223> OTHER INFORMATION: Synthetic construct

<400> SEQUENCE: 121
gacatccaga tgacccagtc tccatcctcc ctgtctgcat ctgtaggaga cagagtcacc      60
atcacttgcc aggcgagtca ggacattagc aactatttaa attggtatca gcagaaacca    120
```

```
gggaaagccc ctaagctcct gatctacgat gcatccaatt tggaaacagg ggtcccatca      180
aggttcagtg gaagtggatc tgggacagat tttactttca ccatcagcag cctgcagcct      240
gaagatattg caacatatta ctgtcagcag tccgatcact accctacttt tggcggaggg      300
accaaggttg agatcaaa                                                    318

<210> SEQ ID NO 122
<211> LENGTH: 324
<212> TYPE: DNA
<213> ORGANISM: Artificial
<220> FEATURE:
<223> OTHER INFORMATION: Synthetic construct

<400> SEQUENCE: 122
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatagc gcatccacca gggccactgg tatcccagcc     180
aggttcagtg gcagtgggtc tgggacagag ttcactctca ccatcagcag cctgcagtct     240
gaagattttg cagtttatta ctgtcagcag cacaatgtct accctcctta cacttttggc     300
ggagggacca aggttgagat caaa                                            324

<210> SEQ ID NO 123
<211> LENGTH: 324
<212> TYPE: DNA
<213> ORGANISM: Artificial
<220> FEATURE:
<223> OTHER INFORMATION: Synthetic construct

<400> SEQUENCE: 123
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtccgaac gaagcccttt cacttttggc     300
ggagggacca aggttgagat caaa                                            324

<210> SEQ ID NO 124
<211> LENGTH: 321
<212> TYPE: DNA
<213> ORGANISM: Artificial
<220> FEATURE:
<223> OTHER INFORMATION: Synthetic construct

<400> SEQUENCE: 124
gaaattgtgt tgacacagtc tccagccacc ctgtctttgt ctccagggga aagagccacc      60
ctctcctgca gggccagtca gagtgttagc agctacttag cctggttcca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag gcattctcca tgcctcctac ttttggcgga     300
gggaccaagg ttgagatcaa a                                               321

<210> SEQ ID NO 125
<211> LENGTH: 321
<212> TYPE: DNA
<213> ORGANISM: Artificial
```

<220> FEATURE:
<223> OTHER INFORMATION: Synthetic construct

<400> SEQUENCE: 125

| | | | | | |
|---|---|---|---|---|---|
| gacatccaga | tgacccagtc | tccttccacc | ctgtctgcat | ctgtaggaga | cagagtcacc | 60 |
| atcacttgcc | gggccagtca | gagtattagt | agctggttgg | cctggtatca | gcagaaacca | 120 |
| gggaaagccc | ctaagctcct | gatctatgat | gcctccagtt | tggaaagtgg | ggtcccatca | 180 |
| aggttcagcg | gcagtggatc | tgggacagaa | ttcactctca | ccatcagcag | cctgcagcct | 240 |
| gatgattttg | caacttatta | ctgccagcag | ttccaaagtt | actcttacac | ttttggcgga | 300 |
| gggaccaagg | ttgagatcaa | a | | | | 321 |

<210> SEQ ID NO 126
<211> LENGTH: 321
<212> TYPE: DNA
<213> ORGANISM: Artificial
<220> FEATURE:
<223> OTHER INFORMATION: Synthetic construct

<400> SEQUENCE: 126

| | | | | | |
|---|---|---|---|---|---|
| gaaatagtga | tgacgcagtc | tccagccacc | ctgtctgtgt | ctccagggga | aagagccacc | 60 |
| ctctcctgca | gggccagtca | gagtgttagc | agcaacttag | cctggtacca | gcagaaacct | 120 |
| ggccaggctc | ccaggctcct | catctatggt | gcatccacca | gggccactgg | tatcccagcc | 180 |
| aggttcagtg | gcagtgggtc | tgggacagag | ttcactctca | ccatcagcag | cctgcagtct | 240 |
| gaagattttg | cagtttatta | ctgtcagcag | taccacgcct | ggcctcctac | ttttggcgga | 300 |
| gggaccaagg | ttgagatcaa | a | | | | 321 |

<210> SEQ ID NO 127
<211> LENGTH: 321
<212> TYPE: DNA
<213> ORGANISM: Artificial
<220> FEATURE:
<223> OTHER INFORMATION: Synthetic construct

<400> SEQUENCE: 127

| | | | | | |
|---|---|---|---|---|---|
| gaaattgtgt | tgacgcagtc | tccaggcacc | ctgtctttgt | ctccagggga | aagagccacc | 60 |
| ctctcctgca | gggccagtca | gagtgttagc | agcagctact | tagcctggta | ccagcagaaa | 120 |
| cctggccagg | ctcccaggct | cctcatctat | ggtgcatcca | gcagggccac | tggcatccca | 180 |
| gacaggttca | gtggcagtgg | gtctgggaca | gacttcactc | tcaccatcag | cagactggag | 240 |
| cctgaagatt | ttgcagtgta | ttactgtcag | cagttcgaca | gcagtcctac | ttttggcgga | 300 |
| gggaccaagg | ttgagatcaa | a | | | | 321 |

<210> SEQ ID NO 128
<211> LENGTH: 324
<212> TYPE: DNA
<213> ORGANISM: Artificial
<220> FEATURE:
<223> OTHER INFORMATION: Synthetic construct

<400> SEQUENCE: 128

| | | | | | |
|---|---|---|---|---|---|
| gaaattgtgt | tgacgcagtc | tccaggcacc | ctgtctttgt | ctccagggga | aagagccacc | 60 |
| ctctcctgca | gggccagtca | gagtgttagc | agcagcttct | tagcctggta | ccagcagaaa | 120 |
| cctggccagg | ctcccaggct | cctcatctat | ggtgcatcca | gcagggccac | tggcatccca | 180 |
| gacaggttca | gtggcagtgg | gtctgggaca | gacttcactc | tcaccatcag | cagactggag | 240 |

```
cctgaagatt ttgcagtgta ttactgtcag cagtacgacg tcttccctat cacttttggc    300
ggagggacca aggttgagat caaa                                           324
```

<210> SEQ ID NO 129
<211> LENGTH: 321
<212> TYPE: DNA
<213> ORGANISM: Artificial
<220> FEATURE:
<223> OTHER INFORMATION: Synthetic construct

<400> SEQUENCE: 129

```
gacatccaga tgacccagtc tccatcctcc ctgtctgcat ctgtaggaga cagagtcacc     60
atcacttgcc aggcgagtca ggacattagc aactatttaa attggtatca gcagaaacca   120
gggaaagccc ctaagctcct gatctacgat gcatccaatt tggaaacagg gtcccatca    180 aggttcagtg gaagtggatc tgggacagat tttactttca ccatcagcag cctgcagcct   240
gaagatattg caacatatta ctgtcagcag cccgccaccc taccttggac ttttggcgga   300
gggaccaagg ttgagatcaa a                                             321
```

<210> SEQ ID NO 130
<211> LENGTH: 106
<212> TYPE: PRT
<213> ORGANISM: Artificial
<220> FEATURE:
<223> OTHER INFORMATION: Synthetic construct

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp His Tyr Pro Thr
                85                  90                  95

Phe Gly Gly Gly Thr Lys Val Glu Ile Lys
            100                 105

<210> SEQ ID NO 131
<211> LENGTH: 108
<212> TYPE: PRT
<213> ORGANISM: Artificial
<220> FEATURE:
<223> OTHER INFORMATION: Synthetic construct

<400> SEQUENCE: 131

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

-continued

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Asn Val Tyr Pro Pro
                85                  90                  95

Tyr Thr Phe Gly Gly Gly Thr Lys Val Glu Ile Lys
            100                 105

<210> SEQ ID NO 132
<211> LENGTH: 108
<212> TYPE: PRT
<213> ORGANISM: Artificial
<220> FEATURE:
<223> OTHER INFORMATION: Synthetic construct

<400> SEQUENCE: 132

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Glu Arg Ser Pro
                85                  90                  95

Phe Thr Phe Gly Gly Gly Thr Lys Val Glu Ile Lys
            100                 105

<210> SEQ ID NO 133
<211> LENGTH: 107
<212> TYPE: PRT
<213> ORGANISM: Artificial
<220> FEATURE:
<223> OTHER INFORMATION: Synthetic construct

<400> SEQUENCE: 133

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Phe Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ala Phe Ser Met Pro Pro
                85                  90                  95

Thr Phe Gly Gly Gly Thr Lys Val Glu Ile Lys
            100                 105

<210> SEQ ID NO 134
<211> LENGTH: 107
<212> TYPE: PRT
<213> ORGANISM: Artificial
<220> FEATURE:
<223> OTHER INFORMATION: Synthetic construct -continued

<400> SEQUENCE: 134

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Phe Gln Ser Tyr Ser Tyr
                85                  90                  95

Thr Phe Gly Gly Gly Thr Lys Val Glu Ile Lys
            100                 105

<210> SEQ ID NO 135
<211> LENGTH: 107
<212> TYPE: PRT
<213> ORGANISM: Artificial
<220> FEATURE:
<223> OTHER INFORMATION: Synthetic construct

<400> SEQUENCE: 135

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ala Trp Pro Pro
                85                  90                  95

Thr Phe Gly Gly Gly Thr Lys Val Glu Ile Lys
            100                 105

<210> SEQ ID NO 136
<211> LENGTH: 107
<212> TYPE: PRT
<213> ORGANISM: Artificial
<220> FEATURE:
<223> OTHER INFORMATION: Synthetic construct

<400> SEQUENCE: 136

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Asp Ser Ser Pro
            85                  90                  95

Thr Phe Gly Gly Gly Thr Lys Val Glu Ile Lys
            100                 105

<210> SEQ ID NO 137
<211> LENGTH: 108
<212> TYPE: PRT
<213> ORGANISM: Artificial
<220> FEATURE:
<223> OTHER INFORMATION: Synthetic construct

<400> SEQUENCE: 137

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Val Phe Pro
                85                  90                  95

Ile Thr Phe Gly Gly Gly Thr Lys Val Glu Ile Lys
            100                 105

<210> SEQ ID NO 138
<211> LENGTH: 107
<212> TYPE: PRT
<213> ORGANISM: Artificial
<220> FEATURE:
<223> OTHER INFORMATION: Synthetic construct

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Pro Ala Thr Leu Pro Trp
                85                  90                  95

Thr Phe Gly Gly Gly Thr Lys Val Glu Ile Lys
            100                 105

<210> SEQ ID NO 139
<211> LENGTH: 449
<212> TYPE: PRT
<213> ORGANISM: Artificial
<220> FEATURE:
<223> OTHER INFORMATION: Synthetic construct

<400> SEQUENCE: 139

Gln Val Gln Leu Val Glu Ser Gly Gly Gly Val Val Gln Pro Gly Arg

-continued

```
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
            35                  40                  45
Ala Val Ile Ser Tyr Asp Gly Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Gly Arg Pro Trp Tyr Ser Glu Thr Gly Thr Ser Ala Phe Asp
            100                 105                 110
Ile Trp Gly Gln Gly Thr Met Val Thr Val Ser Ala Ser Thr Lys
            115                 120                 125
Gly Pro Ser Val Phe Pro Leu Ala Pro Cys Ser Arg Ser Thr Ser Glu
 130                 135                 140
Ser Thr Ala Ala Leu Gly Cys Leu Val Lys Asp Tyr Phe Pro Glu Pro
 145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Asn Phe Gly Thr Gln Thr Tyr Thr Cys Asn
            195                 200                 205
Val Asp His Lys Pro Ser Asn Thr Lys Val Asp Lys Thr Val Glu Arg
 210                 215                 220
Lys Cys Cys Val Glu Cys Pro Pro Cys Pro Ala Pro Pro Val Ala Gly
 225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Gln Phe Asn Trp Tyr Val Asp Gly Val Glu Val His
            275                 280                 285
Asn Ala Lys Thr Lys Pro Arg Glu Glu Gln Phe Asn Ser Thr Phe Arg
 290                 295                 300
Val Val Ser Val Leu Thr Val Val His Gln Asp Trp Leu Asn Gly Lys
 305                 310                 315                 320
Glu Tyr Lys Cys Lys Val Ser Asn Lys Gly Leu Pro Ala Pro Ile Glu
                325                 330                 335
Lys Thr Ile Ser Lys Thr Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
 370                 375                 380
Glu Ser Asn Gly Gln Pro Glu Asn Asn Tyr Lys Thr Thr Pro Pro Met
 385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
            435                 440                 445
Gly

<210> SEQ ID NO 140
<211> LENGTH: 454
<212> TYPE: PRT
<213> ORGANISM: Artificial
<220> FEATURE:
<223> OTHER INFORMATION: Synthetic construct

<400> SEQUENCE: 140

Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Val Tyr
                20                  25                  30

Asn Met His Trp Val Arg Gln Ala Pro Gly Lys Gly Leu Glu Trp Val
            35                  40                  45

Ala Val Ile Ala Tyr Asp Gly Ser Ala Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Ala Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335
```

```
Ala Pro Ile Glu Lys Thr Ile Ser Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Lys
            450

<210> SEQ ID NO 141
<211> LENGTH: 449
<212> TYPE: PRT
<213> ORGANISM: Artificial
<220> FEATURE:
<223> OTHER INFORMATION: Synthetic construct

<400> SEQUENCE: 141

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30

Asn Met His Trp Val Arg Gln Ala Pro Gly Lys Gly Leu Glu Trp Val
        35                  40                  45

Ala Val Ile Ala Tyr Asp Gly Ser Ala Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240
```

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 142
<211> LENGTH: 454
<212> TYPE: PRT
<213> ORGANISM: Artificial
<220> FEATURE:
<223> OTHER INFORMATION: Synthetic construct

<400> SEQUENCE: 142

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Arg
            20                  25                  30

Asn Met His Trp Val Arg Gln Ala Pro Gly Lys Gly Leu Glu Trp Val
        35                  40                  45

Ala Val Ile Ala Tyr Asp Gly Ser Leu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
```

```
                145                 150                 155                 160
Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Lys Ala Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 143
<211> LENGTH: 449
<212> TYPE: PRT
<213> ORGANISM: Artificial
<220> FEATURE:
<223> OTHER INFORMATION: Synthetic construct

<400> SEQUENCE: 143

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Arg
                20                  25                  30

Asn Met His Trp Val Arg Gln Ala Pro Gly Lys Gly Leu Glu Trp Val
            35                  40                  45

Ala Val Ile Ala Tyr Asp Gly Ser Leu Lys Tyr Tyr Ala Asp Ser Val
```

```
                50             55              60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Gly Arg Pro Trp Tyr Ser Glu Thr Gly Thr Ser Ala Phe Asp
                100                 105                 110

Ile Trp Gly Gln Gly Thr Met Val Thr Val Ser Ser Ala Ser Thr Lys
            115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Asn Phe Gly Thr Gln Thr Tyr Thr Cys Asn
                195                 200                 205

Val Asp His Lys Pro Ser Asn Thr Lys Val Asp Lys Thr Val Glu Arg
210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Phe Arg
290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 144
<211> LENGTH: 454
```

```
<212> TYPE: PRT
<213> ORGANISM: Artificial
<220> FEATURE:
<223> OTHER INFORMATION: Synthetic construct

<400> SEQUENCE: 144
```

| | | | | | | | | | | | |
|---|---|---|---|---|---|---|---|---|---|---|---|
| Gln | Val | Gln | Leu | Val | Glu | Ser | Gly | Gly | Val | Gln | Pro | Gly | Arg |
| 1 | | | | 5 | | | | | 10 | | | | 15 |
| Ser | Leu | Arg | Leu | Ser | Cys | Ala | Ala | Ser | Gly | Phe | Thr | Phe | Val | Ser | Tyr |
| | | 20 | | | | | 25 | | | | | 30 | | | |
| Asn | Met | His | Trp | Val | Arg | Gln | Ala | Pro | Gly | Lys | Gly | Leu | Glu | Trp | Val |
| | | 35 | | | | | 40 | | | | | 45 | | | |
| Ala | Val | Ile | Ala | Tyr | Asp | Gly | Ser | Val | Lys | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Gly | Arg | Pro | Trp | Tyr | Ser | Glu | Thr | Gly | Thr | Ser | Ala | Phe | Asp |
| | | | 100 | | | | | 105 | | | | | 110 | | |
| Ile | Trp | Gly | Gln | Gly | Thr | Met | Val | Thr | Val | Ser | Ser | Ala | Ser | Thr | Lys |
| | | | 115 | | | | | 120 | | | | | 125 | | |
| Gly | Pro | Ser | Val | Phe | Pro | Leu | Ala | Pro | Ser | Ser | Lys | Ser | Thr | Ser | Gly |
| | 130 | | | | | 135 | | | | | 140 | | | | |
| Gly | Thr | Ala | Ala | Leu | Gly | Cys | Leu | Val | Lys | Asp | Tyr | Phe | Pro | Glu | Pro |
| 145 | | | | | 150 | | | | | 155 | | | | | 160 |
| Val | Thr | Val | Ser | Trp | Asn | Ser | Gly | Ala | Leu | Thr | Ser | Gly | Val | His | Thr |
| | | | | 165 | | | | | 170 | | | | | 175 | |
| Phe | Pro | Ala | Val | Leu | Gln | Ser | Ser | Gly | Leu | Tyr | Ser | Leu | Ser | Ser | Val |
| | | | 180 | | | | | 185 | | | | | 190 | | |
| Val | Thr | Val | Pro | Ser | Ser | Ser | Leu | Gly | Thr | Gln | Thr | Tyr | Ile | Cys | Asn |
| | | 195 | | | | | 200 | | | | | 205 | | | |
| Val | Asn | His | Lys | Pro | Ser | Asn | Thr | Lys | Val | Asp | Lys | Lys | Ala | Glu | Pro |
| | 210 | | | | | 215 | | | | | 220 | | | | |
| Lys | Ser | Cys | Asp | Lys | Thr | His | Thr | Cys | Pro | Pro | Cys | Pro | Ala | Pro | Glu |
| 225 | | | | | 230 | | | | | 235 | | | | | 240 |
| Leu | Leu | Gly | Gly | Pro | Ser | Val | Phe | Leu | Phe | Pro | Pro | Lys | Pro | Lys | Asp |
| | | | | 245 | | | | | 250 | | | | | 255 | |
| Thr | Leu | Met | Ile | Ser | Arg | Thr | Pro | Glu | Val | Thr | Cys | Val | Val | Val | Asp |
| | | | 260 | | | | | 265 | | | | | 270 | | |
| Val | Ser | His | Glu | Asp | Pro | Glu | Val | Lys | Phe | Asn | Trp | Tyr | Val | Asp | Gly |
| | | 275 | | | | | 280 | | | | | 285 | | | |
| Val | Glu | Val | His | Asn | Ala | Lys | Thr | Lys | Pro | Arg | Glu | Glu | Gln | Tyr | Asn |
| | 290 | | | | | 295 | | | | | 300 | | | | |
| Ser | Thr | Tyr | Arg | Val | Val | Ser | Val | Leu | Thr | Val | Leu | His | Gln | Asp | Trp |
| 305 | | | | | 310 | | | | | 315 | | | | | 320 |
| Leu | Asn | Gly | Lys | Glu | Tyr | Lys | Cys | Lys | Val | Ser | Asn | Lys | Ala | Leu | Pro |
| | | | | 325 | | | | | 330 | | | | | 335 | |
| Ala | Pro | Ile | Glu | Lys | Thr | Ile | Ser | Lys | Ala | Lys | Gly | Gln | Pro | Arg | Glu |
| | | | 340 | | | | | 345 | | | | | 350 | | |
| Pro | Gln | Val | Tyr | Thr | Leu | Pro | Pro | Ser | Arg | Asp | Glu | Leu | Thr | Lys | Asn |
| | | 355 | | | | | 360 | | | | | 365 | | | |
| Gln | Val | Ser | Leu | Thr | Cys | Leu | Val | Lys | Gly | Phe | Tyr | Pro | Ser | Asp | Ile |
| | 370 | | | | | 375 | | | | | 380 | | | | |

```
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 145
<211> LENGTH: 449
<212> TYPE: PRT
<213> ORGANISM: Artificial
<220> FEATURE:
<223> OTHER INFORMATION: Synthetic construct

<400> SEQUENCE: 145

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Val Ser Tyr
            20                  25                  30

Asn Met His Trp Val Arg Gln Ala Pro Gly Lys Gly Leu Glu Trp Val
        35                  40                  45

Ala Val Ile Ala Tyr Asp Gly Ser Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Arg Pro Trp Tyr Ser Glu Thr Gly Thr Ser Ala Phe Asp
        100                 105                 110

Ile Trp Gly Gln Gly Thr Met Val Thr Val Ser Ser Ala Ser Thr Lys
    115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Asn Phe Gly Thr Gln Thr Tyr Thr Cys Asn
    195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Val Ala Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Gln Phe Asn Trp Tyr Val Asp Gly Val Glu Val His
    275                 280                 285
```

```
Asn Ala Lys Thr Lys Pro Arg Glu Glu Gln Phe Asn Ser Thr Phe Arg
    290                 295                 300

Val Val Ser Val Leu Thr Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 146
<211> LENGTH: 454
<212> TYPE: PRT
<213> ORGANISM: Artificial
<220> FEATURE:
<223> OTHER INFORMATION: Synthetic construct

<400> SEQUENCE: 146

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Val Ser Tyr
                20                  25                  30

Asn Met His Trp Val Arg Gln Ala Pro Gly Lys Gly Leu Glu Trp Val
            35                  40                  45

Ala Val Ile Met Tyr Asp Gly Ser Ala Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
                100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
```

```
            195                 200                 205
Val Asn His Lys Pro Ser Asn Thr Lys Val Asp Lys Lys Ala Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Lys
    450

<210> SEQ ID NO 147
<211> LENGTH: 449
<212> TYPE: PRT
<213> ORGANISM: Artificial
<220> FEATURE:
<223> OTHER INFORMATION: Synthetic construct

<400> SEQUENCE: 147

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Val Ser Tyr
            20                  25                  30

Asn Met His Trp Val Arg Gln Ala Pro Gly Lys Gly Leu Glu Trp Val
        35                  40                  45

Ala Val Ile Met Tyr Asp Gly Ser Ala Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
```

```
            100                 105                 110
Ile Trp Gly Gln Gly Thr Met Val Thr Val Ser Ser Ala Ser Thr Lys
            115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 148
<211> LENGTH: 454
<212> TYPE: PRT
<213> ORGANISM: Artificial
<220> FEATURE:
<223> OTHER INFORMATION: Synthetic construct

<400> SEQUENCE: 148

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Arg Ser Tyr
            20                  25                  30

Asp Met His Trp Val Arg Gln Ala Pro Gly Lys Gly Leu Glu Trp Val
            35                  40                  45

Ala Tyr Ile Ala Tyr Asp Gly Ser Asn Lys Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Ala Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430
```

```
Ser Val Met His Glu Ala Leu His Asn His Tyr Thr Gln Lys Ser Leu
            435                 440                 445
Ser Leu Ser Pro Gly Lys
            450

<210> SEQ ID NO 149
<211> LENGTH: 449
<212> TYPE: PRT
<213> ORGANISM: Artificial
<220> FEATURE:
<223> OTHER INFORMATION: Synthetic construct

<400> SEQUENCE: 149

Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Arg Ser Tyr
                20                  25                  30

Asp Met His Trp Val Arg Gln Ala Pro Gly Lys Gly Leu Glu Trp Val
            35                  40                  45

Ala Tyr Ile Ala Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335
```

```
Lys Thr Ile Ser Lys Thr Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 150
<211> LENGTH: 452
<212> TYPE: PRT
<213> ORGANISM: Artificial
<220> FEATURE:
<223> OTHER INFORMATION: Synthetic construct

<400> SEQUENCE: 150

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Val Gly Tyr Pro His Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Ala Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
```

```
                    245                 250                 255
Met Ile Ser Arg Thr Pro Glu Val Thr Cys Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
        450

<210> SEQ ID NO 151
<211> LENGTH: 447
<212> TYPE: PRT
<213> ORGANISM: Artificial
<220> FEATURE:
<223> OTHER INFORMATION: Synthetic construct

<400> SEQUENCE: 151

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Val Gly Tyr Pro His Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
```

```
                145                 150                 155                 160
Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Asn Phe Gly Thr Gln Thr Tyr Thr Cys Asn Val Asp
                195                 200                 205

His Lys Pro Ser Asn Thr Lys Val Asp Lys Thr Val Glu Arg Lys Cys
            210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Phe Arg Val Val
            290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
            435                 440                 445

<210> SEQ ID NO 152
<211> LENGTH: 452
<212> TYPE: PRT
<213> ORGANISM: Artificial
<220> FEATURE:
<223> OTHER INFORMATION: Synthetic construct

<400> SEQUENCE: 152

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Ser Gly
                20                  25                  30

Ala Tyr Tyr Trp Ser Trp Ile Arg Gln His Pro Gly Lys Gly Leu Glu
            35                  40                  45

Trp Ile Gly Tyr Ile Tyr Tyr Asp Gly Gln Thr Tyr Tyr Asn Pro Ser
        50                  55                  60

Leu Lys Ser Arg Val Thr Ile Ser Val Asp Thr Ser Lys Asn Gln Phe
```

```
            65                  70                  75                  80
        Ser Leu Lys Leu Ser Ser Val Thr Ala Ala Asp Thr Ala Val Tyr Tyr
                        85                  90                  95

Cys Ala Arg Asp Val Gly Tyr Pro His Tyr Tyr Gly Met Asp Val Trp
                        100                 105                 110

Gly Gln Gly Thr Thr Val Thr Val Ser Ser Ala Ser Thr Lys Gly Pro
                        115                 120                 125

Ser Val Phe Pro Leu Ala Pro Ser Ser Lys Ser Thr Ser Gly Gly Thr
                130                 135                 140

Ala Ala Leu Gly Cys Leu Val Lys Asp Tyr Phe Pro Glu Pro Val Thr
        145                 150                 155                 160

Val Ser Trp Asn Ser Gly Ala Leu Thr Ser Gly Val His Thr Phe Pro
                        165                 170                 175

Ala Val Leu Gln Ser Ser Gly Leu Tyr Ser Leu Ser Ser Val Val Thr
                        180                 185                 190

Val Pro Ser Ser Ser Leu Gly Thr Gln Thr Tyr Ile Cys Asn Val Asn
                        195                 200                 205

His Lys Pro Ser Asn Thr Lys Val Asp Lys Lys Ala Glu Pro Lys Ser
                210                 215                 220

Cys Asp Lys Thr His Thr Cys Pro Pro Cys Pro Ala Pro Glu Leu Leu
        225                 230                 235                 240

Gly Gly Pro Ser Val Phe Leu Phe Pro Pro Lys Pro Lys Asp Thr Leu
                        245                 250                 255

Met Ile Ser Arg Thr Pro Glu Val Thr Cys Val Val Val Asp Val Ser
                        260                 265                 270

His Glu Asp Pro Glu Val Lys Phe Asn Trp Tyr Val Asp Gly Val Glu
                        275                 280                 285

Val His Asn Ala Lys Thr Lys Pro Arg Glu Glu Gln Tyr Asn Ser Thr
                290                 295                 300

Tyr Arg Val Val Ser Val Leu Thr Val Leu His Gln Asp Trp Leu Asn
        305                 310                 315                 320

Gly Lys Glu Tyr Lys Cys Lys Val Ser Asn Lys Ala Leu Pro Ala Pro
                        325                 330                 335

Ile Glu Lys Thr Ile Ser Lys Ala Lys Gly Gln Pro Arg Glu Pro Gln
                        340                 345                 350

Val Tyr Thr Leu Pro Pro Ser Arg Asp Glu Leu Thr Lys Asn Gln Val
                        355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
        385                 390                 395                 400

Pro Val Leu Asp Ser Asp Gly Ser Phe Phe Leu Tyr Ser Lys Leu Thr
                        405                 410                 415

Val Asp Lys Ser Arg Trp Gln Gln Gly Asn Val Phe Ser Cys Ser Val
                        420                 425                 430

Met His Glu Ala Leu His Asn His Tyr Thr Gln Lys Ser Leu Ser Leu
                        435                 440                 445

Ser Pro Gly Lys
                450

<210> SEQ ID NO 153
<211> LENGTH: 447
<212> TYPE: PRT
<213> ORGANISM: Artificial
```

<220> FEATURE:
<223> OTHER INFORMATION: Synthetic construct

<400> SEQUENCE: 153

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Ser Gly
            20                  25                  30

Ala Tyr Tyr Trp Ser Trp Ile Arg Gln His Pro Gly Lys Gly Leu Glu
        35                  40                  45

Trp Ile Gly Tyr Ile Tyr Tyr Asp Gly Gln Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Val Gly Tyr Pro His Tyr Tyr Gly Met Asp Val Trp
        100                 105                 110

Gly Gln Gly Thr Thr Val Thr Val Ser Ser Ala Ser Thr Lys Gly Pro
    115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Asn Phe Gly Thr Gln Thr Tyr Thr Cys Asn Val Asp
    195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Phe Arg Val Val
290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
            325                 330                 335

Ile Ser Lys Thr Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400
```

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 154
<211> LENGTH: 452
<212> TYPE: PRT
<213> ORGANISM: Artificial
<220> FEATURE:
<223> OTHER INFORMATION: Synthetic construct

<400> SEQUENCE: 154

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ala Ser Tyr Trp Ser Trp Ile Arg Gln His Pro Gly Lys Gly Leu Glu
            35                  40                  45

Trp Ile Gly Tyr Ile Tyr Tyr Ser Gly Glu Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Val Gly Tyr Pro His Tyr Tyr Gly Met Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Ala Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320
```

```
Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 155
<211> LENGTH: 447
<212> TYPE: PRT
<213> ORGANISM: Artificial
<220> FEATURE:
<223> OTHER INFORMATION: Synthetic construct

<400> SEQUENCE: 155

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ala Ser Tyr Trp Ser Trp Ile Arg Gln His Pro Gly Lys Gly Leu Glu
        35                  40                  45

Trp Ile Gly Tyr Ile Tyr Tyr Ser Gly Glu Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Val Gly Tyr Pro His Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220
```

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Phe Arg Val Val
290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
            325                 330                 335

Ile Ser Lys Thr Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
    435                 440                 445

<210> SEQ ID NO 156
<211> LENGTH: 452
<212> TYPE: PRT
<213> ORGANISM: Artificial
<220> FEATURE:
<223> OTHER INFORMATION: Synthetic construct

<400> SEQUENCE: 156

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Ser Tyr Trp Ser Trp Ile Arg Gln His Pro Gly Lys Gly Leu Glu
        35                  40                  45

Trp Ile Gly Tyr Ile Tyr Met Ser Gly Glu Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Val Gly Tyr Pro His Tyr Tyr Gly Met Asp Val Trp
        100                 105                 110

Gly Gln Gly Thr Thr Val Thr Val Ser Ser Ala Ser Thr Lys Gly Pro
    115                 120                 125

Ser Val Phe Pro Leu Ala Pro Ser Ser Lys Ser Thr Ser Gly Gly Thr
130                 135                 140

```
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Leu Gly Thr Gln Thr Tyr Ile Cys Asn Val Asn
    195                 200                 205

His Lys Pro Ser Asn Thr Lys Val Asp Lys Lys Ala Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 157
<211> LENGTH: 447
<212> TYPE: PRT
<213> ORGANISM: Artificial
<220> FEATURE:
<223> OTHER INFORMATION: Synthetic construct

<400> SEQUENCE: 157

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Ser Tyr Trp Ser Trp Ile Arg Gln His Pro Gly Lys Gly Leu Glu
        35                  40                  45
```

Trp Ile Gly Tyr Ile Tyr Met Ser Gly Glu Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Val Gly Tyr Pro His Tyr Tyr Gly Met Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Phe Arg Val Val
290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 158
<211> LENGTH: 453

```
<212> TYPE: PRT
<213> ORGANISM: Artificial
<220> FEATURE:
<223> OTHER INFORMATION: Synthetic construct

<400> SEQUENCE: 158
```

| | | | | | | | | | | | | | | |
|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Glu |
| 1 | | | | 5 | | | | | 10 | | | | | 15 |
| Thr | Leu | Ser | Leu | Thr | Cys | Thr | Val | Ser | Gly | Gly | Ser | Ile | Ser | Ser | Tyr |
| | | | 20 | | | | | 25 | | | | | 30 | |
| Tyr | Trp | Ser | Trp | Ile | Arg | Gln | Pro | Pro | Gly | Lys | Gly | Leu | Glu | Trp | Ile |
| | | 35 | | | | | 40 | | | | | 45 | | |
| Gly | Tyr | Ile | Tyr | Ser | Ser | Gly | Ser | Thr | Asn | Tyr | Asn | Pro | Ser | Leu | Lys |
| | 50 | | | | | 55 | | | | | 60 | | | |
| Ser | Arg | Val | Thr | Ile | Ser | Val | Asp | Thr | Ser | Lys | Asn | Gln | Phe | Ser | Leu |
| 65 | | | | | 70 | | | | | 75 | | | | | 80 |
| Lys | Leu | Ser | Ser | Val | Thr | Ala | Ala | Asp | Thr | Ala | Val | Tyr | Tyr | Cys | Ala |
| | | | | 85 | | | | | 90 | | | | | 95 | |
| Arg | Asp | Ala | Pro | Gly | Gly | Ser | Ser | Tyr | Gln | Asp | Tyr | Tyr | Met | Asp | Val |
| | | | 100 | | | | | 105 | | | | | 110 | | |
| Trp | Gly | Lys | Gly | Thr | Thr | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Ser | Ser | Lys | Ser | Thr | Ser | Gly | Gly |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | 195 | | | | | 200 | | | | | 205 | | | |
| Asn | His | Lys | Pro | Ser | Asn | Thr | Lys | Val | Asp | Lys | Lys | Ala | Glu | Pro | Lys |
| | 210 | | | | | 215 | | | | | 220 | | | | |
| Ser | Cys | Asp | Lys | Thr | His | Thr | Cys | Pro | Pro | Cys | Pro | Ala | Pro | Glu | Leu |
| 225 | | | | | 230 | | | | | 235 | | | | | 240 |
| Leu | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | 275 | | | | | 280 | | | | | 285 | | | |
| Glu | Val | His | Asn | Ala | Lys | Thr | Lys | Pro | Arg | Glu | Glu | Gln | Tyr | Asn | Ser |
| | 290 | | | | | 295 | | | | | 300 | | | | |
| Thr | Tyr | Arg | Val | Val | Ser | Val | Leu | Thr | Val | Leu | His | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Ala | Leu | Pro | Ala |
| | | | | 325 | | | | | 330 | | | | | 335 | |
| Pro | Ile | Glu | Lys | Thr | Ile | Ser | Lys | Ala | Lys | Gly | Gln | Pro | Arg | Glu | Pro |
| | | | 340 | | | | | 345 | | | | | 350 | | |
| Gln | Val | Tyr | Thr | Leu | Pro | Pro | Ser | Arg | Asp | Glu | Leu | Thr | Lys | Asn | Gln |
| | | 355 | | | | | 360 | | | | | 365 | | | |
| Val | Ser | Leu | Thr | Cys | Leu | Val | Lys | Gly | Phe | Tyr | Pro | Ser | Asp | Ile | Ala |
| | 370 | | | | | 375 | | | | | 380 | | | | |

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 159
<211> LENGTH: 448
<212> TYPE: PRT
<213> ORGANISM: Artificial
<220> FEATURE:
<223> OTHER INFORMATION: Synthetic construct

<400> SEQUENCE: 159

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Ser Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Asp Ala Pro Gly Ser Ser Tyr Gln Asp Tyr Tyr Met Asp Val
        100                 105                 110

Trp Gly Lys Gly Thr Thr Val Thr Val Ser Ser Ala Ser Thr Lys Gly
    115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Asn Phe Gly Thr Gln Thr Tyr Thr Cys Asn Val
    195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Gln Phe Asn Trp Tyr Val Asp Gly Val Glu Val His Asn
    275                 280                 285

```
Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445
```

<210> SEQ ID NO 160
<211> LENGTH: 452
<212> TYPE: PRT
<213> ORGANISM: Artificial
<220> FEATURE:
<223> OTHER INFORMATION: Synthetic construct

<400> SEQUENCE: 160

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Leu Gly Tyr Ser Trp Glu Tyr Phe Asp Leu Trp
            100                 105                 110

Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

His Lys Pro Ser Asn Thr Lys Val Asp Lys Lys Ala Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 161
<211> LENGTH: 447
<212> TYPE: PRT
<213> ORGANISM: Artificial
<220> FEATURE:
<223> OTHER INFORMATION: Synthetic construct

<400> SEQUENCE: 161

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
            20                  25                  30
Ser Met Asn Trp Val Arg Gln Ala Pro Gly Lys Gly Leu Glu Trp Val
        35                  40                  45
Ser Ser Ile Ser Ser Ser Ser Asn Tyr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Ala Pro Leu Gly Tyr Ser Trp Glu Tyr Phe Asp Leu Trp
            100                 105                 110

Gly Arg Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 162
<211> LENGTH: 450
<212> TYPE: PRT
<213> ORGANISM: Artificial
<220> FEATURE:
<223> OTHER INFORMATION: Synthetic construct

<400> SEQUENCE: 162

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

-continued

```
Tyr Trp Ser Trp Ile Arg Gln Pro Gly Lys Gly Leu Glu Trp Ile
         35                  40                  45
Gly Glu Ile Asp His Ser Gly Ser Thr Asn Tyr Asn Pro Ser Leu Lys
 50                  55                  60
Ser Arg Val Thr Ile Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                 85                  90                  95
Arg Asp Gly Gly Gly Tyr Ala Ser Pro Phe Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Ala Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
```

-continued

```
                450

<210> SEQ ID NO 163
<211> LENGTH: 445
<212> TYPE: PRT
<213> ORGANISM: Artificial
<220> FEATURE:
<223> OTHER INFORMATION: Synthetic construct

<400> SEQUENCE: 163
```

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Gly Gly Tyr Ala Ser Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val

```
                355                 360                 365
Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 164
<211> LENGTH: 453
<212> TYPE: PRT
<213> ORGANISM: Artificial
<220> FEATURE:
<223> OTHER INFORMATION: Synthetic construct

<400> SEQUENCE: 164

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Gly Tyr Ser Ala Ser Pro Asn Trp Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Ala Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
```

-continued

```
            275                 280                 285
Glu Val His Asn Ala Lys Thr Lys Pro Arg Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 165
<211> LENGTH: 448
<212> TYPE: PRT
<213> ORGANISM: Artificial
<220> FEATURE:
<223> OTHER INFORMATION: Synthetic construct

<400> SEQUENCE: 165

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Gly Tyr Ser Ala Ser Pro Asn Trp Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

```
                180             185             190
Thr Val Pro Ser Ser Asn Phe Gly Thr Gln Thr Tyr Thr Cys Asn Val
            195             200             205
Asp His Lys Pro Ser Asn Thr Lys Val Asp Lys Thr Val Glu Arg Lys
        210              215             220
Cys Cys Val Glu Cys Pro Cys Pro Ala Pro Val Ala Gly Pro
225             230             235             240
Ser Val Phe Leu Phe Pro Pro Lys Pro Lys Asp Thr Leu Met Ile Ser
            245             250             255
Arg Thr Pro Glu Val Thr Cys Val Val Asp Val Ser His Glu Asp
        260             265             270
Pro Glu Val Gln Phe Asn Trp Tyr Val Asp Gly Val Glu Val His Asn
        275             280             285
Ala Lys Thr Lys Pro Arg Glu Glu Gln Phe Asn Ser Thr Phe Arg Val
        290             295             300
Val Ser Val Leu Thr Val Val His Gln Asp Trp Leu Asn Gly Lys Glu
305             310             315             320
Tyr Lys Cys Lys Val Ser Asn Lys Gly Leu Pro Ala Pro Ile Glu Lys
                325             330             335
Thr Ile Ser Lys Thr Lys Gly Gln Pro Arg Glu Pro Gln Val Tyr Thr
                340             345             350
Leu Pro Pro Ser Arg Glu Glu Met Thr Lys Asn Gln Val Ser Leu Thr
            355             360             365
Cys Leu Val Lys Gly Phe Tyr Pro Ser Asp Ile Ala Val Glu Trp Glu
        370             375             380
Ser Asn Gly Gln Pro Glu Asn Asn Tyr Lys Thr Thr Pro Pro Met Leu
385             390             395             400
Asp Ser Asp Gly Ser Phe Phe Leu Tyr Ser Lys Leu Thr Val Asp Lys
                405             410             415
Ser Arg Trp Gln Gln Gly Asn Val Phe Ser Cys Ser Val Met His Glu
                420             425             430
Ala Leu His Asn His Tyr Thr Gln Lys Ser Leu Ser Leu Ser Pro Gly
            435             440             445

<210> SEQ ID NO 166
<211> LENGTH: 451
<212> TYPE: PRT
<213> ORGANISM: Artificial
<220> FEATURE:
<223> OTHER INFORMATION: Synthetic construct

<400> SEQUENCE: 166

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Ala Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Ser Gly Gly Gly Ser Gly Pro Asn Trp Phe Asp Pro Trp Gly
```

100                 105                 110
Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Ala Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 167
<211> LENGTH: 446
<212> TYPE: PRT
<213> ORGANISM: Artificial
<220> FEATURE:
<223> OTHER INFORMATION: Synthetic construct

<400> SEQUENCE: 167

Gln Val Gln Leu Val Gln Ser Gly Ala Glu Val Lys Lys Pro Gly Ala

-continued

```
1               5                   10                  15
Ser Val Lys Val Ser Cys Lys Ala Ser Gly Tyr Thr Phe Thr Ser Tyr
            20                  25                  30
Ala Ile Ser Trp Val Arg Gln Ala Pro Gly Gln Gly Leu Glu Trp Met
            35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Ser Gly Gly Ser Gly Pro Asn Trp Phe Asp Pro Trp Gly
                100                 105                 110
Gln Gly Thr Leu Val Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Asn Phe Gly Thr Gln Thr Tyr Thr Cys Asn Val Asp His
    195                 200                 205
Lys Pro Ser Asn Thr Lys Val Asp Lys Thr Val Glu Arg Lys Cys Cys
210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Gln Phe Asn Trp Tyr Val Asp Gly Val Glu Val His Asn Ala Lys
    275                 280                 285
Thr Lys Pro Arg Glu Glu Gln Phe Asn Ser Thr Phe Arg Val Val Ser
290                 295                 300
Val Leu Thr Val Val His Gln Asp Trp Leu Asn Gly Lys Glu Tyr Lys
305                 310                 315                 320
Cys Lys Val Ser Asn Lys Gly Leu Pro Ala Pro Ile Glu Lys Thr Ile
                325                 330                 335
Ser Lys Thr Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
    355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
```

His Asn His Tyr Thr Gln Lys Ser Leu Ser Leu Ser Pro Gly
            435                 440                 445

<210> SEQ ID NO 168
<211> LENGTH: 213
<212> TYPE: PRT
<213> ORGANISM: Artificial
<220> FEATURE:
<223> OTHER INFORMATION: Synthetic construct

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp His Tyr Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 169
<211> LENGTH: 215
<212> TYPE: PRT
<213> ORGANISM: Artificial
<220> FEATURE:
<223> OTHER INFORMATION: Synthetic construct

<400> SEQUENCE: 169

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu

```
                65                  70                  75                  80
Pro Glu Asp Phe Ala Val Tyr Tyr Cys Gln Gln Ser Glu Arg Ser Pro
                    85                  90                  95

Phe Thr Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 170
<211> LENGTH: 214
<212> TYPE: PRT
<213> ORGANISM: Artificial
<220> FEATURE:
<223> OTHER INFORMATION: Synthetic construct

<400> SEQUENCE: 170

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Phe Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ala Phe Ser Met Pro Pro
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
```

<210> SEQ ID NO 171
<211> LENGTH: 214
<212> TYPE: PRT
<213> ORGANISM: Artificial
<220> FEATURE:
<223> OTHER INFORMATION: Synthetic construct

<400> SEQUENCE: 171

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Phe Gln Ser Tyr Ser Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 172
<211> LENGTH: 214
<212> TYPE: PRT
<213> ORGANISM: Artificial
<220> FEATURE:
<223> OTHER INFORMATION: Synthetic construct

<400> SEQUENCE: 172

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ala Trp Pro Pro
            85                  90                  95

Thr Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 173
<211> LENGTH: 214
<212> TYPE: PRT
<213> ORGANISM: Artificial
<220> FEATURE:
<223> OTHER INFORMATION: Synthetic construct

<400> SEQUENCE: 173

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 174
<211> LENGTH: 215
<212> TYPE: PRT
<213> ORGANISM: Artificial
<220> FEATURE:
<223> OTHER INFORMATION: Synthetic construct

<400> SEQUENCE: 174

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Val Phe Pro
                85                  90                  95

Ile Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 175
<211> LENGTH: 214
<212> TYPE: PRT
<213> ORGANISM: Artificial
<220> FEATURE:
<223> OTHER INFORMATION: Synthetic construct

<400> SEQUENCE: 175

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Pro Ala Thr Leu Pro Trp
                85                  90                  95
```

```
Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 176
<211> LENGTH: 215
<212> TYPE: PRT
<213> ORGANISM: Artificial
<220> FEATURE:
<223> OTHER INFORMATION: Synthetic construct

<400> SEQUENCE: 176

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Asn Val Tyr Pro Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 177
```

<211> LENGTH: 468
<212> TYPE: PRT
<213> ORGANISM: Artificial
<220> FEATURE:
<223> OTHER INFORMATION: Synthetic construct

<400> SEQUENCE: 177

```
Met Gly Trp Ser Leu Ile Leu Leu Phe Leu Val Ala Val Ala Thr Arg
1               5                   10                  15

Val Leu Ser Glu Val Arg Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Ala Met Gly Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Thr Ser Arg Asp Asp Ser Lys Asn
                85                  90                  95

Ala Leu Tyr Leu Gln Met Asn Ser Leu Arg Ala Glu Asp Thr Ala Val
            100                 105                 110

Tyr Tyr Cys Ala Arg Gly Gly Pro Gly Trp Tyr Ala Ala Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Ala Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380
```

```
Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 178
<211> LENGTH: 465
<212> TYPE: PRT
<213> ORGANISM: Artificial
<220> FEATURE:
<223> OTHER INFORMATION: Synthetic construct

<400> SEQUENCE: 178

Met Gly Trp Ser Leu Ile Leu Leu Phe Leu Val Ala Val Ala Thr Arg
1               5                   10                  15

Val Leu Ser Glu Val Arg Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Ala Met Gly Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Thr Ser Arg Asp Asp Ser Lys Asn
                85                  90                  95

Ala Leu Tyr Leu Gln Met Asn Ser Leu Arg Ala Glu Asp Thr Ala Val
            100                 105                 110

Tyr Tyr Cys Ala Arg Gly Gly Pro Gly Trp Tyr Ala Ala Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270
```

```
Arg Thr Pro Glu Val Thr Cys Val Val Asp Val Ser Gln Glu Asp
        275                 280                 285
Pro Glu Val Gln Phe Asn Trp Tyr Val Asp Gly Val Glu Val His Asn
290                 295                 300
Ala Lys Thr Lys Pro Arg Glu Glu Gln Phe Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Gly Leu Pro Ser Ser Ile Glu Lys
            340                 345                 350
Thr Ile Ser Lys Ala Lys Gly Gln Pro Arg Glu Pro Gln Val Tyr Thr
        355                 360                 365
Leu Pro Pro Ser Gln Glu Glu Met Thr Lys Asn Gln Val Ser Leu Thr
370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Arg Leu Thr Val Asp Lys
            420                 425                 430
Ser Arg Trp Gln Glu Gly Asn Val Phe Ser Cys Ser Val Met His Glu
        435                 440                 445
Ala Leu His Asn His Tyr Thr Gln Lys Ser Leu Ser Leu Ser Leu Gly
    450                 455                 460
Lys
465

<210> SEQ ID NO 179
<211> LENGTH: 236
<212> TYPE: PRT
<213> ORGANISM: Artificial
<220> FEATURE:
<223> OTHER INFORMATION: Synthetic construct

<400> SEQUENCE: 179

Met Asp Phe Gln Val Gln Ile Ile Ser Phe Leu Leu Ile Ser Ala Ser
1               5                   10                  15
Val Ile Met Ser Arg Gly Asp Ile Gln Met Thr Gln Ser Pro Ser Ser
            20                  25                  30
Leu Ser Ala Ser Val Gly Asp Arg Val Thr Ile Thr Cys Arg Ala Ser
        35                  40                  45
Gln Ser Ile Ser Ser Tyr Leu Asn Trp Tyr Gln Gln Lys Pro Gly Lys
    50                  55                  60
Ala Pro Lys Leu Leu Ile Tyr Ala Ala Ser Ser Leu Gln Ser Gly Val
65                  70                  75                  80
Pro Ser Arg Phe Ser Gly Ser Gly Ser Gly Thr Asp Phe Thr Leu Thr
                85                  90                  95
Ile Ser Ser Leu Gln Pro Glu Asp Phe Ala Thr Tyr Tyr Cys Gln Gln
            100                 105                 110
Ala Asp Leu Pro Ala Phe Ala Phe Gly Gly Gly Thr Lys Val Glu Ile
        115                 120                 125
Lys Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
```

```
Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
        180                 185                 190

Ser Thr Tyr Ser Leu Ser Ser Thr Leu Thr Leu Ser Lys Ala Asp Tyr
    195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 180
<211> LENGTH: 463
<212> TYPE: PRT
<213> ORGANISM: Artificial
<220> FEATURE:
<223> OTHER INFORMATION: Synthetic construct

<400> SEQUENCE: 180

Met Gly Trp Ser Leu Ile Leu Leu Phe Leu Val Ala Val Ala Thr Arg
1               5                   10                  15

Val Leu Ser Gln Leu Gln Leu Gln Lys Ser Gly Pro Gly Leu Val Lys
            20                  25                  30

Pro Ser Glu Thr Leu Ser Leu Thr Cys Thr Val Ser Gly Phe Thr Phe
        35                  40                  45

Ser Asn Tyr Ala Met Gly Trp Ile Arg Gln Pro Pro Gly Lys Gly Leu
    50                  55                  60

Glu Trp Ile Gly Ala Ile Ser Gly Ser Gly Gly Ser Thr Tyr Tyr Ala
65                  70                  75                  80

Asp Ser Val Lys Gly Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Gly Gly Pro Gly Trp Tyr Ala Ala Asp Val Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285
```

Glu Val Gln Phe Asn Trp Tyr Val Asp Gly Val Glu Val His Asn Ala
            290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly
    450                 455                 460

<210> SEQ ID NO 181
<211> LENGTH: 236
<212> TYPE: PRT
<213> ORGANISM: Artificial
<220> FEATURE:
<223> OTHER INFORMATION: Synthetic construct

<400> SEQUENCE: 181

Met Asp Phe Gln Val Gln Ile Ile Ser Phe Leu Leu Ile Ser Ala Ser
1               5                   10                  15

Val Ile Met Ser Arg Gly Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Gln Ser Ile Ser Ser Tyr Leu Asn Trp Tyr Gln Gln Lys Pro Gly Gln
    50                  55                  60

Ala Pro Arg Leu Leu Ile Tyr Ala Ala Ser Ser Leu Gln Ser Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Ala Asp Leu Pro Ala Phe Ala Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 182
<211> LENGTH: 20
<212> TYPE: PRT
<213> ORGANISM: Artificial
<220> FEATURE:
<223> OTHER INFORMATION: Synthetic construct

<400> SEQUENCE: 182

Met Glu Thr Asp Thr Leu Leu Leu Trp Val Leu Leu Leu Trp Val Pro
1               5                   10                  15

Gly Ser Thr Gly
            20

<210> SEQ ID NO 183
<211> LENGTH: 14
<212> TYPE: PRT
<213> ORGANISM: Artificial
<220> FEATURE:
<223> OTHER INFORMATION: Synthetic construct

<400> SEQUENCE: 183

Trp Val Arg Gln Ala Pro Gly Lys Gly Leu Glu Trp Val Ala
1               5                   10

<210> SEQ ID NO 184
<211> LENGTH: 14
<212> TYPE: PRT
<213> ORGANISM: Artificial
<220> FEATURE:
<223> OTHER INFORMATION: Synthetic construct

<400> SEQUENCE: 184

Trp Ile Arg Gln His Pro Gly Lys Gly Leu Glu Trp Ile Gly
1               5                   10

<210> SEQ ID NO 185
<211> LENGTH: 14
<212> TYPE: PRT
<213> ORGANISM: Artificial
<220> FEATURE:
<223> OTHER INFORMATION: Synthetic construct

<400> SEQUENCE: 185

Trp Ile Arg Gln Pro Pro Gly Lys Gly Leu Glu Trp Ile Gly
1               5                   10

<210> SEQ ID NO 186
<211> LENGTH: 14
<212> TYPE: PRT
<213> ORGANISM: Artificial
<220> FEATURE:
<223> OTHER INFORMATION: Synthetic construct

<400> SEQUENCE: 186

Trp Val Arg Gln Ala Pro Gly Lys Gly Leu Glu Trp Val Ser
1               5                   10

<210> SEQ ID NO 187
<211> LENGTH: 14
<212> TYPE: PRT
<213> ORGANISM: Artificial
<220> FEATURE:
<223> OTHER INFORMATION: Synthetic construct

<400> SEQUENCE: 187

Trp Val Arg Gln Ala Pro Gly Gln Gly Leu Glu Trp Met Gly
1               5                   10

<210> SEQ ID NO 188
<211> LENGTH: 26
<212> TYPE: PRT
<213> ORGANISM: Artificial
<220> FEATURE:
<223> OTHER INFORMATION: Synthetic construct

<400> SEQUENCE: 188

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 189
<211> LENGTH: 454
<212> TYPE: PRT
<213> ORGANISM: Artificial
<220> FEATURE:
<223> OTHER INFORMATION: Synthetic construct

<400> SEQUENCE: 189

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Ala Glu Pro
    210                 215                 220

```
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```